US010647972B2

(12) United States Patent
Moyer

(10) Patent No.: US 10,647,972 B2
(45) **Date of Patent: *May 12, 2020**

(54) METHODS FOR OBTAINING POSITIVE TRANSFORMANTS OF A FILAMENTOUS FUNGAL HOST CELL

(71) Applicant: Novozymes, Inc., Davis, CA (US)

(72) Inventor: Donna Moyer, Davis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/211,689

(22) Filed: Dec. 6, 2018

(65) Prior Publication Data

US 2019/0093094 A1 Mar. 28, 2019

Related U.S. Application Data

(62) Division of application No. 15/197,049, filed on Jun. 29, 2016, now Pat. No. 10,190,109, which is a division of application No. 14/238,681, filed as application No. PCT/US2012/052146 on Aug. 23, 2012, now Pat. No. 9,404,101.

(60) Provisional application No. 61/526,804, filed on Aug. 24, 2011.

(51) Int. Cl.

| | |
|---|---|
| ***C12N 9/42*** | (2006.01) |
| ***C12N 15/80*** | (2006.01) |
| ***C12N 9/24*** | (2006.01) |

(52) U.S. Cl.

CPC ......... *C12N 9/2445* (2013.01); *C12N 9/2402* (2013.01); *C12N 15/80* (2013.01); *C12Y 302/01* (2013.01); *C12Y 302/01021* (2013.01)

(58) Field of Classification Search

None

See application file for complete search history.

(56) References Cited

U.S. PATENT DOCUMENTS 5,958,727 A 9/1999 Brody et al.
6,323,002 B1 11/2001 Brody et al.
6,590,078 B2 7/2003 Ward et al.
7,001,751 B1 2/2006 Pfaller
7,163,804 B1 1/2007 Royer et al.
8,415,119 B2 4/2013 Hansen et al.
8,680,252 B2 3/2014 Emalfarb et al.
8,686,218 B2 4/2014 Romaine et al.
9,404,101 B2 * 8/2016 Moyer .................. C12N 15/80
9,499,820 B2 11/2016 Brody et al.
9,624,554 B2 4/2017 Collins et al.
10,190,109 B2 * 1/2019 Moyer .................. C12N 15/80
10,273,515 B2 * 4/2019 Shasky .................. C12P 19/02
10,301,310 B2 * 5/2019 Reddington ......... C07D 471/06
10,385,352 B2 * 8/2019 Jin ....................... C12N 15/902
2003/0092131 A1 5/2003 Ward et al.
2003/0182678 A1 9/2003 Mitsky et al.
2010/0178671 A1 7/2010 Nguyen et al.
2011/0223671 A1 9/2011 Yoder et al.
2013/0109055 A1 5/2013 Ryding et al.
2014/0206086 A1 * 7/2014 Moyer .................. C12N 15/80 435/471
2014/0303036 A1 10/2014 Roubos et al.
2015/0211013 A1 7/2015 Emalfarb et al.
2016/0304850 A1 * 10/2016 Moyer .................. C12N 15/80
2017/0015986 A1 * 1/2017 Yaver .................... C12N 15/80
2017/0029821 A1 2/2017 Brody et al.
2017/0037417 A9 2/2017 Emalfarb et al.
2017/0204441 A1 * 7/2017 Shasky .................. C12P 19/02
2018/0037897 A1 * 2/2018 Jin ........................ C12N 15/79
2019/0218584 A1 * 7/2019 Shasky ................ C12N 9/0004
2019/0249161 A1 * 8/2019 Yaver .................. C12N 9/2402

FOREIGN PATENT DOCUMENTS

DE 102006052204 A1 5/2008
EP 2 371 963 3/2010
EP 2 840 139 8/2013
WO 1994003072 A1 2/1994
WO 2005093050 A2 10/2005
WO 2007136865 A2 11/2007
WO 2008009728 A1 1/2008
WO 2010039889 A2 4/2010
WO 2011090731 A1 7/2011
WO 2011120952 A1 10/2011
WO WO-2013028912 A2 * 2/2013 ............ C12N 15/80
WO WO-2013028915 A2 * 2/2013 ............ C12N 15/80
WO 2013111754 A1 8/2013
WO 2014145768 A2 9/2014

(Continued)

OTHER PUBLICATIONS

Wang et al, World J. Microbiol. Biotechnol., 2011, 27:1817-1826. published online: Dec. 28, 2010 (Year: 2011).*
Sakai et al, 2008, J Biosci Bioengg 106 (5), 466-472.
Lubertozzi et al, 2009, Biotechnol Adv 27 (1), 53-75.
Bjarne et al, 2011, Appl Environ Microbiol 77(9), 3044-3051.
Zhang et al, 2011, China Biotechnol 31(1), 40-45 (Abstract).
De Vries et al, 2004, Appl Environ Microbiol 70(7), 3954-3959.
Devchand et al, 1991, J Biotechnol 17, 3-10.
Gerngross et al, 2004, Nature Biotechnol 22(11), 1409-1414.
Granado et al, 1997, Mol Gen Genet 256, 28-36.
Hondel et al, 1991, NY Academic Press, 396-428.
Hua et al,2011, China Biotechnol 31(1), 40-45, Abstract.

(Continued)

*Primary Examiner* — Nita M. Minnifield

(74) *Attorney, Agent, or Firm* — Eric Fechter

(57) ABSTRACT

The present invention relates to methods for obtaining positive transformants of a filamentous fungal host cell, comprising: transforming a tandem construct into a population of cells of the filamentous fungal host a tandem construct and isolating a transformant of the filamentous fungal host cell comprising the tandem construct. The present invention also relates to such tandem constructs, filamentous fungal host cells comprising such tandem constructs, and methods of producing multiple recombinant proteins.

13 Claims, 6 Drawing Sheets

Specification includes a Sequence Listing.

(56) References Cited

FOREIGN PATENT DOCUMENTS

WO WO-2015187935 A1 * 12/2015
WO WO-2016145084 A1 * 9/2016 ............. C12N 15/79

OTHER PUBLICATIONS

Kues et al, Coprinus Cinereus.
Menzella et al, 2007, Curr Opin Microbiol 10(3), 238-245.
Nykanen et al, 1997, Appl Environ Microbiol 63(12), 4929-4937.
Nyyssonen et al, 1995, ACS Symposium Series 108-122.
Paloheimo et al, 2007, Appl Environ Microbiol 73(10), 3215-3224.
Punt et al, 2002, Trends Biotechnol 20(5), 200-206.
Read et al, 2007, Appl Environ Microbiol 73(16), 5088-5096.
Timberlake et al, 1989, Sci 244, 1313-1317.
Wang et al, 2005, Biotechnol Adv 23, 115-129.
Perkins et al, 1993, Genetics 134, 729-736.
Yang et al, 2004, Chinese Journal of Immunology 20(2), 79-82.
Duan et al, 2009, World J Microbiol Biotechnol 25, 1779-1783.
Gouka et al, 1999, Nature Biotechnol 17, 598-601.
Jiang et al, 2005, Appl Environ Microbiol 71, 2962-1969.
Kim et al, 2004, Protein Sci 13, 1698-1703.
Kimura et al, 1993, J Bacteriol 175, 4427-4435.
Scheich et al, 2007, Nucleic Acids Res 35(6), e43.
Sharma et al, 2006, Biotechnol Appl Biochem 43, 181-186.

* cited by examiner

SEQUENCE LISTING

```
<160> NUMBER OF SEQ ID NOS: 170

<210> SEQ ID NO 1
<211> LENGTH: 1377
<212> TYPE: DNA
<213> ORGANISM: Trichoderma reesei

<400> SEQUENCE: 1

atggcgccct cagttacact gccgttgacc acggccatcc tggccattgc ccggctcgtc      60

gccgcccagc aaccgggtac cagcaccccc gaggtccatc ccaagttgac aacctacaag     120

tgtacaaagt ccgggggggtg cgtggcccag gacacctcgg tggtccttga ctggaactac     180

cgctggatgc acgacgcaaa ctacaactcg tgcaccgtca acggcggcgt caacaccacg     240

ctctgccctg acgaggcgac ctgtggcaag aactgcttca tcgagggcgt cgactacgcc     300

gcctcgggcg tcacgacctc gggcagcagc ctcaccatga accagtacat gcccagcagc     360

tctggcggct acagcagcgt ctctcctcgg ctgtatctcc tggactctga cggtgagtac     420

gtgatgctga agctcaacgg ccaggagctg agcttcgacg tcgacctctc tgctctgccg     480

tgtggagaga acggctcgct ctacctgtct cagatggacg agaacggggg cgccaaccag     540

tataacacgg ccggtgccaa ctacgggagc ggctactgcg atgctcagtg ccccgtccag     600

acatggagga acggcaccct caacactagc caccagggct tctgctgcaa cgagatggat     660

atcctggagg gcaactcgag ggcgaatgcc ttgacccctc actcttgcac ggccacggcc     720

tgcgactctg ccggttgcgg cttcaacccc tatggcagcg gctacaaaag ctactacggc     780

cccggagata ccgttgacac ctccaagacc ttcaccatca tcacccagtt caacacggac     840

aacggctcgc cctcgggcaa ccttgtgagc atcacccgca agtaccagca aaacggcgtc     900

gacatcccca gcgcccagcc cggcggcgac accatctcgt cctgcccgtc cgcctcagcc     960

tacggcggcc tcgccaccat gggcaaggcc ctgagcagcg gcatggtgct cgtgttcagc    1020

atttggaacg acaacagcca gtacatgaac tggctcgaca gcggcaacgc cggcccctgc    1080

agcagcaccg agggcaaccc atccaacatc ctggccaaca accccaacac gcacgtcgtc    1140

ttctccaaca tccgctgggg agacattggg tctactacga actcgactgc gcccccgccc    1200

ccgcctgcgt ccagcacgac gttttcgact acacggagga gctcgacgac ttcgagcagc    1260
```

```
ccgagctgca cgcagactca ctgggggcag tgcggtggca ttgggtacag cgggtgcaag   1320

acgtgcacgt cgggcactac gtgccagtat agcaacgact actactcgca atgcctt      1377


<210> SEQ ID NO 2
<211> LENGTH: 459
<212> TYPE: PRT
<213> ORGANISM: Trichoderma reesei

<400> SEQUENCE: 2

Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
```

```
        355                 360                 365

Asn Ile Leu Ala Asn Asn Pro Asn Thr His Val Val Phe Ser Asn Ile
    370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
    450                 455


<210> SEQ ID NO 3
<211> LENGTH: 1254
<212> TYPE: DNA
<213> ORGANISM: Trichoderma reesei

<400> SEQUENCE: 3

atgaacaagt ccgtggctcc attgctgctt gcagcgtcca tactatatgg cggcgccgtc     60

gcacagcaga ctgtctgggg ccagtgtgga ggtattggtt ggagcggacc tacgaattgt    120

gctcctggct cagcttgttc gaccctcaat ccttattatg cgcaatgtat tccgggagcc    180

actactatca ccacttcgac ccggccacca tccggtccaa ccaccaccac cagggctacc    240

tcaacaagct catcaactcc acccacgagc tctggggtcc gatttgccgg cgttaacatc    300

gcgggttttg actttggctg taccacagat ggcacttgcg ttacctcgaa ggtttatcct    360

ccgttgaaga acttcaccgg ctcaaacaac taccccgatg gcatcggcca gatgcagcac    420

ttcgtcaacg aggacgggat gactattttc cgcttacctg tcggatggca gtacctcgtc    480

aacaacaatt tgggcggcaa tcttgattcc acgagcattt ccaagtatga tcagcttgtt    540

caggggtgcc tgtctctggg cgcatactgc atcgtcgaca tccacaatta tgctcgatgg    600

aacggtggga tcattggtca gggcggccct actaatgctc aattcacgag cctttggtcg    660

cagttggcat caaagtacgc atctcagtcg agggtgtggt tcggcatcat gaatgagccc    720

cacgacgtga acatcaacac ctgggctgcc acggtccaag aggttgtaac cgcaatccgc    780

aacgctggtg ctacgtcgca attcatctct ttgcctggaa atgattggca atctgctggg    840

gctttcatat ccgatggcag tgcagccgcc ctgtctcaag tcacgaaccc ggatgggtca    900

acaacgaatc tgatttttga cgtgcacaaa tacttggact cagacaactc cggtactcac    960

gccgaatgta ctacaaataa cattgacggc gccttttctc cgcttgccac ttggctccga   1020

cagaacaatc gccaggctat cctgacagaa accggtggtg gcaacgttca gtcctgcata   1080

caagacatgt gccagcaaat ccaatatctc aaccagaact cagatgtcta tcttggctat   1140

gttggttggg gtgccggatc atttgatagc acgtatgtcc tgacggaaac accgactagc   1200

agtggtaact catggacgga cacatccttg gtcagctcgt gtctcgcaag aaag         1254


<210> SEQ ID NO 4
<211> LENGTH: 418
<212> TYPE: PRT
<213> ORGANISM: Trichoderma reesei

<400> SEQUENCE: 4

Met Asn Lys Ser Val Ala Pro Leu Leu Leu Ala Ala Ser Ile Leu Tyr
```

-continued

```
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Ser
385                 390                 395                 400

Ser Gly Asn Ser Trp Thr Asp Thr Ser Leu Val Ser Ser Cys Leu Ala
                405                 410                 415

Arg Lys
```

<210> SEQ ID NO 5
<211> LENGTH: 702
<212> TYPE: DNA
<213> ORGANISM: Trichoderma reesei

<400> SEQUENCE: 5

```
atgaagttcc ttcaagtcct ccctgccctc ataccggccg ccctggccca aaccagctgt     60

gaccagtggg caaccttcac tggcaacggc tacacagtca gcaacaacct ttggggagca    120

tcagccggct ctggatttgg ctgcgtgacg gcggtatcgc tcagcggcgg ggcctcctgg    180

cacgcagact ggcagtggtc cggcggccag aacaacgtca agtcgtacca gaactctcag    240

attgccattc cccagaagag gaccgtcaac agcatcagca gcatgcccac cactgccagc    300

tggagctaca gcgggagcaa catccgcgct aatgttgcgt atgacttgtt caccgcagcc    360

aacccgaatc atgtcacgta ctcgggagac tacgaactca tgatctggct tggcaaatac    420

ggcgatattg ggccgattgg gtcctcacag ggaacagtca acgtcggtgg ccagagctgg    480

acgctctact atggctacaa cggagccatg caagtctatt cctttgtggc ccagaccaac    540

actaccaact acagcggaga tgtcaagaac ttcttcaatt atctccgaga caataaagga    600

tacaacgctg caggccaata tgttcttagc taccaatttg gtaccgagcc cttcacgggc    660

agtggaactc tgaacgtcgc atcctggacc gcatctatca ac                       702
```

<210> SEQ ID NO 6
<211> LENGTH: 234
<212> TYPE: PRT
<213> ORGANISM: Trichoderma reesei

<400> SEQUENCE: 6

```
Met Lys Phe Leu Gln Val Leu Pro Ala Leu Ile Pro Ala Ala Leu Ala
1               5                   10                  15

Gln Thr Ser Cys Asp Gln Trp Ala Thr Phe Thr Gly Asn Gly Tyr Thr
            20                  25                  30

Val Ser Asn Asn Leu Trp Gly Ala Ser Ala Gly Ser Gly Phe Gly Cys
        35                  40                  45

Val Thr Ala Val Ser Leu Ser Gly Gly Ala Ser Trp His Ala Asp Trp
    50                  55                  60

Gln Trp Ser Gly Gly Gln Asn Asn Val Lys Ser Tyr Gln Asn Ser Gln
65                  70                  75                  80

Ile Ala Ile Pro Gln Lys Arg Thr Val Asn Ser Ile Ser Ser Met Pro
                85                  90                  95

Thr Thr Ala Ser Trp Ser Tyr Ser Gly Ser Asn Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
    130                 135                 140

Pro Ile Gly Ser Ser Gln Gly Thr Val Asn Val Gly Gly Gln Ser Trp
145                 150                 155                 160

Thr Leu Tyr Tyr Gly Tyr Asn Gly Ala Met Gln Val Tyr Ser Phe Val
                165                 170                 175

Ala Gln Thr Asn Thr Thr Asn Tyr Ser Gly Asp Val Lys Asn Phe Phe
            180                 185                 190

Asn Tyr Leu Arg Asp Asn Lys Gly Tyr Asn Ala Ala Gly Gln Tyr Val
        195                 200                 205
```

```
Leu Ser Tyr Gln Phe Gly Thr Glu Pro Phe Thr Gly Ser Gly Thr Leu
    210                 215                 220

Asn Val Ala Ser Trp Thr Ala Ser Ile Asn
225                 230


<210> SEQ ID NO 7
<211> LENGTH: 726
<212> TYPE: DNA
<213> ORGANISM: Trichoderma reesei

<400> SEQUENCE: 7

atgaaggcaa ctctggttct cggctccctc attgtaggcg ccgtttccgc gtacaaggcc      60

accaccacgc gctactacga tgggcaggag ggtgcttgcg gatgcggctc gagctccggc     120

gcattcccgt ggcagctcgg catcggcaac ggagtctaca cggctgccgg ctcccaggct     180

ctcttcgaca cggccggagc ttcatggtgc ggcgccggct gcggtaaatg ctaccagctc     240

acctcgacgg gccaggcgcc ctgctccagc tgcggcacgg gcggtgctgc tggccagagc     300

atcatcgtca tggtgaccaa cctgtgcccg aacaatggga acgcgcagtg gtgcccggtg     360

gtcggcggca ccaaccaata cggctacagc taccatttcg acatcatggc gcagaacgag     420

atctttggag acaatgtcgt cgtcgacttt gagcccattg cttgccccgg gcaggctgcc     480

tctgactggg ggacgtgcct ctgcgtggga cagcaagaga cggatcccac gcccgtcctc     540

ggcaacgaca cgggctcaac tcctcccggg agctcgccgc cagcgacatc gtcgagtccg     600

ccgtctggcg gcggccagca gacgctctat ggccagtgtg gaggtgccgg ctggacggga     660

cctacgacgt gccaggcccc agggacctgc aaggttcaga accagtggta ctcccagtgt     720

cttcct                                                                726


<210> SEQ ID NO 8
<211> LENGTH: 242
<212> TYPE: PRT
<213> ORGANISM: Trichoderma reesei

<400> SEQUENCE: 8

Met Lys Ala Thr Leu Val Leu Gly Ser Leu Ile Val Gly Ala Val Ser
1               5                   10                  15

Ala Tyr Lys Ala Thr Thr Thr Arg Tyr Tyr Asp Gly Gln Glu Gly Ala
            20                  25                  30

Cys Gly Cys Gly Ser Ser Ser Gly Ala Phe Pro Trp Gln Leu Gly Ile
        35                  40                  45

Gly Asn Gly Val Tyr Thr Ala Ala Gly Ser Gln Ala Leu Phe Asp Thr
    50                  55                  60

Ala Gly Ala Ser Trp Cys Gly Ala Gly Cys Gly Lys Cys Tyr Gln Leu
65                  70                  75                  80

Thr Ser Thr Gly Gln Ala Pro Cys Ser Ser Cys Gly Thr Gly Gly Ala
                85                  90                  95

Ala Gly Gln Ser Ile Ile Val Met Val Thr Asn Leu Cys Pro Asn Asn
            100                 105                 110

Gly Asn Ala Gln Trp Cys Pro Val Val Gly Gly Thr Asn Gln Tyr Gly
        115                 120                 125

Tyr Ser Tyr His Phe Asp Ile Met Ala Gln Asn Glu Ile Phe Gly Asp
    130                 135                 140

Asn Val Val Val Asp Phe Glu Pro Ile Ala Cys Pro Gly Gln Ala Ala
145                 150                 155                 160

Ser Asp Trp Gly Thr Cys Leu Cys Val Gly Gln Gln Glu Thr Asp Pro
```

-continued

```
            165                 170                 175

Thr Pro Val Leu Gly Asn Asp Thr Gly Ser Thr Pro Pro Gly Ser Ser
            180                 185                 190

Pro Pro Ala Thr Ser Ser Ser Pro Pro Ser Gly Gly Gly Gln Gln Thr
        195                 200                 205

Leu Tyr Gly Gln Cys Gly Gly Ala Gly Trp Thr Gly Pro Thr Thr Cys
    210                 215                 220

Gln Ala Pro Gly Thr Cys Lys Val Gln Asn Gln Trp Tyr Ser Gln Cys
225                 230                 235                 240

Leu Pro


<210> SEQ ID NO 9
<211> LENGTH: 923
<212> TYPE: DNA
<213> ORGANISM: Humicola insolens

<400> SEQUENCE: 9

atgcgttcct cccccctcct ccgctccgcc gttgtggccg ccctgccggt gttggccctt      60

gccgctgatg gcaggtccac ccgctactgg gactgctgca agccttcgtg cggctgggcc     120

aagaaggctc ccgtgaacca gcctgtcttt tcctgcaacg ccaacttcca gcgtatcacg     180

gacttcgacg ccaagtccgg ctgcgagccg ggcggtgtcg cctactcgtg cgccgaccag     240

accccatggg ctgtgaacga cgacttcgcg ctcggttttg ctgccacctc tattgccggc     300

agcaatgagg cgggctggtg ctgcgcctgc tacgagctca ccttcacatc cggtcctgtt     360

gctggcaaga agatggtcgt ccagtccacc agcactggcg gtgatcttgg cagcaaccac     420

ttcgatctca acatccccgg cggcggcgtc ggcatcttcg acggatgcac tccccagttc     480

ggcggtctgc ccggccagcg ctacggcggc atctcgtccc gcaacgagtg cgatcggttc     540

cccgacgccc tcaagcccgg ctgctactgg cgcttcgact ggttcaagaa cgccgacaat     600

ccgagcttca gcttccgtca ggtccagtgc ccagccgagc tcgtcgctcg caccggatgc     660

cgccgcaacg acgacggcaa cttccctgcc gtccagatcc cctccagcag caccagctct     720

ccggtcaacc agcctaccag caccagcacc acgtccacct ccaccacctc gagcccgcca     780

gtccagccta cgactcccag cggctgcact gctgagaggt gggctcagtg cggcggcaat     840

ggctggagcg gctgcaccac ctgcgtcgct ggcagcactt gcacgaagat taatgactgg     900

taccatcagt gcctgtagaa ttc                                             923


<210> SEQ ID NO 10
<211> LENGTH: 305
<212> TYPE: PRT
<213> ORGANISM: Humicola insolens

<400> SEQUENCE: 10

Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80
```

```
Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Ser Thr Ser Ser
225                 230                 235                 240

Pro Val Asn Gln Pro Thr Ser Thr Ser Thr Thr Ser Thr Ser Thr Thr
                245                 250                 255

Ser Ser Pro Pro Val Gln Pro Thr Thr Pro Ser Gly Cys Thr Ala Glu
            260                 265                 270

Arg Trp Ala Gln Cys Gly Gly Asn Gly Trp Ser Gly Cys Thr Thr Cys
        275                 280                 285

Val Ala Gly Ser Thr Cys Thr Lys Ile Asn Asp Trp Tyr His Gln Cys
    290                 295                 300

Leu
305
```

<210> SEQ ID NO 11
<211> LENGTH: 1188
<212> TYPE: DNA
<213> ORGANISM: Myceliopthora thermophila

<400> SEQUENCE: 11

```
cgacttgaaa cgccccaaat gaagtcctcc atcctcgcca gcgtcttcgc cacgggcgcc      60

gtggctcaaa gtggtccgtg gcagcaatgt ggtggcatcg gatggcaagg atcgaccgac     120

tgtgtgtcgg gctaccactg cgtctaccag aacgattggt acagccagtg cgtgcctggc     180

gcggcgtcga caacgctgca gacatcgacc acgtccaggc ccaccgccac cagcaccgcc     240

cctccgtcgt ccaccacctc gcctagcaag ggcaagctga agtggctcgg cagcaacgag     300

tcgggcgccg agttcgggga gggcaattac cccggcctct ggggcaagca cttcatcttc     360

ccgtcgactt cggcgattca gacgctcatc aatgatggat acaacatctt ccggatcgac     420

ttctcgatgg agcgtctggt gcccaaccag ttgacgtcgt ccttcgacca gggttacctc     480

cgcaacctga ccgaggtggt caacttcgtg acgaacgcgg gcaagtacgc cgtcctggac     540

ccgcacaact acggccggta ctacggcaac atcatcacgg acacgaacgc gttccggacc     600

ttctggacca acctggccaa gcagttcgcc tccaactcgc tcgtcatctt cgacaccaac     660

aacgagtaca acacgatgga ccagaccctg gtgctcaacc tcaaccaggc cgccatcgac     720

ggcatccggg ccgccggcgc gacctcgcag tacatcttcg tcgagggcaa cgcgtggagc     780
```

```
ggggcctgga gctggaacac gaccaacacc aacatggccg ccctgacgga cccgcagaac    840

aagatcgtgt acgagatgca ccagtacctc gactcggaca gctcgggcac ccacgccgag    900

tgcgtcagca gcaccatcgg cgcccagcgc gtcgtcggag ccacccagtg gctccgcgcc    960

aacggcaagc tcggcgtcct cggcgagttc gccggcggcg ccaacgccgt ctgccagcag   1020

gccgtcaccg gcctcctcga ccacctccag gacaacagcg acgtctggct gggtgccctc   1080

tggtgggccg ccggtccctg gtggggcgac tacatgtact cgttcgagcc tccttcgggc   1140

accggctatg tcaactacaa ctcgatcttg aagaagtact tgccgtaa                1188


<210> SEQ ID NO 12
<211> LENGTH: 389
<212> TYPE: PRT
<213> ORGANISM: Myceliopthora thermophila

<400> SEQUENCE: 12

Met Lys Ser Ser Ile Leu Ala Ser Val Phe Ala Thr Gly Ala Val Ala
1               5                   10                  15

Gln Ser Gly Pro Trp Gln Gln Cys Gly Gly Ile Gly Trp Gln Gly Ser
            20                  25                  30

Thr Asp Cys Val Ser Gly Tyr His Cys Val Tyr Gln Asn Asp Trp Tyr
        35                  40                  45

Ser Gln Cys Val Pro Gly Ala Ala Ser Thr Thr Leu Gln Thr Ser Thr
    50                  55                  60

Thr Ser Arg Pro Thr Ala Thr Ser Thr Ala Pro Pro Ser Ser Thr Thr
65                  70                  75                  80

Ser Pro Ser Lys Gly Lys Leu Lys Trp Leu Gly Ser Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
        115                 120                 125

Asn Ile Phe Arg Ile Asp Phe Ser Met Glu Arg Leu Val Pro Asn Gln
    130                 135                 140

Leu Thr Ser Ser Phe Asp Gln Gly Tyr Leu Arg Asn Leu Thr Glu Val
145                 150                 155                 160

Val Asn Phe Val Thr Asn Ala Gly Lys Tyr Ala Val Leu Asp Pro His
                165                 170                 175

Asn Tyr Gly Arg Tyr Tyr Gly Asn Ile Ile Thr Asp Thr Asn Ala Phe
            180                 185                 190

Arg Thr Phe Trp Thr Asn Leu Ala Lys Gln Phe Ala Ser Asn Ser Leu
        195                 200                 205

Val Ile Phe Asp Thr Asn Asn Glu Tyr Asn Thr Met Asp Gln Thr Leu
    210                 215                 220

Val Leu Asn Leu Asn Gln Ala Ala Ile Asp Gly Ile Arg Ala Ala Gly
225                 230                 235                 240

Ala Thr Ser Gln Tyr Ile Phe Val Glu Gly Asn Ala Trp Ser Gly Ala
                245                 250                 255

Trp Ser Trp Asn Thr Thr Asn Thr Asn Met Ala Ala Leu Thr Asp Pro
            260                 265                 270

Gln Asn Lys Ile Val Tyr Glu Met His Gln Tyr Leu Asp Ser Asp Ser
        275                 280                 285

Ser Gly Thr His Ala Glu Cys Val Ser Ser Thr Ile Gly Ala Gln Arg
    290                 295                 300
```

```
Val Val Gly Ala Thr Gln Trp Leu Arg Ala Asn Gly Lys Leu Gly Val
305                 310                 315                 320

Leu Gly Glu Phe Ala Gly Gly Ala Asn Ala Val Cys Gln Gln Ala Val
                325                 330                 335

Thr Gly Leu Leu Asp His Leu Gln Asp Asn Ser Asp Val Trp Leu Gly
            340                 345                 350

Ala Leu Trp Trp Ala Ala Gly Pro Trp Trp Gly Asp Tyr Met Tyr Ser
        355                 360                 365

Phe Glu Pro Pro Ser Gly Thr Gly Tyr Val Asn Tyr Asn Ser Ile Leu
    370                 375                 380

Lys Lys Tyr Leu Pro
385


<210> SEQ ID NO 13
<211> LENGTH: 1232
<212> TYPE: DNA
<213> ORGANISM: BASIDIOMYCETE CBS 495.95

<400> SEQUENCE: 13

ggatccactt agtaacggcc gccagtgtgc tggaaagcat gaagtctctc ttcctgtcac     60

ttgtagcgac cgtcgcgctc agctcgccag tattctctgt cgcagtctgg gggcaatgcg    120

gcggcattgg cttcagcgga agcaccgtct gtgatgcagg cgccggctgt gtgaagctca    180

acgactatta ctctcaatgc caacccggcg ctcccactgc tacatccgcg gcgccaagta    240

gcaacgcacc gtccggcact tcgacggcct cggccccctc ctccagcctt tgctctggca    300

gccgcacgcc gttccagttc ttcggtgtca acgaatccgg cgcggagttc ggcaacctga    360

acatccccgg tgttctgggc accgactaca cctggccgtc gccatccagc attgacttct    420

tcatgggcaa gggaatgaat accttccgta ttccgttcct catggagcgt cttgtccccc    480

ctgccactgg catcacagga cctctcgacc agacgtactt gggcggcctg cagacgattg    540

tcaactacat caccggcaaa ggcggctttg ctctcattga cccgcacaac tttatgatct    600

acaatggcca gacgatctcc agtaccagcg acttccagaa gttctggcag aacctcgcag    660

gagtgtttaa atcgaacagt cacgtcatct tcgatgttat gaacgagcct cacgatattc    720

ccgcccagac cgtgttccaa ctgaaccaag ccgctgtcaa tggcatccgt gcgagcggtg    780

cgacgtcgca gctcattctg gtcgagggca caagctggac tggagcctgg acctggacga    840

cctctggcaa cagcgatgca ttcggtgcca ttaaggatcc caacaacaac gtcgcgatcc    900

agatgcatca gtacctggat agcgatggct ctggcacttc gcagacctgc gtgtctccca    960

ccatcggtgc cgagcggttg caggctgcga ctcaatggtt gaagcagaac aacctcaagg   1020

gcttcctggg cgagatcggc gccggctcta actccgcttg catcagcgct gtgcagggtg   1080

cgttgtgttc gatgcagcaa tctggtgtgt ggctcggcgc tctctggtgg gctgcgggcc   1140

cgtggtgggg cgactactac cagtccatcg agccgccctc tggcccggcg gtgtccgcga   1200

tcctcccgca ggccctgctg ccgttcgcgt aa                                 1232


<210> SEQ ID NO 14
<211> LENGTH: 397
<212> TYPE: PRT
<213> ORGANISM: BASIDIOMYCETE CBS 495.95

<400> SEQUENCE: 14

Met Lys Ser Leu Phe Leu Ser Leu Val Ala Thr Val Ala Leu Ser Ser
1               5                   10                  15
```

```
Pro Val Phe Ser Val Ala Val Trp Gly Gln Cys Gly Gly Ile Gly Phe
            20                  25                  30

Ser Gly Ser Thr Val Cys Asp Ala Gly Ala Gly Cys Val Lys Leu Asn
        35                  40                  45

Asp Tyr Tyr Ser Gln Cys Gln Pro Gly Ala Pro Thr Ala Thr Ser Ala
    50                  55                  60

Ala Pro Ser Ser Asn Ala Pro Ser Gly Thr Ser Thr Ala Ser Ala Pro
65                  70                  75                  80

Ser Ser Ser Leu Cys Ser Gly Ser Arg Thr Pro Phe Gln Phe Phe Gly
                85                  90                  95

Val Asn Glu Ser Gly Ala Glu Phe Gly Asn Leu Asn Ile Pro Gly Val
            100                 105                 110

Leu Gly Thr Asp Tyr Thr Trp Pro Ser Pro Ser Ser Ile Asp Phe Phe
        115                 120                 125

Met Gly Lys Gly Met Asn Thr Phe Arg Ile Pro Phe Leu Met Glu Arg
    130                 135                 140

Leu Val Pro Pro Ala Thr Gly Ile Thr Gly Pro Leu Asp Gln Thr Tyr
145                 150                 155                 160

Leu Gly Gly Leu Gln Thr Ile Val Asn Tyr Ile Thr Gly Lys Gly Gly
                165                 170                 175

Phe Ala Leu Ile Asp Pro His Asn Phe Met Ile Tyr Asn Gly Gln Thr
            180                 185                 190

Ile Ser Ser Thr Ser Asp Phe Gln Lys Phe Trp Gln Asn Leu Ala Gly
        195                 200                 205

Val Phe Lys Ser Asn Ser His Val Ile Phe Asp Val Met Asn Glu Pro
    210                 215                 220

His Asp Ile Pro Ala Gln Thr Val Phe Gln Leu Asn Gln Ala Ala Val
225                 230                 235                 240

Asn Gly Ile Arg Ala Ser Gly Ala Thr Ser Gln Leu Ile Leu Val Glu
                245                 250                 255

Gly Thr Ser Trp Thr Gly Ala Trp Thr Trp Thr Thr Ser Gly Asn Ser
            260                 265                 270

Asp Ala Phe Gly Ala Ile Lys Asp Pro Asn Asn Asn Val Ala Ile Gln
        275                 280                 285

Met His Gln Tyr Leu Asp Ser Asp Gly Ser Gly Thr Ser Gln Thr Cys
    290                 295                 300

Val Ser Pro Thr Ile Gly Ala Glu Arg Leu Gln Ala Ala Thr Gln Trp
305                 310                 315                 320

Leu Lys Gln Asn Asn Leu Lys Gly Phe Leu Gly Glu Ile Gly Ala Gly
                325                 330                 335

Ser Asn Ser Ala Cys Ile Ser Ala Val Gln Gly Ala Leu Cys Ser Met
            340                 345                 350

Gln Gln Ser Gly Val Trp Leu Gly Ala Leu Trp Trp Ala Ala Gly Pro
        355                 360                 365

Trp Trp Gly Asp Tyr Tyr Gln Ser Ile Glu Pro Pro Ser Gly Pro Ala
    370                 375                 380

Val Ser Ala Ile Leu Pro Gln Ala Leu Leu Pro Phe Ala
385                 390                 395
```

<210> SEQ ID NO 15
<211> LENGTH: 1303
<212> TYPE: DNA
<213> ORGANISM: BASIDIOMYCETE CBS 495.95

<400> SEQUENCE: 15

```
ggaaagcgtc agtatggtga aatttgcgct tgtggcaact gtcggcgcaa tcttgagcgc     60
ttctgcggcc aatgcggctt ctatctacca gcaatgtgga ggcattggat ggtctgggtc    120
cactgtttgc gacgccggtc tcgcttgcgt tatcctcaat gcgtactact ttcagtgctt    180
gacgcccgcc gcgggccaga caacgacggg ctcgggcgca ccggcgtcaa catcaacctc    240
tcactcaacg gtcactacgg ggagctcaca ctcaacaacc gggacgacgg cgacgaaaac    300
aactaccact ccgtcgacca ccacgaccct acccgccatc tctgtgtctg gtcgcgtctg    360
ctctggctcc aggacgaagt tcaagttctt cggtgtgaat gaaagcggcg ccgaattcgg    420
gaacactgct tggccagggc agctcgggaa agactataca tggccttcgc ctagcagcgt    480
ggactacttc atgggggctg gattcaatac attccgtatc accttcttga tggagcgtat    540
gagccctccg gctaccggac tcactggccc attcaaccag acgtacctgt cgggcctcac    600
caccattgtc gactacatca cgaacaaagg aggatacgct cttattgacc cccacaactt    660
catgcgttac aacaacggca taatcagcag cacatctgac ttcgcgactt ggtggagcaa    720
tttggccact gtattcaaat ccacgaagaa cgccatcttc gacatccaga acgagccgta    780
cggaatcgat gcgcagaccg tatacgaact gaatcaagct gccatcaatt cgatccgcgc    840
cgctggcgct acgtcacagt tgattctggt tgaaggaacg tcatacactg gagcttggac    900
gtgggtctcg tccggaaacg gagctgcttt cgcggccgtt acggatcctt acaacaacac    960
ggcaattgaa atgcaccaat acctcgacag cgacggttct gggacaaacg aagactgtgt   1020
ctcctccacc attgggtcgc aacgtctcca agctgccact gcgtggctgc aacaaacagg   1080
actcaaggga ttcctcggag agacgggtgc tgggtcgaat tcccagtgca tcgacgccgt   1140
gttcgatgaa ctttgctata tgcaacagca aggcggctcc tggatcggtg cactctggtg   1200
ggctgcgggt ccctggtggg gcacgtacat ttactcgatt gaacctccga gcggtgccgc   1260
tatcccagaa gtccttcctc agggtctcgc tccattcctc tag                     1303
```

```
<210> SEQ ID NO 16
<211> LENGTH: 429
<212> TYPE: PRT
<213> ORGANISM: BASIDIOMYCETE CBS 495.95

<400> SEQUENCE: 16

Met Val Lys Phe Ala Leu Val Ala Thr Val Gly Ala Ile Leu Ser Ala
1               5                   10                  15

Ser Ala Ala Asn Ala Ala Ser Ile Tyr Gln Gln Cys Gly Gly Ile Gly
            20                  25                  30

Trp Ser Gly Ser Thr Val Cys Asp Ala Gly Leu Ala Cys Val Ile Leu
        35                  40                  45

Asn Ala Tyr Tyr Phe Gln Cys Leu Thr Pro Ala Ala Gly Gln Thr Thr
    50                  55                  60

Thr Gly Ser Gly Ala Pro Ala Ser Thr Ser Thr Ser His Ser Thr Val
65                  70                  75                  80

Thr Thr Gly Ser Ser His Ser Thr Thr Gly Thr Thr Ala Thr Lys Thr
                85                  90                  95

Thr Thr Thr Pro Ser Thr Thr Thr Thr Leu Pro Ala Ile Ser Val Ser
            100                 105                 110

Gly Arg Val Cys Ser Gly Ser Arg Thr Lys Phe Lys Phe Phe Gly Val
        115                 120                 125

Asn Glu Ser Gly Ala Glu Phe Gly Asn Thr Ala Trp Pro Gly Gln Leu
    130                 135                 140
```

```
Gly Lys Asp Tyr Thr Trp Pro Ser Pro Ser Ser Val Asp Tyr Phe Met
145                 150                 155                 160

Gly Ala Gly Phe Asn Thr Phe Arg Ile Thr Phe Leu Met Glu Arg Met
                165                 170                 175

Ser Pro Pro Ala Thr Gly Leu Thr Gly Pro Phe Asn Gln Thr Tyr Leu
            180                 185                 190

Ser Gly Leu Thr Thr Ile Val Asp Tyr Ile Thr Asn Lys Gly Gly Tyr
        195                 200                 205

Ala Leu Ile Asp Pro His Asn Phe Met Arg Tyr Asn Asn Gly Ile Ile
    210                 215                 220

Ser Ser Thr Ser Asp Phe Ala Thr Trp Trp Ser Asn Leu Ala Thr Val
225                 230                 235                 240

Phe Lys Ser Thr Lys Asn Ala Ile Phe Asp Ile Gln Asn Glu Pro Tyr
                245                 250                 255

Gly Ile Asp Ala Gln Thr Val Tyr Glu Leu Asn Gln Ala Ala Ile Asn
            260                 265                 270

Ser Ile Arg Ala Ala Gly Ala Thr Ser Gln Leu Ile Leu Val Glu Gly
        275                 280                 285

Thr Ser Tyr Thr Gly Ala Trp Thr Trp Val Ser Ser Gly Asn Gly Ala
    290                 295                 300

Ala Phe Ala Ala Val Thr Asp Pro Tyr Asn Asn Thr Ala Ile Glu Met
305                 310                 315                 320

His Gln Tyr Leu Asp Ser Asp Gly Ser Gly Thr Asn Glu Asp Cys Val
                325                 330                 335

Ser Ser Thr Ile Gly Ser Gln Arg Leu Gln Ala Ala Thr Ala Trp Leu
            340                 345                 350

Gln Gln Thr Gly Leu Lys Gly Phe Leu Gly Glu Thr Gly Ala Gly Ser
        355                 360                 365

Asn Ser Gln Cys Ile Asp Ala Val Phe Asp Glu Leu Cys Tyr Met Gln
    370                 375                 380

Gln Gln Gly Gly Ser Trp Ile Gly Ala Leu Trp Trp Ala Ala Gly Pro
385                 390                 395                 400

Trp Trp Gly Thr Tyr Ile Tyr Ser Ile Glu Pro Pro Ser Gly Ala Ala
                405                 410                 415

Ile Pro Glu Val Leu Pro Gln Gly Leu Ala Pro Phe Leu
            420                 425
```

<210> SEQ ID NO 17
<211> LENGTH: 1580
<212> TYPE: DNA
<213> ORGANISM: Thielavia terrestris

<400> SEQUENCE: 17

```
agccccccgt tcaggcacac ttggcatcag atcagcttag cagcgcctgc acagcatgaa      60

gctctcgcag tcggccgcgc tggcggcact caccgcgacg gcgctcgccg ccccctcgcc     120

cacgacgccg caggcgccga ggcaggcttc agccggctgc tcgtctgcgg tcacgctcga     180

cgccagcacc aacgtttgga agaagtacac gctgcacccc aacagctact accgcaagga     240

ggttgaggcc gcggtggcgc agatctcgga cccggacctc gccgccaagg ccaagaaggt     300

ggccgacgtc ggcaccttcc tgtggctcga ctcgatcgag aacatcggca agctggagcc     360

ggcgatccag gacgtgccct gcgagaacat cctgggcctg gtcatctacg acctgccggg     420

ccgcgactgc gcggccaagg cgtccaacgg cgagctcaag gtcggcgaga tcgaccgcta     480
```

```
caagaccgag tacatcgaca gtgagtgctg ccccccgggt tcgagaagag cgtgggggaa    540
agggaaaggg ttgactgact gacacggcgc actgcagaga tcgtgtcgat cctcaaggca    600
caccccaaca cggcgttcgc gctggtcatc gagccggact cgctgcccaa cctggtgacc    660
aacagcaact tggacacgtg ctcgagcagc gcgtcgggct accgcgaagg cgtggcttac    720
gccctcaaga acctcaacct gcccaacgtg atcatgtacc tcgacgccgg ccacggcggc    780
tggctcggct gggacgccaa cctgcagccc ggcgcgcagg agctagccaa ggcgtacaag    840
aacgccggct cgcccaagca gctccgcggc ttctcgacca acgtggccgg ctggaactcc    900
tggtgagctt ttttccattc catttcttct tcctcttctc tcttcgctcc cactctgcag    960
ccccccctcc cccaagcacc cactggcgtt ccggcttgct gactcggcct ccctttcccc   1020
gggcaccagg gatcaatcgc ccggcgaatt ctcccaggcg tccgacgcca agtacaacaa   1080
gtgccagaac gagaagatct acgtcagcac cttcggctcc gcgctccagt cggccggcat   1140
gcccaaccac gccatcgtcg acacgggccg caacggcgtc accggcctgc gcaaggagtg   1200
gggtgactgg tgcaacgtca acggtgcagg ttcgttgtct tctttttctc ctcttttgtt   1260
tgcacgtcgt ggtccttttc aagcagccgt gtttggttgg gggagatgga ctccggctga   1320
tgttctgctt cctctctagg cttcggcgtg cgcccgacga gcaacacggg cctcgagctg   1380
gccgacgcgt tcgtgtgggt caagcccggc ggcgagtcgg acggcaccag cgacagctcg   1440
tcgccgcgct acgacagctt ctgcggcaag gacgacgcct tcaagccctc gcccgaggcc   1500
ggcacctgga acgaggccta cttcgagatg ctgctcaaga acgccgtgcc gtcgttctaa   1560
gacggtccag catcatccgg                                                1580


<210> SEQ ID NO 18
<211> LENGTH: 396
<212> TYPE: PRT
<213> ORGANISM: Thielavia terrestris

<400> SEQUENCE: 18

Met Lys Leu Ser Gln Ser Ala Ala Leu Ala Ala Leu Thr Ala Thr Ala
1               5                   10                  15

Leu Ala Ala Pro Ser Pro Thr Thr Pro Gln Ala Pro Arg Gln Ala Ser
            20                  25                  30

Ala Gly Cys Ser Ser Ala Val Thr Leu Asp Ala Ser Thr Asn Val Trp
        35                  40                  45

Lys Lys Tyr Thr Leu His Pro Asn Ser Tyr Tyr Arg Lys Glu Val Glu
    50                  55                  60

Ala Ala Val Ala Gln Ile Ser Asp Pro Asp Leu Ala Ala Lys Ala Lys
65                  70                  75                  80

Lys Val Ala Asp Val Gly Thr Phe Leu Trp Leu Asp Ser Ile Glu Asn
                85                  90                  95

Ile Gly Lys Leu Glu Pro Ala Ile Gln Asp Val Pro Cys Glu Asn Ile
            100                 105                 110

Leu Gly Leu Val Ile Tyr Asp Leu Pro Gly Arg Asp Cys Ala Ala Lys
        115                 120                 125

Ala Ser Asn Gly Glu Leu Lys Val Gly Glu Ile Asp Arg Tyr Lys Thr
    130                 135                 140

Glu Tyr Ile Asp Lys Ile Val Ser Ile Leu Lys Ala His Pro Asn Thr
145                 150                 155                 160

Ala Phe Ala Leu Val Ile Glu Pro Asp Ser Leu Pro Asn Leu Val Thr
                165                 170                 175
```

```
Asn Ser Asn Leu Asp Thr Cys Ser Ser Ser Ala Ser Gly Tyr Arg Glu
            180                 185                 190

Gly Val Ala Tyr Ala Leu Lys Asn Leu Asn Leu Pro Asn Val Ile Met
        195                 200                 205

Tyr Leu Asp Ala Gly His Gly Gly Trp Leu Gly Trp Asp Ala Asn Leu
    210                 215                 220

Gln Pro Gly Ala Gln Glu Leu Ala Lys Ala Tyr Lys Asn Ala Gly Ser
225                 230                 235                 240

Pro Lys Gln Leu Arg Gly Phe Ser Thr Asn Val Ala Gly Trp Asn Ser
                245                 250                 255

Trp Asp Gln Ser Pro Gly Glu Phe Ser Gln Ala Ser Asp Ala Lys Tyr
            260                 265                 270

Asn Lys Cys Gln Asn Glu Lys Ile Tyr Val Ser Thr Phe Gly Ser Ala
        275                 280                 285

Leu Gln Ser Ala Gly Met Pro Asn His Ala Ile Val Asp Thr Gly Arg
    290                 295                 300

Asn Gly Val Thr Gly Leu Arg Lys Glu Trp Gly Asp Trp Cys Asn Val
305                 310                 315                 320

Asn Gly Ala Gly Phe Gly Val Arg Pro Thr Ser Asn Thr Gly Leu Glu
                325                 330                 335

Leu Ala Asp Ala Phe Val Trp Val Lys Pro Gly Gly Glu Ser Asp Gly
            340                 345                 350

Thr Ser Asp Ser Ser Ser Pro Arg Tyr Asp Ser Phe Cys Gly Lys Asp
        355                 360                 365

Asp Ala Phe Lys Pro Ser Pro Glu Ala Gly Thr Trp Asn Glu Ala Tyr
    370                 375                 380

Phe Glu Met Leu Leu Lys Asn Ala Val Pro Ser Phe
385                 390                 395
```

<210> SEQ ID NO 19
<211> LENGTH: 1203
<212> TYPE: DNA
<213> ORGANISM: Thielavia terrestris

<400> SEQUENCE: 19

```
atgaagtacc tcaacctcct cgcagctctc ctcgccgtcg ctcctctctc cctcgctgca     60

cccagcatcg aggccagaca gtcgaacgtc aacccataca tcggcaagag cccgctcgtt    120

attaggtcgt acgcccaaaa gcttgaggag accgtcagga ccttccagca acgtggcgac    180

cagctcaacg ctgcgaggac acggacggtg cagaacgttg cgactttcgc ctggatctcg    240

gataccaatg gtattggagc cattcgacct ctcatccaag atgctctcgc ccagcaggct    300

cgcactggac agaaggtcat cgtccaaatc gtcgtctaca acctcccaga tcgcgactgc    360

tctgccaacg cctcgactgg agagttcacc gtaggaaacg acggtctcaa ccgatacaag    420

aactttgtca acaccatcgc ccgcgagctc tcgactgctg acgctgacaa gctccacttt    480

gccctcctcc tcgaacccga cgcacttgcc aacctcgtca ccaacgcgaa tgcccccagg    540

tgccgaatcg ccgctcccgc ttacaaggag ggtatcgcct acaccctcgc caccttgtcc    600

aagcccaacg tcgacgtcta catcgacgcc gccaacggtg gctggctcgg ctggaacgac    660

aacctccgcc ccttcgccga actcttcaag gaagtctacg acctcgcccg ccgcatcaac    720

cccaacgcca aggtccgcgg cgtccccgtc aacgtctcca actacaacca gtaccgcgct    780

gaagtccgcg agcccttcac cgagtggaag gacgcctggg acgagagccg ctacgtcaac    840

gtcctcaccc cgcacctcaa cgccgtcggc ttctccgcgc acttcatcgt tgaccaggga    900
```

```
cgcggtggca agggcggtat caggacggag tggggccagt ggtgcaacgt taggaacgct    960

gggttcggta tcaggcctac tgcggatcag ggcgtgctcc agaacccgaa tgtggatgcg   1020

attgtgtggg ttaagccggg tggagagtcg gatggcacga gtgatttgaa ctcgaacagg   1080

tatgatccta cgtgcaggag tccggtggcg catgttcccg ctcctgaggc tggccagtgg   1140

ttcaacgagt atgttgttaa cctcgttttg aacgctaacc cccctcttga gcctacctgg   1200

taa                                                                 1203


<210> SEQ ID NO 20
<211> LENGTH: 400
<212> TYPE: PRT
<213> ORGANISM: Thielavia terrestris

<400> SEQUENCE: 20

Met Lys Tyr Leu Asn Leu Leu Ala Ala Leu Leu Ala Val Ala Pro Leu
1               5                   10                  15

Ser Leu Ala Ala Pro Ser Ile Glu Ala Arg Gln Ser Asn Val Asn Pro
            20                  25                  30

Tyr Ile Gly Lys Ser Pro Leu Val Ile Arg Ser Tyr Ala Gln Lys Leu
        35                  40                  45

Glu Glu Thr Val Arg Thr Phe Gln Gln Arg Gly Asp Gln Leu Asn Ala
    50                  55                  60

Ala Arg Thr Arg Thr Val Gln Asn Val Ala Thr Phe Ala Trp Ile Ser
65                  70                  75                  80

Asp Thr Asn Gly Ile Gly Ala Ile Arg Pro Leu Ile Gln Asp Ala Leu
                85                  90                  95

Ala Gln Gln Ala Arg Thr Gly Gln Lys Val Ile Val Gln Ile Val Val
            100                 105                 110

Tyr Asn Leu Pro Asp Arg Asp Cys Ser Ala Asn Ala Ser Thr Gly Glu
        115                 120                 125

Phe Thr Val Gly Asn Asp Gly Leu Asn Arg Tyr Lys Asn Phe Val Asn
    130                 135                 140

Thr Ile Ala Arg Glu Leu Ser Thr Ala Asp Ala Asp Lys Leu His Phe
145                 150                 155                 160

Ala Leu Leu Leu Glu Pro Asp Ala Leu Ala Asn Leu Val Thr Asn Ala
                165                 170                 175

Asn Ala Pro Arg Cys Arg Ile Ala Ala Pro Ala Tyr Lys Glu Gly Ile
            180                 185                 190

Ala Tyr Thr Leu Ala Thr Leu Ser Lys Pro Asn Val Asp Val Tyr Ile
        195                 200                 205

Asp Ala Ala Asn Gly Gly Trp Leu Gly Trp Asn Asp Asn Leu Arg Pro
    210                 215                 220

Phe Ala Glu Leu Phe Lys Glu Val Tyr Asp Leu Ala Arg Arg Ile Asn
225                 230                 235                 240

Pro Asn Ala Lys Val Arg Gly Val Pro Val Asn Val Ser Asn Tyr Asn
                245                 250                 255

Gln Tyr Arg Ala Glu Val Arg Glu Pro Phe Thr Glu Trp Lys Asp Ala
            260                 265                 270

Trp Asp Glu Ser Arg Tyr Val Asn Val Leu Thr Pro His Leu Asn Ala
        275                 280                 285

Val Gly Phe Ser Ala His Phe Ile Val Asp Gln Gly Arg Gly Gly Lys
    290                 295                 300

Gly Gly Ile Arg Thr Glu Trp Gly Gln Trp Cys Asn Val Arg Asn Ala
```

-continued

```
305                 310                 315                 320

Gly Phe Gly Ile Arg Pro Thr Ala Asp Gln Gly Val Leu Gln Asn Pro
                325                 330                 335

Asn Val Asp Ala Ile Val Trp Val Lys Pro Gly Gly Glu Ser Asp Gly
            340                 345                 350

Thr Ser Asp Leu Asn Ser Asn Arg Tyr Asp Pro Thr Cys Arg Ser Pro
        355                 360                 365

Val Ala His Val Pro Ala Pro Glu Ala Gly Gln Trp Phe Asn Glu Tyr
    370                 375                 380

Val Val Asn Leu Val Leu Asn Ala Asn Pro Pro Leu Glu Pro Thr Trp
385                 390                 395                 400


<210> SEQ ID NO 21
<211> LENGTH: 1501
<212> TYPE: DNA
<213> ORGANISM: Thielavia terrestris

<400> SEQUENCE: 21

gccgttgtca agatgggcca gaagacgctg cacggattcg ccgccacggc tttggccgtt      60

ctcccctttg tgaaggctca gcagcccggc aacttcacgc cggaggtgca cccgcaactg     120

ccaacgtgga agtgcacgac cgccggcggc tgcgttcagc aggacacttc ggtggtgctc     180

gactggaact accgttggat ccacaatgcc gacggcaccg cctcgtgcac gacgtccagc     240

ggggtcgacc acacgctgtg tccagatgag gcgacctgcg cgaagaactg cttcgtggaa     300

ggcgtcaact acacgagcag cggtgtcacc acatccggca gttcgctgac gatgaggcag     360

tatttcaagg ggagcaacgg gcagaccaac agcgtttcgc ctcgtctcta cctgctcggc     420

tcggatggaa actacgtaat gctcaagctg ctcggccagg agctgagctt cgatgtcgat     480

ctctccacgc tcccctgcgg cgagaacggc gcgctgtacc tgtccgagat ggacgcgacc     540

ggtggcagga accagtacaa caccggcggt gccaactacg gctcgggcta ctgtgacgcc     600

cagtgtcccg tgcagacgtg gatgaacggc acgctgaaca ccaacgggca gggctactgc     660

tgcaacgaga tggacatcct cgaggccaac tcccgcgcca acgcgatgac acctcacccc     720

tgcgccaacg gcagctgcga caagagcggg tgcggactca acccctacgc cgagggctac     780

aagagctact acggaccggg cctcacggtt gacacgtcga agcccttcac catcattacc     840

cgcttcatca ccgacgacgg cacgaccagc ggcaccctca accagatcca gcggatctat     900

gtgcagaatg gcaagacggt cgcgtcggct gcgtccggag gcgacatcat cacggcatcc     960

ggctgcacct cggcccaggc gttcggcggg ctggccaaca tgggcgcggc gcttggacgg    1020

ggcatggtgc tgaccttcag catctggaac gacgctgggg gctacatgaa ctggctcgac    1080

agcggcaaca acggcccgtg cagcagcacc gagggcaacc cgtccaacat cctggccaac    1140

tacccggaca cccacgtggt cttctccaac atccgctggg gagacatcgg ctcgacggtc    1200

caggtctcgg gaggcggcaa cggcggctcg accaccacca cgtcgaccac cacgctgagg    1260

acctcgacca cgaccaccac caccgccccg acggccactg ccacgcactg ggacaatgc     1320

ggcggaatcg ggtacgtcaa accgcctcct gcattctgtt gaggaagtta actaacgtgg    1380

cctacgcagt ggactggacc gaccgtctgc gaatcgccgt acgcatgcaa ggagctgaac    1440

ccctggtact accagtgcct ctaaagtatt gcagtgaagc catactccgt gctcggcatg    1500

g                                                                    1501


<210> SEQ ID NO 22
```

```
<211> LENGTH: 464
<212> TYPE: PRT
<213> ORGANISM: Thielavia terrestris

<400> SEQUENCE: 22

Met Gly Gln Lys Thr Leu His Gly Phe Ala Ala Thr Ala Leu Ala Val
1               5                   10                  15

Leu Pro Phe Val Lys Ala Gln Gln Pro Gly Asn Phe Thr Pro Glu Val
            20                  25                  30

His Pro Gln Leu Pro Thr Trp Lys Cys Thr Thr Ala Gly Gly Cys Val
        35                  40                  45

Gln Gln Asp Thr Ser Val Val Leu Asp Trp Asn Tyr Arg Trp Ile His
    50                  55                  60

Asn Ala Asp Gly Thr Ala Ser Cys Thr Thr Ser Ser Gly Val Asp His
65                  70                  75                  80

Thr Leu Cys Pro Asp Glu Ala Thr Cys Ala Lys Asn Cys Phe Val Glu
                85                  90                  95

Gly Val Asn Tyr Thr Ser Ser Gly Val Thr Thr Ser Gly Ser Ser Leu
            100                 105                 110

Thr Met Arg Gln Tyr Phe Lys Gly Ser Asn Gly Gln Thr Asn Ser Val
        115                 120                 125

Ser Pro Arg Leu Tyr Leu Leu Gly Ser Asp Gly Asn Tyr Val Met Leu
    130                 135                 140

Lys Leu Leu Gly Gln Glu Leu Ser Phe Asp Val Asp Leu Ser Thr Leu
145                 150                 155                 160

Pro Cys Gly Glu Asn Gly Ala Leu Tyr Leu Ser Glu Met Asp Ala Thr
                165                 170                 175

Gly Gly Arg Asn Gln Tyr Asn Thr Gly Gly Ala Asn Tyr Gly Ser Gly
            180                 185                 190

Tyr Cys Asp Ala Gln Cys Pro Val Gln Thr Trp Met Asn Gly Thr Leu
        195                 200                 205

Asn Thr Asn Gly Gln Gly Tyr Cys Cys Asn Glu Met Asp Ile Leu Glu
    210                 215                 220

Ala Asn Ser Arg Ala Asn Ala Met Thr Pro His Pro Cys Ala Asn Gly
225                 230                 235                 240

Ser Cys Asp Lys Ser Gly Cys Gly Leu Asn Pro Tyr Ala Glu Gly Tyr
                245                 250                 255

Lys Ser Tyr Tyr Gly Pro Gly Leu Thr Val Asp Thr Ser Lys Pro Phe
            260                 265                 270

Thr Ile Ile Thr Arg Phe Ile Thr Asp Asp Gly Thr Thr Ser Gly Thr
        275                 280                 285

Leu Asn Gln Ile Gln Arg Ile Tyr Val Gln Asn Gly Lys Thr Val Ala
    290                 295                 300

Ser Ala Ala Ser Gly Gly Asp Ile Ile Thr Ala Ser Gly Cys Thr Ser
305                 310                 315                 320

Ala Gln Ala Phe Gly Gly Leu Ala Asn Met Gly Ala Ala Leu Gly Arg
                325                 330                 335

Gly Met Val Leu Thr Phe Ser Ile Trp Asn Asp Ala Gly Gly Tyr Met
            340                 345                 350

Asn Trp Leu Asp Ser Gly Asn Asn Gly Pro Cys Ser Ser Thr Glu Gly
        355                 360                 365

Asn Pro Ser Asn Ile Leu Ala Asn Tyr Pro Asp Thr His Val Val Phe
    370                 375                 380

Ser Asn Ile Arg Trp Gly Asp Ile Gly Ser Thr Val Gln Val Ser Gly
```

```
385                 390                 395                 400

Gly Gly Asn Gly Gly Ser Thr Thr Thr Thr Ser Thr Thr Thr Leu Arg
                405                 410                 415

Thr Ser Thr Thr Thr Thr Thr Thr Ala Pro Thr Ala Thr Ala Thr His
            420                 425                 430

Trp Gly Gln Cys Gly Gly Ile Gly Trp Thr Gly Pro Thr Val Cys Glu
        435                 440                 445

Ser Pro Tyr Ala Cys Lys Glu Leu Asn Pro Trp Tyr Tyr Gln Cys Leu
    450                 455                 460


<210> SEQ ID NO 23
<211> LENGTH: 1368
<212> TYPE: DNA
<213> ORGANISM: Thielavia terrestris

<400> SEQUENCE: 23

accgatccgc tcgaagatgg cgcccaagtc tacagttctg gccgcctggc tgctctcctc     60

gctggccgcg gcccagcaga tcggcaaagc cgtgcccgag gtccacccca aactgacaac    120

gcagaagtgc actctccgcg gcgggtgcaa gcctgtccgc acctcggtcg tgctcgactc    180

gtccgcgcgc tcgctgcaca aggtcgggga ccccaacacc agctgcagcg tcggcggcga    240

cctgtgctcg gacgcgaagt cgtgcggcaa gaactgcgcg ctcgagggcg tcgactacgc    300

ggcccacggc gtggcgacca agggcgacgc cctcacgctg caccagtggc tcaagggggc    360

cgacggcacc tacaggaccg tctcgccgcg cgtatacctc ctgggcgagg acgggaagaa    420

ctacgaggac ttcaagctgc tcaacgccga gctcagcttc gacgtcgacg tgtcccagct    480

cgtctgcggc atgaacggcg ccctgtactt ctccgagatg gagatggacg gcggccgcag    540

cccgctgaac ccggcgggcg ccacgtacgg cacgggctac tgcgacgcgc agtgccccaa    600

gttggacttt atcaacggcg aggtatttct tctctcttct gtttttcttt tccatcgctt    660

tttctgaccg gaatccgccc tcttagctca acaccaacca cacgtacggg gcgtgctgca    720

acgagatgga catctgggag gccaacgcgc tggcgcaggc gctcacgccg cacccgtgca    780

acgcgacgcg ggtgtacaag tgcgacacgg cggacgagtg cgggcagccg gtgggcgtgt    840

gcgacgaatg ggggtgctcg tacaacccgt ccaacttcgg ggtcaaggac tactacgggc    900

gcaacctgac ggtggacacg aaccgcaagt tcacggtgac gacgcagttc gtgacgtcca    960

acgggcgggc ggacggcgag ctgaccgaga tccggcggct gtacgtgcag gacggcgtgg   1020

tgatccagaa ccacgcggtc acggcgggcg gggcgacgta cgacagcatc acggacggct   1080

tctgcaacgc gacggccacc tggacgcagc agcggggcgg gctcgcgcgc atgggcgagg   1140

ccatcggccg cggcatggtg ctcatcttca gcctgtgggt tgacaacggc ggcttcatga   1200

actggctcga cagcggcaac gccgggccct gcaacgccac cgagggcgac ccggccctga   1260

tcctgcagca gcacccggac gccagcgtca ccttctccaa catccgatgg ggcgagatcg   1320

gcagcacgta caagagcgag tgcagccact agagtagagc ttgtaatt                1368


<210> SEQ ID NO 24
<211> LENGTH: 423
<212> TYPE: PRT
<213> ORGANISM: Thielavia terrestris

<400> SEQUENCE: 24

Met Ala Pro Lys Ser Thr Val Leu Ala Ala Trp Leu Leu Ser Ser Leu
1               5                   10                  15
```

-continued

```
Ala Ala Ala Gln Gln Ile Gly Lys Ala Val Pro Glu Val His Pro Lys
            20                  25                  30

Leu Thr Thr Gln Lys Cys Thr Leu Arg Gly Gly Cys Lys Pro Val Arg
        35                  40                  45

Thr Ser Val Val Leu Asp Ser Ser Ala Arg Ser Leu His Lys Val Gly
    50                  55                  60

Asp Pro Asn Thr Ser Cys Ser Val Gly Gly Asp Leu Cys Ser Asp Ala
65                  70                  75                  80

Lys Ser Cys Gly Lys Asn Cys Ala Leu Glu Gly Val Asp Tyr Ala Ala
                85                  90                  95

His Gly Val Ala Thr Lys Gly Asp Ala Leu Thr Leu His Gln Trp Leu
            100                 105                 110

Lys Gly Ala Asp Gly Thr Tyr Arg Thr Val Ser Pro Arg Val Tyr Leu
        115                 120                 125

Leu Gly Glu Asp Gly Lys Asn Tyr Glu Asp Phe Lys Leu Leu Asn Ala
    130                 135                 140

Glu Leu Ser Phe Asp Val Asp Val Ser Gln Leu Val Cys Gly Met Asn
145                 150                 155                 160

Gly Ala Leu Tyr Phe Ser Glu Met Glu Met Asp Gly Gly Arg Ser Pro
                165                 170                 175

Leu Asn Pro Ala Gly Ala Thr Tyr Gly Thr Gly Tyr Cys Asp Ala Gln
            180                 185                 190

Cys Pro Lys Leu Asp Phe Ile Asn Gly Glu Leu Asn Thr Asn His Thr
        195                 200                 205

Tyr Gly Ala Cys Cys Asn Glu Met Asp Ile Trp Glu Ala Asn Ala Leu
    210                 215                 220

Ala Gln Ala Leu Thr Pro His Pro Cys Asn Ala Thr Arg Val Tyr Lys
225                 230                 235                 240

Cys Asp Thr Ala Asp Glu Cys Gly Gln Pro Val Gly Val Cys Asp Glu
                245                 250                 255

Trp Gly Cys Ser Tyr Asn Pro Ser Asn Phe Gly Val Lys Asp Tyr Tyr
            260                 265                 270

Gly Arg Asn Leu Thr Val Asp Thr Asn Arg Lys Phe Thr Val Thr Thr
        275                 280                 285

Gln Phe Val Thr Ser Asn Gly Arg Ala Asp Gly Glu Leu Thr Glu Ile
    290                 295                 300

Arg Arg Leu Tyr Val Gln Asp Gly Val Val Ile Gln Asn His Ala Val
305                 310                 315                 320

Thr Ala Gly Gly Ala Thr Tyr Asp Ser Ile Thr Asp Gly Phe Cys Asn
                325                 330                 335

Ala Thr Ala Thr Trp Thr Gln Gln Arg Gly Gly Leu Ala Arg Met Gly
            340                 345                 350

Glu Ala Ile Gly Arg Gly Met Val Leu Ile Phe Ser Leu Trp Val Asp
        355                 360                 365

Asn Gly Gly Phe Met Asn Trp Leu Asp Ser Gly Asn Ala Gly Pro Cys
    370                 375                 380

Asn Ala Thr Glu Gly Asp Pro Ala Leu Ile Leu Gln Gln His Pro Asp
385                 390                 395                 400

Ala Ser Val Thr Phe Ser Asn Ile Arg Trp Gly Glu Ile Gly Ser Thr
                405                 410                 415

Tyr Lys Ser Glu Cys Ser His
            420
```

```
<210> SEQ ID NO 25
<211> LENGTH: 1011
<212> TYPE: DNA
<213> ORGANISM: Thielavia terrestris

<400> SEQUENCE: 25

atgaccctac ggctccctgt catcagcctg ctggcctcgc tggcagcagg cgccgtcgtc     60

gtcccacggg cggagtttca cccccctctc ccgacttgga aatgcacgac ctccgggggc    120

tgcgtgcagc agaacaccag cgtcgtcctg gaccgtgact cgaagtacgc cgcacacagc    180

gccggctcgc ggacggaatc ggattacgcg gcaatgggag tgtccacttc gggcaatgcc    240

gtgacgctgt accactacgt caagaccaac ggcaccctcg tccccgcttc gccgcgcatc    300

tacctcctgg gcgcggacgg caagtacgtg cttatggacc tcctcaacca ggagctgtcg    360

gtggacgtcg acttctcggc gctgccgtgc ggcgagaacg gggccttcta cctgtccgag    420

atggcggcgg acgggcgggg cgacgcgggg gcgggcgacg ggtactgcga cgcgcagtgc    480

cagggctact gctgcaacga gatggacatc ctcgaggcca actcgatggc gacggccatg    540

acgccgcacc cgtgcaaggg caacaactgc gaccgcagcg gctgcggcta caacccgtac    600

gccagcggcc agcgcggctt ctacgggccc ggcaagacgg tcgacacgag caagcccttc    660

accgtcgtca cgcagttcgc cgccagcggc ggcaagctga cccagatcac ccgcaagtac    720

atccagaacg gccgggagat cggcggcggc ggcaccatct ccagctgcgg ctccgagtct    780

tcgacgggcg gcctgaccgg catgggcgag gcgctggggc gcggaatggt gctggccatg    840

agcatctgga acgacgcggc ccaggagatg gcatggctcg atgccggcaa caacggccct    900

tgcgccagtg gccagggcag cccgtccgtc attcagtcgc agcatcccga cacccacgtc    960

gtcttctcca acatcaggtg gggcgacatc gggtctacca cgaagaacta g            1011


<210> SEQ ID NO 26
<211> LENGTH: 336
<212> TYPE: PRT
<213> ORGANISM: Thielavia terrestris

<400> SEQUENCE: 26

Met Thr Leu Arg Leu Pro Val Ile Ser Leu Leu Ala Ser Leu Ala Ala
1               5                   10                  15

Gly Ala Val Val Val Pro Arg Ala Glu Phe His Pro Pro Leu Pro Thr
            20                  25                  30

Trp Lys Cys Thr Thr Ser Gly Gly Cys Val Gln Gln Asn Thr Ser Val
        35                  40                  45

Val Leu Asp Arg Asp Ser Lys Tyr Ala Ala His Ser Ala Gly Ser Arg
    50                  55                  60

Thr Glu Ser Asp Tyr Ala Ala Met Gly Val Ser Thr Ser Gly Asn Ala
65                  70                  75                  80

Val Thr Leu Tyr His Tyr Val Lys Thr Asn Gly Thr Leu Val Pro Ala
                85                  90                  95

Ser Pro Arg Ile Tyr Leu Leu Gly Ala Asp Gly Lys Tyr Val Leu Met
            100                 105                 110

Asp Leu Leu Asn Gln Glu Leu Ser Val Asp Val Asp Phe Ser Ala Leu
        115                 120                 125

Pro Cys Gly Glu Asn Gly Ala Phe Tyr Leu Ser Glu Met Ala Ala Asp
    130                 135                 140

Gly Arg Gly Asp Ala Gly Ala Gly Asp Gly Tyr Cys Asp Ala Gln Cys
145                 150                 155                 160
```

```
Gln Gly Tyr Cys Cys Asn Glu Met Asp Ile Leu Glu Ala Asn Ser Met
                165                 170                 175

Ala Thr Ala Met Thr Pro His Pro Cys Lys Gly Asn Asn Cys Asp Arg
            180                 185                 190

Ser Gly Cys Gly Tyr Asn Pro Tyr Ala Ser Gly Gln Arg Gly Phe Tyr
        195                 200                 205

Gly Pro Gly Lys Thr Val Asp Thr Ser Lys Pro Phe Thr Val Val Thr
    210                 215                 220

Gln Phe Ala Ala Ser Gly Gly Lys Leu Thr Gln Ile Thr Arg Lys Tyr
225                 230                 235                 240

Ile Gln Asn Gly Arg Glu Ile Gly Gly Gly Gly Thr Ile Ser Ser Cys
                245                 250                 255

Gly Ser Glu Ser Ser Thr Gly Gly Leu Thr Gly Met Gly Glu Ala Leu
            260                 265                 270

Gly Arg Gly Met Val Leu Ala Met Ser Ile Trp Asn Asp Ala Ala Gln
        275                 280                 285

Glu Met Ala Trp Leu Asp Ala Gly Asn Asn Gly Pro Cys Ala Ser Gly
    290                 295                 300

Gln Gly Ser Pro Ser Val Ile Gln Ser Gln His Pro Asp Thr His Val
305                 310                 315                 320

Val Phe Ser Asn Ile Arg Trp Gly Asp Ile Gly Ser Thr Thr Lys Asn
                325                 330                 335
```

```
<210> SEQ ID NO 27
<211> LENGTH: 1480
<212> TYPE: DNA
<213> ORGANISM: Cladorrhinum foecundissimum

<400> SEQUENCE: 27

gatccgaatt cctcctctcg ttctttagtc acagaccaga catctgccca cgatggttca      60

caagttcgcc ctcctcaccg gcctcgccgc ctccctcgca tctgcccagc agatcggcac     120

cgtcgtcccc gagtctcacc ccaagcttcc caccaagcgc tgcactctcg ccggtggctg     180

ccagaccgtc gacacctcca tcgtcatcga cgccttccag cgtcccctcc acaagatcgg     240

cgacccttcc actccttgcg tcgtcggcgg ccctctctgc cccgacgcca agtcctgcgc     300

tgagaactgc gcgctcgagg gtgtcgacta tgcctcctgg ggcatcaaga ccgagggcga     360

cgccctaact ctcaaccagt ggatgcccga cccggcgaac cctggccagt acaagacgac     420

tactccccgt acttaccttg ttgctgagga cggcaagaac tacgaggatg tgaagctcct     480

ggctaaggag atctcgtttg atgccgatgt cagcaacctt ccctgcggca tgaacggtgc     540

tttctacttg tctgagatgt tgatggatgg tggacgtggc gacctcaacc ctgctggtgc     600

cgagtatggt accggttact gtgatgcgca gtgcttcaag ttggatttca tcaacggcga     660

ggccaacatc gaccaaaagc acggcgcctg ctgcaacgaa atggacattt tcgaatccaa     720

ctcgcgcgcc aagaccttcg tcccccaccc ctgcaacatc acgcaggtct acaagtgcga     780

aggcgaagac gagtgcggcc agcccgtcgg cgtgtgcgac aagtgggggt gcggcttcaa     840

cgagtacaaa tggggcgtcg agtccttcta cggccggggc tcgcagttcg ccatcgactc     900

ctccaagaag ttcaccgtca ccacgcagtt cctgaccgac aacggcaagg aggacggcgt     960

cctcgtcgag atccgccgct tgtggcacca ggatggcaag ctgatcaaga acaccgctat    1020

ccaggttgag gagaactaca gcacggactc ggtgagcacc gagttctgcg agaagactgc    1080

ttctttcacc atgcagcgcg gtggtctcaa ggcgatgggc gaggctatcg gtcgtggtat    1140
```

```
ggtgctggtt ttcagcatct gggcggatga ttcgggtttt atgaactggt tggatgcgga   1200

gggtaatggc ccttgcagcg cgactgaggg cgatccgaag gagattgtca agaataagcc   1260

ggatgctagg gttacgttct caaacattag gattggtgag gttggtagca cgtatgctcc   1320

gggtgggaag tgcggtgtta agagcagggt tgctaggggg cttactgctt cttaaggggg   1380

gtgtgaagag aggaggaggt gttgttgggg gttggagatg ataattgggc gagatggtgt   1440

agagcgggtt ggttggatat gaatacgttg aattggatgt                         1480
```

<210> SEQ ID NO 28
<211> LENGTH: 440
<212> TYPE: PRT
<213> ORGANISM: Cladorrhinum foecundissimum

<400> SEQUENCE: 28

```
Met Val His Lys Phe Ala Leu Leu Thr Gly Leu Ala Ala Ser Leu Ala
1               5                   10                  15

Ser Ala Gln Gln Ile Gly Thr Val Val Pro Glu Ser His Pro Lys Leu
            20                  25                  30

Pro Thr Lys Arg Cys Thr Leu Ala Gly Gly Cys Gln Thr Val Asp Thr
        35                  40                  45

Ser Ile Val Ile Asp Ala Phe Gln Arg Pro Leu His Lys Ile Gly Asp
    50                  55                  60

Pro Ser Thr Pro Cys Val Val Gly Gly Pro Leu Cys Pro Asp Ala Lys
65                  70                  75                  80

Ser Cys Ala Glu Asn Cys Ala Leu Glu Gly Val Asp Tyr Ala Ser Trp
                85                  90                  95

Gly Ile Lys Thr Glu Gly Asp Ala Leu Thr Leu Asn Gln Trp Met Pro
            100                 105                 110

Asp Pro Ala Asn Pro Gly Gln Tyr Lys Thr Thr Thr Pro Arg Thr Tyr
        115                 120                 125

Leu Val Ala Glu Asp Gly Lys Asn Tyr Glu Asp Val Lys Leu Leu Ala
    130                 135                 140

Lys Glu Ile Ser Phe Asp Ala Asp Val Ser Asn Leu Pro Cys Gly Met
145                 150                 155                 160

Asn Gly Ala Phe Tyr Leu Ser Glu Met Leu Met Asp Gly Gly Arg Gly
                165                 170                 175

Asp Leu Asn Pro Ala Gly Ala Glu Tyr Gly Thr Gly Tyr Cys Asp Ala
            180                 185                 190

Gln Cys Phe Lys Leu Asp Phe Ile Asn Gly Glu Ala Asn Ile Asp Gln
        195                 200                 205

Lys His Gly Ala Cys Cys Asn Glu Met Asp Ile Phe Glu Ser Asn Ser
    210                 215                 220

Arg Ala Lys Thr Phe Val Pro His Pro Cys Asn Ile Thr Gln Val Tyr
225                 230                 235                 240

Lys Cys Glu Gly Glu Asp Glu Cys Gly Gln Pro Val Gly Val Cys Asp
                245                 250                 255

Lys Trp Gly Cys Gly Phe Asn Glu Tyr Lys Trp Gly Val Glu Ser Phe
            260                 265                 270

Tyr Gly Arg Gly Ser Gln Phe Ala Ile Asp Ser Ser Lys Lys Phe Thr
        275                 280                 285

Val Thr Thr Gln Phe Leu Thr Asp Asn Gly Lys Glu Asp Gly Val Leu
    290                 295                 300

Val Glu Ile Arg Arg Leu Trp His Gln Asp Gly Lys Leu Ile Lys Asn
305                 310                 315                 320
```

```
Thr Ala Ile Gln Val Glu Glu Asn Tyr Ser Thr Asp Ser Val Ser Thr
                325                 330                 335

Glu Phe Cys Glu Lys Thr Ala Ser Phe Thr Met Gln Arg Gly Gly Leu
            340                 345                 350

Lys Ala Met Gly Glu Ala Ile Gly Arg Gly Met Val Leu Val Phe Ser
        355                 360                 365

Ile Trp Ala Asp Asp Ser Gly Phe Met Asn Trp Leu Asp Ala Glu Gly
    370                 375                 380

Asn Gly Pro Cys Ser Ala Thr Glu Gly Asp Pro Lys Glu Ile Val Lys
385                 390                 395                 400

Asn Lys Pro Asp Ala Arg Val Thr Phe Ser Asn Ile Arg Ile Gly Glu
                405                 410                 415

Val Gly Ser Thr Tyr Ala Pro Gly Gly Lys Cys Gly Val Lys Ser Arg
            420                 425                 430

Val Ala Arg Gly Leu Thr Ala Ser
        435                 440
```

<210> SEQ ID NO 29
<211> LENGTH: 1380
<212> TYPE: DNA
<213> ORGANISM: Trichoderma reesei

<400> SEQUENCE: 29

```
atggcgccct cagttacact gccgttgacc acggccatcc tggccattgc ccggctcgtc     60

gccgcccagc aaccgggtac cagcaccccc gaggtccatc ccaagttgac aacctacaag    120

tgtacaaagt ccggggggtg cgtggcccag gacacctcgg tggtccttga ctggaactac    180

cgctggatgc acgacgcaaa ctacaactcg tgcaccgtca acggcggcgt caacaccacg    240

ctctgccctg acgaggcgac ctgtggcaag aactgcttca tcgagggcgt cgactacgcc    300

gcctcgggcg tcacgacctc gggcagcagc ctcaccatga accagtacat gcccagcagc    360

tctggcggct acagcagcgt ctctcctcgg ctgtatctcc tggactctga cggtgagtac    420

gtgatgctga agctcaacgg ccaggagctg agcttcgacg tcgacctctc tgctctgccg    480

tgtggagaga acggctcgct ctacctgtct cagatggacg agaacggggg cgccaaccag    540

tataacacgg ccggtgccaa ctacgggagc ggctactgcg atgctcagtg ccccgtccag    600

acatggagga acggcaccct caacactagc caccagggct tctgctgcaa cgagatggat    660

atcctggagg gcaactcgag ggcgaatgcc ttgacccctc actcttgcac ggccacggcc    720

tgcgactctg ccggttgcgg cttcaacccc tatggcagcg gctacaaaag ctactacggc    780

cccggagata ccgttgacac ctccaagacc ttcaccatca tcacccagtt caacacggac    840

aacggctcgc cctcgggcaa ccttgtgagc atcacccgca agtaccagca aaacggcgtc    900

gacatcccca gcgcccagcc cggcggcgac accatctcgt cctgcccgtc cgcctcagcc    960

tacggcggcc tcgccaccat gggcaaggcc ctgagcagcg gcatggtgct cgtgttcagc   1020

atttggaacg acaacagcca gtacatgaac tggctcgaca gcggcaacgc cggcccctgc   1080

agcagcaccg agggcaaccc atccaacatc ctggccaaca accccaacac gcacgtcgtc   1140

ttctccaaca tccgctgggg agacattggg tctactacga actcgactgc gcccccgccc   1200

ccgcctgcgt ccagcacgac gttttcgact acacggagga gctcgacgac ttcgagcagc   1260

ccgagctgca cgcagactca ctgggggcag tgcggtggca ttgggtacag cgggtgcaag   1320

acgtgcacgt cgggcactac gtgccagtat agcaacgact actactcgca atgcctttag   1380
```

<210> SEQ ID NO 30
<211> LENGTH: 459
<212> TYPE: PRT
<213> ORGANISM: Trichoderma reesei

<400> SEQUENCE: 30

```
Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
    370                 375                 380
```

```
Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
    450                 455


<210> SEQ ID NO 31
<211> LENGTH: 1545
<212> TYPE: DNA
<213> ORGANISM: Trichoderma reesei

<400> SEQUENCE: 31

atgtatcgga agttggccgt catctcggcc ttcttggcca cagctcgtgc tcagtcggcc     60

tgcactctcc aatcggagac tcacccgcct ctgacatggc agaaatgctc gtctggtggc    120

acgtgcactc aacagacagg ctccgtggtc atcgacgcca actggcgctg gactcacgct    180

acgaacagca gcacgaactg ctacgatggc aacacttgga gctcgaccct atgtcctgac    240

aacgagacct gcgcgaagaa ctgctgtctg gacggtgccg cctacgcgtc cacgtacgga    300

gttaccacga gcggtaacag cctctccatt ggctttgtca cccagtctgc gcagaagaac    360

gttggcgctc gcctttacct tatggcgagc gacacgacct accaggaatt caccctgctt    420

ggcaacgagt tctctttcga tgttgatgtt tcgcagctgc cgtgcggctt gaacggagct    480

ctctacttcg tgtccatgga cgcggatggt ggcgtgagca agtatcccac caacaccgct    540

ggcgccaagt acggcacggg gtactgtgac agccagtgtc cccgcgatct gaagttcatc    600

aatggccagg ccaacgttga gggctgggag ccgtcatcca acaacgcgaa cacgggcatt    660

ggaggacacg gaagctgctg ctctgagatg gatatctggg aggccaactc catctccgag    720

gctcttaccc cccacccttg cacgactgtc ggccaggaga tctgcgaggg tgatgggtgc    780

ggcggaactt actccgataa cagatatggc ggcacttgcg atcccgatgg ctgcgactgg    840

aacccatacc gcctgggcaa caccagcttc tacggccctg gctcaagctt taccctcgat    900

accaccaaga aattgaccgt tgtcacccag ttcgagacgt cgggtgccat caaccgatac    960

tatgtccaga atggcgtcac tttccagcag cccaacgccg agcttggtag ttactctggc   1020

aacgagctca acgatgatta ctgcacagct gaggaggcag aattcggcgg atcctctttc   1080

tcagacaagg gcggcctgac tcagttcaag aaggctacct ctggcggcat ggttctggtc   1140

atgagtctgt gggatgatta ctacgccaac atgctgtggc tggactccac ctacccgaca   1200

aacgagacct cctccacacc cggtgccgtg cgcggaagct gctccaccag ctccggtgtc   1260

cctgctcagg tcgaatctca gtctcccaac gccaaggtca ccttctccaa catcaagttc   1320

ggacccattg gcagcaccgg caaccctagc ggcggcaacc ctcccggcgg aaacccgcct   1380

ggcaccacca ccacccgccg cccagccact accactggaa gctctcccgg acctacccag   1440

tctcactacg gccagtgcgg cggtattggc tacagcggcc ccacggtctg cgccagcggc   1500

acaacttgcc aggtcctgaa cccttactac tctcagtgcc tgtaa                   1545


<210> SEQ ID NO 32
<211> LENGTH: 514
```

<212> TYPE: PRT
<213> ORGANISM: Trichoderma reesei

<400> SEQUENCE: 32

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400
```

```
Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu


<210> SEQ ID NO 33
<211> LENGTH: 1611
<212> TYPE: DNA
<213> ORGANISM: Trichoderma reesei

<400> SEQUENCE: 33

atgattgtcg gcattctcac cacgctggct acgctggcca cactcgcagc tagtgtgcct     60

ctagaggagc ggcaagcttg ctcaagcgtc tggtaattat gtgaaccctc tcaagagacc    120

caaatactga gatatgtcaa ggggccaatg tggtggccag aattggtcgg gtccgacttg    180

ctgtgcttcc ggaagcacat gcgtctactc caacgactat tactcccagt gtcttcccgg    240

cgctgcaagc tcaagctcgt ccacgcgcgc cgcgtcgacg acttctcgag tatcccccac    300

aacatcccgg tcgagctccg cgacgcctcc acctggttct actactacca gagtacctcc    360

agtcggatcg ggaaccgcta cgtattcagg caaccctttt gttggggtca ctccttgggc    420

caatgcatat tacgcctctg aagttagcag cctcgctatt cctagcttga ctggagccat    480

ggccactgct gcagcagctg tcgcaaaggt tccctctttt atgtggctgt aggtcctccc    540

ggaaccaagg caatctgtta ctgaaggctc atcattcact gcagagatac tcttgacaag    600

acccctctca tggagcaaac cttggccgac atccgcaccg ccaacaagaa tggcggtaac    660

tatgccggac agtttgtggt gtatgacttg ccggatcgcg attgcgctgc ccttgcctcg    720

aatggcgaat actctattgc cgatggtggc gtcgccaaat ataagaacta tatcgacacc    780

attcgtcaaa ttgtcgtgga atattccgat atccggaccc tcctggttat tggtatgagt    840

ttaaacacct gcctcccccc cccccttccct tcctttcccg ccggcatctt gtcgttgtgc    900

taactattgt tccctcttcc agagcctgac tctcttgcca acctggtgac caacctcggt    960

actccaaagt gtgccaatgc tcagtcagcc taccttgagt gcatcaacta cgccgtcaca   1020

cagctgaacc ttccaaatgt tgcgatgtat ttggacgctg gccatgcagg atggcttggc   1080

tggccggcaa accaagaccc ggccgctcag ctatttgcaa atgtttacaa gaatgcatcg   1140

tctccgagag ctcttcgcgg attggcaacc aatgtcgcca actacaacgg gtggaacatt   1200

accagccccc catcgtacac gcaaggcaac gctgtctaca acgagaagct gtacatccac   1260

gctattggac gtcttcttgc caatcacggc tggtccaacg ccttcttcat cactgatcaa   1320

ggtcgatcgg gaaagcagcc taccggacag caacagtggg gagactggtg caatgtgatc   1380

ggcaccggat ttggtattcg cccatccgca aacactgggg actcgttgct ggattcgttt   1440
```

```
gtctgggtca agccaggcgg cgagtgtgac ggcaccagcg acagcagtgc gccacgattt   1500

gactcccact gtgcgctccc agatgccttg caaccggcgc ctcaagctgg tgcttggttc   1560

caagcctact ttgtgcagct tctcacaaac gcaaacccat cgttcctgta a             1611


<210> SEQ ID NO 34
<211> LENGTH: 471
<212> TYPE: PRT
<213> ORGANISM: Trichoderma reesei

<400> SEQUENCE: 34

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
```

```
            340                 345                 350

Tyr Ile His Ala Ile Gly Arg Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470


<210> SEQ ID NO 35
<211> LENGTH: 2046
<212> TYPE: DNA
<213> ORGANISM: Humicola insolens

<400> SEQUENCE: 35

gccgtgacct tgcgcgcttt gggtggcggt ggcgagtcgt ggacggtgct tgctggtcgc      60

cggccttccc ggcgatccgc gtgatgagag ggccaccaac ggcgggatga tgctccatgg     120

ggaacttccc catggagaag agagagaaac ttgcggagcc gtgatctggg gaaagatgct     180

ccgtgtctcg tctatataac tcgagtctcc ccgagccctc aacaccacca gctctgatct     240

caccatcccc atcgacaatc acgcaaacac agcagttgtc gggccattcc ttcagacaca     300

tcagtcaccc tccttcaaaa tgcgtaccgc caagttcgcc accctcgccg cccttgtggc     360

ctcggccgcc gcccagcagg cgtgcagtct caccaccgag aggcaccctt ccctctcttg     420

gaacaagtgc accgccggcg gccagtgcca gaccgtccag gcttccatca ctctcgactc     480

caactggcgc tggactcacc aggtgtctgg ctccaccaac tgctacacgg gcaacaagtg     540

ggatactagc atctgcactg atgccaagtc gtgcgctcag aactgctgcg tcgatggtgc     600

cgactacacc agcacctatg gcatcaccac caacggtgat tccctgagcc tcaagttcgt     660

caccaagggc cagcactcga ccaacgtcgg ctcgcgtacc tacctgatgg acggcgagga     720

caagtatcag agtacgttct atcttcagcc ttctcgcgcc ttgaatcctg gctaacgttt     780

acacttcaca gccttcgagc tcctcggcaa cgagttcacc ttcgatgtcg atgtctccaa     840

catcggctgc ggtctcaacg gcgccctgta cttcgtctcc atggacgccg atggtggtct     900

cagccgctat cctggcaaca aggctggtgc caagtacggt accggctact gcgatgctca     960

gtgcccccgt gacatcaagt tcatcaacgg cgaggccaac attgagggct ggaccggctc    1020

caccaacgac cccaacgccg gcgcgggccg ctatggtacc tgctgctctg agatggatat    1080

ctgggaagcc aacaacatgg ctactgcctt cactcctcac ccttgcacca tcattggcca    1140

gagccgctgc gagggcgact cgtgcggtgg cacctacagc aacgagcgct acgccggcgt    1200

ctgcgacccc gatggctgcg acttcaactc gtaccgccag ggcaacaaga ccttctacgg    1260

caagggcatg accgtcgaca ccaccaagaa gatcactgtc gtcacccagt tcctcaagga    1320

tgccaacggc gatctcggcg agatcaagcg cttctacgtc caggatggca agatcatccc    1380
```

```
caactccgag tccaccatcc ccggcgtcga gggcaattcc atcacccagg actggtgcga   1440

ccgccagaag gttgcctttg gcgacattga cgacttcaac cgcaagggcg gcatgaagca   1500

gatgggcaag gccctcgccg gccccatggt cctggtcatg tccatctggg atgaccacgc   1560

ctccaacatg ctctggctcg actcgacctt ccctgtcgat gccgctggca agcccggcgc   1620

cgagcgcggt gcctgcccga ccacctcggg tgtccctgct gaggttgagg ccgaggcccc   1680

caacagcaac gtcgtcttct ccaacatccg cttcggcccc atcggctcga ccgttgctgg   1740

tctccccggc gcgggcaacg gcggcaacaa cggcggcaac cccccgcccc ccaccaccac   1800

cacctcctcg gctccggcca ccaccaccac cgccagcgct ggccccaagg ctggccgctg   1860

gcagcagtgc ggcggcatcg gcttcactgg cccgacccag tgcgaggagc cctacatttg   1920

caccaagctc aacgactggt actctcagtg cctgtaaatt ctgagtcgct gactcgacga   1980

tcacggccgg tttttgcatg aaaggaaaca aacgaccgcg ataaaaatgg agggtaatga   2040

gatgtc                                                              2046
```

<210> SEQ ID NO 36
<211> LENGTH: 525
<212> TYPE: PRT
<213> ORGANISM: Humicola insolens

<400> SEQUENCE: 36

```
Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
            20                  25                  30

Ser Trp Asn Lys Cys Thr Ala Gly Gly Gln Cys Gln Thr Val Gln Ala
        35                  40                  45

Ser Ile Thr Leu Asp Ser Asn Trp Arg Trp Thr His Gln Val Ser Gly
    50                  55                  60

Ser Thr Asn Cys Tyr Thr Gly Asn Lys Trp Asp Thr Ser Ile Cys Thr
65                  70                  75                  80

Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
            100                 105                 110

Phe Val Thr Lys Gly Gln His Ser Thr Asn Val Gly Ser Arg Thr Tyr
        115                 120                 125

Leu Met Asp Gly Glu Asp Lys Tyr Gln Thr Phe Glu Leu Leu Gly Asn
    130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
                165                 170                 175

Tyr Pro Gly Asn Lys Ala Gly Ala Lys Tyr Gly Thr Gly Tyr Cys Asp
            180                 185                 190

Ala Gln Cys Pro Arg Asp Ile Lys Phe Ile Asn Gly Glu Ala Asn Ile
        195                 200                 205

Glu Gly Trp Thr Gly Ser Thr Asn Asp Pro Asn Ala Gly Ala Gly Arg
    210                 215                 220

Tyr Gly Thr Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
```

```
                245                 250                 255

Cys Glu Gly Asp Ser Cys Gly Gly Thr Tyr Ser Asn Glu Arg Tyr Ala
            260                 265                 270

Gly Val Cys Asp Pro Asp Gly Cys Asp Phe Asn Ser Tyr Arg Gln Gly
        275                 280                 285

Asn Lys Thr Phe Tyr Gly Lys Gly Met Thr Val Asp Thr Thr Lys Lys
    290                 295                 300

Ile Thr Val Val Thr Gln Phe Leu Lys Asp Ala Asn Gly Asp Leu Gly
305                 310                 315                 320

Glu Ile Lys Arg Phe Tyr Val Gln Asp Gly Lys Ile Ile Pro Asn Ser
                325                 330                 335

Glu Ser Thr Ile Pro Gly Val Glu Gly Asn Ser Ile Thr Gln Asp Trp
            340                 345                 350

Cys Asp Arg Gln Lys Val Ala Phe Gly Asp Ile Asp Asp Phe Asn Arg
        355                 360                 365

Lys Gly Gly Met Lys Gln Met Gly Lys Ala Leu Ala Gly Pro Met Val
    370                 375                 380

Leu Val Met Ser Ile Trp Asp Asp His Ala Ser Asn Met Leu Trp Leu
385                 390                 395                 400

Asp Ser Thr Phe Pro Val Asp Ala Ala Gly Lys Pro Gly Ala Glu Arg
                405                 410                 415

Gly Ala Cys Pro Thr Thr Ser Gly Val Pro Ala Glu Val Glu Ala Glu
            420                 425                 430

Ala Pro Asn Ser Asn Val Val Phe Ser Asn Ile Arg Phe Gly Pro Ile
        435                 440                 445

Gly Ser Thr Val Ala Gly Leu Pro Gly Ala Gly Asn Gly Gly Asn Asn
    450                 455                 460

Gly Gly Asn Pro Pro Pro Pro Thr Thr Thr Thr Ser Ser Ala Pro Ala
465                 470                 475                 480

Thr Thr Thr Thr Ala Ser Ala Gly Pro Lys Ala Gly Arg Trp Gln Gln
                485                 490                 495

Cys Gly Gly Ile Gly Phe Thr Gly Pro Thr Gln Cys Glu Glu Pro Tyr
            500                 505                 510

Ile Cys Thr Lys Leu Asn Asp Trp Tyr Ser Gln Cys Leu
        515                 520                 525
```

<210> SEQ ID NO 37
<211> LENGTH: 1812
<212> TYPE: DNA
<213> ORGANISM: Myceliophthora thermophila

<400> SEQUENCE: 37

```
atggccaaga agcttttcat caccgccgcc cttgcggctg ccgtgttggc ggcccccgtc      60

attgaggagc gccagaactg cggcgctgtg tggtaagaaa gcccggtctg agtttcccat     120

gactttctca tcgagtaatg gcataaggcc cacccccttcg actgactgtg agaatcgatc     180

aaatccagga ctcaatgcgg cggcaacggg tggcagggtc ccacatgctg cgcctcgggc     240

tcgacctgcg ttgcgcagaa cgagtggtac tctcagtgcc tgcccaacaa tcaggtgacg     300

agttccaaca ctccgtcgtc gacttccacc tcgcagcgca gcagcagcac ctccagcagc     360

agcaccagga gcggcagctc ctcctcctcc accaccacgc cccctcccgt ctccagcccc     420

gtgactagca ttcccggcgg tgcgaccacc acggcgagct actctggcaa cccccttctcg     480

ggcgtccggc tcttcgccaa cgactactac aggtccgagg tccacaatct cgccattcct     540
```

```
agcatgaccg gtactctggc ggccaaggct tccgccgtcg ccgaagtccc tagcttccag    600
tggctcgacc ggaacgtcac catcgacacc ctgatggtcc agactctgtc ccagatccgg    660
gctgccaata atgccggtgc caatcctccc tatgctggtg agttacatgg cggcgacttg    720
ccttctcgtc ccccaccttt cttgacggga tcggttacct gacctggagg caaaacaaaa    780
ccagcccaac ttgtcgtcta cgacctcccc gaccgtgact gcgccgccgc tgcgtccaac    840
ggcgagtttt cgattgcaaa cggcggcgcc gccaactaca ggagctacat cgacgctatc    900
cgcaagcaca tcattgagta ctcggacatc cggatcatcc tggttatcga gcccgactcg    960
atggccaaca tggtgaccaa catgaacgtg gccaagtgca gcaacgccgc gtcgacgtac   1020
cacgagttga ccgtgtacgc gctcaagcag ctgaacctgc ccaacgtcgc catgtatctc   1080
gacgccggcc acgccggctg gctcggctgg cccgccaaca tccagcccgc cgccgacctg   1140
tttgccggca tctacaatga cgccggcaag ccggctgccg tccgcggcct ggccactaac   1200
gtcgccaact acaacgcctg gagtatcgct tcggccccgt cgtacacgtc ccctaaccct   1260
aactacgacg agaagcacta catcgaggcc ttcagcccgc tcctgaacgc ggccggcttc   1320
cccgcacgct tcattgtcga cactggccgc aacggcaaac aacctaccgg tatggttttt   1380
ttcttttttt ttctctgttc cctcccccct tccccttcag ttggcgtcca caaggtctct   1440
tagtcttgct tcttctcgga ccaaccttcc cccaccccca aaacgcaccg cccacaaccg   1500
ttcgactcta tactcttggg aatgggcgcc gaaactgacc gttcgacagg ccaacaacag   1560
tggggtgact ggtgcaatgt caagggcact ggctttggcg tgcgcccgac ggccaacacg   1620
ggccacgacc tggtcgatgc ctttgtctgg gtcaagcccg gcggcgagtc cgacggcaca   1680
agcgacacca gcgccgcccg ctacgactac cactgcggcc tgtccgatgc cctgcagcct   1740
gctccggagg ctggacagtg gttccaggcc tacttcgagc agctgctcac caacgccaac   1800
ccgccccttct aa                                                        1812
```

```
<210> SEQ ID NO 38
<211> LENGTH: 482
<212> TYPE: PRT
<213> ORGANISM: Myceliophthora thermophila

<400> SEQUENCE: 38

Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Asn Gln Val Thr Ser Ser Asn Thr Pro Ser Ser Thr Ser Thr Ser Gln
65                  70                  75                  80

Arg Ser Ser Ser Thr Ser Ser Ser Ser Thr Arg Ser Gly Ser Ser Ser
                85                  90                  95

Ser Ser Thr Thr Thr Pro Pro Pro Val Ser Ser Pro Val Thr Ser Ile
            100                 105                 110

Pro Gly Gly Ala Thr Thr Thr Ala Ser Tyr Ser Gly Asn Pro Phe Ser
        115                 120                 125

Gly Val Arg Leu Phe Ala Asn Asp Tyr Tyr Arg Ser Glu Val His Asn
    130                 135                 140
```

```
Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Ile Arg Ala Ala Asn Asn
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Asp Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

Ala Phe Ser Pro Leu Leu Asn Ala Ala Gly Phe Pro Ala Arg Phe Ile
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Asp Leu Val Asp Ala Phe Val Trp Val Lys Pro
            420                 425                 430

Gly Gly Glu Ser Asp Gly Thr Ser Asp Thr Ser Ala Ala Arg Tyr Asp
        435                 440                 445

Tyr His Cys Gly Leu Ser Asp Ala Leu Gln Pro Ala Pro Glu Ala Gly
    450                 455                 460

Gln Trp Phe Gln Ala Tyr Phe Glu Gln Leu Leu Thr Asn Ala Asn Pro
465                 470                 475                 480

Pro Phe


<210> SEQ ID NO 39
<211> LENGTH: 1802
<212> TYPE: DNA
<213> ORGANISM: Myceliophthora thermophila

<400> SEQUENCE: 39

atggccaaga agcttttcat caccgccgcg cttgcggctg ccgtgttggc ggcccccgtc      60

attgaggagc gccagaactg cggcgctgtg tggtaagaaa gcccggtccg agtctcccat     120

gattttctcg tcgagtaatg gcataagggc caccccttcg actgaccgtg agaatcgatc     180
```

```
aaatccagga ctcaatgcgg cggtaacggg tggcaaggtc ccacatgctg cgcctcgggc     240
tcgacctgcg ttgcgcagaa cgagtggtac tctcagtgcc tgcccaacag ccaggtgacg     300
agttccacca ctccgtcgtc gacttccacc tcgcagcgca gcaccagcac ctccagcagc     360
accaccagga gcggcagctc ctcctcctcc tccaccacgc ccccgcccgt ctccagcccc     420
gtgaccagca ttcccggcgg tgcgacctcc acggcgagct actctggcaa ccccttctcg     480
ggcgtccggc tcttcgccaa cgactactac aggtccgagg tccacaatct cgccattcct     540
agcatgactg gtactctggc ggccaaggct tccgccgtcg ccgaagtccc tagcttccag     600
tggctcgacc ggaacgtcac catcgacacc ctgatggtcc agactctgtc ccaggtccgg     660
gctctcaata aggccggtgc caatcctccc tatgctggtg agttacatgg cgacttgcct     720
tctcgtcccc tacctttctt gacgggatcg gttacctgac ctggaggcaa aacaacaaca     780
gcccaactcg tcgtctacga cctccccgac cgtgactgtg ccgccgctgc gtccaacggc     840
gagttttcga ttgcaaacgg cggcgccgcc aactacagga gctacatcga cgctatccgc     900
aagcacatca ttgagtactc ggacatccgg atcatcctgg ttatcgagcc cgactcgatg     960
gccaacatgg tgaccaacat gaacgtggcc aagtgcagca acgccgcgtc gacgtaccac    1020
gagttgaccg tgtacgcgct caagcagctg aacctgccca acgtcgccat gtatctcgac    1080
gccggccacg ccggctggct cggctggccc gccaacatcc agcccgccgc cgagctgttt    1140
gccggcatct acaatgatgc cggcaagccg gctgccgtcc gcggcctggc cactaacgtc    1200
gccaactaca acgcctggag catcgcttcg gccccgtcgt acacgtcgcc taaccctaac    1260
tacgacgaga agcactacat cgaggccttc agcccgctct tgaactcggc cggcttcccc    1320
gcacgcttca ttgtcgacac tggccgcaac ggcaaacaac ctaccggtat gttttttttt    1380
cttttgtctc tgtccccccc ttttctcccc cttcagttgg cgtccacaag gtctcttagt    1440
cctgcttcat ctgtgaccaa cctccccccc cccggcaccg cccacaaccg tttgactcta    1500
tactcttggg aatgggcgcc gaaactgacc gttccacagg ccaacaacag tggggtgact    1560
ggtgcaatgt caagggcacc ggctttggcg tgcgcccgac ggccaacacg ggccacgagc    1620
tggtcgatgc ctttgtctgg gtcaagcccg gcggcgagtc cgacggcaca agcgacacca    1680
gcgccgcccg ctacgactac cactgcggcc tgtccgatgc cctgcagcct gcccccgagg    1740
ctggacagtg gttccaggcc tacttcgagc agctgctcac caacgccaac ccgcccttct    1800
aa                                                                  1802
```

<210> SEQ ID NO 40
<211> LENGTH: 481
<212> TYPE: PRT
<213> ORGANISM: Myceliophthora thermophila

<400> SEQUENCE: 40

```
Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Ser Gln Val Thr Ser Ser Thr Thr Pro Ser Ser Thr Ser Thr Ser Gln
65                  70                  75                  80
```

```
Arg Ser Thr Ser Thr Ser Ser Ser Thr Thr Arg Ser Gly Ser Ser Ser
                85                  90                  95

Ser Ser Ser Thr Thr Pro Pro Pro Val Ser Ser Pro Val Thr Ser Ile
            100                 105                 110

Pro Gly Gly Ala Thr Ser Thr Ala Ser Tyr Ser Gly Asn Pro Phe Ser
        115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Val Arg Ala Leu Asn Lys
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Glu Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

Ala Phe Ser Pro Leu Leu Asn Ser Ala Gly Phe Pro Ala Arg Phe Ile
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Glu Leu Val Asp Ala Phe Val Trp Val Lys Pro
            420                 425                 430

Gly Gly Glu Ser Asp Gly Thr Ser Asp Thr Ser Ala Ala Arg Tyr Asp
        435                 440                 445

Tyr His Cys Gly Leu Ser Asp Ala Leu Gln Pro Ala Pro Glu Ala Gly
    450                 455                 460

Gln Trp Phe Gln Ala Tyr Phe Glu Gln Leu Leu Thr Asn Ala Asn Pro
465                 470                 475                 480

Pro

<210> SEQ ID NO 41
```

<211> LENGTH: 1446
<212> TYPE: DNA
<213> ORGANISM: Thielavia terrestris

<400> SEQUENCE: 41

```
atggctcaga agctccttct cgccgccgcc cttgcggcca gcgccctcgc tgctcccgtc     60

gtcgaggagc gccagaactg cggttccgtc tggagccaat gcggcggcat tggctggtcc    120

ggcgcgacct gctgcgcttc gggcaatacc tgcgttgagc tgaacccgta ctactcgcag    180

tgcctgccca acagccaggt gactacctcg accagcaaga ccacctccac caccaccagg    240

agcagcacca ccagccacag cagcggtccc accagcacga gcaccaccac caccagcagt    300

cccgtggtca ctaccccgcc gagtacctcc atccccggcg gtgcctcgtc aacggccagc    360

tggtccggca acccgttctc gggcgtgcag atgtgggcca acgactacta cgcctccgag    420

gtctcgtcgc tggccatccc cagcatgacg ggcgccatgg ccaccaaggc ggccgaggtg    480

gccaaggtgc ccagcttcca gtggcttgac cgcaacgtca ccatcgacac gctgttcgcc    540

cacacgctgt cgcagatccg cgcggccaac cagaaaggcg ccaacccgcc ctacgcgggc    600

atcttcgtgg tctacgacct tccggaccgc gactgcgccg ccgccgcgtc caacggcgag    660

ttctccatcg cgaacaacgg ggcggccaac tacaagacgt acatcgacgc gatccggagc    720

ctcgtcatcc agtactcaga catccgcatc atcttcgtca tcgagcccga ctcgctggcc    780

aacatggtga ccaacctgaa cgtggccaag tgcgccaacg ccgagtcgac ctacaaggag    840

ttgaccgtct acgcgctgca gcagctgaac ctgcccaacg tggccatgta cctggacgcc    900

ggccacgccg gctggctcgg ctggcccgcc aacatccagc cggccgccaa cctcttcgcc    960

gagatctaca cgagcgccgg caagccggcc gccgtgcgcg gcctcgccac caacgtggcc   1020

aactacaacg gctggagcct ggccacgccg ccctcgtaca cccagggcga ccccaactac   1080

gacgagagcc actacgtcca ggccctcgcc ccgctgctca ccgccaacgg cttccccgcc   1140

cacttcatca ccgacaccgg ccgcaacggc aagcagccga ccggacaacg gcaatgggga   1200

gactggtgca acgttatcgg aactggcttc ggcgtgcgcc cgacgacaaa caccggcctc   1260

gacatcgagg acgccttcgt ctgggtcaag cccggcggcg agtgcgacgg cacgagcaac   1320

acgacctctc cccgctacga ctaccactgc ggcctgtcgg acgcgctgca gcctgctccg   1380

gaggccggca cttggttcca ggcctacttc gagcagctcc tgaccaacgc caacccgccc   1440

ttttaa                                                               1446
```

<210> SEQ ID NO 42
<211> LENGTH: 481
<212> TYPE: PRT
<213> ORGANISM: Thielavia terrestris

<400> SEQUENCE: 42

```
Met Ala Gln Lys Leu Leu Leu Ala Ala Ala Leu Ala Ala Ser Ala Leu
1               5                   10                  15

Ala Ala Pro Val Val Glu Glu Arg Gln Asn Cys Gly Ser Val Trp Ser
            20                  25                  30

Gln Cys Gly Gly Ile Gly Trp Ser Gly Ala Thr Cys Cys Ala Ser Gly
        35                  40                  45

Asn Thr Cys Val Glu Leu Asn Pro Tyr Tyr Ser Gln Cys Leu Pro Asn
    50                  55                  60

Ser Gln Val Thr Thr Ser Thr Ser Lys Thr Thr Ser Thr Thr Thr Arg
65                  70                  75                  80
```

```
Ser Ser Thr Thr Ser His Ser Ser Gly Pro Thr Ser Thr Ser Thr Thr
                85                  90                  95

Thr Thr Ser Ser Pro Val Val Thr Thr Pro Pro Ser Thr Ser Ile Pro
            100                 105                 110

Gly Gly Ala Ser Ser Thr Ala Ser Trp Ser Gly Asn Pro Phe Ser Gly
        115                 120                 125

Val Gln Met Trp Ala Asn Asp Tyr Tyr Ala Ser Glu Val Ser Ser Leu
    130                 135                 140

Ala Ile Pro Ser Met Thr Gly Ala Met Ala Thr Lys Ala Ala Glu Val
145                 150                 155                 160

Ala Lys Val Pro Ser Phe Gln Trp Leu Asp Arg Asn Val Thr Ile Asp
                165                 170                 175

Thr Leu Phe Ala His Thr Leu Ser Gln Ile Arg Ala Ala Asn Gln Lys
            180                 185                 190

Gly Ala Asn Pro Pro Tyr Ala Gly Ile Phe Val Val Tyr Asp Leu Pro
        195                 200                 205

Asp Arg Asp Cys Ala Ala Ala Ala Ser Asn Gly Glu Phe Ser Ile Ala
    210                 215                 220

Asn Asn Gly Ala Ala Asn Tyr Lys Thr Tyr Ile Asp Ala Ile Arg Ser
225                 230                 235                 240

Leu Val Ile Gln Tyr Ser Asp Ile Arg Ile Ile Phe Val Ile Glu Pro
                245                 250                 255

Asp Ser Leu Ala Asn Met Val Thr Asn Leu Asn Val Ala Lys Cys Ala
            260                 265                 270

Asn Ala Glu Ser Thr Tyr Lys Glu Leu Thr Val Tyr Ala Leu Gln Gln
        275                 280                 285

Leu Asn Leu Pro Asn Val Ala Met Tyr Leu Asp Ala Gly His Ala Gly
    290                 295                 300

Trp Leu Gly Trp Pro Ala Asn Ile Gln Pro Ala Ala Asn Leu Phe Ala
305                 310                 315                 320

Glu Ile Tyr Thr Ser Ala Gly Lys Pro Ala Ala Val Arg Gly Leu Ala
                325                 330                 335

Thr Asn Val Ala Asn Tyr Asn Gly Trp Ser Leu Ala Thr Pro Pro Ser
            340                 345                 350

Tyr Thr Gln Gly Asp Pro Asn Tyr Asp Glu Ser His Tyr Val Gln Ala
        355                 360                 365

Leu Ala Pro Leu Leu Thr Ala Asn Gly Phe Pro Ala His Phe Ile Thr
    370                 375                 380

Asp Thr Gly Arg Asn Gly Lys Gln Pro Thr Gly Gln Arg Gln Trp Gly
385                 390                 395                 400

Asp Trp Cys Asn Val Ile Gly Thr Gly Phe Gly Val Arg Pro Thr Thr
                405                 410                 415

Asn Thr Gly Leu Asp Ile Glu Asp Ala Phe Val Trp Val Lys Pro Gly
            420                 425                 430

Gly Glu Cys Asp Gly Thr Ser Asn Thr Thr Ser Pro Arg Tyr Asp Tyr
        435                 440                 445

His Cys Gly Leu Ser Asp Ala Leu Gln Pro Ala Pro Glu Ala Gly Thr
    450                 455                 460

Trp Phe Gln Ala Tyr Phe Glu Gln Leu Leu Thr Asn Ala Asn Pro Pro
465                 470                 475                 480

Phe
```

<210> SEQ ID NO 43

<211> LENGTH: 1593
<212> TYPE: DNA
<213> ORGANISM: Chaetomium thermophilum

<400> SEQUENCE: 43

```
atgatgtaca agaagttcgc cgctctcgcc gccctcgtgg ctggcgccgc cgcccagcag      60
gcttgctccc tcaccactga gacccacccc agactcactt ggaagcgctg cacctctggc     120
ggcaactgct cgaccgtgaa cggcgccgtc accatcgatg ccaactggcg ctggactcac     180
actgtttccg gctcgaccaa ctgctacacc ggcaacgagt gggatacctc catctgctct     240
gatggcaaga gctgcgccca gacctgctgc gtcgacggcg ctgactactc ttcgacctat     300
ggtatcacca ccagcggtga ctccctgaac ctcaagttcg tcaccaagca ccagcacggc     360
accaatgtcg gctctcgtgt ctacctgatg gagaacgaca ccaagtacca gatgttcgag     420
ctcctcggca acgagttcac cttcgatgtc gatgtctcta acctgggctg cggtctcaac     480
ggcgccctct acttcgtctc catggacgct gatggtggta tgagcaagta ctctggcaac     540
aaggctggcg ccaagtacgg taccggctac tgcgatgctc agtgcccgcg cgaccttaag     600
ttcatcaacg gcgaggccaa cattgagaac tggacccctt cgaccaatga tgccaacgcc     660
ggtttcggcc gctatggcag ctgctgctct gagatggata tctgggatgc caacaacatg     720
gctactgcct tcactcctca cccttgcacc attatcggcc agagccgctg cgagggcaac     780
agctgcggtg gcacctacag ctctgagcgc tatgctggtg tttgcgatcc tgatggctgc     840
gacttcaacg cctaccgcca gggcgacaag accttctacg gcaagggcat gaccgtcgac     900
accaccaaga agatgaccgt cgtcacccag ttccacaaga actcggctgg cgtcctcagc     960
gagatcaagc gcttctacgt tcaggacggc aagatcattg ccaacgccga gtccaagatc    1020
cccggcaacc ccggcaactc catcacccag gagtggtgcg atgcccagaa ggtcgccttc    1080
ggtgacatcg atgacttcaa ccgcaagggc ggtatggctc agatgagcaa ggccctcgag    1140
ggccctatgg tcctggtcat gtccgtctgg gatgaccact acgccaacat gctctggctc    1200
gactcgacct accccattga caaggccggc acccccggcg ccgagcgcgg tgcttgcccg    1260
accacctccg gtgtccctgc cgagattgag gcccaggtcc ccaacagcaa cgttatcttc    1320
tccaacatcc gcttcggccc catcggctcg accgtccctg gcctcgacgg cagcaccccc    1380
agcaacccga ccgccaccgt tgctcctccc acttctacca ccaccagcgt gagaagcagc    1440
actactcaga tttccacccc gactagccag cccggcggct gcaccaccca gaagtggggc    1500
cagtgcggtg gtatcggcta caccggctgc actaactgcg ttgctggcac tacctgcact    1560
gagctcaacc cctggtacag ccagtgcctg taa                                 1593
```

<210> SEQ ID NO 44
<211> LENGTH: 530
<212> TYPE: PRT
<213> ORGANISM: Chaetomium thermophilum

<400> SEQUENCE: 44

```
Met Met Tyr Lys Lys Phe Ala Ala Leu Ala Ala Leu Val Ala Gly Ala
1               5                   10                  15

Ala Ala Gln Gln Ala Cys Ser Leu Thr Thr Glu Thr His Pro Arg Leu
            20                  25                  30

Thr Trp Lys Arg Cys Thr Ser Gly Gly Asn Cys Ser Thr Val Asn Gly
        35                  40                  45

Ala Val Thr Ile Asp Ala Asn Trp Arg Trp Thr His Thr Val Ser Gly
    50                  55                  60
```

```
Ser Thr Asn Cys Tyr Thr Gly Asn Glu Trp Asp Thr Ser Ile Cys Ser
65                  70                  75                  80

Asp Gly Lys Ser Cys Ala Gln Thr Cys Cys Val Asp Gly Ala Asp Tyr
                85                  90                  95

Ser Ser Thr Tyr Gly Ile Thr Thr Ser Gly Asp Ser Leu Asn Leu Lys
            100                 105                 110

Phe Val Thr Lys His Gln His Gly Thr Asn Val Gly Ser Arg Val Tyr
        115                 120                 125

Leu Met Glu Asn Asp Thr Lys Tyr Gln Met Phe Glu Leu Leu Gly Asn
    130                 135                 140

Glu Phe Thr Phe Asp Val Asp Val Ser Asn Leu Gly Cys Gly Leu Asn
145                 150                 155                 160

Gly Ala Leu Tyr Phe Val Ser Met Asp Ala Asp Gly Gly Met Ser Lys
                165                 170                 175

Tyr Ser Gly Asn Lys Ala Gly Ala Lys Tyr Gly Thr Gly Tyr Cys Asp
            180                 185                 190

Ala Gln Cys Pro Arg Asp Leu Lys Phe Ile Asn Gly Glu Ala Asn Ile
        195                 200                 205

Glu Asn Trp Thr Pro Ser Thr Asn Asp Ala Asn Ala Gly Phe Gly Arg
    210                 215                 220

Tyr Gly Ser Cys Cys Ser Glu Met Asp Ile Trp Asp Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asn Ser Cys Gly Gly Thr Tyr Ser Ser Glu Arg Tyr Ala
            260                 265                 270

Gly Val Cys Asp Pro Asp Gly Cys Asp Phe Asn Ala Tyr Arg Gln Gly
        275                 280                 285

Asp Lys Thr Phe Tyr Gly Lys Gly Met Thr Val Asp Thr Thr Lys Lys
    290                 295                 300

Met Thr Val Val Thr Gln Phe His Lys Asn Ser Ala Gly Val Leu Ser
305                 310                 315                 320

Glu Ile Lys Arg Phe Tyr Val Gln Asp Gly Lys Ile Ile Ala Asn Ala
                325                 330                 335

Glu Ser Lys Ile Pro Gly Asn Pro Gly Asn Ser Ile Thr Gln Glu Trp
            340                 345                 350

Cys Asp Ala Gln Lys Val Ala Phe Gly Asp Ile Asp Asp Phe Asn Arg
        355                 360                 365

Lys Gly Gly Met Ala Gln Met Ser Lys Ala Leu Glu Gly Pro Met Val
    370                 375                 380

Leu Val Met Ser Val Trp Asp Asp His Tyr Ala Asn Met Leu Trp Leu
385                 390                 395                 400

Asp Ser Thr Tyr Pro Ile Asp Lys Ala Gly Thr Pro Gly Ala Glu Arg
                405                 410                 415

Gly Ala Cys Pro Thr Thr Ser Gly Val Pro Ala Glu Ile Glu Ala Gln
            420                 425                 430

Val Pro Asn Ser Asn Val Ile Phe Ser Asn Ile Arg Phe Gly Pro Ile
        435                 440                 445

Gly Ser Thr Val Pro Gly Leu Asp Gly Ser Thr Pro Ser Asn Pro Thr
    450                 455                 460

Ala Thr Val Ala Pro Pro Thr Ser Thr Thr Thr Ser Val Arg Ser Ser
465                 470                 475                 480
```

```
Thr Thr Gln Ile Ser Thr Pro Thr Ser Gln Pro Gly Gly Cys Thr Thr
                485                 490                 495

Gln Lys Trp Gly Gln Cys Gly Gly Ile Gly Tyr Thr Gly Cys Thr Asn
            500                 505                 510

Cys Val Ala Gly Thr Thr Cys Thr Glu Leu Asn Pro Trp Tyr Ser Gln
        515                 520                 525

Cys Leu
    530


<210> SEQ ID NO 45
<211> LENGTH: 1434
<212> TYPE: DNA
<213> ORGANISM: Chaetomium thermophilum

<400> SEQUENCE: 45

atggctaagc agctgctgct cactgccgct cttgcggcca cttcgctggc tgcccctctc      60

cttgaggagc gccagagctg ctcctccgtc tggggtcaat gcggtggcat caattacaac     120

ggcccgacct gctgccagtc cggcagtgtt tgcacttacc tgaatgactg gtacagccag     180

tgcattcccg gtcaggctca gcccggcacg actagcacca cggctcggac caccagcacc     240

agcaccacca gcacttcgtc ggtccgcccg accacctcga atacccctgt gacgactgct     300

cccccgacga ccaccatccc gggcggcgcc tcgagcacgg ccagctacaa cggcaacccg     360

ttttcgggtg ttcaactttg ggccaacacc tactactcgt ccgaggtgca cactttggcc     420

atccccagct tgtctcctga gctggctgcc aaggccgcca aggtcgctga ggttcccagc     480

ttccagtggc tcgaccgcaa tgtgactgtt gacactctct tctccggcac tcttgccgaa     540

atccgcgccg ccaaccagcg cggtgccaac ccgccttatg ccggcatttt cgtggtttat     600

gacttaccag accgtgattg cgcggctgct gcttcgaacg gcgagtggtc tatcgccaac     660

aatggtgcca acaactacaa gcgctacatc gaccggatcc gtgagctcct tatccagtac     720

tccgatatcc gcactattct ggtcattgaa cctgattccc tggccaacat ggtcaccaac     780

atgaacgtcc agaagtgctc gaacgctgcc tccacttaca aggagcttac tgtctatgcc     840

ctcaaacagc tcaatcttcc tcacgttgcc atgtacatgg atgctggcca cgctggctgg     900

cttggctggc ccgccaacat ccagcctgct gctgagctct ttgctcaaat ctaccgcgac     960

gctggcaggc ccgctgctgt ccgcggtctt gcgaccaacg ttgccaacta caatgcttgg    1020

tcgatcgcca gccctccgtc ctacacctct cctaacccga actacgacga gaagcactat    1080

attgaggcct ttgctcctct tctccgcaac cagggcttcg acgcaaagtt catcgtcgac    1140

accggccgta acggcaagca gcccactggc cagcttgaat ggggtcactg gtgcaatgtc    1200

aagggaactg gcttcggtgt gcgccctact gctaacactg ggcatgaact tgttgatgct    1260

ttcgtgtggg tcaagcccgg tggcgagtcc gacggcacca gtgcggacac cagcgctgct    1320

cgttatgact atcactgcgg cctttccgac gcactgactc cggcgcctga ggctggccaa    1380

tggttccagg cttatttcga acagctgctc atcaatgcca accctccgct ctga          1434


<210> SEQ ID NO 46
<211> LENGTH: 477
<212> TYPE: PRT
<213> ORGANISM: Chaetomium thermophilum

<400> SEQUENCE: 46

Met Ala Lys Gln Leu Leu Leu Thr Ala Ala Leu Ala Ala Thr Ser Leu
1               5                   10                  15
```

```
Ala Ala Pro Leu Leu Glu Glu Arg Gln Ser Cys Ser Ser Val Trp Gly
            20                  25                  30

Gln Cys Gly Gly Ile Asn Tyr Asn Gly Pro Thr Cys Cys Gln Ser Gly
        35                  40                  45

Ser Val Cys Thr Tyr Leu Asn Asp Trp Tyr Ser Gln Cys Ile Pro Gly
    50                  55                  60

Gln Ala Gln Pro Gly Thr Thr Ser Thr Thr Ala Arg Thr Thr Ser Thr
65                  70                  75                  80

Ser Thr Thr Ser Thr Ser Ser Val Arg Pro Thr Thr Ser Asn Thr Pro
                85                  90                  95

Val Thr Thr Ala Pro Pro Thr Thr Thr Ile Pro Gly Gly Ala Ser Ser
            100                 105                 110

Thr Ala Ser Tyr Asn Gly Asn Pro Phe Ser Gly Val Gln Leu Trp Ala
        115                 120                 125

Asn Thr Tyr Tyr Ser Ser Glu Val His Thr Leu Ala Ile Pro Ser Leu
    130                 135                 140

Ser Pro Glu Leu Ala Ala Lys Ala Ala Lys Val Ala Glu Val Pro Ser
145                 150                 155                 160

Phe Gln Trp Leu Asp Arg Asn Val Thr Val Asp Thr Leu Phe Ser Gly
                165                 170                 175

Thr Leu Ala Glu Ile Arg Ala Ala Asn Gln Arg Gly Ala Asn Pro Pro
            180                 185                 190

Tyr Ala Gly Ile Phe Val Val Tyr Asp Leu Pro Asp Arg Asp Cys Ala
        195                 200                 205

Ala Ala Ala Ser Asn Gly Glu Trp Ser Ile Ala Asn Asn Gly Ala Asn
    210                 215                 220

Asn Tyr Lys Arg Tyr Ile Asp Arg Ile Arg Glu Leu Leu Ile Gln Tyr
225                 230                 235                 240

Ser Asp Ile Arg Thr Ile Leu Val Ile Glu Pro Asp Ser Leu Ala Asn
                245                 250                 255

Met Val Thr Asn Met Asn Val Gln Lys Cys Ser Asn Ala Ala Ser Thr
            260                 265                 270

Tyr Lys Glu Leu Thr Val Tyr Ala Leu Lys Gln Leu Asn Leu Pro His
        275                 280                 285

Val Ala Met Tyr Met Asp Ala Gly His Ala Gly Trp Leu Gly Trp Pro
    290                 295                 300

Ala Asn Ile Gln Pro Ala Ala Glu Leu Phe Ala Gln Ile Tyr Arg Asp
305                 310                 315                 320

Ala Gly Arg Pro Ala Ala Val Arg Gly Leu Ala Thr Asn Val Ala Asn
                325                 330                 335

Tyr Asn Ala Trp Ser Ile Ala Ser Pro Pro Ser Tyr Thr Ser Pro Asn
            340                 345                 350

Pro Asn Tyr Asp Glu Lys His Tyr Ile Glu Ala Phe Ala Pro Leu Leu
        355                 360                 365

Arg Asn Gln Gly Phe Asp Ala Lys Phe Ile Val Asp Thr Gly Arg Asn
    370                 375                 380

Gly Lys Gln Pro Thr Gly Gln Leu Glu Trp Gly His Trp Cys Asn Val
385                 390                 395                 400

Lys Gly Thr Gly Phe Gly Val Arg Pro Thr Ala Asn Thr Gly His Glu
                405                 410                 415

Leu Val Asp Ala Phe Val Trp Val Lys Pro Gly Gly Glu Ser Asp Gly
            420                 425                 430

Thr Ser Ala Asp Thr Ser Ala Ala Arg Tyr Asp Tyr His Cys Gly Leu
```

```
        435                 440                 445

Ser Asp Ala Leu Thr Pro Ala Pro Glu Ala Gly Gln Trp Phe Gln Ala
    450                 455                 460

Tyr Phe Glu Gln Leu Leu Ile Asn Ala Asn Pro Pro Leu
465                 470                 475
```

<210> SEQ ID NO 47
<211> LENGTH: 1599
<212> TYPE: DNA
<213> ORGANISM: Aspergillus fumigatus

<400> SEQUENCE: 47

```
atgctggcct ccaccttctc ctaccgcatg tacaagaccg cgctcatcct ggccgccctt     60

ctgggctctg gccaggctca gcaggtcggt acttcccagg cggaagtgca tccgtccatg    120

acctggcaga gctgcacggc tggcggcagc tgcaccacca acaacggcaa ggtggtcatc    180

gacgcgaact ggcgttgggt gcacaaagtc ggcgactaca ccaactgcta caccggcaac    240

acctgggaca cgactatctg ccctgacgat gcgacctgcg catccaactg cgcccttgag    300

ggtgccaact acgaatccac ctatggtgtg accgccagcg gcaattccct ccgcctcaac    360

ttcgtcacca ccagccagca gaagaacatt ggctcgcgtc tgtacatgat gaaggacgac    420

tcgacctacg agatgtttaa gctgctgaac caggagttca ccttcgatgt cgatgtctcc    480

aacctcccct gcggtctcaa cggtgctctg tactttgtcg ccatggacgc cgacggtggc    540

atgtccaagt acccaaccaa caaggccggt gccaagtacg gtactggata ctgtgactcg    600

cagtgccctc gcgacctcaa gttcatcaac ggtcaggcca acgtcgaagg gtggcagccc    660

tcctccaacg atgccaatgc gggtaccggc aaccacgggt cctgctgcgc ggagatggat    720

atctgggagg ccaacagcat ctccacggcc ttcacccccc atccgtgcga cacgcccggc    780

caggtgatgt gcaccggtga tgcctgcggt ggcacctaca gctccgaccg ctacggcggc    840

acctgcgacc ccgacggatg tgatttcaac tccttccgcc agggcaacaa gaccttctac    900

ggccctggca tgaccgtcga caccaagagc aagtttaccg tcgtcaccca gttcatcacc    960

gacgacggca cctccagcgg caccctcaag gagatcaagc gcttctacgt gcagaacggc   1020

aaggtgatcc ccaactcgga gtcgacctgg accggcgtca gcggcaactc catcaccacc   1080

gagtactgca ccgcccagaa gagcctgttc caggaccaga acgtcttcga aaagcacggc   1140

ggcctcgagg gcatgggtgc tgccctcgcc cagggtatgg ttctcgtcat gtccctgtgg   1200

gatgatcact cggccaacat gctctggctc gacagcaact acccgaccac tgcctcttcc   1260

accactcccg gcgtcgcccg tggtacctgc gacatctcct ccggcgtccc tgcggatgtc   1320

gaggcgaacc accccgacgc ctacgtcgtc tactccaaca tcaaggtcgg ccccatcggc   1380

tcgaccttca acagcggtgg ctcgaacccc ggtggcggaa ccaccacgac aactaccacc   1440

cagcctacta ccaccacgac cacggctgga aaccctggcg gcaccggagt cgcacagcac   1500

tatggccagt gtggtggaat cggatggacc ggacccacaa cctgtgccag cccttatacc   1560

tgccagaagc tgaatgatta ttactctcag tgcctgtag                          1599
```

<210> SEQ ID NO 48
<211> LENGTH: 532
<212> TYPE: PRT
<213> ORGANISM: Aspergillus fumigatus

<400> SEQUENCE: 48

```
Met Leu Ala Ser Thr Phe Ser Tyr Arg Met Tyr Lys Thr Ala Leu Ile
```

-continued

```
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430
```

```
Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
        515                 520                 525

Ser Gln Cys Leu
    530


<210> SEQ ID NO 49
<211> LENGTH: 1713
<212> TYPE: DNA
<213> ORGANISM: Aspergillus fumigatus

<400> SEQUENCE: 49

atgaagcacc ttgcatcttc catcgcattg actctactgt tgcctgccgt gcaggcccag     60

cagaccgtat ggggccaatg tatgttctgg ctgtcactgg aataagactg tatcaactgc    120

tgatatgctt ctaggtggcg gccaaggctg gtctggcccg acgagctgtg ttgccggcgc    180

agcctgtagc acactgaatc cctgtatgtt agatatcgtc ctgagtggag acttatactg    240

acttccttag actacgctca gtgtatcccg ggagccaccg cgacgtccac caccctcacg    300

acgacgacgg cggcgacgac gacatcccag accaccacca aacctaccac gactggtcca    360

actacatccg cacccaccgt gaccgcatcc ggtaaccctt tcagcggcta ccagctgtat    420

gccaacccct actactcctc cgaggtccat actctggcca tgccttctct gcccagctcg    480

ctgcagccca aggctagtgc tgttgctgaa gtgccctcat ttgtttggct gtaagtggcc    540

ttatcccaat actgagacca actctctgac agtcgtagcg acgttgccgc caaggtgccc    600

actatgggaa cctacctggc cgacattcag gccaagaaca aggccggcgc caaccctcct    660

atcgctggta tcttcgtggt ctacgacttg ccggaccgtg actgcgccgc tctggccagt    720

aatggcgagt actcaattgc caacaacggt gtggccaact acaaggcgta cattgacgcc    780

atccgtgctc agctggtgaa gtactctgac gttcacacca tcctcgtcat cggtaggccg    840

tacacctccg ttgcgcgccg cctttctctg acatcttgca gaacccgaca gcttggccaa    900

cctggtgacc aacctcaacg tcgccaaatg cgccaatgcg cagagcgcct acctggagtg    960

tgtcgactat gctctgaagc agctcaacct gcccaacgtc gccatgtacc tcgacgcagg   1020

tatgcctcac ttcccgcatt ctgtatccct tccagacact aactcatcag gccatgcggg   1080

ctggctcgga tggcccgcca acttgggccc cgccgcaaca ctcttcgcca aagtctacac   1140

cgacgcgggt tcccccgcgg ctgttcgtgg cctggccacc aacgtcgcca actacaacgc   1200

ctggtcgctc agtacctgcc cctcctacac ccagggagac cccaactgcg acgagaagaa   1260

gtacatcaac gccatggcgc ctcttctcaa ggaagccggc ttcgatgccc acttcatcat   1320

ggatacctgt aagtgcttat tccaatcgcc gatgtgtgcc gactaatcaa tgtttcagcc   1380

cggaatggcg tccagcccac gaagcaaaac gcctggggtg actggtgcaa cgtcatcggc   1440

accggcttcg gtgttcgccc ctcgactaac accggcgatc cgctccagga tgcctttgtg   1500
```

```
tggatcaagc ccggtggaga gagtgatggc acgtccaact cgacttcccc ccggtatgac   1560

gcgcactgcg gatatagtga tgctctgcag cctgctcctg aggctggtac ttggttccag   1620

gtatgtcatc cattagccag atgagggata agtgactgac ggacctaggc ctactttgag   1680

cagcttctga ccaacgctaa cccgtccttt taa                                1713


<210> SEQ ID NO 50
<211> LENGTH: 454
<212> TYPE: PRT
<213> ORGANISM: Aspergillus fumigatus

<400> SEQUENCE: 50

Met Lys His Leu Ala Ser Ser Ile Ala Leu Thr Leu Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335
```

```
Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
    450


<210> SEQ ID NO 51
<211> LENGTH: 2586
<212> TYPE: DNA
<213> ORGANISM: Aspergillus oryzae

<400> SEQUENCE: 51

atgaagcttg gttggatcga ggtggccgca ttggcggctg cctcagtagt cagtgccaag     60

gatgatctcg cgtactcccc tcctttctac ccttccccat gggcagatgg tcagggtgaa    120

tgggcggaag tatacaaacg cgctgtagac atagtttccc agatgacgtt gacagagaaa    180

gtcaacttaa cgactggaac aggatggcaa ctagagaggt gtgttggaca aactggcagt    240

gttcccagac tcaacatccc cagcttgtgt ttgcaggata gtcctcttgg tattcgtttc    300

tcggactaca attcagcttt ccctgcgggt gttaatgtcg ctgccacctg ggacaagacg    360

ctcgcctacc ttcgtggtca ggcaatgggt gaggagttca gtgataaggg tattgacgtt    420

cagctgggtc ctgctgctgg ccctctcggt gctcatccgg atggcggtag aaactgggaa    480

ggtttctcac cagatccagc cctcaccggt gtactttttg cggagacgat taagggtatt    540

caagatgctg gtgtcattgc gacagctaag cattatatca tgaacgaaca agagcatttc    600

cgccaacaac ccgaggctgc gggttacgga ttcaacgtaa gcgacagttt gagttccaac    660

gttgatgaca agactatgca tgaattgtac ctctggccct tcgcggatgc agtacgcgct    720

ggagtcggtg ctgtcatgtg ctcttacaac caaatcaaca acagctacgg ttgcgagaat    780

agcgaaactc tgaacaagct tttgaaggcg gagcttggtt tccaaggctt cgtcatgagt    840

gattggaccg ctcatcacag cggcgtaggc gctgctttag caggtctgga tatgtcgatg    900

cccggtgatg ttaccttcga tagtggtacg tctttctggg gtgcaaactt gacggtcggt    960

gtccttaacg gtacaatccc ccaatggcgt gttgatgaca tggctgtccg tatcatggcc   1020

gcttattaca aggttggccg cgacaccaaa tacacccctc ccaacttcag ctcgtggacc   1080

agggacgaat atggtttcgc gcataaccat gtttcggaag gtgcttacga gagggtcaac   1140

gaattcgtgg acgtgcaacg cgatcatgcc gacctaatcc gtcgcatcgg cgcgcagagc   1200

actgttctgc tgaagaacaa gggtgccttg cccttgagcc gcaaggaaaa gctggtcgcc   1260

cttctgggag aggatgcggg ttccaactcg tggggcgcta acggctgtga tgaccgtggt   1320

tgcgataacg gtacccttgc catggcctgg ggtagcggta ctgcgaattt cccatacctc   1380
```

```
gtgacaccag agcaggcgat tcagaacgaa gttcttcagg gccgtggtaa tgtcttcgcc   1440
gtgaccgaca gttgggcgct cgacaagatc gctgcggctg cccgccaggc cagcgtatct   1500
ctcgtgttcg tcaactccga ctcaggagaa ggctatctta gtgtggatgg aaatgagggc   1560
gatcgtaaca acatcactct gtggaagaac ggcgacaatg tggtcaagac cgcagcgaat   1620
aactgtaaca acaccgttgt catcatccac tccgtcggac cagttttgat cgatgaatgg   1680
tatgaccacc ccaatgtcac tggtattctc tgggctggtc tgccaggcca ggagtctggt   1740
aactccattg ccgatgtgct gtacggtcgt gtcaaccctg gcgccaagtc tcctttcact   1800
tggggcaaga cccgggagtc gtatggttct cccttggtca aggatgccaa caatggcaac   1860
ggagcgcccc agtctgattt cacccagggt gttttcatcg attaccgcca tttcgataag   1920
ttcaatgaga cccctatcta cgagtttggc tacggcttga gctacaccac cttcgagctc   1980
tccgacctcc atgttcagcc cctgaacgcg tcccgataca ctcccaccag tggcatgact   2040
gaagctgcaa agaactttgg tgaaattggc gatgcgtcgg agtacgtgta tccggagggg   2100
ctggaaagga tccatgagtt tatctatccc tggatcaact ctaccgacct gaaggcatcg   2160
tctgacgatt ctaactacgg ctgggaagac tccaagtata ttcccgaagg cgccacggat   2220
gggtctgccc agccccgttt gcccgctagt ggtggtgccg gaggaaaccc cggtctgtac   2280
gaggatcttt tccgcgtctc tgtgaaggtc aagaacacgg gcaatgtcgc cggtgatgaa   2340
gttcctcagc tgtacgtttc cctaggcggc ccgaatgagc ccaaggtggt actgcgcaag   2400
tttgagcgta ttcacttggc cccttcgcag gaggccgtgt ggacaacgac ccttacccgt   2460
cgtgaccttg caaactggga cgtttcggct caggactgga ccgtcactcc ttaccccaag   2520
acgatctacg ttggaaactc ctcacggaaa ctgccgctcc aggcctcgct gcctaaggcc   2580
cagtaa                                                              2586
```

```
<210> SEQ ID NO 52
<211> LENGTH: 861
<212> TYPE: PRT
<213> ORGANISM: Aspergillus oryzae

<400> SEQUENCE: 52

Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125

Met Gly Glu Glu Phe Ser Asp Lys Gly Ile Asp Val Gln Leu Gly Pro
    130                 135                 140

Ala Ala Gly Pro Leu Gly Ala His Pro Asp Gly Gly Arg Asn Trp Glu
145                 150                 155                 160
```

```
Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Gln Pro Glu Ala Ala Gly
        195                 200                 205

Tyr Gly Phe Asn Val Ser Asp Ser Leu Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270

Gly Phe Gln Gly Phe Val Met Ser Asp Trp Thr Ala His His Ser Gly
        275                 280                 285

Val Gly Ala Ala Leu Ala Gly Leu Asp Met Ser Met Pro Gly Asp Val
    290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Asp Met Ala Val
                325                 330                 335

Arg Ile Met Ala Ala Tyr Tyr Lys Val Gly Arg Asp Thr Lys Tyr Thr
            340                 345                 350

Pro Pro Asn Phe Ser Ser Trp Thr Arg Asp Glu Tyr Gly Phe Ala His
        355                 360                 365

Asn His Val Ser Glu Gly Ala Tyr Glu Arg Val Asn Glu Phe Val Asp
    370                 375                 380

Val Gln Arg Asp His Ala Asp Leu Ile Arg Arg Ile Gly Ala Gln Ser
385                 390                 395                 400

Thr Val Leu Leu Lys Asn Lys Gly Ala Leu Pro Leu Ser Arg Lys Glu
                405                 410                 415

Lys Leu Val Ala Leu Leu Gly Glu Asp Ala Gly Ser Asn Ser Trp Gly
            420                 425                 430

Ala Asn Gly Cys Asp Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Ala Arg Gln
                485                 490                 495

Ala Ser Val Ser Leu Val Phe Val Asn Ser Asp Ser Gly Glu Gly Tyr
            500                 505                 510

Leu Ser Val Asp Gly Asn Glu Gly Asp Arg Asn Asn Ile Thr Leu Trp
        515                 520                 525

Lys Asn Gly Asp Asn Val Val Lys Thr Ala Ala Asn Asn Cys Asn Asn
    530                 535                 540

Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
                565                 570                 575
```

```
Gln Glu Ser Gly Asn Ser Ile Ala Asp Val Leu Tyr Gly Arg Val Asn
            580                 585                 590

Pro Gly Ala Lys Ser Pro Phe Thr Trp Gly Lys Thr Arg Glu Ser Tyr
        595                 600                 605

Gly Ser Pro Leu Val Lys Asp Ala Asn Asn Gly Asn Gly Ala Pro Gln
    610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Arg
            660                 665                 670

Tyr Thr Pro Thr Ser Gly Met Thr Glu Ala Ala Lys Asn Phe Gly Glu
        675                 680                 685

Ile Gly Asp Ala Ser Glu Tyr Val Tyr Pro Glu Gly Leu Glu Arg Ile
    690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
                725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
        755                 760                 765

Lys Val Lys Asn Thr Gly Asn Val Ala Gly Asp Glu Val Pro Gln Leu
    770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                805                 810                 815

Thr Leu Thr Arg Arg Asp Leu Ala Asn Trp Asp Val Ser Ala Gln Asp
            820                 825                 830

Trp Thr Val Thr Pro Tyr Pro Lys Thr Ile Tyr Val Gly Asn Ser Ser
        835                 840                 845

Arg Lys Leu Pro Leu Gln Ala Ser Leu Pro Lys Ala Gln
    850                 855                 860


<210> SEQ ID NO 53
<211> LENGTH: 3060
<212> TYPE: DNA
<213> ORGANISM: Aspergillus fumigatus

<400> SEQUENCE: 53

atgagattcg gttggctcga ggtggccgct ctgacggccg cttctgtagc caatgcccag      60

gtttgtgatg ctttcccgtc attgtttcgg atatagttga caatagtcat ggaaataatc     120

aggaattggc tttctctcca ccattctacc cttcgccttg ggctgatggc cagggagagt     180

gggcagatgc ccatcgacgc gccgtcgaga tcgtttctca gatgacactg gcggagaagg     240

ttaaccttac aacgggtact gggtgggttg cgactttttt gttgacagtg agctttcttc     300

actgaccatc tacacagatg ggaaatggac cgatgcgtcg gtcaaaccgg cagcgttccc     360

aggtaagctt gcaattctgc aacaacgtgc aagtgtagtt gctaaaacgc ggtggtgcag     420

acttggtatc aactggggtc tttgtggcca ggattcccct ttgggtatcc gtttctgtga     480

gctatacccg cggagtcttt cagtccttgt attatgtgct gatgattgtc tctgtatagc     540
```

-continued

```
tgacctcaac tccgccttcc ctgctggtac taatgtcgcc gcgacatggg acaagacact    600
cgcctacctt cgtggcaagg ccatgggtga ggaattcaac gacaagggcg tggacatttt    660
gctggggcct gctgctggtc ctctcggcaa atacccggac ggcggcagaa tctgggaagg    720
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg gatatggtta caacatcacg gagacgatca gctccaacgt    900
ggatgacaag accatgcacg agttgtacct ttggtgagta gttgacactg caaatgagga    960
ccttgattga tttgactgac ctggaatgca ggccctttgc agatgctgtg cgcggtaaga   1020
ttttccgtag acttgacctc gcgacgaaga aatcgctgac gaaccatcgt agctggcgtt   1080
ggcgctgtca tgtgttccta caatcaaatc aacaacagct acggttgtca aaacagtcaa   1140
actctcaaca agctcctcaa ggctgagctg ggcttccaag gcttcgtcat gagtgactgg   1200
agcgctcacc acagcggtgt cggcgctgcc ctcgctgggt tggatatgtc gatgcctgga   1260
gacatttcct tcgacgacgg actctccttc tggggcacga acctaactgt cagtgttctt   1320
aacggcaccg ttccagcctg gcgtgtcgat gacatggctg ttcgtatcat gaccgcgtac   1380
tacaaggttg gtcgtgaccg tcttcgtatt ccccctaact tcagctcctg gacccgggat   1440
gagtacggct gggagcattc tgctgtctcc gagggagcct ggaccaaggt gaacgacttc   1500
gtcaatgtgc agcgcagtca ctctcagatc atccgtgaga ttggtgccgc tagtacagtg   1560
ctcttgaaga acacgggtgc tcttcctttg accggcaagg aggttaaagt gggtgttctc   1620
ggtgaagacg ctggttccaa cccgtggggt gctaacggct gccccgaccg cggctgtgat   1680
aacggcactc ttgctatggc ctggggtagt ggtactgcca acttccctta ccttgtcacc   1740
cccgagcagg ctatccagcg agaggtcatc agcaacggcg gcaatgtctt tgctgtgact   1800
gataacgggg ctctcagcca gatggcagat gttgcatctc aatccaggtg agtgcgggct   1860
cttagaaaaa gaacgttctc tgaatgaagt tttttaacca ttgcgaacag cgtgtctttg   1920
gtgtttgtca acgccgactc tggagagggt ttcatcagtg tcgacggcaa cgagggtgac   1980
cgcaaaaatc tcactctgtg gaagaacggc gaggccgtca ttgacactgt tgtcagccac   2040
tgcaacaaca cgattgtggt tattcacagt gttgggcccg tcttgatcga ccggtggtat   2100
gataacccca acgtcactgc catcatctgg gccggcttgc ccggtcagga gagtggcaac   2160
tccctggtcg acgtgctcta tggccgcgtc aaccccagcg ccaagacccc gttcacctgg   2220
ggcaagactc gggagtctta cggggctccc ttgctcaccg agcctaacaa tggcaatggt   2280
gctccccagg atgatttcaa cgagggcgtc ttcattgact accgtcactt tgacaagcgc   2340
aatgagaccc ccatttatga gtttggccat ggcttgagct acaccacctt tggttactct   2400
caccttcggg ttcaggccct caatagttcg agttcggcat atgtcccgac tagcggagag   2460
accaagcctg cgccaaccta tggtgagatc ggtagtgccg ccgactacct gtatcccgag   2520
ggtctcaaaa gaattaccaa gtttatttac ccttggctca actcgaccga cctcgaggat   2580
tcttctgacg acccgaacta cggctgggag gactcggagt acattcccga aggcgctagg   2640
gatgggtctc ctcaacccct cctgaaggct ggcggcgctc ctggtggtaa ccctaccctt   2700
tatcaggatc ttgttagggt gtcggccacc ataaccaaca ctggtaacgt cgccggttat   2760
gaagtccctc aattggtgag tgacccgcat gttccttgcg ttgcaatttg gctaactcgc   2820
ttctagtatg tttcactggg cggaccgaac gagcctcggg tcgttctgcg caagttcgac   2880
```

```
cgaatcttcc tggctcctgg ggagcaaaag gtttggacca cgactcttaa ccgtcgtgat   2940

ctcgccaatt gggatgtgga ggctcaggac tgggtcatca caaagtaccc caagaaagtg   3000

cacgtcggca gctcctcgcg taagctgcct ctgagagcgc ctctgccccg tgtctactag   3060


<210> SEQ ID NO 54
<211> LENGTH: 863
<212> TYPE: PRT
<213> ORGANISM: Aspergillus fumigatus

<400> SEQUENCE: 54

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350
```

```
Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
    610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
    690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765
```

```
Ser Ala Thr Ile Thr Asn Thr Gly Asn Val Ala Gly Tyr Glu Val Pro
    770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860


<210> SEQ ID NO 55
<211> LENGTH: 2800
<212> TYPE: DNA
<213> ORGANISM: Penicillium brasilianum

<400> SEQUENCE: 55

tgaaaatgca gggttctaca atctttctgg ctttcgcctc atgggcgagc caggttgctg      60

ccattgcgca gcccatacag aagcacgagg tttgttttat cttgctcatg gacgtgcttt     120

gacttgacta attgttttac atacagcccg gatttctgca cgggccccaa gccatagaat     180

cgttctcaga accgttctac ccgtcgccct ggatgaatcc tcacgccgag ggctgggagg     240

ccgcatatca gaaagctcaa gattttgtct cgcaactcac tatcttggag aaaataaatc     300

tgaccaccgg tgttgggtaa gtctctccga ctgcttctgg gtcacggtgc gacgagccac     360

tgactttttg aagctgggaa aatgggccgt gtgtaggaaa cactggatca attcctcgtc     420

tcggattcaa aggattttgt acccaggatt caccacaggg tgttcggttc gcagattatt     480

cctccgcttt cacatctagc caaatggccg ccgcaacatt tgaccgctca attctttatc     540

aacgaggcca agccatggca caggaacaca aggctaaggg tatcacaatt caattgggcc     600

ctgttgccgg ccctctcggt cgcatccccg agggcggccg caactgggaa ggattctccc     660

ctgatcctgt cttgactggt atagccatgg ctgagacaat taagggcatg caggatactg     720

gagtgattgc ttgcgctaaa cattatattg gaaacgagca ggagcacttc cgtcaagtgg     780

gtgaagctgc gggtcacgga tacactattt ccgatactat ttcatctaat attgacgacc     840

gtgctatgca tgagctatac ttgtggccat ttgctgatgc cgttcgcgct ggtgtgggtt     900

ctttcatgtg ctcatactct cagatcaaca actcctacgg atgccaaaac agtcagaccc     960

tcaacaagct cctcaagagc gaattgggct tccaaggctt tgtcatgagc gattggggtg    1020

cccatcactc tggagtgtca tcggcgctag ctggacttga tatgagcatg ccgggtgata    1080

ccgaatttga ttctggcttg agcttctggg gctctaacct caccattgca attctgaacg    1140

gcacggttcc cgaatggcgc ctggatgaca tggcgatgcg aattatggct gcatacttca    1200

aagttggcct tactattgag gatcaaccag atgtcaactt caatgcctgg acccatgaca    1260

cctacggata taaatacgct tatagcaagg aagattacga gcaggtcaac tggcatgtcg    1320

atgttcgcag cgaccacaat aagctcattc gcgagactgc cgcgaagggt acagttctgc    1380

tgaagaacaa ctttcatgct ctccctctga agcagcccag gttcgtggcc gtcgttggtc    1440

aggatgccgg gccaaacccc aagggcccta acggctgcgc agaccgagga tgcgaccaag    1500

gcactctcgc aatgggatgg ggctcagggt ctaccgaatt cccttacctg gtcactcctg    1560

acactgctat tcagtcaaag gtcctcgaat acgggggtcg atacgagagt atttttgata    1620
```

```
actatgacga caatgctatc ttgtcgcttg tctcacagcc tgatgcaacc tgtatcgttt   1680

ttgcaaatgc cgattccggt gaaggctaca tcactgtcga caacaactgg ggtgaccgca   1740

acaatctgac cctctggcaa aatgccgatc aagtgattag cactgtcagc tcgcgatgca   1800

acaacacaat cgttgttctc cactctgtcg gaccagtgtt gctaaatggt atatatgagc   1860

acccgaacat cacagctatt gtctgggcag ggatgccagg cgaagaatct ggcaatgctc   1920

tcgtggatat tctttggggc aatgttaacc ctgccggtcg cactccgttc acctgggcca   1980

aaagtcgaga ggactatggc actgatataa tgtacgagcc caacaacggc cagcgtgcgc   2040

ctcagcagga tttcaccgag agcatctacc tcgactaccg ccatttcgac aaagctggta   2100

tcgagccaat ttacgagttt ggattcggcc tctcctatac caccttcgaa tactctgacc   2160

tccgtgttgt gaagaagtat gttcaaccat acagtcccac gaccggcacc ggtgctcaag   2220

caccttccat cggacagcca cctagccaga acctggatac ctacaagttc cctgctacat   2280

acaagtacat caaaaccttc atttatccct acctgaacag cactgtctcc ctccgcgctg   2340

cttccaagga tcccgaatac ggtcgtacag actttatccc accccacgcg cgtgatggct   2400

cccctcaacc tctcaacccc gctggagacc cagtggccag tggtggaaac aacatgctct   2460

acgacgaact ttacgaggtc actgcacaga tcaaaaacac tggcgacgtg gccggcgacg   2520

aagtcgtcca gctttacgta gatctcgggg gtgacaaccc gcctcgtcag ttgagaaact   2580

ttgacaggtt ttatctgctg cccggtcaga gctcaacatt ccgggctaca ttgacgcgcc   2640

gtgatttgag caactgggat attgaggcgc agaactggcg agttacggaa tcgcctaaga   2700

gagtgtatgt tggacggtcg agtcgggatt tgccgctgag ctcacaattg gagtaatgat   2760

catgtctacc aatagatgtt gaatgtctgg tgtggatatt                         2800
```

```
<210> SEQ ID NO 56
<211> LENGTH: 878
<212> TYPE: PRT
<213> ORGANISM: Penicillium brasilianum

<400> SEQUENCE: 56

Met Gln Gly Ser Thr Ile Phe Leu Ala Phe Ala Ser Trp Ala Ser Gln
1               5                   10                  15

Val Ala Ala Ile Ala Gln Pro Ile Gln Lys His Glu Pro Gly Phe Leu
            20                  25                  30

His Gly Pro Gln Ala Ile Glu Ser Phe Ser Glu Pro Phe Tyr Pro Ser
        35                  40                  45

Pro Trp Met Asn Pro His Ala Glu Gly Trp Glu Ala Ala Tyr Gln Lys
    50                  55                  60

Ala Gln Asp Phe Val Ser Gln Leu Thr Ile Leu Glu Lys Ile Asn Leu
65                  70                  75                  80

Thr Thr Gly Val Gly Trp Glu Asn Gly Pro Cys Val Gly Asn Thr Gly
                85                  90                  95

Ser Ile Pro Arg Leu Gly Phe Lys Gly Phe Cys Thr Gln Asp Ser Pro
            100                 105                 110

Gln Gly Val Arg Phe Ala Asp Tyr Ser Ser Ala Phe Thr Ser Ser Gln
        115                 120                 125

Met Ala Ala Ala Thr Phe Asp Arg Ser Ile Leu Tyr Gln Arg Gly Gln
    130                 135                 140

Ala Met Ala Gln Glu His Lys Ala Lys Gly Ile Thr Ile Gln Leu Gly
145                 150                 155                 160
```

```
Pro Val Ala Gly Pro Leu Gly Arg Ile Pro Glu Gly Gly Arg Asn Trp
                165                 170                 175

Glu Gly Phe Ser Pro Asp Pro Val Leu Thr Gly Ile Ala Met Ala Glu
            180                 185                 190

Thr Ile Lys Gly Met Gln Asp Thr Gly Val Ile Ala Cys Ala Lys His
        195                 200                 205

Tyr Ile Gly Asn Glu Gln Glu His Phe Arg Gln Val Gly Glu Ala Ala
    210                 215                 220

Gly His Gly Tyr Thr Ile Ser Asp Thr Ile Ser Ser Asn Ile Asp Asp
225                 230                 235                 240

Arg Ala Met His Glu Leu Tyr Leu Trp Pro Phe Ala Asp Ala Val Arg
                245                 250                 255

Ala Gly Val Gly Ser Phe Met Cys Ser Tyr Ser Gln Ile Asn Asn Ser
            260                 265                 270

Tyr Gly Cys Gln Asn Ser Gln Thr Leu Asn Lys Leu Leu Lys Ser Glu
        275                 280                 285

Leu Gly Phe Gln Gly Phe Val Met Ser Asp Trp Gly Ala His His Ser
    290                 295                 300

Gly Val Ser Ser Ala Leu Ala Gly Leu Asp Met Ser Met Pro Gly Asp
305                 310                 315                 320

Thr Glu Phe Asp Ser Gly Leu Ser Phe Trp Gly Ser Asn Leu Thr Ile
                325                 330                 335

Ala Ile Leu Asn Gly Thr Val Pro Glu Trp Arg Leu Asp Asp Met Ala
            340                 345                 350

Met Arg Ile Met Ala Ala Tyr Phe Lys Val Gly Leu Thr Ile Glu Asp
        355                 360                 365

Gln Pro Asp Val Asn Phe Asn Ala Trp Thr His Asp Thr Tyr Gly Tyr
    370                 375                 380

Lys Tyr Ala Tyr Ser Lys Glu Asp Tyr Glu Gln Val Asn Trp His Val
385                 390                 395                 400

Asp Val Arg Ser Asp His Asn Lys Leu Ile Arg Glu Thr Ala Ala Lys
                405                 410                 415

Gly Thr Val Leu Leu Lys Asn Asn Phe His Ala Leu Pro Leu Lys Gln
            420                 425                 430

Pro Arg Phe Val Ala Val Val Gly Gln Asp Ala Gly Pro Asn Pro Lys
        435                 440                 445

Gly Pro Asn Gly Cys Ala Asp Arg Gly Cys Asp Gln Gly Thr Leu Ala
    450                 455                 460

Met Gly Trp Gly Ser Gly Ser Thr Glu Phe Pro Tyr Leu Val Thr Pro
465                 470                 475                 480

Asp Thr Ala Ile Gln Ser Lys Val Leu Glu Tyr Gly Gly Arg Tyr Glu
                485                 490                 495

Ser Ile Phe Asp Asn Tyr Asp Asp Asn Ala Ile Leu Ser Leu Val Ser
            500                 505                 510

Gln Pro Asp Ala Thr Cys Ile Val Phe Ala Asn Ala Asp Ser Gly Glu
        515                 520                 525

Gly Tyr Ile Thr Val Asp Asn Asn Trp Gly Asp Arg Asn Asn Leu Thr
    530                 535                 540

Leu Trp Gln Asn Ala Asp Gln Val Ile Ser Thr Val Ser Ser Arg Cys
545                 550                 555                 560

Asn Asn Thr Ile Val Val Leu His Ser Val Gly Pro Val Leu Leu Asn
                565                 570                 575

Gly Ile Tyr Glu His Pro Asn Ile Thr Ala Ile Val Trp Ala Gly Met
```

```
            580                 585                 590

Pro Gly Glu Glu Ser Gly Asn Ala Leu Val Asp Ile Leu Trp Gly Asn
        595                 600                 605

Val Asn Pro Ala Gly Arg Thr Pro Phe Thr Trp Ala Lys Ser Arg Glu
    610                 615                 620

Asp Tyr Gly Thr Asp Ile Met Tyr Glu Pro Asn Asn Gly Gln Arg Ala
625                 630                 635                 640

Pro Gln Gln Asp Phe Thr Glu Ser Ile Tyr Leu Asp Tyr Arg His Phe
                645                 650                 655

Asp Lys Ala Gly Ile Glu Pro Ile Tyr Glu Phe Gly Phe Gly Leu Ser
            660                 665                 670

Tyr Thr Thr Phe Glu Tyr Ser Asp Leu Arg Val Val Lys Lys Tyr Val
        675                 680                 685

Gln Pro Tyr Ser Pro Thr Thr Gly Thr Gly Ala Gln Ala Pro Ser Ile
    690                 695                 700

Gly Gln Pro Pro Ser Gln Asn Leu Asp Thr Tyr Lys Phe Pro Ala Thr
705                 710                 715                 720

Tyr Lys Tyr Ile Lys Thr Phe Ile Tyr Pro Tyr Leu Asn Ser Thr Val
                725                 730                 735

Ser Leu Arg Ala Ala Ser Lys Asp Pro Glu Tyr Gly Arg Thr Asp Phe
            740                 745                 750

Ile Pro Pro His Ala Arg Asp Gly Ser Pro Gln Pro Leu Asn Pro Ala
        755                 760                 765

Gly Asp Pro Val Ala Ser Gly Gly Asn Asn Met Leu Tyr Asp Glu Leu
    770                 775                 780

Tyr Glu Val Thr Ala Gln Ile Lys Asn Thr Gly Asp Val Ala Gly Asp
785                 790                 795                 800

Glu Val Val Gln Leu Tyr Val Asp Leu Gly Gly Asp Asn Pro Pro Arg
                805                 810                 815

Gln Leu Arg Asn Phe Asp Arg Phe Tyr Leu Leu Pro Gly Gln Ser Ser
            820                 825                 830

Thr Phe Arg Ala Thr Leu Thr Arg Arg Asp Leu Ser Asn Trp Asp Ile
        835                 840                 845

Glu Ala Gln Asn Trp Arg Val Thr Glu Ser Pro Lys Arg Val Tyr Val
    850                 855                 860

Gly Arg Ser Ser Arg Asp Leu Pro Leu Ser Ser Gln Leu Glu
865                 870                 875
```

<210> SEQ ID NO 57
<211> LENGTH: 2583
<212> TYPE: DNA
<213> ORGANISM: Aspergillus niger

<400> SEQUENCE: 57

```
atgaggttca ctttgatcga ggcggtggct ctgactgccg tctcgctggc cagcgctgat      60

gaattggcct actccccacc gtattaccca tccccttggg ccaatggcca gggcgactgg     120

gcgcaggcat accagcgcgc tgttgatatt gtctcgcaaa tgacattgga tgagaaggtc     180

aatctgacca caggaactgg atgggaattg gaactatgtg ttggtcagac tggcggtgtt     240

ccccgattgg gagttccggg aatgtgttta caggatagcc ctctgggcgt tcgcgactcc     300

gactacaact ctgctttccc tgccggcatg aacgtggctg caacctggga caagaatctg     360

gcataccttc gcggcaaggc tatgggtcag gaatttagtg acaagggtgc cgatatccaa     420

ttgggtccag ctgccggccc tctcggtaga agtcccgacg gtggtcgtaa ctgggagggc     480
```

```
ttctccccag accctgccct aagtggtgtg ctctttgccg agaccatcaa gggtatccaa    540
gatgctggtg tggttgcgac ggctaagcac tacattgctt acgagcaaga gcatttccgt    600
caggcgcctg aagcccaagg ttttggattt aatatttccg agagtggaag tgcgaacctc    660
gatgataaga ctatgcacga gctgtacctc tggcccttcg cggatgccat ccgtgcaggt    720
gctggcgctg tgatgtgctc ctacaaccag atcaacaaca gttatggctg ccagaacagc    780
tacactctga acaagctgct caaggccgag ctgggcttcc agggctttgt catgagtgat    840
tgggctgctc accatgctgg tgtgagtggt gctttggcag gattggatat gtctatgcca    900
ggagacgtcg actacgacag tggtacgtct tactggggta caaacttgac cattagcgtg    960
ctcaacggaa cggtgcccca atggcgtgtt gatgacatgg ctgtccgcat catggccgcc   1020
tactacaagg tcggccgtga ccgtctgtgg actcctccca acttcagctc atggaccaga   1080
gatgaatacg gctacaagta ctactacgtg tcggagggac cgtacgagaa ggtcaaccag   1140
tacgtgaatg tgcaacgcaa ccacagcgaa ctgattcgcc gcattggagc ggacagcacg   1200
gtgctcctca agaacgacgg cgctctgcct ttgactggta aggagcgcct ggtcgcgctt   1260
atcggagaag atgcgggctc caacccttat ggtgccaacg gctgcagtga ccgtggatgc   1320
gacaatggaa cattggcgat gggctgggga agtggtactg ccaacttccc atacctggtg   1380
acccccgagc aggccatctc aaacgaggtg cttaagcaca agaatggtgt attcaccgcc   1440
accgataact gggctatcga tcagattgag gcgcttgcta agaccgccag tgtctctctt   1500
gtctttgtca acgccgactc tggtgagggt tacatcaatg tggacggaaa cctgggtgac   1560
cgcaggaacc tgaccctgtg gaggaacggc gataatgtga tcaaggctgc tgctagcaac   1620
tgcaacaaca caatcgttgt cattcactct gtcggaccag tcttggttaa cgagtggtac   1680
gacaacccca atgttaccgc tatcctctgg ggtggtttgc ccggtcagga gtctggcaac   1740
tctcttgccg acgtcctcta tggccgtgtc aaccccggtg ccaagtcgcc ctttacctgg   1800
ggcaagactc gtgaggccta ccaagactac ttggtcaccg agcccaacaa cggcaacgga   1860
gcccctcagg aagactttgt cgagggcgtc ttcattgact accgtggatt tgacaagcgc   1920
aacgagaccc cgatctacga gttcggctat ggtctgagct acaccacttt caactactcg   1980
aaccttgagg tgcaggtgct gagcgcccct gcatacgagc ctgcttcggg tgagaccgag   2040
gcagcgccaa ccttcggaga ggttggaaat gcgtcggatt acctctaccc cagcggattg   2100
cagagaatta ccaagttcat ctacccctgg ctcaacggta ccgatctcga ggcatcttcc   2160
ggggatgcta gctacgggca ggactcctcc gactatcttc ccgagggagc caccgatggc   2220
tctgcgcaac cgatcctgcc tgccggtggc ggtcctggcg gcaaccctcg cctgtacgac   2280
gagctcatcc gcgtgtcagt gaccatcaag aacaccggca aggttgctgg tgatgaagtt   2340
ccccaactgt atgtttccct tggcggtccc aatgagccca agatcgtgct gcgtcaattc   2400
gagcgcatca cgctgcagcc gtcggaggag acgaagtgga gcacgactct gacgcgccgt   2460
gaccttgcaa actggaatgt tgagaagcag gactgggaga ttacgtcgta tcccaagatg   2520
gtgtttgtcg gaagctcctc gcggaagctg ccgctccggg cgtctctgcc tactgttcac   2580
taa                                                                 2583
```

<210> SEQ ID NO 58
<211> LENGTH: 860
<212> TYPE: PRT
<213> ORGANISM: Aspergillus niger

<400> SEQUENCE: 58

```
Met Arg Phe Thr Leu Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Asp Glu Lys Val Asn Leu Thr Thr
    50                  55                  60

Gly Thr Gly Trp Glu Leu Glu Leu Cys Val Gly Gln Thr Gly Gly Val
65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Phe
        195                 200                 205

Gly Phe Asn Ile Ser Glu Ser Gly Ser Ala Asn Leu Asp Asp Lys Thr
    210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
        275                 280                 285

Ser Gly Ala Leu Ala Gly Leu Asp Met Ser Met Pro Gly Asp Val Asp
    290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Tyr Gly Tyr Lys Tyr Tyr
        355                 360                 365

Tyr Val Ser Glu Gly Pro Tyr Glu Lys Val Asn Gln Tyr Val Asn Val
    370                 375                 380

Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
                405                 410                 415
```

```
Leu Val Ala Leu Ile Gly Glu Asp Ala Gly Ser Asn Pro Tyr Gly Ala
            420                 425                 430

Asn Gly Cys Ser Asp Arg Gly Cys Asp Asn Gly Thr Leu Ala Met Gly
        435                 440                 445

Trp Gly Ser Gly Thr Ala Asn Phe Pro Tyr Leu Val Thr Pro Glu Gln
    450                 455                 460

Ala Ile Ser Asn Glu Val Leu Lys His Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
            500                 505                 510

Asn Val Asp Gly Asn Leu Gly Asp Arg Arg Asn Leu Thr Leu Trp Arg
        515                 520                 525

Asn Gly Asp Asn Val Ile Lys Ala Ala Ala Ser Asn Cys Asn Asn Thr
    530                 535                 540

Ile Val Val Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
        595                 600                 605

Asp Tyr Leu Val Thr Glu Pro Asn Asn Gly Asn Gly Ala Pro Gln Glu
    610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
            660                 665                 670

Glu Pro Ala Ser Gly Glu Thr Glu Ala Ala Pro Thr Phe Gly Glu Val
        675                 680                 685

Gly Asn Ala Ser Asp Tyr Leu Tyr Pro Ser Gly Leu Gln Arg Ile Thr
    690                 695                 700

Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Ser Asp Tyr Leu Pro Glu Gly
                725                 730                 735

Ala Thr Asp Gly Ser Ala Gln Pro Ile Leu Pro Ala Gly Gly Gly Pro
            740                 745                 750

Gly Gly Asn Pro Arg Leu Tyr Asp Glu Leu Ile Arg Val Ser Val Thr
        755                 760                 765

Ile Lys Asn Thr Gly Lys Val Ala Gly Asp Glu Val Pro Gln Leu Tyr
    770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Lys Trp Ser Thr Thr
                805                 810                 815

Leu Thr Arg Arg Asp Leu Ala Asn Trp Asn Val Glu Lys Gln Asp Trp
            820                 825                 830
```

```
Glu Ile Thr Ser Tyr Pro Lys Met Val Phe Val Gly Ser Ser Ser Arg
        835                 840                 845

Lys Leu Pro Leu Arg Ala Ser Leu Pro Thr Val His
    850                 855                 860


<210> SEQ ID NO 59
<211> LENGTH: 2583
<212> TYPE: DNA
<213> ORGANISM: Aspergillus aculeatus

<400> SEQUENCE: 59

atgaagctca gttggcttga ggcggctgcc ttgacggctg cttcagtcgt cagcgctgat      60

gaactggcgt tctctcctcc tttctacccc tctccgtggg ccaatggcca gggagagtgg     120

gcggaagcct accagcgtgc agtggccatt gtatcccaga tgactctgga tgagaaggtc     180

aacctgacca ccggaactgg atgggagctg gagaagtgcg tcggtcagac tggtggtgtc     240

ccaagactga acatcggtgg catgtgtctt caggacagtc ccttgggaat tcgtgatagt     300

gactacaatt cggctttccc tgctggtgtc aacgttgctg cgacatggga caagaacctt     360

gcttatctac gtggtcaggc tatgggtcaa gagttcagtg acaaaggaat tgatgttcaa     420

ttgggaccgg ccgcgggtcc cctcggcagg agccctgatg gaggtcgcaa ctgggaaggt     480

ttctctccag acccggctct tactggtgtg ctctttgcgg agacgattaa gggtattcaa     540

gacgctggtg tcgtggcgac agccaagcat tacattctca atgagcaaga gcatttccgc     600

caggtcgcag aggctgcggg ctacggattc aatatctccg acacgatcag ctctaacgtt     660

gatgacaaga ccattcatga aatgtacctc tggcccttcg cggatgccgt tcgcgccggc     720

gttggcgcca tcatgtgttc ctacaaccag atcaacaaca gctacggttg ccagaacagt     780

tacactctga acaagcttct gaaggccgag ctcggcttcc agggctttgt gatgtctgac     840

tggggtgctc accacagtgg tgttggctct gctttggccg gcttggatat gtcaatgcct     900

ggcgatatca ccttcgattc tgccactagt ttctggggta ccaacctgac cattgctgtg     960

ctcaacggta ccgtcccgca gtggcgcgtt gacgacatgg ctgtccgtat catggctgcc    1020

tactacaagg ttggccgcga ccgcctgtac cagccgccta acttcagctc ctggactcgc    1080

gatgaatacg gcttcaagta tttctacccc caggaagggc cctatgagaa ggtcaatcac    1140

tttgtcaatg tgcagcgcaa ccacagcgag gttattcgca agttgggagc agacagtact    1200

gttctactga agaacaacaa tgccctgccg ctgaccggaa aggagcgcaa agttgcgatc    1260

ctgggtgaag atgctggatc caactcgtac ggtgccaatg gctgctctga ccgtggctgt    1320

gacaacggta ctcttgctat ggcttggggt agcggcactg ccgaattccc atatctcgtg    1380

acccctgagc aggctattca agccgaggtg ctcaagcata agggcagcgt ctacgccatc    1440

acggacaact gggcgctgag ccaggtggag accctcgcta aacaagccag tgtctctctt    1500

gtatttgtca actcggacgc gggagagggc tatatctccg tggacggaaa cgagggcgac    1560

cgcaacaacc tcaccctctg gaagaacggc gacaacctca tcaaggctgc tgcaaacaac    1620

tgcaacaaca ccatcgttgt catccactcc gttggacctg ttttggttga cgagtggtat    1680

gaccacccca acgttactgc catcctctgg gcgggcttgc ctggccagga gtctggcaac    1740

tccttggctg acgtgctcta cggccgcgtc aacccgggcg ccaaatctcc attcacctgg    1800

ggcaagacga gggaggcgta cggggattac cttgtccgtg agctcaacaa cggcaacgga    1860

gctccccaag atgatttctc ggaaggtgtt ttcattgact accgcggatt cgacaagcgc    1920

aatgagaccc cgatctacga gttcggacat ggtctgagct acaccacttt caactactct    1980
```

```
ggccttcaca tccaggttct caacgcttcc tccaacgctc aagtagccac tgagactggc   2040

gccgctccca ccttcggaca agtcggcaat gcctctgact acgtgtaccc tgagggattg   2100

accagaatca gcaagttcat ctatccctgg cttaattcca cagacctgaa ggcctcatct   2160

ggcgacccgt actatggagt cgacaccgcg gagcacgtgc ccgagggtgc tactgatggc   2220

tctccgcagc ccgttctgcc tgccggtggt ggctctggtg gtaacccgcg cctctacgat   2280

gagttgatcc gtgtttcggt gacagtcaag aacactggtc gtgttgccgg tgatgctgtg   2340

cctcaattgt atgtttccct tggtggaccc aatgagccca aggttgtgtt gcgcaaattc   2400

gaccgcctca ccctcaagcc ctccgaggag acggtgtgga cgactaccct gacccgccgc   2460

gatctgtcta actgggacgt tgcggctcag gactgggtca tcacttctta cccgaagaag   2520

gtccatgttg gtagctcttc gcgtcagctg ccccttcacg cggcgctccc gaaggtgcaa   2580

tga                                                                 2583
```

```
<210> SEQ ID NO 60
<211> LENGTH: 860
<212> TYPE: PRT
<213> ORGANISM: Aspergillus aculeatus

<400> SEQUENCE: 60

Met Lys Leu Ser Trp Leu Glu Ala Ala Ala Leu Thr Ala Ala Ser Val
1               5                   10                  15

Val Ser Ala Asp Glu Leu Ala Phe Ser Pro Pro Phe Tyr Pro Ser Pro
            20                  25                  30

Trp Ala Asn Gly Gln Gly Glu Trp Ala Glu Ala Tyr Gln Arg Ala Val
        35                  40                  45

Ala Ile Val Ser Gln Met Thr Leu Asp Glu Lys Val Asn Leu Thr Thr
    50                  55                  60

Gly Thr Gly Trp Glu Leu Glu Lys Cys Val Gly Gln Thr Gly Gly Val
65                  70                  75                  80

Pro Arg Leu Asn Ile Gly Gly Met Cys Leu Gln Asp Ser Pro Leu Gly
                85                  90                  95

Ile Arg Asp Ser Asp Tyr Asn Ser Ala Phe Pro Ala Gly Val Asn Val
            100                 105                 110

Ala Ala Thr Trp Asp Lys Asn Leu Ala Tyr Leu Arg Gly Gln Ala Met
        115                 120                 125

Gly Gln Glu Phe Ser Asp Lys Gly Ile Asp Val Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Thr Gly Val Leu Phe Ala Glu Thr Ile
                165                 170                 175

Lys Gly Ile Gln Asp Ala Gly Val Val Ala Thr Ala Lys His Tyr Ile
            180                 185                 190

Leu Asn Glu Gln Glu His Phe Arg Gln Val Ala Glu Ala Ala Gly Tyr
        195                 200                 205

Gly Phe Asn Ile Ser Asp Thr Ile Ser Ser Asn Val Asp Asp Lys Thr
    210                 215                 220

Ile His Glu Met Tyr Leu Trp Pro Phe Ala Asp Ala Val Arg Ala Gly
225                 230                 235                 240

Val Gly Ala Ile Met Cys Ser Tyr Asn Gln Ile Asn Asn Ser Tyr Gly
                245                 250                 255
```

```
Cys Gln Asn Ser Tyr Thr Leu Asn Lys Leu Leu Lys Ala Glu Leu Gly
            260                 265                 270

Phe Gln Gly Phe Val Met Ser Asp Trp Gly Ala His His Ser Gly Val
        275                 280                 285

Gly Ser Ala Leu Ala Gly Leu Asp Met Ser Met Pro Gly Asp Ile Thr
    290                 295                 300

Phe Asp Ser Ala Thr Ser Phe Trp Gly Thr Asn Leu Thr Ile Ala Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Tyr Gln Pro
            340                 345                 350

Pro Asn Phe Ser Ser Trp Thr Arg Asp Glu Tyr Gly Phe Lys Tyr Phe
        355                 360                 365

Tyr Pro Gln Glu Gly Pro Tyr Glu Lys Val Asn His Phe Val Asn Val
    370                 375                 380

Gln Arg Asn His Ser Glu Val Ile Arg Lys Leu Gly Ala Asp Ser Thr
385                 390                 395                 400

Val Leu Leu Lys Asn Asn Asn Ala Leu Pro Leu Thr Gly Lys Glu Arg
                405                 410                 415

Lys Val Ala Ile Leu Gly Glu Asp Ala Gly Ser Asn Ser Tyr Gly Ala
            420                 425                 430

Asn Gly Cys Ser Asp Arg Gly Cys Asp Asn Gly Thr Leu Ala Met Ala
        435                 440                 445

Trp Gly Ser Gly Thr Ala Glu Phe Pro Tyr Leu Val Thr Pro Glu Gln
    450                 455                 460

Ala Ile Gln Ala Glu Val Leu Lys His Lys Gly Ser Val Tyr Ala Ile
465                 470                 475                 480

Thr Asp Asn Trp Ala Leu Ser Gln Val Glu Thr Leu Ala Lys Gln Ala
                485                 490                 495

Ser Val Ser Leu Val Phe Val Asn Ser Asp Ala Gly Glu Gly Tyr Ile
            500                 505                 510

Ser Val Asp Gly Asn Glu Gly Asp Arg Asn Asn Leu Thr Leu Trp Lys
        515                 520                 525

Asn Gly Asp Asn Leu Ile Lys Ala Ala Ala Asn Asn Cys Asn Asn Thr
    530                 535                 540

Ile Val Val Ile His Ser Val Gly Pro Val Leu Val Asp Glu Trp Tyr
545                 550                 555                 560

Asp His Pro Asn Val Thr Ala Ile Leu Trp Ala Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gly
        595                 600                 605

Asp Tyr Leu Val Arg Glu Leu Asn Asn Gly Asn Gly Ala Pro Gln Asp
    610                 615                 620

Asp Phe Ser Glu Gly Val Phe Ile Asp Tyr Arg Gly Phe Asp Lys Arg
625                 630                 635                 640

Asn Glu Thr Pro Ile Tyr Glu Phe Gly His Gly Leu Ser Tyr Thr Thr
                645                 650                 655

Phe Asn Tyr Ser Gly Leu His Ile Gln Val Leu Asn Ala Ser Ser Asn
            660                 665                 670

Ala Gln Val Ala Thr Glu Thr Gly Ala Ala Pro Thr Phe Gly Gln Val
```

```
        675                 680                 685

Gly Asn Ala Ser Asp Tyr Val Tyr Pro Glu Gly Leu Thr Arg Ile Ser
    690                 695                 700

Lys Phe Ile Tyr Pro Trp Leu Asn Ser Thr Asp Leu Lys Ala Ser Ser
705                 710                 715                 720

Gly Asp Pro Tyr Tyr Gly Val Asp Thr Ala Glu His Val Pro Glu Gly
                725                 730                 735

Ala Thr Asp Gly Ser Pro Gln Pro Val Leu Pro Ala Gly Gly Gly Ser
            740                 745                 750

Gly Gly Asn Pro Arg Leu Tyr Asp Glu Leu Ile Arg Val Ser Val Thr
        755                 760                 765

Val Lys Asn Thr Gly Arg Val Ala Gly Asp Ala Val Pro Gln Leu Tyr
    770                 775                 780

Val Ser Leu Gly Gly Pro Asn Glu Pro Lys Val Val Leu Arg Lys Phe
785                 790                 795                 800

Asp Arg Leu Thr Leu Lys Pro Ser Glu Glu Thr Val Trp Thr Thr Thr
                805                 810                 815

Leu Thr Arg Arg Asp Leu Ser Asn Trp Asp Val Ala Ala Gln Asp Trp
            820                 825                 830

Val Ile Thr Ser Tyr Pro Lys Lys Val His Val Gly Ser Ser Ser Arg
        835                 840                 845

Gln Leu Pro Leu His Ala Ala Leu Pro Lys Val Gln
    850                 855                 860


<210> SEQ ID NO 61
<211> LENGTH: 3294
<212> TYPE: DNA
<213> ORGANISM: Aspergillus oryzae

<400> SEQUENCE: 61

atgcgttcct cccccctcct ccgctccgcc gttgtggccg ccctgccggt gttggccctt      60

gccgctgatg gcaggtccac ccgctactgg gactgctgca agccttcgtg cggctgggcc     120

aagaaggctc ccgtgaacca gcctgtcttt tcctgcaacg ccaacttcca gcgtatcacg     180

gacttcgacg ccaagtccgg ctgcgagccg ggcggtgtcg cctactcgtg cgccgaccag     240

accccatggg ctgtgaacga cgacttcgcg ctcggttttg ctgccacctc tattgccggc     300

agcaatgagg cgggctggtg ctgcgcctgc tacgagctca ccttcacatc cggtcctgtt     360

gctggcaaga agatggtcgt ccagtccacc agcactggcg gtgatcttgg cagcaaccac     420

ttcgatctca acatccccgg cggcggcgtc ggcatcttcg acggatgcac tccccagttc     480

ggtggtctgc ccggccagcg ctacggcggc atctcgtccc gcaacgagtg cgatcggttc     540

cccgacgccc tcaagcccgg ctgctactgg cgcttcgact ggttcaagaa cgccgacaat     600

ccgagcttca gcttccgtca ggtccagtgc ccagccgagc tcgtcgctcg caccggatgc     660

cgccgcaacg acgacggcaa cttccctgcc gtccagatcc ccatgcgttc ctcccccctc     720

ctccgctccg ccgttgtggc cgccctgccg gtgttggccc ttgccaagga tgatctcgcg     780

tactcccctc ctttctaccc ttccccatgg gcagatggtc agggtgaatg ggcggaagta     840

tacaaacgcg ctgtagacat agtttcccag atgacgttga cagagaaagt caacttaacg     900

actggaacag gatggcaact agagaggtgt gttggacaaa ctggcagtgt tcccagactc     960

aacatcccca gcttgtgttt gcaggatagt cctcttggta ttcgtttctc ggactacaat    1020

tcagctttcc ctgcgggtgt taatgtcgct gccacctggg acaagacgct cgcctacctt    1080
```

```
cgtggtcagg caatgggtga ggagttcagt gataagggta ttgacgttca gctgggtcct   1140
gctgctggcc ctctcggtgc tcatccggat ggcggtagaa actgggaagg tttctcacca   1200
gatccagccc tcaccggtgt actttttgcg gagacgatta agggtattca agatgctggt   1260
gtcattgcga cagctaagca ttatatcatg aacgaacaag agcatttccg ccaacaaccc   1320
gaggctgcgg gttacggatt caacgtaagc gacagtttga gttccaacgt tgatgacaag   1380
actatgcatg aattgtacct ctggcccttc gcggatgcag tacgcgctgg agtcggtgct   1440
gtcatgtgct cttacaacca aatcaacaac agctacggtt gcgagaatag cgaaactctg   1500
aacaagcttt tgaaggcgga gcttggtttc caaggcttcg tcatgagtga ttggaccgct   1560
catcacagcg gcgtaggcgc tgctttagca ggtctggata tgtcgatgcc cggtgatgtt   1620
accttcgata gtggtacgtc tttctggggt gcaaacttga cggtcggtgt ccttaacggt   1680
acaatccccc aatggcgtgt tgatgacatg gctgtccgta tcatggccgc ttattacaag   1740
gttggccgcg acaccaaata cacccctccc aacttcagct cgtggaccag ggacgaatat   1800
ggtttcgcgc ataaccatgt ttcggaaggt gcttacgaga gggtcaacga attcgtggac   1860
gtgcaacgcg atcatgccga cctaatccgt cgcatcggcg cgcagagcac tgttctgctg   1920
aagaacaagg gtgccttgcc cttgagccgc aaggaaaagc tggtcgccct tctgggagag   1980
gatgcgggtt ccaactcgtg gggcgctaac ggctgtgatg accgtggttg cgataacggt   2040
acccttgcca tggcctgggg tagcggtact gcgaatttcc catacctcgt gacaccagag   2100
caggcgattc agaacgaagt tcttcagggc cgtggtaatg tcttcgccgt gaccgacagt   2160
tgggcgctcg acaagatcgc tgcggctgcc cgccaggcca gcgtatctct cgtgttcgtc   2220
aactccgact caggagaagg ctatcttagt gtggatggaa atgagggcga tcgtaacaac   2280
atcactctgt ggaagaacgg cgacaatgtg gtcaagaccg cagcgaataa ctgtaacaac   2340
accgttgtca tcatccactc cgtcggacca gttttgatcg atgaatggta tgaccacccc   2400
aatgtcactg gtattctctg ggctggtctg ccaggccagg agtctggtaa ctccattgcc   2460
gatgtgctgt acggtcgtgt caaccctggc gccaagtctc ctttcacttg ggcaagacc    2520
cgggagtcgt atggttctcc cttggtcaag gatgccaaca atggcaacgg agcgccccag   2580
tctgatttca cccagggtgt tttcatcgat taccgccatt tcgataagtt caatgagacc   2640
cctatctacg agtttggcta cggcttgagc tacaccacct tcgagctctc cgacctccat   2700
gttcagcccc tgaacgcgtc ccgatacact cccaccagtg gcatgactga agctgcaaag   2760
aactttggtg aaattggcga tgcgtcggag tacgtgtatc cggaggggct ggaaaggatc   2820
catgagttta tctatccctg gatcaactct accgacctga aggcatcgtc tgacgattct   2880
aactacggct gggaagactc caagtatatt cccgaaggcg ccacggatgg gtctgcccag   2940
ccccgtttgc ccgctagtgg tggtgccgga ggaaaccccg gtctgtacga ggatcttttc   3000
cgcgtctctg tgaaggtcaa gaacacgggc aatgtcgccg gtgatgaagt tcctcagctg   3060
tacgtttccc taggcggccc gaatgagccc aaggtggtac tgcgcaagtt tgagcgtatt   3120
cacttggccc cttcgcagga ggccgtgtgg acaacgaccc ttacccgtcg tgaccttgca   3180
aactgggacg tttcggctca ggactggacc gtcactcctt accccaagac gatctacgtt   3240
ggaaactcct cacggaaact gccgctccag gcctcgctgc ctaaggccca gtaa         3294
```

<210> SEQ ID NO 62
<211> LENGTH: 1097
<212> TYPE: PRT
<213> ORGANISM: Aspergillus oryzae

<400> SEQUENCE: 62

```
Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Pro Trp Ala Asp
            260                 265                 270

Gly Gln Gly Glu Trp Ala Glu Val Tyr Lys Arg Ala Val Asp Ile Val
        275                 280                 285

Ser Gln Met Thr Leu Thr Glu Lys Val Asn Leu Thr Thr Gly Thr Gly
    290                 295                 300

Trp Gln Leu Glu Arg Cys Val Gly Gln Thr Gly Ser Val Pro Arg Leu
305                 310                 315                 320

Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
            340                 345                 350

Trp Asp Lys Thr Leu Ala Tyr Leu Arg Gly Gln Ala Met Gly Glu Glu
        355                 360                 365

Phe Ser Asp Lys Gly Ile Asp Val Gln Leu Gly Pro Ala Ala Gly Pro
    370                 375                 380

Leu Gly Ala His Pro Asp Gly Gly Arg Asn Trp Glu Gly Phe Ser Pro
385                 390                 395                 400

Asp Pro Ala Leu Thr Gly Val Leu Phe Ala Glu Thr Ile Lys Gly Ile
```

```
                405                 410                 415

Gln Asp Ala Gly Val Ile Ala Thr Ala Lys His Tyr Ile Met Asn Glu
            420                 425                 430

Gln Glu His Phe Arg Gln Gln Pro Glu Ala Ala Gly Tyr Gly Phe Asn
        435                 440                 445

Val Ser Asp Ser Leu Ser Ser Asn Val Asp Asp Lys Thr Met His Glu
    450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
                485                 490                 495

Ser Glu Thr Leu Asn Lys Leu Leu Lys Ala Glu Leu Gly Phe Gln Gly
            500                 505                 510

Phe Val Met Ser Asp Trp Thr Ala His His Ser Gly Val Gly Ala Ala
        515                 520                 525

Leu Ala Gly Leu Asp Met Ser Met Pro Gly Asp Val Thr Phe Asp Ser
    530                 535                 540

Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
            580                 585                 590

Ser Ser Trp Thr Arg Asp Glu Tyr Gly Phe Ala His Asn His Val Ser
        595                 600                 605

Glu Gly Ala Tyr Glu Arg Val Asn Glu Phe Val Asp Val Gln Arg Asp
    610                 615                 620

His Ala Asp Leu Ile Arg Arg Ile Gly Ala Gln Ser Thr Val Leu Leu
625                 630                 635                 640

Lys Asn Lys Gly Ala Leu Pro Leu Ser Arg Lys Glu Lys Leu Val Ala
                645                 650                 655

Leu Leu Gly Glu Asp Ala Gly Ser Asn Ser Trp Gly Ala Asn Gly Cys
            660                 665                 670

Asp Asp Arg Gly Cys Asp Asn Gly Thr Leu Ala Met Ala Trp Gly Ser
        675                 680                 685

Gly Thr Ala Asn Phe Pro Tyr Leu Val Thr Pro Glu Gln Ala Ile Gln
    690                 695                 700

Asn Glu Val Leu Gln Gly Arg Gly Asn Val Phe Ala Val Thr Asp Ser
705                 710                 715                 720

Trp Ala Leu Asp Lys Ile Ala Ala Ala Ala Arg Gln Ala Ser Val Ser
                725                 730                 735

Leu Val Phe Val Asn Ser Asp Ser Gly Glu Gly Tyr Leu Ser Val Asp
            740                 745                 750

Gly Asn Glu Gly Asp Arg Asn Asn Ile Thr Leu Trp Lys Asn Gly Asp
        755                 760                 765

Asn Val Val Lys Thr Ala Ala Asn Asn Cys Asn Asn Thr Val Val Ile
    770                 775                 780

Ile His Ser Val Gly Pro Val Leu Ile Asp Glu Trp Tyr Asp His Pro
785                 790                 795                 800

Asn Val Thr Gly Ile Leu Trp Ala Gly Leu Pro Gly Gln Glu Ser Gly
                805                 810                 815

Asn Ser Ile Ala Asp Val Leu Tyr Gly Arg Val Asn Pro Gly Ala Lys
            820                 825                 830
```

```
Ser Pro Phe Thr Trp Gly Lys Thr Arg Glu Ser Tyr Gly Ser Pro Leu
        835                 840                 845

Val Lys Asp Ala Asn Asn Gly Asn Gly Ala Pro Gln Ser Asp Phe Thr
    850                 855                 860

Gln Gly Val Phe Ile Asp Tyr Arg His Phe Asp Lys Phe Asn Glu Thr
865                 870                 875                 880

Pro Ile Tyr Glu Phe Gly Tyr Gly Leu Ser Tyr Thr Thr Phe Glu Leu
                885                 890                 895

Ser Asp Leu His Val Gln Pro Leu Asn Ala Ser Arg Tyr Thr Pro Thr
            900                 905                 910

Ser Gly Met Thr Glu Ala Ala Lys Asn Phe Gly Glu Ile Gly Asp Ala
        915                 920                 925

Ser Glu Tyr Val Tyr Pro Glu Gly Leu Glu Arg Ile His Glu Phe Ile
    930                 935                 940

Tyr Pro Trp Ile Asn Ser Thr Asp Leu Lys Ala Ser Ser Asp Asp Ser
945                 950                 955                 960

Asn Tyr Gly Trp Glu Asp Ser Lys Tyr Ile Pro Glu Gly Ala Thr Asp
                965                 970                 975

Gly Ser Ala Gln Pro Arg Leu Pro Ala Ser Gly Gly Ala Gly Gly Asn
            980                 985                 990

Pro Gly Leu Tyr Glu Asp Leu Phe  Arg Val Ser Val Lys  Val Lys Asn
        995                 1000                1005

Thr Gly  Asn Val Ala Gly Asp  Glu Val Pro Gln Leu  Tyr Val Ser
    1010                1015                1020

Leu Gly  Gly Pro Asn Glu Pro  Lys Val Val Leu Arg  Lys Phe Glu
    1025                1030                1035

Arg Ile  His Leu Ala Pro Ser  Gln Glu Ala Val Trp  Thr Thr Thr
    1040                1045                1050

Leu Thr  Arg Arg Asp Leu Ala  Asn Trp Asp Val Ser  Ala Gln Asp
    1055                1060                1065

Trp Thr  Val Thr Pro Tyr Pro  Lys Thr Ile Tyr Val  Gly Asn Ser
    1070                1075                1080

Ser Arg  Lys Leu Pro Leu Gln  Ala Ser Leu Pro Lys  Ala Gln
    1085                1090                1095
```

<210> SEQ ID NO 63
<211> LENGTH: 3294
<212> TYPE: DNA
<213> ORGANISM: Aspergillus oryzae

<400> SEQUENCE: 63

```
atgcgttcct ccccctcct ccgctccgcc gttgtggccg ccctgccggt gttggccctt      60

gccgctgatg gcaggtccac ccgctactgg gactgctgca agccttcgtg cggctgggcc    120

aagaaggctc ccgtgaacca gcctgtcttt tcctgcaacg ccaacttcca gcgtatcacg    180

gacttcgacg ccaagtccgg ctgcgagccg ggcggtgtcg cctactcgtg cgccgaccag    240

accccatggg ctgtgaacga cgacttcgcg ctcggttttg ctgccacctc tattgccggc    300

agcaatgagg cgggctggtg ctgcgcctgc tacgagctca ccttcacatc cggtcctgtt    360

gctggcaaga agatggtcgt ccagtccacc agcactggcg gtgatcttgg cagcaaccac    420

ttcgatctca acatccccgg cggcggcgtc ggcatcttcg acggatgcac tccccagttc    480

ggtggtctgc ccggccagcg ctacggcggc atctcgtccc gcaacgagtg cgatcggttc    540

cccgacgccc tcaagcccgg ctgctactgg cgcttcgact ggttcaagaa cgccgacaat    600
```

```
ccgagcttca gcttccgtca ggtccagtgc ccagccgagc tcgtcgctcg caccggatgc    660
cgccgcaacg acgacggcaa cttccctgcc gtccagatcc ccatgcgttc ctccccccctc    720
ctccgctccg ccgttgtggc cgccctgccg gtgttggccc ttgccaagga tgatctcgcg    780
tactcccctc ctttctaccc ttccccatgg gcagatggtc agggtgaatg ggcggaagta    840
tacaaacgcg ctgtagacat agtttcccag atgacgttga cagagaaagt caacttaacg    900
actggaacag gatggcaact agagaggtgt gttggacaaa ctggcagtgt tcccagactc    960
aacatcccca gcttgtgttt gcaggatagt cctcttggta ttcgtttctc ggactacaat   1020
tcagctttcc ctgcgggtgt taatgtcgct gccacctggg acaagacgct cgcctacctt   1080
cgtggtcagg caatgggtga ggagttcagt gataagggta ttgacgttca gctgggtcct   1140
gctgctggcc ctctcggtgc tcatccggat ggcggtagaa actgggaaag tttctcacca   1200
gatccagccc tcaccggtgt actttttgcg gagacgatta agggtattca agatgctggt   1260
gtcattgcga cagctaagca ttatatcatg aacgaacaag agcatttccg ccaacaaccc   1320
gaggctgcgg gttacggatt caacgtaagc gacagtttga gttccaacgt tgatgacaag   1380
actatgcatg aattgtacct ctggcccttc gcggatgcag tacgcgctgg agtcggtgct   1440
gttatgtgct cttacaacca aatcaacaac agctacggtt gcgagaatag cgaaactctg   1500
aacaagcttt tgaaggcgga gcttggtttc caaggcttcg tcatgagtga ttggaccgct   1560
caacacagcg gcgtaggcgc tgctttagca ggtctggata tgtcgatgcc cggtgatgtt   1620
accttcgata gtggtacgtc tttctggggt gcaaacttga cggtcggtgt ccttaacggt   1680
acaatccccc aatggcgtgt tgatgacatg gctgtccgta tcatggccgc ttattacaag   1740
gttggccgcg acaccaaata cacccctccc aacttcagct cgtggaccag ggacgaatat   1800
ggtttcgcgc ataaccatgt ttcggaaggt gcttacgaga gggtcaacga attcgtggac   1860
gtgcaacgcg atcatgccga cctaatccgt cgcatcggcg cgcagagcac tgttctgctg   1920
aagaacaagg gtgccttgcc cttgagccgc aaggaaaagc tggtcgccct tctgggagag   1980
gatgcgggtt ccaactcgtg gggcgctaac ggctgtgatg accgtggttg cgataacggt   2040
acccttgcca tggcctgggg tagcggtact gcgaatttcc catacctcgt gacaccagag   2100
caggcgattc agaacgaagt tcttcagggc cgtggtaatg tcttcgccgt gaccgacagt   2160
tgggcgctcg acaagatcgc tgcggctgcc cgccaggcca gcgtatctct cgtgttcgtc   2220
aactccgact caggagaagg ctatcttagt gtggatggaa atgagggcga tcgtaacaac   2280
atcactctgt ggaagaacgg cgacaatgtg gtcaagaccg cagcgaataa ctgtaacaac   2340
accgttgtca tcatccactc cgtcggacca gttttgatcg atgaatggta tgaccacccc   2400
aatgtcactg gtattctctg ggctggtctg ccaggccagg agtctggtaa ctccattgcc   2460
gatgtgctgt acggtcgtgt caaccctggc gccaagtctc ctttcacttg gggcaagacc   2520
cgggagtcgt atggttctcc cttggtcaag gatgccaaca atggcaacgg agcgccccag   2580
tctgatttca cccagggtgt tttcatcgat taccgccatt tcgataagtt caatgagacc   2640
cctatctacg agtttggcta cggcttgagc tacaccacct tcgagctctc cgacctccat   2700
gttcagcccc tgaacgcgtc ccgatacact cccaccagtg gcatgactga agctgcaaag   2760
aactttggtg aaattggcga tgcgtcggag tacgtgtatc cggaggggct ggaaaggatc   2820
catgagttta tctatccctg gatcaactct accgacctga aggcatcgtc tgacgattct   2880
aactacggct gggaagactc caagtatatt cccgaaggcg ccacggatgg gtctgcccag   2940
```

```
ccccgtttgc ccgctagtgg tggtgccgga ggaaaccccg gtctgtacga ggatcttttc   3000

cgcgtctctg tgaaggtcaa gaacacgggc aatgtcgccg gtgatgaagt tcctcagctg   3060

tacgtttccc taggcggccc gaatgagccc aaggtggtac tgcgcaagtt tgagcgtatt   3120

cacttggccc cttcgcagga ggccgtgtgg acaacgaccc ttacccgtcg tgaccttgca   3180

aactgggacg tttcggctca ggactggacc gtcactcctt accccaagac gatctacgtt   3240

ggaaactcct cacggaaact gccgctccag gcctcgctgc ctaaggccca gtaa         3294
```

<210> SEQ ID NO 64
<211> LENGTH: 1097
<212> TYPE: PRT
<213> ORGANISM: Aspergillus oryzae

<400> SEQUENCE: 64

```
Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Pro Trp Ala Asp
            260                 265                 270

Gly Gln Gly Glu Trp Ala Glu Val Tyr Lys Arg Ala Val Asp Ile Val
        275                 280                 285

Ser Gln Met Thr Leu Thr Glu Lys Val Asn Leu Thr Thr Gly Thr Gly
    290                 295                 300

Trp Gln Leu Glu Arg Cys Val Gly Gln Thr Gly Ser Val Pro Arg Leu
305                 310                 315                 320
```

```
Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
            340                 345                 350

Trp Asp Lys Thr Leu Ala Tyr Leu Arg Gly Gln Ala Met Gly Glu Glu
        355                 360                 365

Phe Ser Asp Lys Gly Ile Asp Val Gln Leu Gly Pro Ala Ala Gly Pro
    370                 375                 380

Leu Gly Ala His Pro Asp Gly Gly Arg Asn Trp Glu Ser Phe Ser Pro
385                 390                 395                 400

Asp Pro Ala Leu Thr Gly Val Leu Phe Ala Glu Thr Ile Lys Gly Ile
                405                 410                 415

Gln Asp Ala Gly Val Ile Ala Thr Ala Lys His Tyr Ile Met Asn Glu
            420                 425                 430

Gln Glu His Phe Arg Gln Gln Pro Glu Ala Ala Gly Tyr Gly Phe Asn
        435                 440                 445

Val Ser Asp Ser Leu Ser Ser Asn Val Asp Asp Lys Thr Met His Glu
    450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
                485                 490                 495

Ser Glu Thr Leu Asn Lys Leu Leu Lys Ala Glu Leu Gly Phe Gln Gly
            500                 505                 510

Phe Val Met Ser Asp Trp Thr Ala Gln His Ser Gly Val Gly Ala Ala
        515                 520                 525

Leu Ala Gly Leu Asp Met Ser Met Pro Gly Asp Val Thr Phe Asp Ser
    530                 535                 540

Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
            580                 585                 590

Ser Ser Trp Thr Arg Asp Glu Tyr Gly Phe Ala His Asn His Val Ser
        595                 600                 605

Glu Gly Ala Tyr Glu Arg Val Asn Glu Phe Val Asp Val Gln Arg Asp
    610                 615                 620

His Ala Asp Leu Ile Arg Arg Ile Gly Ala Gln Ser Thr Val Leu Leu
625                 630                 635                 640

Lys Asn Lys Gly Ala Leu Pro Leu Ser Arg Lys Glu Lys Leu Val Ala
                645                 650                 655

Leu Leu Gly Glu Asp Ala Gly Ser Asn Ser Trp Gly Ala Asn Gly Cys
            660                 665                 670

Asp Asp Arg Gly Cys Asp Asn Gly Thr Leu Ala Met Ala Trp Gly Ser
        675                 680                 685

Gly Thr Ala Asn Phe Pro Tyr Leu Val Thr Pro Glu Gln Ala Ile Gln
    690                 695                 700

Asn Glu Val Leu Gln Gly Arg Gly Asn Val Phe Ala Val Thr Asp Ser
705                 710                 715                 720

Trp Ala Leu Asp Lys Ile Ala Ala Ala Ala Arg Gln Ala Ser Val Ser
                725                 730                 735
```

```
Leu Val Phe Val Asn Ser Asp Ser Gly Glu Gly Tyr Leu Ser Val Asp
            740                 745                 750

Gly Asn Glu Gly Asp Arg Asn Asn Ile Thr Leu Trp Lys Asn Gly Asp
        755                 760                 765

Asn Val Val Lys Thr Ala Ala Asn Asn Cys Asn Asn Thr Val Val Ile
    770                 775                 780

Ile His Ser Val Gly Pro Val Leu Ile Asp Glu Trp Tyr Asp His Pro
785                 790                 795                 800

Asn Val Thr Gly Ile Leu Trp Ala Gly Leu Pro Gly Gln Glu Ser Gly
                805                 810                 815

Asn Ser Ile Ala Asp Val Leu Tyr Gly Arg Val Asn Pro Gly Ala Lys
            820                 825                 830

Ser Pro Phe Thr Trp Gly Lys Thr Arg Glu Ser Tyr Gly Ser Pro Leu
        835                 840                 845

Val Lys Asp Ala Asn Asn Gly Asn Gly Ala Pro Gln Ser Asp Phe Thr
    850                 855                 860

Gln Gly Val Phe Ile Asp Tyr Arg His Phe Asp Lys Phe Asn Glu Thr
865                 870                 875                 880

Pro Ile Tyr Glu Phe Gly Tyr Gly Leu Ser Tyr Thr Thr Phe Glu Leu
                885                 890                 895

Ser Asp Leu His Val Gln Pro Leu Asn Ala Ser Arg Tyr Thr Pro Thr
            900                 905                 910

Ser Gly Met Thr Glu Ala Ala Lys Asn Phe Gly Glu Ile Gly Asp Ala
        915                 920                 925

Ser Glu Tyr Val Tyr Pro Glu Gly Leu Glu Arg Ile His Glu Phe Ile
    930                 935                 940

Tyr Pro Trp Ile Asn Ser Thr Asp Leu Lys Ala Ser Ser Asp Asp Ser
945                 950                 955                 960

Asn Tyr Gly Trp Glu Asp Ser Lys Tyr Ile Pro Glu Gly Ala Thr Asp
                965                 970                 975

Gly Ser Ala Gln Pro Arg Leu Pro Ala Ser Gly Gly Ala Gly Gly Asn
            980                 985                 990

Pro Gly Leu Tyr Glu Asp Leu Phe  Arg Val Ser Val Lys  Val Lys Asn
        995                 1000                 1005

Thr Gly  Asn Val Ala Gly Asp  Glu Val Pro Gln Leu  Tyr Val Ser
    1010                 1015                 1020

Leu Gly  Gly Pro Asn Glu Pro  Lys Val Val Leu Arg  Lys Phe Glu
    1025                 1030                 1035

Arg Ile  His Leu Ala Pro Ser  Gln Glu Ala Val Trp  Thr Thr Thr
    1040                 1045                 1050

Leu Thr  Arg Arg Asp Leu Ala  Asn Trp Asp Val Ser  Ala Gln Asp
    1055                 1060                 1065

Trp Thr  Val Thr Pro Tyr Pro  Lys Thr Ile Tyr Val  Gly Asn Ser
    1070                 1075                 1080

Ser Arg  Lys Leu Pro Leu Gln  Ala Ser Leu Pro Lys  Ala Gln
    1085                 1090                 1095


<210> SEQ ID NO 65
<211> LENGTH: 1846
<212> TYPE: DNA
<213> ORGANISM: Thielavia terrestris

<400> SEQUENCE: 65

aattgaagga gggagtggcg gagtggccac caagtcaggc ggctgtcaac taaccaagga      60
```

-continued

```
tgggaacagt tcggctcgcc ttgcccgagg gcagcgttcc ctgatgggga cgaaccatgg    120

gactggggtc agctgctgta taaaagttca aatcgatgat ctctcagatg gcgctgctgg    180

ggtgttctgc gcttttccat cctcgcaacc tggtatccca ctagtccagc gttcggcacc    240

atgaagtcgt tcaccattgc cgccttggca gccctatggg cccaggaggc cgccgcccac    300

gcgaccttcc aggacctctg gattgatgga gtcgactacg gctcgcaatg tgtccgcctc    360

ccggcgtcca actcccccgt caccaatgtt gcgtccgacg atatccgatg caatgtcggc    420

acctcgaggc ccaccgtcaa gtgcccggtc aaggccggct ccacggtcac gatcgagatg    480

caccaggttc gcacgcctct ctgcgtaggc cccccagcta ctatatggca ctaacacgac    540

ctccagcaac ctggcgaccg gtcttgcgcc aacgaggcta tcggcggcga ccactacggc    600

cccgtaatgg tgtacatgtc caaggtcgat gacgcggtga cagccgacgg ttcatcgggc    660

tggttcaagg tgttccagga cagctgggcc aagaacccgt cgggttcgac gggcgacgac    720

gactactggg gcaccaagga cctcaactcg tgctgcggca agatgaacgt caagatcccc    780

gaagacatcg agccgggcga ctacctgctc cgcgccgagg ttatcgcgct gcacgtggcc    840

gccagctcgg gcggcgcgca gttctacatg tcctgctacc agctgaccgt gacgggctcc    900

ggcagcgcca ccccctcgac cgtgaatttc ccgggcgcct actcggccag cgacccgggc    960

atcctgatca acatccacgc gcccatgtcg acctacgtcg tcccgggccc gaccgtgtac   1020

gcgggcggct cgaccaagtc ggctggcagc tcctgctccg gctgcgaggc gacctgcacg   1080

gttggttccg gccccagcgc gacactgacg cagcccacct ccaccgcgac cgcgacctcc   1140

gcccctggcg gcggcggctc cggctgcacg gcggccaagt accagcagtg cggcggcacc   1200

ggctacactg ggtgcaccac ctgcgctgta agttccctcg tgatatgcag cggaacaccg   1260

tctggactgt tttgctaact cgcgtcgtag tccgggtcta cctgcagcgc cgtctcgcct   1320

ccgtactact cgcagtgcct ctaagccggg agcgcttgct cagcgggctg ctgtgaagga   1380

gctccatgtc cccatgccgc catggccgga gtaccgggct gagcgcccaa ttcttgtata   1440

tagttgagtt ttcccaatca tgaatacata tgcatctgca tggactgttg cgtcgtcagt   1500

ctacatcctt tgctccactg aactgtgaga ccccatgtca tccggaccat tcgatcggtg   1560

ctcgctctac catctcggtt gatgggtctg ggcttgagag tcactggcac gtcctcggcg   1620

gtaatgaaat gtggaggaaa gtgtgagctg tctgacgcac tcggcgctga tgagacgttg   1680

agcgcggccc acactggtgt tctgtaagcc agcacacaaa agaatactcc aggatggccc   1740

atagcggcaa atatacagta tcagggatgc aaaaagtgca aaagtaaggg gctcaatcgg   1800

ggatcgaacc cgagacctcg cacatgactt atttcaagtc aggggt                  1846
```

<210> SEQ ID NO 66
<211> LENGTH: 326
<212> TYPE: PRT
<213> ORGANISM: Thielavia terrestris

<400> SEQUENCE: 66

```
Met Lys Ser Phe Thr Ile Ala Ala Leu Ala Ala Leu Trp Ala Gln Glu
1               5                   10                  15

Ala Ala Ala His Ala Thr Phe Gln Asp Leu Trp Ile Asp Gly Val Asp
            20                  25                  30

Tyr Gly Ser Gln Cys Val Arg Leu Pro Ala Ser Asn Ser Pro Val Thr
        35                  40                  45

Asn Val Ala Ser Asp Asp Ile Arg Cys Asn Val Gly Thr Ser Arg Pro
    50                  55                  60
```

```
Thr Val Lys Cys Pro Val Lys Ala Gly Ser Thr Val Thr Ile Glu Met
65                  70                  75                  80

His Gln Gln Pro Gly Asp Arg Ser Cys Ala Asn Glu Ala Ile Gly Gly
                85                  90                  95

Asp His Tyr Gly Pro Val Met Val Tyr Met Ser Lys Val Asp Asp Ala
            100                 105                 110

Val Thr Ala Asp Gly Ser Ser Gly Trp Phe Lys Val Phe Gln Asp Ser
        115                 120                 125

Trp Ala Lys Asn Pro Ser Gly Ser Thr Gly Asp Asp Asp Tyr Trp Gly
    130                 135                 140

Thr Lys Asp Leu Asn Ser Cys Cys Gly Lys Met Asn Val Lys Ile Pro
145                 150                 155                 160

Glu Asp Ile Glu Pro Gly Asp Tyr Leu Leu Arg Ala Glu Val Ile Ala
                165                 170                 175

Leu His Val Ala Ala Ser Ser Gly Gly Ala Gln Phe Tyr Met Ser Cys
            180                 185                 190

Tyr Gln Leu Thr Val Thr Gly Ser Gly Ser Ala Thr Pro Ser Thr Val
        195                 200                 205

Asn Phe Pro Gly Ala Tyr Ser Ala Ser Asp Pro Gly Ile Leu Ile Asn
    210                 215                 220

Ile His Ala Pro Met Ser Thr Tyr Val Val Pro Gly Pro Thr Val Tyr
225                 230                 235                 240

Ala Gly Gly Ser Thr Lys Ser Ala Gly Ser Ser Cys Ser Gly Cys Glu
                245                 250                 255

Ala Thr Cys Thr Val Gly Ser Gly Pro Ser Ala Thr Leu Thr Gln Pro
            260                 265                 270

Thr Ser Thr Ala Thr Ala Thr Ser Ala Pro Gly Gly Gly Gly Ser Gly
        275                 280                 285

Cys Thr Ala Ala Lys Tyr Gln Gln Cys Gly Gly Thr Gly Tyr Thr Gly
    290                 295                 300

Cys Thr Thr Cys Ala Ser Gly Ser Thr Cys Ser Ala Val Ser Pro Pro
305                 310                 315                 320

Tyr Tyr Ser Gln Cys Leu
                325
```

<210> SEQ ID NO 67
<211> LENGTH: 880
<212> TYPE: DNA
<213> ORGANISM: Thielavia terrestris

<400> SEQUENCE: 67

```
accccgggat cactgcccct aggaaccagc acacctcggt ccaatcatgc ggttcgacgc     60

cctctccgcc ctcgctcttg cgccgcttgt ggctggccac ggcgccgtga ccagctacat    120

catcggcggc aaaacctatc ccggctacga gggcttctcg cctgcctcga gcccgccgac    180

gatccagtac cagtggcccg actacaaccc gaccctgagc gtgaccgacc cgaagatgcg    240

ctgcaacggc ggcacctcgg cagagctcag cgcgcccgtc caggccggcg agaacgtgac    300

ggccgtctgg aagcagtgga cccaccagca aggccccgtc atggtctgga tgttcaagtg    360

ccccggcgac ttctcgtcgt gccacggcga cggcaagggc tggttcaaga tcgaccagct    420

gggcctgtgg ggcaacaacc tcaactcgaa caactggggc accgcgatcg tctacaagac    480

cctccagtgg agcaacccga tccccaagaa cctcgcgccg ggcaactacc tcatccgcca    540

cgagctgctc gccctgcacc aggccaacac gccgcagttc tacgccgagt gcgcccagct    600
```

```
ggtcgtctcc ggcagcggct ccgccctgcc cccgtccgac tacctctaca gcatccccgt    660

ctacgcgccc cagaacgacc ccggcatcac cgtgagtggg cttccgttcc gcggcgagct    720

ctgtggaaat cttgctgacg atgggctagg ttgacatcta caacggcggg cttacctcct    780

acaccccgcc cggcggcccc gtctggtctg gcttcgagtt ttaggcgcat tgagtcgggg    840

gctacgaggg gaaggcatct gttcgcatga gcgtgggtac                          880


<210> SEQ ID NO 68
<211> LENGTH: 239
<212> TYPE: PRT
<213> ORGANISM: Thielavia terrestris

<400> SEQUENCE: 68

Met Arg Phe Asp Ala Leu Ser Ala Leu Ala Leu Ala Pro Leu Val Ala
1               5                   10                  15

Gly His Gly Ala Val Thr Ser Tyr Ile Ile Gly Gly Lys Thr Tyr Pro
            20                  25                  30

Gly Tyr Glu Gly Phe Ser Pro Ala Ser Ser Pro Pro Thr Ile Gln Tyr
        35                  40                  45

Gln Trp Pro Asp Tyr Asn Pro Thr Leu Ser Val Thr Asp Pro Lys Met
    50                  55                  60

Arg Cys Asn Gly Gly Thr Ser Ala Glu Leu Ser Ala Pro Val Gln Ala
65                  70                  75                  80

Gly Glu Asn Val Thr Ala Val Trp Lys Gln Trp Thr His Gln Gln Gly
                85                  90                  95

Pro Val Met Val Trp Met Phe Lys Cys Pro Gly Asp Phe Ser Ser Ser
            100                 105                 110

His Gly Asp Gly Lys Gly Trp Phe Lys Ile Asp Gln Leu Gly Leu Trp
        115                 120                 125

Gly Asn Asn Leu Asn Ser Asn Asn Trp Gly Thr Ala Ile Val Tyr Lys
    130                 135                 140

Thr Leu Gln Trp Ser Asn Pro Ile Pro Lys Asn Leu Ala Pro Gly Asn
145                 150                 155                 160

Tyr Leu Ile Arg His Glu Leu Leu Ala Leu His Gln Ala Asn Thr Pro
                165                 170                 175

Gln Phe Tyr Ala Glu Cys Ala Gln Leu Val Val Ser Gly Ser Gly Ser
            180                 185                 190

Ala Leu Pro Pro Ser Asp Tyr Leu Tyr Ser Ile Pro Val Tyr Ala Pro
        195                 200                 205

Gln Asn Asp Pro Gly Ile Thr Val Asp Ile Tyr Asn Gly Gly Leu Thr
    210                 215                 220

Ser Tyr Thr Pro Pro Gly Gly Pro Val Trp Ser Gly Phe Glu Phe
225                 230                 235


<210> SEQ ID NO 69
<211> LENGTH: 1000
<212> TYPE: DNA
<213> ORGANISM: Thielavia terrestris

<400> SEQUENCE: 69

ctcctgttcc tgggccaccg cttgttgcct gcactattgg tagagttggt ctattgctag     60

agttggccat gcttctcaca tcagtcctcg gctcggctgc cctgcttgct agcggcgctg    120

cggcacacgg cgccgtgacc agctacatca tcgccggcaa gaattacccg gggtgggtag    180

ctgattattg agggcgcatt caaggttcat accggtgtgc atggctgaca accggctggc    240
```

```
agataccaag gcttttctcc tgcgaactcg ccgaacgtca tccaatggca atggcatgac    300

tacaaccccg tcttgtcgtg cagcgactcg aagcttcgct gcaacggcgg cacgtcggcc    360

accctgaacg ccacggccgc accgggcgac accatcaccg ccatctgggc gcagtggacg    420

cacagccagg gccccatcct ggtgtggatg tacaagtgcc cgggctcctt cagctcctgt    480

gacggctccg gcgctggctg gttcaagatc gacgaggccg gcttccacgg cgacggcgtc    540

aaggtcttcc tcgacaccga gaacccgtcc ggctgggaca tcgccaagct cgtcggcggc    600

aacaagcagt ggagcagcaa ggtccccgag ggcctcgccc ccggcaacta cctcgtccgc    660

cacgagttga tcgccctgca ccaggccaac aacccgcagt tctacccgga gtgcgcccag    720

gtcgtcatca ccggctccgg caccgcgcag ccggatgcct catacaaggc ggctatcccc    780

ggctactgca accagaatga cccgaacatc aaggtgagat ccaggcgtaa tgcagtctac    840

tgctggaaag aaagtggtcc aagctaaacc gcgctccagg tgcccatcaa cgaccactcc    900

atccctcaga cctacaagat tcccggccct cccgtcttca agggcaccgc cagcaagaag    960

gcccgggact tcaccgcctg aagttgttga atcgatggag                         1000


<210> SEQ ID NO 70
<211> LENGTH: 258
<212> TYPE: PRT
<213> ORGANISM: Thielavia terrestris

<400> SEQUENCE: 70

Met Leu Leu Thr Ser Val Leu Gly Ser Ala Ala Leu Leu Ala Ser Gly
1               5                   10                  15

Ala Ala Ala His Gly Ala Val Thr Ser Tyr Ile Ile Ala Gly Lys Asn
            20                  25                  30

Tyr Pro Gly Tyr Gln Gly Phe Ser Pro Ala Asn Ser Pro Asn Val Ile
        35                  40                  45

Gln Trp Gln Trp His Asp Tyr Asn Pro Val Leu Ser Cys Ser Asp Ser
    50                  55                  60

Lys Leu Arg Cys Asn Gly Gly Thr Ser Ala Thr Leu Asn Ala Thr Ala
65                  70                  75                  80

Ala Pro Gly Asp Thr Ile Thr Ala Ile Trp Ala Gln Trp Thr His Ser
                85                  90                  95

Gln Gly Pro Ile Leu Val Trp Met Tyr Lys Cys Pro Gly Ser Phe Ser
            100                 105                 110

Ser Cys Asp Gly Ser Gly Ala Gly Trp Phe Lys Ile Asp Glu Ala Gly
        115                 120                 125

Phe His Gly Asp Gly Val Lys Val Phe Leu Asp Thr Glu Asn Pro Ser
    130                 135                 140

Gly Trp Asp Ile Ala Lys Leu Val Gly Gly Asn Lys Gln Trp Ser Ser
145                 150                 155                 160

Lys Val Pro Glu Gly Leu Ala Pro Gly Asn Tyr Leu Val Arg His Glu
                165                 170                 175

Leu Ile Ala Leu His Gln Ala Asn Asn Pro Gln Phe Tyr Pro Glu Cys
            180                 185                 190

Ala Gln Val Val Ile Thr Gly Ser Gly Thr Ala Gln Pro Asp Ala Ser
        195                 200                 205

Tyr Lys Ala Ala Ile Pro Gly Tyr Cys Asn Gln Asn Asp Pro Asn Ile
    210                 215                 220

Lys Val Pro Ile Asn Asp His Ser Ile Pro Gln Thr Tyr Lys Ile Pro
225                 230                 235                 240
```

Gly Pro Pro Val Phe Lys Gly Thr Ala Ser Lys Lys Ala Arg Asp Phe
245 250 255

Thr Ala

<210> SEQ ID NO 71
<211> LENGTH: 681
<212> TYPE: DNA
<213> ORGANISM: Thielavia terrestris

<400> SEQUENCE: 71
atgctcgcaa acggtgccat cgtcttcctg gccgccgccc tcggcgtcag tggccactac 60
acctggccac gggttaacga cggcgccgac tggcaacagg tccgtaaggc ggacaactgg 120
caggacaacg gctacgtcgg ggatgtcacg tcgccacaga tccgctgttt ccaggcgacc 180
ccgtccccgg ccccatccgt cctcaacacc acggccggct cgaccgtgac ctactgggcc 240
aaccccgacg tctaccaccc cgggcctgtg cagttttaca tggcccgcgt gcccgatggc 300
gaggacatca actcgtggaa cggcgacggc gccgtgtggt tcaaggtgta cgaggaccat 360
cctacctttg gcgctcagct cacatggccc agcacgggca agagctcgtt cgcggttccc 420 atcccccgt gcatcaagtc cggctactac ctcctccggg cggagcaaat cggcctgcac 480
gtcgcccaga gcgtaggcgg agcgcagttc tacatctcat gcgcccagct cagcgtcacc 540
ggcggcggca gcaccgagcc gccgaacaag gtggccttcc ccggcgctta cagtgcgacg 600
gacccgggca ttctgatcaa catctactac cctgttccca cgtcctacca gaaccccggc 660
ccggccgtct tcagctgctg a 681

<210> SEQ ID NO 72
<211> LENGTH: 226
<212> TYPE: PRT
<213> ORGANISM: Thielavia terrestris

<400> SEQUENCE: 72

Met Leu Ala Asn Gly Ala Ile Val Phe Leu Ala Ala Ala Leu Gly Val
1 5 10 15

Ser Gly His Tyr Thr Trp Pro Arg Val Asn Asp Gly Ala Asp Trp Gln
20 25 30

Gln Val Arg Lys Ala Asp Asn Trp Gln Asp Asn Gly Tyr Val Gly Asp
35 40 45

Val Thr Ser Pro Gln Ile Arg Cys Phe Gln Ala Thr Pro Ser Pro Ala
50 55 60

Pro Ser Val Leu Asn Thr Thr Ala Gly Ser Thr Val Thr Tyr Trp Ala
65 70 75 80

Asn Pro Asp Val Tyr His Pro Gly Pro Val Gln Phe Tyr Met Ala Arg
85 90 95

Val Pro Asp Gly Glu Asp Ile Asn Ser Trp Asn Gly Asp Gly Ala Val
100 105 110

Trp Phe Lys Val Tyr Glu Asp His Pro Thr Phe Gly Ala Gln Leu Thr
115 120 125

Trp Pro Ser Thr Gly Lys Ser Ser Phe Ala Val Pro Ile Pro Pro Cys
130 135 140

Ile Lys Ser Gly Tyr Tyr Leu Leu Arg Ala Glu Gln Ile Gly Leu His
145 150 155 160

Val Ala Gln Ser Val Gly Gly Ala Gln Phe Tyr Ile Ser Cys Ala Gln
165 170 175

```
Leu Ser Val Thr Gly Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile
        195                 200                 205

Tyr Tyr Pro Val Pro Thr Ser Tyr Gln Asn Pro Gly Pro Ala Val Phe
    210                 215                 220

Ser Cys
225
```

```
<210> SEQ ID NO 73
<211> LENGTH: 960
<212> TYPE: DNA
<213> ORGANISM: Thielavia terrestris

<400> SEQUENCE: 73

atgaagggac ttttcagtgc cgccgccctc tccctggccg tcggccaggc ttcggcccat     60

tacatcttcc agcaactctc catcaacggg aaccagtttc cggtgtacca atatattcgc    120

aagaacacca attataacag tcccgttacc gatctcacgt ccgacgatct tcggtgcaat    180

gtcggcgccc agggtgctgg gacagacacc gtcacggtga aggccggcga ccagttcacc    240

ttcacccttg acacccctgt ttaccaccag gggcccatct ccatctacat gtccaaggcc    300

ccgggcgcgg cgtcagacta cgatggcagc ggcggctggt tcaagatcaa ggactggggc    360

ccgactttca acgccgacgg cacggccacc tgggacatgg ccggctcata cacctacaac    420

atcccgacct gcattcccga cggcgactat ctgctccgca tccagtcgct ggccatccac    480

aacccctggc cggcgggcat cccgcagttc tacatctcct gcgcccagat caccgtgacc    540

ggcggcggca acggcaaccc tggcccgacg gccctcatcc ccggcgcctt caaggacacc    600

gacccgggct acacggtgaa catctacacg aacttccaca actacacggt tcccggcccg    660

gaggtcttca gctgcaacgg cggcggctcg aacccgcccc cgccggtgag tagcagcacg    720

cccgcgacca cgacgctggt cacgtcgacg cgcaccacgt cctccacgtc ctccgcctcg    780

acgccggcct cgaccggcgg ctgcaccgtc gccaagtggg gccagtgcgg cggcaacggg    840

tacaccggct gcacgacctg cgcggccggg tccacctgca gcaagcagaa cgactactac    900

tcgcagtgct tgtaagggag gccgcaaagc atgaggtgtt tgaagaggag gagaggggtc    960
```

```
<210> SEQ ID NO 74
<211> LENGTH: 304
<212> TYPE: PRT
<213> ORGANISM: Thielavia terrestris

<400> SEQUENCE: 74

Met Lys Gly Leu Phe Ser Ala Ala Ala Leu Ser Leu Ala Val Gly Gln
1               5                   10                  15

Ala Ser Ala His Tyr Ile Phe Gln Gln Leu Ser Ile Asn Gly Asn Gln
            20                  25                  30

Phe Pro Val Tyr Gln Tyr Ile Arg Lys Asn Thr Asn Tyr Asn Ser Pro
        35                  40                  45

Val Thr Asp Leu Thr Ser Asp Asp Leu Arg Cys Asn Val Gly Ala Gln
    50                  55                  60

Gly Ala Gly Thr Asp Thr Val Thr Val Lys Ala Gly Asp Gln Phe Thr
65                  70                  75                  80

Phe Thr Leu Asp Thr Pro Val Tyr His Gln Gly Pro Ile Ser Ile Tyr
                85                  90                  95

Met Ser Lys Ala Pro Gly Ala Ala Ser Asp Tyr Asp Gly Ser Gly Gly
```

```
            100                 105                 110

Trp Phe Lys Ile Lys Asp Trp Gly Pro Thr Phe Asn Ala Asp Gly Thr
        115                 120                 125

Ala Thr Trp Asp Met Ala Gly Ser Tyr Thr Tyr Asn Ile Pro Thr Cys
    130                 135                 140

Ile Pro Asp Gly Asp Tyr Leu Leu Arg Ile Gln Ser Leu Ala Ile His
145                 150                 155                 160

Asn Pro Trp Pro Ala Gly Ile Pro Gln Phe Tyr Ile Ser Cys Ala Gln
                165                 170                 175

Ile Thr Val Thr Gly Gly Gly Asn Gly Asn Pro Gly Pro Thr Ala Leu
            180                 185                 190

Ile Pro Gly Ala Phe Lys Asp Thr Asp Pro Gly Tyr Thr Val Asn Ile
        195                 200                 205

Tyr Thr Asn Phe His Asn Tyr Thr Val Pro Gly Pro Glu Val Phe Ser
    210                 215                 220

Cys Asn Gly Gly Gly Ser Asn Pro Pro Pro Pro Val Ser Ser Ser Thr
225                 230                 235                 240

Pro Ala Thr Thr Thr Leu Val Thr Ser Thr Arg Thr Thr Ser Ser Thr
                245                 250                 255

Ser Ser Ala Ser Thr Pro Ala Ser Thr Gly Gly Cys Thr Val Ala Lys
            260                 265                 270

Trp Gly Gln Cys Gly Gly Asn Gly Tyr Thr Gly Cys Thr Thr Cys Ala
        275                 280                 285

Ala Gly Ser Thr Cys Ser Lys Gln Asn Asp Tyr Tyr Ser Gln Cys Leu
    290                 295                 300


<210> SEQ ID NO 75
<211> LENGTH: 954
<212> TYPE: DNA
<213> ORGANISM: Thielavia terrestris

<400> SEQUENCE: 75

atgaagggcc tcagcctcct cgccgctgcg tcggcagcga ctgctcatac catcttcgtg      60

cagctcgagt caggggggaac gacctatccg gtatcctacg gcatccggga ccctagctac     120

gacggtccca tcaccgacgt cacctccgac tcactggctt gcaatggtcc cccgaacccc     180

acgacgccgt ccccgtacat catcaacgtc accgccggca ccacggtcgc ggcgatctgg     240

aggcacaccc tcacatccgg ccccgacgat gtcatggacg ccagccacaa ggggccgacc     300

ctggcctacc tcaagaaggt cgatgatgcc ttgaccgaca cgggtatcgg cggcggctgg     360

ttcaagatcc aggaggccgg ttacgacaat ggcaattggg ctaccagcac ggtgatcacc     420

aacggtggct tccaatatat tgacatcccc gcctgcattc ccaacggcca gtatctgctc     480

cgcgccgaga tgatcgcgct ccacgccgcc agcacgcagg gtggtgccca gctctacatg     540

gagtgcgcgc agatcaacgt ggtgggcggc tccggcagcg ccagcccgca gacgtacagc     600

atcccgggca tctaccaggc aaccgacccg ggcctgctga tcaacatcta ctccatgacg     660

ccgtccagcc agtacaccat tccgggtccg cccctgttca cctgcagcgg cagcggcaac     720

aacggcggcg gcagcaaccc gtcgggcggg cagaccacga cggcgaagcc cacgacgacg     780

acggcggcga cgaccacctc ctccgccgct cctaccagca gccagggggg cagcagcggt     840

tgcaccgttc cccagtggca gcagtgcggt ggcatctcgt tcaccggctg caccacctgc     900

gcggcgggct acacctgcaa gtatctgaac gactattact cgcaatgcca gtaa           954
```

<210> SEQ ID NO 76
<211> LENGTH: 317
<212> TYPE: PRT
<213> ORGANISM: Thielavia terrestris

<400> SEQUENCE: 76

```
Met Lys Gly Leu Ser Leu Leu Ala Ala Ala Ser Ala Ala Thr Ala His
1               5                   10                  15

Thr Ile Phe Val Gln Leu Glu Ser Gly Gly Thr Thr Tyr Pro Val Ser
            20                  25                  30

Tyr Gly Ile Arg Asp Pro Ser Tyr Asp Gly Pro Ile Thr Asp Val Thr
        35                  40                  45

Ser Asp Ser Leu Ala Cys Asn Gly Pro Pro Asn Pro Thr Thr Pro Ser
    50                  55                  60

Pro Tyr Ile Ile Asn Val Thr Ala Gly Thr Thr Val Ala Ala Ile Trp
65                  70                  75                  80

Arg His Thr Leu Thr Ser Gly Pro Asp Asp Val Met Asp Ala Ser His
                85                  90                  95

Lys Gly Pro Thr Leu Ala Tyr Leu Lys Lys Val Asp Asp Ala Leu Thr
            100                 105                 110

Asp Thr Gly Ile Gly Gly Gly Trp Phe Lys Ile Gln Glu Ala Gly Tyr
        115                 120                 125

Asp Asn Gly Asn Trp Ala Thr Ser Thr Val Ile Thr Asn Gly Gly Phe
    130                 135                 140

Gln Tyr Ile Asp Ile Pro Ala Cys Ile Pro Asn Gly Gln Tyr Leu Leu
145                 150                 155                 160

Arg Ala Glu Met Ile Ala Leu His Ala Ala Ser Thr Gln Gly Gly Ala
                165                 170                 175

Gln Leu Tyr Met Glu Cys Ala Gln Ile Asn Val Val Gly Gly Ser Gly
            180                 185                 190

Ser Ala Ser Pro Gln Thr Tyr Ser Ile Pro Gly Ile Tyr Gln Ala Thr
        195                 200                 205

Asp Pro Gly Leu Leu Ile Asn Ile Tyr Ser Met Thr Pro Ser Ser Gln
    210                 215                 220

Tyr Thr Ile Pro Gly Pro Pro Leu Phe Thr Cys Ser Gly Ser Gly Asn
225                 230                 235                 240

Asn Gly Gly Gly Ser Asn Pro Ser Gly Gly Gln Thr Thr Thr Ala Lys
                245                 250                 255

Pro Thr Thr Thr Thr Ala Ala Thr Thr Thr Ser Ser Ala Ala Pro Thr
            260                 265                 270

Ser Ser Gln Gly Gly Ser Ser Gly Cys Thr Val Pro Gln Trp Gln Gln
        275                 280                 285

Cys Gly Gly Ile Ser Phe Thr Gly Cys Thr Thr Cys Ala Ala Gly Tyr
    290                 295                 300

Thr Cys Lys Tyr Leu Asn Asp Tyr Tyr Ser Gln Cys Gln
305                 310                 315
```

<210> SEQ ID NO 77
<211> LENGTH: 799
<212> TYPE: DNA
<213> ORGANISM: Thermoascus aurantiacus

<400> SEQUENCE: 77

```
atgtcctttt ccaagataat tgctactgcc ggcgttcttg cctctgcttc tctagtggct      60

ggccatggct tcgttcagaa catcgtgatt gatggtaaaa agtatgtcat tgcaagacgc     120
```

```
acataagcgg caacagctga caatcgacag ttatggcggg tatctagtga accagtatcc    180

atacatgtcc aatcctccag aggtcatcgc ctggtctact acggcaactg atcttggatt    240

tgtggacggt actggatacc aaaccccaga tatcatctgc catagggggcg ccaagcctgg    300

agccctgact gctccagtct ctccaggagg aactgttgag cttcaatgga ctccatggcc    360

tgattctcac catggcccag ttatcaacta ccttgctccg tgcaatggtg attgttccac    420

tgtggataag acccaattag aattcttcaa aattgccgag agcggtctca tcaatgatga    480

caatcctcct gggatctggg cttcagacaa tctgatagca gccaacaaca gctggactgt    540

caccattcca accacaattg cacctggaaa ctatgttctg aggcatgaga ttattgctct    600

tcactcagct cagaaccagg atggtgccca gaactatccc cagtgcatca atctgcaggt    660

cactggaggt ggttctgata accctgctgg aactcttgga acggcactct accacgatac    720

cgatcctgga attctgatca acatctatca gaaactttcc agctatatca tccctggtcc    780

tcctctgtat actggttaa                                                 799
```

```
<210> SEQ ID NO 78
<211> LENGTH: 249
<212> TYPE: PRT
<213> ORGANISM: Thermoascus aurantiacus

<400> SEQUENCE: 78

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
            20                  25                  30

Lys Tyr Tyr Gly Gly Tyr Leu Val Asn Gln Tyr Pro Tyr Met Ser Asn
        35                  40                  45

Pro Pro Glu Val Ile Ala Trp Ser Thr Thr Ala Thr Asp Leu Gly Phe
    50                  55                  60

Val Asp Gly Thr Gly Tyr Gln Thr Pro Asp Ile Ile Cys His Arg Gly
65                  70                  75                  80

Ala Lys Pro Gly Ala Leu Thr Ala Pro Val Ser Pro Gly Gly Thr Val
                85                  90                  95

Glu Leu Gln Trp Thr Pro Trp Pro Asp Ser His His Gly Pro Val Ile
            100                 105                 110

Asn Tyr Leu Ala Pro Cys Asn Gly Asp Cys Ser Thr Val Asp Lys Thr
        115                 120                 125

Gln Leu Glu Phe Phe Lys Ile Ala Glu Ser Gly Leu Ile Asn Asp Asp
    130                 135                 140

Asn Pro Pro Gly Ile Trp Ala Ser Asp Asn Leu Ile Ala Ala Asn Asn
145                 150                 155                 160

Ser Trp Thr Val Thr Ile Pro Thr Thr Ile Ala Pro Gly Asn Tyr Val
                165                 170                 175

Leu Arg His Glu Ile Ile Ala Leu His Ser Ala Gln Asn Gln Asp Gly
            180                 185                 190

Ala Gln Asn Tyr Pro Gln Cys Ile Asn Leu Gln Val Thr Gly Gly Gly
        195                 200                 205

Ser Asp Asn Pro Ala Gly Thr Leu Gly Thr Ala Leu Tyr His Asp Thr
    210                 215                 220

Asp Pro Gly Ile Leu Ile Asn Ile Tyr Gln Lys Leu Ser Ser Tyr Ile
225                 230                 235                 240

Ile Pro Gly Pro Pro Leu Tyr Thr Gly
                245
```

<210> SEQ ID NO 79
<211> LENGTH: 1172
<212> TYPE: DNA
<213> ORGANISM: Trichoderma reesei

<400> SEQUENCE: 79

```
ggatctaagc cccatcgata tgaagtcctg cgccattctt gcagcccttg gctgtcttgc      60

cgggagcgtt ctcggccatg gacaagtcca aaacttcacg atcaatggac aatacaatca     120

gggtttcatt ctcgattact actatcagaa gcagaatact ggtcacttcc ccaacgttgc     180

tggctggtac gccgaggacc tagacctggg cttcatctcc cctgaccaat acaccacgcc     240

cgacattgtc tgtcacaaga acgcggcccc aggtgccatt tctgccactg cagcggccgg     300

cagcaacatc gtcttccaat ggggccctgg cgtctggcct caccccctacg gtcccatcgt     360

tacctacgtg gctgagtgca gcggatcgtg cacgaccgtg aacaagaaca acctgcgctg     420

ggtcaagatt caggaggccg gcatcaacta taacacccaa gtctgggcgc agcaggatct     480

gatcaaccag ggcaacaagt ggactgtgaa gatcccgtcg agcctcaggc ccggaaacta     540

tgtcttccgc catgaacttc ttgctgccca tggtgcctct agtgcgaacg gcatgcagaa     600

ctatcctcag tgcgtgaaca tcgccgtcac aggctcgggc acgaaagcgc tccctgccgg     660

aactcctgca actcagctct acaagcccac tgaccctggc atcttgttca acccttacac     720

aacaatcacg agctacacca tccctggccc agccctgtgg caaggctaga tccaggggta     780

cggtgttggc gttcgtgaag tcggagctgt tgacaaggat atctgatgat gaacggagag     840

gactgatggg cgtgactgag tgtatatatt tttgatgacc aaattgtata cgaaatccga     900

acgcatggtg atcattgttt atccctgtag tatattgtct ccaggctgct aagagcccac     960

cgggtgtatt acggcaacaa agtcaggaat ttgggtggca atgaacgcag gtctccatga    1020

atgtatatgt gaagaggcat cggctggcat gggcattacc agatataggc cctgtgaaac    1080

atatagtact tgaacgtgct actggaacgg atcataagca agtcatcaac atgtgaaaaa    1140

acactacatg taaaaaaaaa aaaaaaaaaa aa                                  1172
```

<210> SEQ ID NO 80
<211> LENGTH: 249
<212> TYPE: PRT
<213> ORGANISM: Trichoderma reesei

<400> SEQUENCE: 80

```
Met Lys Ser Cys Ala Ile Leu Ala Ala Leu Gly Cys Leu Ala Gly Ser
1               5                   10                  15

Val Leu Gly His Gly Gln Val Gln Asn Phe Thr Ile Asn Gly Gln Tyr
            20                  25                  30

Asn Gln Gly Phe Ile Leu Asp Tyr Tyr Tyr Gln Lys Gln Asn Thr Gly
        35                  40                  45

His Phe Pro Asn Val Ala Gly Trp Tyr Ala Glu Asp Leu Asp Leu Gly
    50                  55                  60

Phe Ile Ser Pro Asp Gln Tyr Thr Thr Pro Asp Ile Val Cys His Lys
65                  70                  75                  80

Asn Ala Ala Pro Gly Ala Ile Ser Ala Thr Ala Ala Ala Gly Ser Asn
                85                  90                  95

Ile Val Phe Gln Trp Gly Pro Gly Val Trp Pro His Pro Tyr Gly Pro
            100                 105                 110

Ile Val Thr Tyr Val Val Glu Cys Ser Gly Ser Cys Thr Thr Val Asn
```

```
        115                 120                 125

Lys Asn Asn Leu Arg Trp Val Lys Ile Gln Glu Ala Gly Ile Asn Tyr
    130                 135                 140

Asn Thr Gln Val Trp Ala Gln Gln Asp Leu Ile Asn Gln Gly Asn Lys
145                 150                 155                 160

Trp Thr Val Lys Ile Pro Ser Ser Leu Arg Pro Gly Asn Tyr Val Phe
                165                 170                 175

Arg His Glu Leu Leu Ala Ala His Gly Ala Ser Ser Ala Asn Gly Met
            180                 185                 190

Gln Asn Tyr Pro Gln Cys Val Asn Ile Ala Val Thr Gly Ser Gly Thr
        195                 200                 205

Lys Ala Leu Pro Ala Gly Thr Pro Ala Thr Gln Leu Tyr Lys Pro Thr
    210                 215                 220

Asp Pro Gly Ile Leu Phe Asn Pro Tyr Thr Thr Ile Thr Ser Tyr Thr
225                 230                 235                 240

Ile Pro Gly Pro Ala Leu Trp Gln Gly
                245
```

<210> SEQ ID NO 81
<211> LENGTH: 924
<212> TYPE: DNA
<213> ORGANISM: Myceliophthora thermophila

<400> SEQUENCE: 81

```
atgaagttca cctcgtccct cgctgtcctg gccgctgccg gcgcccaggc tcactgttag     60

tcgaccctcg aacccaacac ccccctcccc cctttctcc tccatctcct cggcctcact    120

tagtagccgc tgacaacgac tagatacctt ccctagggcc ggcactggtg gctcgctctc    180

tggcgagtgg gaggtggtcc gcatgaccga gaaccattac tcgcacggcc cggtcaccga    240

tgtcaccagc cccgagatga cctgctatca gtccggcgtg cagggtgcgc cccagaccgt    300

ccaggtcaag gcgggctccc aattcacctt cagcgtggat ccctcgatcg gccaccccgg    360

ccctctccag ttctacatgg ctaaggtgcc gtcgggccag acggccgcca cctttgacgg    420

cacgggagcc gtgtggttca agatctacca agacggcccg aacggcctcg gcaccgacag    480

cattacctgg cccagcgccg gttcgtgact tcctccccac tcgctttttt tttttattt    540

tttatttttt tttctttcgg aactcaagaa tctttctctc tctctcccgt ctttggcctt    600

gaacaacact aaaactcttc cttactgtat taattaggca aaaccgaggt ctcggtcacc    660

atccccagct gcatcgatga tggcgagtac ctgctccggg tcgagcacat cgcgctccac    720

agcgccagca gcgtgggcgg cgctcagttc tacattgcct gcgcccagct ctccgtcacc    780

ggcggctccg gcaccctcaa cacgggctcg ctcgtctccc tgcccggcgc ctacaaggcc    840

accgacccgg gcatcctctt ccagctctac tggcccatcc cgaccgagta catcaacccc    900

ggcccggccc ccgtctcttg ctaa                                          924
```

<210> SEQ ID NO 82
<211> LENGTH: 232
<212> TYPE: PRT
<213> ORGANISM: Myceliophthora thermophila

<400> SEQUENCE: 82

```
Met Lys Phe Thr Ser Ser Leu Ala Val Leu Ala Ala Ala Gly Ala Gln
1               5                   10                  15

Ala His Tyr Thr Phe Pro Arg Ala Gly Thr Gly Gly Ser Leu Ser Gly
            20                  25                  30
```

```
Glu Trp Glu Val Val Arg Met Thr Glu Asn His Tyr Ser His Gly Pro
        35                  40                  45

Val Thr Asp Val Thr Ser Pro Glu Met Thr Cys Tyr Gln Ser Gly Val
    50                  55                  60

Gln Gly Ala Pro Gln Thr Val Gln Val Lys Ala Gly Ser Gln Phe Thr
65                  70                  75                  80

Phe Ser Val Asp Pro Ser Ile Gly His Pro Gly Pro Leu Gln Phe Tyr
                85                  90                  95

Met Ala Lys Val Pro Ser Gly Gln Thr Ala Ala Thr Phe Asp Gly Thr
            100                 105                 110

Gly Ala Val Trp Phe Lys Ile Tyr Gln Asp Gly Pro Asn Gly Leu Gly
        115                 120                 125

Thr Asp Ser Ile Thr Trp Pro Ser Ala Gly Lys Thr Glu Val Ser Val
    130                 135                 140

Thr Ile Pro Ser Cys Ile Asp Asp Gly Glu Tyr Leu Leu Arg Val Glu
145                 150                 155                 160

His Ile Ala Leu His Ser Ala Ser Ser Val Gly Gly Ala Gln Phe Tyr
                165                 170                 175

Ile Ala Cys Ala Gln Leu Ser Val Thr Gly Gly Ser Gly Thr Leu Asn
            180                 185                 190

Thr Gly Ser Leu Val Ser Leu Pro Gly Ala Tyr Lys Ala Thr Asp Pro
        195                 200                 205

Gly Ile Leu Phe Gln Leu Tyr Trp Pro Ile Pro Thr Glu Tyr Ile Asn
    210                 215                 220

Pro Gly Pro Ala Pro Val Ser Cys
225                 230

<210> SEQ ID NO 83
<211> LENGTH: 854
<212> TYPE: DNA
<213> ORGANISM: Myceliophthora thermophila

<400> SEQUENCE: 83

atgaaggccc tctctctcct tgcggctgcc tcggcagtct ctgcgcatac catcttcgtc      60

cagctcgaag cagacggcac gaggtacccg gtctcgtacg ggatccggga cccaagctac     120

gacggcccca tcaccgacgt cacatccaac gacgttgctt gcaacggcgg gccgaacccg     180

acgacccccct ccagcgacgt catcaccgtc accgcgggca ccacggtcaa ggccatctgg     240

aggcacaccc tccaatccgg cccggacgat gtcatggacg ccagccacaa gggcccgacc     300

ctggcctacc tcaagaaggt cggcgatgcc accaaggact cgggcgtcgg cggtggctgg     360

ttcaagattc aggaggacgg ctacaacaac ggccagtggg gcaccagcac cgttatctcc     420

aacggcggcg agcactacat gtgagccatt cctccgagag aagaccaaga ctcttgacga     480

tctcgctgac ccgtgcaaca agtgacatcc cggcctgcat ccccgagggt cagtacctcc     540

tccgcgccga gatgatcgcc ctccacgcgg ccgggtcccc cggcggtgcc cagctctacg     600

taagcctctg cccttccccc cttcctcttg atcgaatcgg actgcccacc cccctttttcg     660

actccgacta acaccgttgc cagatggaat gtgcccagat caacatcgtc ggcggctccg     720

gctcggtgcc cagctcgacc gtcagcttcc ccggcgcgta cagccccaac gacccgggtc     780

tcctcatcaa catctattcc atgtcgccct cgagctcgta caccatcccg ggcccgcccg     840

tcttcaagtg ctag                                                        854
```

<210> SEQ ID NO 84
<211> LENGTH: 235
<212> TYPE: PRT
<213> ORGANISM: Myceliophthora thermophila

<400> SEQUENCE: 84

```
Met Lys Ala Leu Ser Leu Leu Ala Ala Ala Ser Ala Val Ser Ala His
1               5                   10                  15

Thr Ile Phe Val Gln Leu Glu Ala Asp Gly Thr Arg Tyr Pro Val Ser
            20                  25                  30

Tyr Gly Ile Arg Asp Pro Ser Tyr Asp Gly Pro Ile Thr Asp Val Thr
        35                  40                  45

Ser Asn Asp Val Ala Cys Asn Gly Gly Pro Asn Pro Thr Thr Pro Ser
    50                  55                  60

Ser Asp Val Ile Thr Val Thr Ala Gly Thr Thr Val Lys Ala Ile Trp
65                  70                  75                  80

Arg His Thr Leu Gln Ser Gly Pro Asp Asp Val Met Asp Ala Ser His
                85                  90                  95

Lys Gly Pro Thr Leu Ala Tyr Leu Lys Lys Val Gly Asp Ala Thr Lys
            100                 105                 110

Asp Ser Gly Val Gly Gly Gly Trp Phe Lys Ile Gln Glu Asp Gly Tyr
        115                 120                 125

Asn Asn Gly Gln Trp Gly Thr Ser Thr Val Ile Ser Asn Gly Gly Glu
    130                 135                 140

His Tyr Ile Asp Ile Pro Ala Cys Ile Pro Glu Gly Gln Tyr Leu Leu
145                 150                 155                 160

Arg Ala Glu Met Ile Ala Leu His Ala Ala Gly Ser Pro Gly Gly Ala
                165                 170                 175

Gln Leu Tyr Met Glu Cys Ala Gln Ile Asn Ile Val Gly Gly Ser Gly
            180                 185                 190

Ser Val Pro Ser Ser Thr Val Ser Phe Pro Gly Ala Tyr Ser Pro Asn
        195                 200                 205

Asp Pro Gly Leu Leu Ile Asn Ile Tyr Ser Met Ser Pro Ser Ser Ser
    210                 215                 220

Tyr Thr Ile Pro Gly Pro Pro Val Phe Lys Cys
225                 230                 235
```

<210> SEQ ID NO 85
<211> LENGTH: 1242
<212> TYPE: DNA
<213> ORGANISM: Myceliophthora thermophila

<400> SEQUENCE: 85

```
atgaagtcct tcgccctcac cactctggcc gccctggccg gcaacgccgc cgctcacgcg      60

accttccagg ccctctgggt cgacggcgtc gactacggcg cgcagtgtgc ccgtctgccc     120

gcgtccaact ccccggtcac cgacgtgacc tccaacgcga tccgctgcaa cgccaacccg     180

tcgcccgctc ggggcaagtg cccggtcaag gccggctcga ccgttacggt cgagatgcat     240

caggtacgtt ggatgaatga aaggggaaag gaagcagagg cagaagggga aggcgaaggg     300

aaagaaaaag aaaaagaaat ggaaaagaaa aagaaatgga aaagaaaaag aaaaatgaaa     360

aagaaagtgg aaaccgtcag actaactggg gctcctcccc cccacccctc ctttgatatc     420

agcaacccgg tgaccggtcg tgcagcagcg aggcgatcgg cggggcgcac tacggccccg     480

tcatggtgta catgtccaag gtgtcggacg cggcgtcggc ggacgggtcg tcgggctggt     540

tcaaggtgtt cgaggacggc tggggccaaga acccgtccgg cgggtcgggc gacgacgact     600
```

```
actggggcac caaggacctg aactcgtgct gcgggaagat gaacgtcaag atccccgccg    660

acctgccctc gggcgactac ctgctccggg ccgaggccct cgcgctgcac acggcgggca    720

gcgccggcgg cgcccagttc tacatgacgt gctaccagct caccgtgacg ggctccggca    780

gcgccagccc gcccaccgtc tccttcccgg gcgcctacaa ggccaccgac ccgggcatcc    840

tcgtcaacat ccacgccccg ctgtccggct acaccgtgcc cggcccggcc gtctactccg    900

gcggctccac caagaaggcc ggcagcgcct gcaccggctg cgagtccacc tgcgccgtcg    960

gctccggccc caccgccacc gtctcccagt cgcccggttc caccgccacc tccgcccccg   1020

gcggcggcgg cggctgcacc gtccagaagt accagcagtg cggcggcgag ggctacaccg   1080

gctgcaccaa ctgcgcggta cgtttttcaa ccccgttttt ttttttcctt ccctacctta   1140

tttggttacc taattaatta ctttccggct gctgactttt tgctttagtc cggctctacc   1200

tgcagcgccg tctcgccgcc ctactactcg cagtgcgtct aa                      1242
```

<210> SEQ ID NO 86
<211> LENGTH: 323
<212> TYPE: PRT
<213> ORGANISM: Myceliophthora thermophila

<400> SEQUENCE: 86

```
Met Lys Ser Phe Ala Leu Thr Thr Leu Ala Ala Leu Ala Gly Asn Ala
1               5                   10                  15

Ala Ala His Ala Thr Phe Gln Ala Leu Trp Val Asp Gly Val Asp Tyr
            20                  25                  30

Gly Ala Gln Cys Ala Arg Leu Pro Ala Ser Asn Ser Pro Val Thr Asp
        35                  40                  45

Val Thr Ser Asn Ala Ile Arg Cys Asn Ala Asn Pro Ser Pro Ala Arg
    50                  55                  60

Gly Lys Cys Pro Val Lys Ala Gly Ser Thr Val Thr Val Glu Met His
65                  70                  75                  80

Gln Gln Pro Gly Asp Arg Ser Cys Ser Ser Glu Ala Ile Gly Gly Ala
                85                  90                  95

His Tyr Gly Pro Val Met Val Tyr Met Ser Lys Val Ser Asp Ala Ala
            100                 105                 110

Ser Ala Asp Gly Ser Ser Gly Trp Phe Lys Val Phe Glu Asp Gly Trp
        115                 120                 125

Ala Lys Asn Pro Ser Gly Gly Ser Gly Asp Asp Asp Tyr Trp Gly Thr
    130                 135                 140

Lys Asp Leu Asn Ser Cys Cys Gly Lys Met Asn Val Lys Ile Pro Ala
145                 150                 155                 160

Asp Leu Pro Ser Gly Asp Tyr Leu Leu Arg Ala Glu Ala Leu Ala Leu
                165                 170                 175

His Thr Ala Gly Ser Ala Gly Gly Ala Gln Phe Tyr Met Thr Cys Tyr
            180                 185                 190

Gln Leu Thr Val Thr Gly Ser Gly Ser Ala Ser Pro Pro Thr Val Ser
        195                 200                 205

Phe Pro Gly Ala Tyr Lys Ala Thr Asp Pro Gly Ile Leu Val Asn Ile
    210                 215                 220

His Ala Pro Leu Ser Gly Tyr Thr Val Pro Gly Pro Ala Val Tyr Ser
225                 230                 235                 240

Gly Gly Ser Thr Lys Lys Ala Gly Ser Ala Cys Thr Gly Cys Glu Ser
                245                 250                 255
```

```
Thr Cys Ala Val Gly Ser Gly Pro Thr Ala Thr Val Ser Gln Ser Pro
            260                 265                 270

Gly Ser Thr Ala Thr Ser Ala Pro Gly Gly Gly Gly Gly Cys Thr Val
        275                 280                 285

Gln Lys Tyr Gln Gln Cys Gly Gly Glu Gly Tyr Thr Gly Cys Thr Asn
    290                 295                 300

Cys Ala Ser Gly Ser Thr Cys Ser Ala Val Ser Pro Pro Tyr Tyr Ser
305                 310                 315                 320

Gln Cys Val


<210> SEQ ID NO 87
<211> LENGTH: 1253
<212> TYPE: DNA
<213> ORGANISM: Myceliophthora thermophila

<400> SEQUENCE: 87

atgaagcctt ttagcctcgt cgccctggcg accgccgtga gcggccatgc catcttccag      60

cgggtgtcgg tcaacgggca ggaccagggc cagctcaagg gggtgcgggc gccgtcgagc     120

aactccccga tccagaacgt caacgatgcc aacatggcct gcaacgccaa cattgtgtac     180

cacgacagca ccatcatcaa ggtgcccgcg ggagcccgcg tcggcgcgtg gtggcagcac     240

gtcatcggcg ggccgcaggg cgccaacgac ccggacaacc cgatcgcggc ctcccacaag     300

ggtatgatga tcgatgatgc ctctctcttc ccccgttctt gatggacagg cgatggctcc     360

caggaacacg cgtgactgac caccgaatcc aggccccatc caggtctacc tggccaaggt     420

ggacaacgcg gcgacggcgt cgccgtcggg cctcaggtgg ttcaaggtgg ccgagcgcgg     480

cctgaacaac ggcgtgtggg ccgtcgatga gctcatcgcc aacaacggct ggcactactt     540

cgacctgccg tcgtgcgtgg cccccggcca gtacctgatg cgcgtcgagc tgctcgccct     600

gcacagcgcc tcaagccccg gcggcgccca gttctacatg ggctgcgcac agatcgaagg     660

tgcgtcgatc tttgttctcc ttccgtgtcc tctctgatcc tttctctctt ctttttcttt     720

cttttactcc ctttccttcc atcttcggag aagcaacgaa gggggaaagg gatagaagag     780

aggaatgaga gacgacgaaa gagaggattg ggaaagaca agacagggaa aaaaagacaa     840

gaaaaaaaaa aaaaaaaaaa aacagagtga gctaacaaga acaatcagtc actggctccg     900

gcaccaactc gggctccgac tttgtctcgt tccccggcgc ctactcggcc aacgatccgg     960

gcatcttgct aagcatctac gacagctcgg gcaagcccac caacggcggg cgctcgtacc    1020

cgatccccgg cccgcgcccc atctcctgct ccggcagcgg cgacggcggc aacaacggcg    1080

gcggcggcga cgacaacaac aataacaacg gtggtggcaa caacggcggc ggcggcggcg    1140

gcagcgtccc cctgtacggg cagtgcggcg gcatcggcta cacgggcccg accacctgtg    1200

cccagggaac ttgcaaggtg tcgaacgaat actacagcca gtgcctcccc tag           1253


<210> SEQ ID NO 88
<211> LENGTH: 310
<212> TYPE: PRT
<213> ORGANISM: Myceliophthora thermophila

<400> SEQUENCE: 88

Met Lys Pro Phe Ser Leu Val Ala Leu Ala Thr Ala Val Ser Gly His
1               5                   10                  15

Ala Ile Phe Gln Arg Val Ser Val Asn Gly Gln Asp Gln Gly Gln Leu
            20                  25                  30

Lys Gly Val Arg Ala Pro Ser Ser Asn Ser Pro Ile Gln Asn Val Asn
```

```
        35                  40                  45

Asp Ala Asn Met Ala Cys Asn Ala Asn Ile Val Tyr His Asp Ser Thr
    50                  55                  60

Ile Ile Lys Val Pro Ala Gly Ala Arg Val Gly Ala Trp Trp Gln His
65                  70                  75                  80

Val Ile Gly Gly Pro Gln Gly Ala Asn Asp Pro Asp Asn Pro Ile Ala
                85                  90                  95

Ala Ser His Lys Gly Pro Ile Gln Val Tyr Leu Ala Lys Val Asp Asn
            100                 105                 110

Ala Ala Thr Ala Ser Pro Ser Gly Leu Arg Trp Phe Lys Val Ala Glu
        115                 120                 125

Arg Gly Leu Asn Asn Gly Val Trp Ala Val Asp Glu Leu Ile Ala Asn
    130                 135                 140

Asn Gly Trp His Tyr Phe Asp Leu Pro Ser Cys Val Ala Pro Gly Gln
145                 150                 155                 160

Tyr Leu Met Arg Val Glu Leu Leu Ala Leu His Ser Ala Ser Ser Pro
                165                 170                 175

Gly Gly Ala Gln Phe Tyr Met Gly Cys Ala Gln Ile Glu Val Thr Gly
            180                 185                 190

Ser Gly Thr Asn Ser Gly Ser Asp Phe Val Ser Phe Pro Gly Ala Tyr
        195                 200                 205

Ser Ala Asn Asp Pro Gly Ile Leu Leu Ser Ile Tyr Asp Ser Ser Gly
    210                 215                 220

Lys Pro Thr Asn Gly Gly Arg Ser Tyr Pro Ile Pro Gly Pro Arg Pro
225                 230                 235                 240

Ile Ser Cys Ser Gly Ser Gly Asp Gly Gly Asn Asn Gly Gly Gly Gly
                245                 250                 255

Asp Asp Asn Asn Asn Asn Asn Gly Gly Gly Asn Asn Gly Gly Gly Gly
            260                 265                 270

Gly Gly Ser Val Pro Leu Tyr Gly Gln Cys Gly Gly Ile Gly Tyr Thr
        275                 280                 285

Gly Pro Thr Thr Cys Ala Gln Gly Thr Cys Lys Val Ser Asn Glu Tyr
    290                 295                 300

Tyr Ser Gln Cys Leu Pro
305                 310


<210> SEQ ID NO 89
<211> LENGTH: 814
<212> TYPE: DNA
<213> ORGANISM: Myceliophthora thermophila

<400> SEQUENCE: 89

atgaagctct ccctcttctc cgtcctggcc actgccctca ccgtcgaggg gcatgccatc      60

ttccagaagg tctccgtcaa cggagcggac cagggctccc tcaccggcct ccgcgctccc     120

aacaacaaca accccgtgca ggatgtcaac agccaggaca tgatctgcgg ccagtcggga     180

tcgacgtcga acactatcat cgaggtcaag gccggcgata ggatcggtgc ctggtatcag     240

catgtcatcg gcggtgccca gttccccaac gacccagaca acccgattgc caagtcgcac     300

aagggccccg tcatggccta cctcgccaag gttgacaatg ccgcaaccgc cagcaagacg     360

ggcctgaagt ggtatgtatt cccgcggccc gagggacatc gggttgggca agtcgagact     420

gacggagctc gcttctccgt ataggttcaa gatttgggag gataccttta atcccagcac     480

caagacctgg ggtgtcgaca acctcatcaa taacaacggc tgggtgtact tcaacctccc     540
```

```
gcagtgcatc gccgacggca actacctcct ccgcgtcgag gtcctcgctc tgcactcggc    600

ctactctcag ggccaggctc agttctacca gtcctgcgcc cagatcaacg tatccggcgg    660

cggctccttc acaccgccgt cgactgtcag cttcccgggt gcctacagcg ccagcgaccc    720

cggtatcctg atcaacatct acggcgccac cggccagccc gacaacaacg gccagccgta    780

cactgcccct gggcccgcgc ccatctcctg ctga                                 814


<210> SEQ ID NO 90
<211> LENGTH: 246
<212> TYPE: PRT
<213> ORGANISM: Myceliophthora thermophila

<400> SEQUENCE: 90

Met Lys Leu Ser Leu Phe Ser Val Leu Ala Thr Ala Leu Thr Val Glu
1               5                   10                  15

Gly His Ala Ile Phe Gln Lys Val Ser Val Asn Gly Ala Asp Gln Gly
            20                  25                  30

Ser Leu Thr Gly Leu Arg Ala Pro Asn Asn Asn Asn Pro Val Gln Asp
        35                  40                  45

Val Asn Ser Gln Asp Met Ile Cys Gly Gln Ser Gly Ser Thr Ser Asn
    50                  55                  60

Thr Ile Ile Glu Val Lys Ala Gly Asp Arg Ile Gly Ala Trp Tyr Gln
65                  70                  75                  80

His Val Ile Gly Gly Ala Gln Phe Pro Asn Asp Pro Asp Asn Pro Ile
                85                  90                  95

Ala Lys Ser His Lys Gly Pro Val Met Ala Tyr Leu Ala Lys Val Asp
            100                 105                 110

Asn Ala Ala Thr Ala Ser Lys Thr Gly Leu Lys Trp Phe Lys Ile Trp
        115                 120                 125

Glu Asp Thr Phe Asn Pro Ser Thr Lys Thr Trp Gly Val Asp Asn Leu
    130                 135                 140

Ile Asn Asn Asn Gly Trp Val Tyr Phe Asn Leu Pro Gln Cys Ile Ala
145                 150                 155                 160

Asp Gly Asn Tyr Leu Leu Arg Val Glu Val Leu Ala Leu His Ser Ala
                165                 170                 175

Tyr Ser Gln Gly Gln Ala Gln Phe Tyr Gln Ser Cys Ala Gln Ile Asn
            180                 185                 190

Val Ser Gly Gly Gly Ser Phe Thr Pro Pro Ser Thr Val Ser Phe Pro
        195                 200                 205

Gly Ala Tyr Ser Ala Ser Asp Pro Gly Ile Leu Ile Asn Ile Tyr Gly
    210                 215                 220

Ala Thr Gly Gln Pro Asp Asn Asn Gly Gln Pro Tyr Thr Ala Pro Gly
225                 230                 235                 240

Pro Ala Pro Ile Ser Cys
                245


<210> SEQ ID NO 91
<211> LENGTH: 1115
<212> TYPE: DNA
<213> ORGANISM: Thermoascus aurantiacus

<400> SEQUENCE: 91

atgtcgttct cgaagattgc tgcgatcacc ggggccatta cctatgcgtc tctggccgcc     60

gctcacggtt atgttacagg aatcgtagcc gatggcacct agtatgtaac gctcatgcca    120

agatccgcat tgctgtacta acaattagca gctacggggg ctatatcgtg acccaatacc    180
```

```
cctacatgtc gacaccgccg gatgtcatcg cctggtctac caaagcaact gatcttggtt    240

tcgtggatcc cagtagctat gcttcgtctg atattatctg ccacaagggt gctgagcctg    300

gtgccctgag cgccaaggtg gctgctggag ggaccgtcga gctgcagtgg acggattggc    360

ctgagagtca caagggcccg gtcattgact acctcgccgc ctgtaacggg gactgctcga    420

ctgtcgacaa gaccaaacta gagttcttca agattgatga gagtggccta attgacggca    480

gcagcgcccc aggcacatgg gcctctgaca acttgattgc caataacaac agctggaccg    540

tcaccatccc gagcacgatt gctcccggca actatgtcct gagacatgaa atcattgccc    600

tccactccgc cggaaataca aatggtgctc agaactaccc ccagtgtatc aaccttgagg    660

tcacaggcag tggcaccgac acccctgccg gcaccctcgg aacggagctt tataaggcaa    720

cggaccctgg cattctggtc aacatctacc agaccctgac cagctacgat attcccggcc    780

ctgctctgta caccggtggt agctctggta gctctggttc ctccaacacc gccaaggcca    840

ccacttcgac ggcttctagc tctatcgtga ccccgacgcc tgttaacaac ccaaccgtta    900

ctcagactgc cgttgttgat gtcacccaga ctgtttccca gaatgctgcc gtcgccacca    960

cgactccggc ctccactgca gttgctacag ctgtcccaac gggaaccacc tttagctttg   1020

attcgatgac ctcggatgaa ttcgtcagcc tgatgcgtgc gaccgtgaat tggctgcttt   1080

ctaacaagaa gcatgcccgg gatctttctt actaa                              1115
```

<210> SEQ ID NO 92
<211> LENGTH: 354
<212> TYPE: PRT
<213> ORGANISM: Thermoascus aurantiacus

<400> SEQUENCE: 92

```
Met Ser Phe Ser Lys Ile Ala Ala Ile Thr Gly Ala Ile Thr Tyr Ala
1               5                   10                  15

Ser Leu Ala Ala Ala His Gly Tyr Val Thr Gly Ile Val Ala Asp Gly
            20                  25                  30

Thr Tyr Tyr Gly Gly Tyr Ile Val Thr Gln Tyr Pro Tyr Met Ser Thr
        35                  40                  45

Pro Pro Asp Val Ile Ala Trp Ser Thr Lys Ala Thr Asp Leu Gly Phe
    50                  55                  60

Val Asp Pro Ser Ser Tyr Ala Ser Ser Asp Ile Ile Cys His Lys Gly
65                  70                  75                  80

Ala Glu Pro Gly Ala Leu Ser Ala Lys Val Ala Ala Gly Gly Thr Val
                85                  90                  95

Glu Leu Gln Trp Thr Asp Trp Pro Glu Ser His Lys Gly Pro Val Ile
            100                 105                 110

Asp Tyr Leu Ala Ala Cys Asn Gly Asp Cys Ser Thr Val Asp Lys Thr
        115                 120                 125

Lys Leu Glu Phe Phe Lys Ile Asp Glu Ser Gly Leu Ile Asp Gly Ser
    130                 135                 140

Ser Ala Pro Gly Thr Trp Ala Ser Asp Asn Leu Ile Ala Asn Asn Asn
145                 150                 155                 160

Ser Trp Thr Val Thr Ile Pro Ser Thr Ile Ala Pro Gly Asn Tyr Val
                165                 170                 175

Leu Arg His Glu Ile Ile Ala Leu His Ser Ala Gly Asn Thr Asn Gly
            180                 185                 190

Ala Gln Asn Tyr Pro Gln Cys Ile Asn Leu Glu Val Thr Gly Ser Gly
        195                 200                 205
```

```
Thr Asp Thr Pro Ala Gly Thr Leu Gly Thr Glu Leu Tyr Lys Ala Thr
    210                 215                 220

Asp Pro Gly Ile Leu Val Asn Ile Tyr Gln Thr Leu Thr Ser Tyr Asp
225                 230                 235                 240

Ile Pro Gly Pro Ala Leu Tyr Thr Gly Gly Ser Ser Gly Ser Ser Gly
                245                 250                 255

Ser Ser Asn Thr Ala Lys Ala Thr Thr Ser Thr Ala Ser Ser Ser Ile
            260                 265                 270

Val Thr Pro Thr Pro Val Asn Asn Pro Thr Val Thr Gln Thr Ala Val
        275                 280                 285

Val Asp Val Thr Gln Thr Val Ser Gln Asn Ala Ala Val Ala Thr Thr
    290                 295                 300

Thr Pro Ala Ser Thr Ala Val Ala Thr Ala Val Pro Thr Gly Thr Thr
305                 310                 315                 320

Phe Ser Phe Asp Ser Met Thr Ser Asp Glu Phe Val Ser Leu Met Arg
                325                 330                 335

Ala Thr Val Asn Trp Leu Leu Ser Asn Lys Lys His Ala Arg Asp Leu
            340                 345                 350

Ser Tyr
```

<210> SEQ ID NO 93
<211> LENGTH: 862
<212> TYPE: DNA
<213> ORGANISM: Aspergillus fumigatus

<400> SEQUENCE: 93

```
atgactttgt ccaagatcac ttccattgct ggccttctgg cctcagcgtc tctcgtggct     60

ggccacggct ttgtttctgg cattgttgct gatgggaaat agtatgtgct tgaaccacac    120

aaatgacagc tgcaacagct aacttctatt ccagttacgg agggtacctt gttaaccaat    180

acccctacat gagcaaccct cccgacacca ttgcctggtc caccaccgcc accgacctcg    240

gctttgtgga cggcaccggc taccagtctc cggatattat ctgccacaga gacgcaaaga    300

atggcaagtt gaccgcaacc gttgcagccg gttcacagat cgaattccag tggacgacgt    360

ggccagagtc tcaccatgga ccggtacgac gccgaagaga agagaacata ttgtgaccag    420

ataggctaac atagcatagt tgattactta cctcgctcca tgcaacggcg actgtgccac    480

cgtggacaag accaccctga agtttgtcaa gatcgccgct caaggcttga tcgacggctc    540

caacccacct ggtgtttggg ctgatgatga aatgatcgcc aacaacaaca cggccacagt    600

gaccattcct gcctcctatg cccccggaaa ctacgtcctt cgccacgaga tcatcgccct    660

tcactctgcg ggtaacctga acggcgcgca gaactacccc cagtgtttca acatccaaat    720

caccggtggc ggcagtgctc agggatctgg caccgctggc acgtccctgt acaagaatac    780

tgatcctggc atcaagtttg acatctactc ggatctgagc ggtggatacc ctattcctgg    840

tcctgcactg ttcaacgctt aa                                             862
```

<210> SEQ ID NO 94
<211> LENGTH: 250
<212> TYPE: PRT
<213> ORGANISM: Aspergillus fumigatus

<400> SEQUENCE: 94

```
Met Thr Leu Ser Lys Ile Thr Ser Ile Ala Gly Leu Leu Ala Ser Ala
1               5                   10                  15
```

```
Ser Leu Val Ala Gly His Gly Phe Val Ser Gly Ile Val Ala Asp Gly
            20                  25                  30

Lys Tyr Tyr Gly Gly Tyr Leu Val Asn Gln Tyr Pro Tyr Met Ser Asn
        35                  40                  45

Pro Pro Asp Thr Ile Ala Trp Ser Thr Thr Ala Thr Asp Leu Gly Phe
    50                  55                  60

Val Asp Gly Thr Gly Tyr Gln Ser Pro Asp Ile Ile Cys His Arg Asp
65                  70                  75                  80

Ala Lys Asn Gly Lys Leu Thr Ala Thr Val Ala Ala Gly Ser Gln Ile
                85                  90                  95

Glu Phe Gln Trp Thr Thr Trp Pro Glu Ser His His Gly Pro Leu Ile
            100                 105                 110

Thr Tyr Leu Ala Pro Cys Asn Gly Asp Cys Ala Thr Val Asp Lys Thr
        115                 120                 125

Thr Leu Lys Phe Val Lys Ile Ala Ala Gln Gly Leu Ile Asp Gly Ser
    130                 135                 140

Asn Pro Pro Gly Val Trp Ala Asp Asp Glu Met Ile Ala Asn Asn Asn
145                 150                 155                 160

Thr Ala Thr Val Thr Ile Pro Ala Ser Tyr Ala Pro Gly Asn Tyr Val
                165                 170                 175

Leu Arg His Glu Ile Ile Ala Leu His Ser Ala Gly Asn Leu Asn Gly
            180                 185                 190

Ala Gln Asn Tyr Pro Gln Cys Phe Asn Ile Gln Ile Thr Gly Gly Gly
        195                 200                 205

Ser Ala Gln Gly Ser Gly Thr Ala Gly Thr Ser Leu Tyr Lys Asn Thr
    210                 215                 220

Asp Pro Gly Ile Lys Phe Asp Ile Tyr Ser Asp Leu Ser Gly Gly Tyr
225                 230                 235                 240

Pro Ile Pro Gly Pro Ala Leu Phe Asn Ala
                245                 250


<210> SEQ ID NO 95
<211> LENGTH: 1021
<212> TYPE: DNA
<213> ORGANISM: Penicillium pinophilum

<400> SEQUENCE: 95

atgccttcta ctaaagtcgc tgccctttct gctgttctag ctttggcctc cacggttgct      60

ggccatggtt ttgtgcaaaa catcgttatc gacggtaaat cgtaagcagt gatgcatcca     120

ttattaaact agacatgctt acaaaaaaat cagttactct ggataccttg tgaatcagtt     180

cccctacgag tccaacccac cagctgttat tgggtgggca acaactgcaa ccgacctggg     240

attcgtcgct cccagtgagt acaccaatgc agacattatc tgccacaaga acgccacacc     300

tggcgcgctt tctgctccag ttgctgcagg gggcactgtc gagctccagt ggactacatg     360

gcccgatagt catcacggtc ctgtcatcag ctacctcgcc aactgcaatg gcaattgttc     420

taccgtggat aagactaagc tagactttgt caagattgac caaggtggtt tgatcgacga     480

tactaccccc ccgggtacat gggcttccga caaacttatc gctgccaaca acagctggac     540

tgtaactatc ccctccacca tcgcgcctgg aaactacgtt ttgcgccacg aaatcattgc     600

tcttcactcc gctggaaacg cagacggtgc ccaaaactac cctcaatgca tcaacttgga     660

gatcaccggc agcggaaccg ccgctccctc tggtaccgct ggcgaaaagc tctacacctc     720

tactgacccc ggtatcttgg tcaatatcta ccaatccttg tcgacctacg ttattcccgg     780
```

```
accaactctg tggagcggtg ctgccaatgg cgctgttgcc actggttctg ctactgcggt    840

tgctacgact gccactgctt ctgcgaccgc tactcctacc acacttgtta cctctgtcgc    900

tccagcttca tctacctttg ccactgctgt tgtgaccact gtcgctcctg cagtaactga    960

tgtcgtgact gtcaccgatg tagttaccgt gaccaccgtc atcaccacta ctgtcctttg   1020

a                                                                   1021


<210> SEQ ID NO 96
<211> LENGTH: 322
<212> TYPE: PRT
<213> ORGANISM: Penicillium pinophilum

<400> SEQUENCE: 96

Met Pro Ser Thr Lys Val Ala Ala Leu Ser Ala Val Leu Ala Leu Ala
1               5                   10                  15

Ser Thr Val Ala Gly His Gly Phe Val Gln Asn Ile Val Ile Asp Gly
            20                  25                  30

Lys Ser Tyr Ser Gly Tyr Leu Val Asn Gln Phe Pro Tyr Glu Ser Asn
        35                  40                  45

Pro Pro Ala Val Ile Gly Trp Ala Thr Thr Ala Thr Asp Leu Gly Phe
    50                  55                  60

Val Ala Pro Ser Glu Tyr Thr Asn Ala Asp Ile Ile Cys His Lys Asn
65                  70                  75                  80

Ala Thr Pro Gly Ala Leu Ser Ala Pro Val Ala Ala Gly Gly Thr Val
                85                  90                  95

Glu Leu Gln Trp Thr Thr Trp Pro Asp Ser His His Gly Pro Val Ile
            100                 105                 110

Ser Tyr Leu Ala Asn Cys Asn Gly Asn Cys Ser Thr Val Asp Lys Thr
        115                 120                 125

Lys Leu Asp Phe Val Lys Ile Asp Gln Gly Gly Leu Ile Asp Asp Thr
    130                 135                 140

Thr Pro Pro Gly Thr Trp Ala Ser Asp Lys Leu Ile Ala Ala Asn Asn
145                 150                 155                 160

Ser Trp Thr Val Thr Ile Pro Ser Thr Ile Ala Pro Gly Asn Tyr Val
                165                 170                 175

Leu Arg His Glu Ile Ile Ala Leu His Ser Ala Gly Asn Ala Asp Gly
            180                 185                 190

Ala Gln Asn Tyr Pro Gln Cys Ile Asn Leu Glu Ile Thr Gly Ser Gly
        195                 200                 205

Thr Ala Ala Pro Ser Gly Thr Ala Gly Glu Lys Leu Tyr Thr Ser Thr
    210                 215                 220

Asp Pro Gly Ile Leu Val Asn Ile Tyr Gln Ser Leu Ser Thr Tyr Val
225                 230                 235                 240

Ile Pro Gly Pro Thr Leu Trp Ser Gly Ala Ala Asn Gly Ala Val Ala
                245                 250                 255

Thr Gly Ser Ala Thr Ala Val Ala Thr Thr Ala Thr Ala Ser Ala Thr
            260                 265                 270

Ala Thr Pro Thr Thr Leu Val Thr Ser Val Ala Pro Ala Ser Ser Thr
        275                 280                 285

Phe Ala Thr Ala Val Val Thr Thr Val Ala Pro Ala Val Thr Asp Val
    290                 295                 300

Val Thr Val Thr Asp Val Val Thr Val Thr Thr Val Ile Thr Thr Thr
305                 310                 315                 320

Val Leu
```

<210> SEQ ID NO 97
<211> LENGTH: 1486
<212> TYPE: DNA
<213> ORGANISM: Thermoascus sp.

<400> SEQUENCE: 97

```
atgttgtcgt tcgcttctgc caagtcagct gtgctgacga cccttctact tcttggatcc     60
gctcaggctc acactttgat gaccaccctg tttgtggatg gcgtcaatca gggagatggt    120
gtctgtattc gcatgaacaa caacggtagt actgccaaca cctatatcca gcctgtcacg    180
agcaaggata ttgcctgcgg taagtacagt accggtccag atatcatact ctatttcaat    240
ccgacaacag tcagagctgg agagcaatgc taaacatccc caggcattca aggcgaaatt    300
ggcgccgctc gagtctgtcc agccaaggct tcatccaccc tcacgttcca attccgagag    360
cagccatcca acccgaattc cgctcctctc gatccctcgc acaaaggccc cgctgcggtg    420
tacctgaaaa aggtagactc cgccatcgcg agcaacaacg ccgctggaga cggctggttc    480
aagatctggg agtccgtcta cgacgagtcc acgggcaaat ggggtacgac caagatgatc    540
gagaacaacg ggcacatctc tgtcaaggtc cccgacgata tcgagggtgg gtattatctc    600
gcgcgtacgg agcttctggc gctgcacgcg gcgaacgaag gggatccgca gttctacgtt    660
ggctgcgcgc agctgttcat cgattcagcg gggacagcga aaccgcctac tgtctctatt    720
ggagagggga cctacgatct gagcatgcct gccatgacgt acaatatcta ccagactccg    780
ttggctctac catacccgat gtatgggcct cctgtctaca cacctggctc tggctcgggt    840
tctggctctg gttccgggtc agcttctgca acgagatctt ctgctattcc tactgccacc    900
gctgttacgg actgttcttc cgaagaggac agggaagact cagtcatggc aaccggtgtt    960
cccgttgcaa gaagcacact cagaacctgg gttgacagac tgtcatggca tggtaaggcc   1020
cgtgagaacg tgaaaccagc cgccaggaga agcgcccttg tccagaccga gggtctgaag   1080
ccggaaggct gcatcttcgt caacggcaac tggtgcggtt tcgaggtccc cgattacaac   1140
gatgcggaaa gctgctgggc tgtacgttcc cgtctaatta cttaaaacga aataaaagct   1200
aacagtactt ttctttttct aatcccaggc ctccgacaac tgctggaaac agtccgactc   1260
gtgctggaac cagacccagc ccaccggcta caacaactgc cagatctggc aagaccagaa   1320
atgcaagccc atccaggact cgtgtagcca atccaacccg actggaccgc cgaacaaggg   1380
caaggatata actccaacgt ggccgcccct ggagggctcg atgaagacct tcaccaagcg   1440
cactgtcagt taccgtgatt ggattatgaa aaggaaagga gcataa                   1486
```

<210> SEQ ID NO 98
<211> LENGTH: 444
<212> TYPE: PRT
<213> ORGANISM: Thermoascus sp.

<400> SEQUENCE: 98

```
Met Leu Ser Phe Ala Ser Ala Lys Ser Ala Val Leu Thr Thr Leu Leu
1               5                   10                  15

Leu Leu Gly Ser Ala Gln Ala His Thr Leu Met Thr Thr Leu Phe Val
            20                  25                  30

Asp Gly Val Asn Gln Gly Asp Gly Val Cys Ile Arg Met Asn Asn Asn
        35                  40                  45

Gly Ser Thr Ala Asn Thr Tyr Ile Gln Pro Val Thr Ser Lys Asp Ile
    50                  55                  60
```

```
Ala Cys Gly Ile Gln Gly Glu Ile Gly Ala Ala Arg Val Cys Pro Ala
65                  70                  75                  80

Lys Ala Ser Ser Thr Leu Thr Phe Gln Phe Arg Glu Gln Pro Ser Asn
                85                  90                  95

Pro Asn Ser Ala Pro Leu Asp Pro Ser His Lys Gly Pro Ala Ala Val
            100                 105                 110

Tyr Leu Lys Lys Val Asp Ser Ala Ile Ala Ser Asn Asn Ala Ala Gly
        115                 120                 125

Asp Gly Trp Phe Lys Ile Trp Glu Ser Val Tyr Asp Glu Ser Thr Gly
    130                 135                 140

Lys Trp Gly Thr Thr Lys Met Ile Glu Asn Asn Gly His Ile Ser Val
145                 150                 155                 160

Lys Val Pro Asp Asp Ile Glu Gly Gly Tyr Tyr Leu Ala Arg Thr Glu
                165                 170                 175

Leu Leu Ala Leu His Ala Ala Asn Glu Gly Asp Pro Gln Phe Tyr Val
            180                 185                 190

Gly Cys Ala Gln Leu Phe Ile Asp Ser Ala Gly Thr Ala Lys Pro Pro
        195                 200                 205

Thr Val Ser Ile Gly Glu Gly Thr Tyr Asp Leu Ser Met Pro Ala Met
    210                 215                 220

Thr Tyr Asn Ile Tyr Gln Thr Pro Leu Ala Leu Pro Tyr Pro Met Tyr
225                 230                 235                 240

Gly Pro Pro Val Tyr Thr Pro Gly Ser Gly Ser Gly Ser Gly Ser Gly
                245                 250                 255

Ser Gly Ser Ala Ser Ala Thr Arg Ser Ser Ala Ile Pro Thr Ala Thr
            260                 265                 270

Ala Val Thr Asp Cys Ser Ser Glu Glu Asp Arg Glu Asp Ser Val Met
        275                 280                 285

Ala Thr Gly Val Pro Val Ala Arg Ser Thr Leu Arg Thr Trp Val Asp
    290                 295                 300

Arg Leu Ser Trp His Gly Lys Ala Arg Glu Asn Val Lys Pro Ala Ala
305                 310                 315                 320

Arg Arg Ser Ala Leu Val Gln Thr Glu Gly Leu Lys Pro Glu Gly Cys
                325                 330                 335

Ile Phe Val Asn Gly Asn Trp Cys Gly Phe Glu Val Pro Asp Tyr Asn
            340                 345                 350

Asp Ala Glu Ser Cys Trp Ala Ala Ser Asp Asn Cys Trp Lys Gln Ser
        355                 360                 365

Asp Ser Cys Trp Asn Gln Thr Gln Pro Thr Gly Tyr Asn Asn Cys Gln
    370                 375                 380

Ile Trp Gln Asp Gln Lys Cys Lys Pro Ile Gln Asp Ser Cys Ser Gln
385                 390                 395                 400

Ser Asn Pro Thr Gly Pro Pro Asn Lys Gly Lys Asp Ile Thr Pro Thr
                405                 410                 415

Trp Pro Pro Leu Glu Gly Ser Met Lys Thr Phe Thr Lys Arg Thr Val
            420                 425                 430

Ser Tyr Arg Asp Trp Ile Met Lys Arg Lys Gly Ala
        435                 440
```

<210> SEQ ID NO 99
<211> LENGTH: 835
<212> TYPE: DNA
<213> ORGANISM: Penicillium sp.

<400> SEQUENCE: 99

```
atgctgtctt cgacgactcg caccctcgcc tttacaggcc ttgcgggcct tctgtccgct     60

cccctggtca aggcccatgg ctttgtccag ggcattgtca tcggtgacca attgtaagtc    120

cctctcttgc agttctgtcg attaactgct ggactgcttg cttgactccc tgctgactcc    180

caacagctac agcgggtaca tcgtcaactc gttcccctac gaatccaacc caccccccgt    240

catcggctgg gccacgaccg ccaccgacct gggcttcgtc gacggcacag gataccaagg    300

cccggacatc atctgccacc ggaatgcgac gcccgcgccg ctgacagccc ccgtggccgc    360

cggcggcacc gtcgagctgc agtggacgcc gtggccggac agccaccacg gacccgtcat    420

cacctacctg gcgccgtgca acggcaactg ctcgaccgtc gacaagacga cgctggagtt    480

cttcaagatc gaccagcagg gcctgatcga cgacacgagc ccgccgggca cctgggcgtc    540

ggacaacctc atcgccaaca acaatagctg gaccgtcacc attcccaaca gcgtcgcccc    600

cggcaactac gtcctgcgcc acgagatcat cgccctgcac tcggccaaca acaaggacgg    660

cgcccagaac tacccccagt gcatcaacat cgaggtcacg ggcggcggct ccgacgcgcc    720

tgagggtact ctgggcgagg atctctacca tgacaccgac ccgggcattc tggtcgacat    780

ttacgagccc attgcgacgt ataccattcc ggggccgcct gagccgacgt tctag         835
```

```
<210> SEQ ID NO 100
<211> LENGTH: 253
<212> TYPE: PRT
<213> ORGANISM: Penicillium sp.

<400> SEQUENCE: 100

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220
```

```
Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250


<210> SEQ ID NO 101
<211> LENGTH: 977
<212> TYPE: DNA
<213> ORGANISM: Thielavia terrestris

<400> SEQUENCE: 101

atgaagctgt catcccagct cgccgccctc acgctggccg cggcctccgt gtcaggccac      60

tacatcttcg agcagattgc ccatggcggc accaagttcc caccttacga gtacatccga     120

agaaacacga actataacag ccctgtcacc agtctctcgt cgaacgacct gcgatgcaac     180

gtaggcggcg agacggctgg caacacgacc gtcctcgacg tgaaggcggg cgactccttc     240

accttctact cggacgtggc cgtgtaccac caggggccca tctcactgtg cgtgccccgg     300

gccaactttg atcagtccca agcggactgt ccgctcgcct ggataaccac aattgactga     360

cagcccgcac agctacatgt ccaaggctcc cggctccgtc gtggactacg acggctccgg     420

cgactggttc aagatccacg actggggccc gaccttcagc aacggccagg cctcgtggcc     480

gctgcggggt gcgtcccttc cctttccctc cccttcctc ccccttcctc cccccctttc      540

ccccctttc tgtctggtcg cacgccctgc tgacgtcccc gtagacaact accagtacaa      600

catcccgacg tgcatcccga acggcgagta cctgctgcgc atccagtcgc tggcgatcca     660

caacccgggc gccacgccgc agttctacat cagctgcgcg caggtccggg tctcgggcgg     720

cggcagcgcc tccccctccc caacggccaa gatccccggc gcgttcaagg cgaccgatcc     780

cgggtatacc gcgaatgtga gtgccctatg ttccttgcgc tccttgttcc ttgctccttg     840

ctcggcgtgc ttgaacgcta cgggctgtgg agggagggat ggatggatga ataggatgct     900

gactgatggt gggacaccag atttacaata acttccactc gtatacggtg ccgggtccgg     960

cggtctttca gtgctag                                                     977


<210> SEQ ID NO 102
<211> LENGTH: 223
<212> TYPE: PRT
<213> ORGANISM: Thielavia terrestris

<400> SEQUENCE: 102

Met Lys Leu Ser Ser Gln Leu Ala Ala Leu Thr Leu Ala Ala Ala Ser
1               5                   10                  15

Val Ser Gly His Tyr Ile Phe Glu Gln Ile Ala His Gly Gly Thr Lys
            20                  25                  30

Phe Pro Pro Tyr Glu Tyr Ile Arg Arg Asn Thr Asn Tyr Asn Ser Pro
        35                  40                  45

Val Thr Ser Leu Ser Ser Asn Asp Leu Arg Cys Asn Val Gly Gly Glu
    50                  55                  60

Thr Ala Gly Asn Thr Thr Val Leu Asp Val Lys Ala Gly Asp Ser Phe
65                  70                  75                  80

Thr Phe Tyr Ser Asp Val Ala Val Tyr His Gln Gly Pro Ile Ser Leu
                85                  90                  95

Tyr Met Ser Lys Ala Pro Gly Ser Val Val Asp Tyr Asp Gly Ser Gly
            100                 105                 110

Asp Trp Phe Lys Ile His Asp Trp Gly Pro Thr Phe Ser Asn Gly Gln
        115                 120                 125
```

```
Ala Ser Trp Pro Leu Arg Asp Asn Tyr Gln Tyr Asn Ile Pro Thr Cys
    130                 135                 140

Ile Pro Asn Gly Glu Tyr Leu Leu Arg Ile Gln Ser Leu Ala Ile His
145                 150                 155                 160

Asn Pro Gly Ala Thr Pro Gln Phe Tyr Ile Ser Cys Ala Gln Val Arg
                165                 170                 175

Val Ser Gly Gly Gly Ser Ala Ser Pro Ser Pro Thr Ala Lys Ile Pro
            180                 185                 190

Gly Ala Phe Lys Ala Thr Asp Pro Gly Tyr Thr Ala Asn Ile Tyr Asn
        195                 200                 205

Asn Phe His Ser Tyr Thr Val Pro Gly Pro Ala Val Phe Gln Cys
    210                 215                 220
```

<210> SEQ ID NO 103
<211> LENGTH: 878
<212> TYPE: DNA
<213> ORGANISM: Thielavia terrestris

<400> SEQUENCE: 103

```
atgaagttct cactggtgtc tctgctggct tacggcctct cggtcgaggc gcactccatc     60

ttccaggttc gtctcgcaca tcacgctcaa ctcggctcgt ggcgtaaggg caaggattaa    120

cacggccggc agagagtctc ggtcaacggc caagaccaag gcctgctcac cggcctccgc    180

gctccaagca acaacaaccc agtgcaagat gtcaacagcc agaacatgat ttgcggccag    240

tcgggctcca agtcgcagac cgttatcaac gtcaaggccg gcgacaggat cggctcgctc    300

tggcagcatg tcatcggcgg cgcccagttt tcgggtgacc cggacaaccc gatcgcccac    360

tcgcacaagg gccccgtgat ggcgtacctt gctaaggtcg acaatgccgc gtccgcgagc    420

caaacgggtc tgaagtggta agtagcgggc gacgctcagg ggacggggat cgggggcctg    480

ctccatccga gactaacacc gtggacaggt tcaagatctg gcaggacggg ttcgatacca    540

gcagcaagac atggggcgtc gacaacctga tcaagaacaa cggctgggtg tacttccacc    600

tgccgcagtg cctcgctccg ggccagtatc tcctgcgcgt cgaggttctg gcgctgcact    660

cggcgtacca gcagggccag gcccagttct accagtcctg cgcccagatc aacgtctccg    720

gctccgggtc cttcagcccg tcccagacgg tcagcatccc gggcgtctac agcgccaccg    780

acccgagcat cctcatcaac atctacggca gcacggggca gcccgacaac ggcggcaagg    840

cttacaaccc ccctggaccc gccccgatct cctgctga                            878
```

<210> SEQ ID NO 104
<211> LENGTH: 246
<212> TYPE: PRT
<213> ORGANISM: Thielavia terrestris

<400> SEQUENCE: 104

```
Met Lys Phe Ser Leu Val Ser Leu Leu Ala Tyr Gly Leu Ser Val Glu
1               5                   10                  15

Ala His Ser Ile Phe Gln Arg Val Ser Val Asn Gly Gln Asp Gln Gly
            20                  25                  30

Leu Leu Thr Gly Leu Arg Ala Pro Ser Asn Asn Asn Pro Val Gln Asp
        35                  40                  45

Val Asn Ser Gln Asn Met Ile Cys Gly Gln Ser Gly Ser Lys Ser Gln
    50                  55                  60

Thr Val Ile Asn Val Lys Ala Gly Asp Arg Ile Gly Ser Leu Trp Gln
65                  70                  75                  80
```

```
His Val Ile Gly Gly Ala Gln Phe Ser Gly Asp Pro Asp Asn Pro Ile
                85                  90                  95

Ala His Ser His Lys Gly Pro Val Met Ala Tyr Leu Ala Lys Val Asp
            100                 105                 110

Asn Ala Ala Ser Ala Ser Gln Thr Gly Leu Lys Trp Phe Lys Ile Trp
        115                 120                 125

Gln Asp Gly Phe Asp Thr Ser Ser Lys Thr Trp Gly Val Asp Asn Leu
    130                 135                 140

Ile Lys Asn Asn Gly Trp Val Tyr Phe His Leu Pro Gln Cys Leu Ala
145                 150                 155                 160

Pro Gly Gln Tyr Leu Leu Arg Val Glu Val Leu Ala Leu His Ser Ala
                165                 170                 175

Tyr Gln Gln Gly Gln Ala Gln Phe Tyr Gln Ser Cys Ala Gln Ile Asn
            180                 185                 190

Val Ser Gly Ser Gly Ser Phe Ser Pro Ser Gln Thr Val Ser Ile Pro
        195                 200                 205

Gly Val Tyr Ser Ala Thr Asp Pro Ser Ile Leu Ile Asn Ile Tyr Gly
    210                 215                 220

Ser Thr Gly Gln Pro Asp Asn Gly Gly Lys Ala Tyr Asn Pro Pro Gly
225                 230                 235                 240

Pro Ala Pro Ile Ser Cys
                245
```

<210> SEQ ID NO 105
<211> LENGTH: 1253
<212> TYPE: DNA
<213> ORGANISM: Thielavia terrestris

<400> SEQUENCE: 105

```
atgaggacga cattcgccgc cgcgttggca gccttcgctg cgcaggaagt ggcaggccat     60

gccatcttcc aacagctctg ggtggacggc accgactata tacgtgctcc ccttttcctt    120

ttgtgtttgc ccatcctcga ttgataaccc gaggccatcc aatgctgact cttacagcac    180

ggctcctcct gcgtccgcat gccgctgtcg aactcgcccg tcacgaacgt cggcagcagg    240

gacatgatct gcaacgccgg cacgcgcccc gtcagcggga agtgccccgt caaggccggc    300

ggcaccgtga cggttgagat gcaccaggtg ggctgatttc ctgagcgtcc tattcctccc    360

ggaagcccct ttcccatcct ttgccctggc taacccctcc gcccctccca gcaacccggg    420

gatcggtcgt gtaacaacga agccatcggc ggcgcccact ggggaccggt gcaggtgtac    480

ctcagcaagg tggaggacgc gagcacggcg gacgggtcga cgggctggtt caagatcttc    540

gcggacacgt ggtccaagaa ggcgggcagc tcggtggggg acgacgacaa ctggggcacg    600

cgcgacctca acgcgtgctg cggcaagatg caggtcaaga tcccggcgga catcccgtcg    660

ggcgactacc tgctgcgggc ggaggcgctg gcgctgcaca cggcgggcca ggtgggcggc    720

gcgcagttct acatgagctg ctaccagatc accgtgtcgg gcggcggcag cgccagcccg    780

gccaccgtca agttccccgg cgcctacagc gccaacgacc cgggcatcca catcaacatc    840

cacgcggccg tgtccaacta cgtcgcgccc ggcccggccg tctattccgg cggcacgacc    900

aaggtggccg ggtccgggtg ccaaggctgc gagaacacgt gcaaggtcgg ctcgtcgccc    960

acggcgacgg cgccgtcggg caagagcggc gcgggttccg acggcggcgc tgggaccgac   1020

ggcgggtctt cgtcttcgag ccccgacacg ggcagcgcgt gcagcgtgca ggcctacggg   1080

cagtgcggcg ggaacgggta ctcgggttgc acccagtgcg cggtaagttc ggggtcgtct   1140
```

```
gtcttttgta ggaacatccg agaggcttgg ctgacgaggc gttgttgtag cccggctata   1200

cttgcaaggc ggtctctccg ccgtactatt cgcagtgcgc cccttcttct tag          1253


<210> SEQ ID NO 106
<211> LENGTH: 334
<212> TYPE: PRT
<213> ORGANISM: Thielavia terrestris

<400> SEQUENCE: 106

Met Arg Thr Thr Phe Ala Ala Ala Leu Ala Ala Phe Ala Ala Gln Glu
1               5                   10                  15

Val Ala Gly His Ala Ile Phe Gln Gln Leu Trp His Gly Ser Ser Cys
            20                  25                  30

Val Arg Met Pro Leu Ser Asn Ser Pro Val Thr Asn Val Gly Ser Arg
        35                  40                  45

Asp Met Ile Cys Asn Ala Gly Thr Arg Pro Val Ser Gly Lys Cys Pro
    50                  55                  60

Val Lys Ala Gly Gly Thr Val Thr Val Glu Met His Gln Gln Pro Gly
65                  70                  75                  80

Asp Arg Ser Cys Asn Asn Glu Ala Ile Gly Gly Ala His Trp Gly Pro
                85                  90                  95

Val Gln Val Tyr Leu Ser Lys Val Glu Asp Ala Ser Thr Ala Asp Gly
            100                 105                 110

Ser Thr Gly Trp Phe Lys Ile Phe Ala Asp Thr Trp Ser Lys Lys Ala
        115                 120                 125

Gly Ser Ser Val Gly Asp Asp Asp Asn Trp Gly Thr Arg Asp Leu Asn
    130                 135                 140

Ala Cys Cys Gly Lys Met Gln Val Lys Ile Pro Ala Asp Ile Pro Ser
145                 150                 155                 160

Gly Asp Tyr Leu Leu Arg Ala Glu Ala Leu Ala Leu His Thr Ala Gly
                165                 170                 175

Gln Val Gly Gly Ala Gln Phe Tyr Met Ser Cys Tyr Gln Ile Thr Val
            180                 185                 190

Ser Gly Gly Gly Ser Ala Ser Pro Ala Thr Val Lys Phe Pro Gly Ala
        195                 200                 205

Tyr Ser Ala Asn Asp Pro Gly Ile His Ile Asn Ile His Ala Ala Val
    210                 215                 220

Ser Asn Tyr Val Ala Pro Gly Pro Ala Val Tyr Ser Gly Gly Thr Thr
225                 230                 235                 240

Lys Val Ala Gly Ser Gly Cys Gln Gly Cys Glu Asn Thr Cys Lys Val
                245                 250                 255

Gly Ser Ser Pro Thr Ala Thr Ala Pro Ser Gly Lys Ser Gly Ala Gly
            260                 265                 270

Ser Asp Gly Gly Ala Gly Thr Asp Gly Gly Ser Ser Ser Ser Ser Pro
        275                 280                 285

Asp Thr Gly Ser Ala Cys Ser Val Gln Ala Tyr Gly Gln Cys Gly Gly
    290                 295                 300

Asn Gly Tyr Ser Gly Cys Thr Gln Cys Ala Pro Gly Tyr Thr Cys Lys
305                 310                 315                 320

Ala Val Ser Pro Pro Tyr Tyr Ser Gln Cys Ala Pro Ser Ser
                325                 330


<210> SEQ ID NO 107
<211> LENGTH: 798
```

```
<212> TYPE: DNA
<213> ORGANISM: Thielavia terrestris

<400> SEQUENCE: 107

atgaagctga gcgttgccat cgccgtgctg gcgtcggctc ttgccgaggc tcactgtgag      60

tgcatcgtct cactccagct actgcgaagc ttgctgacga tggtccctag acaccttccc     120

cagcatcgga aacaccgctg actggcagta tgtgcggatt acaacgaact accagagcaa     180

cgggccggtg acggacgtca cctcggatca aattcggtgc tacgaacgga acccaggcac     240

gggagcgcag ggcatataca acgtcaccgc cggccagacc atcaactaca acgcgaaggc     300

gtccatctcc cacccggggc ccatgtcctt ctacattgct aaggttcccg ccggccaaac     360

cgctgcgacc tgggacggta agggggctgt gtggaccaag atctaccagg acatgcccaa     420

gttcggcagc agcctgacct ggcccaccat gggtaagaat tctcaccctg gaaatgaacg     480

cacatttgca cagatctaac atggcctaca ggcgccaagt ctgtccccgt caccatccct     540

cgttgcctcc agaacggcga ttaccttctg cgagccgagc acatcgctct acacagcgcg     600

agcagcgtcg gtggcgccca gttctacctc tcgtgcgccc agcttactgt cagcggcggc     660

agtggcacct ggaaccccaa gaaccgggtc tccttccccg gcgcttacaa ggcaacagac     720

ccgggcatct tgatcaacat ctactacccc gtgccgacca gctactcgcc gcccggcccg     780

ccggctgaga cgtgctaa                                                   798


<210> SEQ ID NO 108
<211> LENGTH: 227
<212> TYPE: PRT
<213> ORGANISM: Thielavia terrestris

<400> SEQUENCE: 108

Met Lys Leu Ser Val Ala Ile Ala Val Leu Ala Ser Ala Leu Ala Glu
1               5                   10                  15

Ala His Tyr Thr Phe Pro Ser Ile Gly Asn Thr Ala Asp Trp Gln Tyr
            20                  25                  30

Val Arg Ile Thr Thr Asn Tyr Gln Ser Asn Gly Pro Val Thr Asp Val
        35                  40                  45

Thr Ser Asp Gln Ile Arg Cys Tyr Glu Arg Asn Pro Gly Thr Gly Ala
    50                  55                  60

Gln Gly Ile Tyr Asn Val Thr Ala Gly Gln Thr Ile Asn Tyr Asn Ala
65                  70                  75                  80

Lys Ala Ser Ile Ser His Pro Gly Pro Met Ser Phe Tyr Ile Ala Lys
                85                  90                  95

Val Pro Ala Gly Gln Thr Ala Ala Thr Trp Asp Gly Lys Gly Ala Val
            100                 105                 110

Trp Thr Lys Ile Tyr Gln Asp Met Pro Lys Phe Gly Ser Ser Leu Thr
        115                 120                 125

Trp Pro Thr Met Gly Ala Lys Ser Val Pro Val Thr Ile Pro Arg Cys
    130                 135                 140

Leu Gln Asn Gly Asp Tyr Leu Leu Arg Ala Glu His Ile Ala Leu His
145                 150                 155                 160

Ser Ala Ser Ser Val Gly Gly Ala Gln Phe Tyr Leu Ser Cys Ala Gln
                165                 170                 175

Leu Thr Val Ser Gly Gly Ser Gly Thr Trp Asn Pro Lys Asn Arg Val
            180                 185                 190

Ser Phe Pro Gly Ala Tyr Lys Ala Thr Asp Pro Gly Ile Leu Ile Asn
        195                 200                 205
```

```
Ile Tyr Tyr Pro Val Pro Thr Ser Tyr Ser Pro Pro Gly Pro Pro Ala
    210                 215                 220

Glu Thr Cys
225


<210> SEQ ID NO 109
<211> LENGTH: 1107
<212> TYPE: DNA
<213> ORGANISM: Thielavia terrestris

<400> SEQUENCE: 109

atgccttctt tcgcctccaa gactctcctt tccaccctgg cgggtgccgc atccgtggcc      60

gcccacgggc acgtgtcgaa catcgtcatc aacggggtct cgtaccaggg ttacgatccg     120

acctccttcc cttacatgca gaacccgccc atcgtggtcg gctggactgc cgccgacacg     180

gacaacggct ttgttgcccc ggatgccttc gccagtggcg atatcatctg ccacaagaac     240

gccaccaacg ccaagggcca cgccgtggtc gccgcgggag acaagatctt catccagtgg     300

aacacatggc ccgagtccca ccacggcccc gtcatcgact acctcgcgag ctgcggcagc     360

gcgtcctgcg agaccgtcga caagaccaag ctcgagttct tcaagatcga cgaggtcggc     420

ctggtcgacg gcagctcggc gcccggtgtg tggggctccg accagctcat cgccaacaac     480

aactcgtggc tcgtcgagat cccgcccacc atcgcgccgg gcaactacgt cctgcgccac     540

gagatcatcg cgctgcacag cgccgaaaac gccgacggcg cccagaacta cccgcagtgc     600

ttcaacctgc agatcaccgg caccggcacc gccacccccct ccggcgtccc cggcacctcg     660

ctctacaccc cgaccgaccc gggcatcctc gtcaacatct acagcgcccc gatcacctac     720

accgtcccgg ggccggccct catctccggc gccgtcagca tcgcccagtc ctcctccgcc     780

atcaccgcct ccggcaccgc cctgaccggc tctgccaccg cacccgccgc cgccgctgct     840

accacaactt ccaccaccaa cgccgcggct gctgctacct ctgctgctgc tgctgctggt     900

acttccacaa ccaccaccag cgccgcggcc gtggtccaga cctcctcctc ctcctcctcc     960

gccccgtcct ctgccgccgc cgccgccacc accaccgcgg ctgccagcgc ccgcccgacc    1020

ggctgctcct ctggccgctc caggaagcag ccgcgccgcc acgcgcggga tatggtggtt    1080

gcgcgagggg ctgaggaggc aaactga                                        1107


<210> SEQ ID NO 110
<211> LENGTH: 368
<212> TYPE: PRT
<213> ORGANISM: Thielavia terrestris

<400> SEQUENCE: 110

Met Pro Ser Phe Ala Ser Lys Thr Leu Leu Ser Thr Leu Ala Gly Ala
1               5                   10                  15

Ala Ser Val Ala Ala His Gly His Val Ser Asn Ile Val Ile Asn Gly
            20                  25                  30

Val Ser Tyr Gln Gly Tyr Asp Pro Thr Ser Phe Pro Tyr Met Gln Asn
        35                  40                  45

Pro Pro Ile Val Val Gly Trp Thr Ala Ala Asp Thr Asp Asn Gly Phe
    50                  55                  60

Val Ala Pro Asp Ala Phe Ala Ser Gly Asp Ile Ile Cys His Lys Asn
65                  70                  75                  80

Ala Thr Asn Ala Lys Gly His Ala Val Val Ala Ala Gly Asp Lys Ile
                85                  90                  95
```

```
Phe Ile Gln Trp Asn Thr Trp Pro Glu Ser His His Gly Pro Val Ile
            100                 105                 110

Asp Tyr Leu Ala Ser Cys Gly Ser Ala Ser Cys Glu Thr Val Asp Lys
        115                 120                 125

Thr Lys Leu Glu Phe Phe Lys Ile Asp Glu Val Gly Leu Val Asp Gly
    130                 135                 140

Ser Ser Ala Pro Gly Val Trp Gly Ser Asp Gln Leu Ile Ala Asn Asn
145                 150                 155                 160

Asn Ser Trp Leu Val Glu Ile Pro Pro Thr Ile Ala Pro Gly Asn Tyr
                165                 170                 175

Val Leu Arg His Glu Ile Ile Ala Leu His Ser Ala Glu Asn Ala Asp
            180                 185                 190

Gly Ala Gln Asn Tyr Pro Gln Cys Phe Asn Leu Gln Ile Thr Gly Thr
        195                 200                 205

Gly Thr Ala Thr Pro Ser Gly Val Pro Gly Thr Ser Leu Tyr Thr Pro
    210                 215                 220

Thr Asp Pro Gly Ile Leu Val Asn Ile Tyr Ser Ala Pro Ile Thr Tyr
225                 230                 235                 240

Thr Val Pro Gly Pro Ala Leu Ile Ser Gly Ala Val Ser Ile Ala Gln
                245                 250                 255

Ser Ser Ser Ala Ile Thr Ala Ser Gly Thr Ala Leu Thr Gly Ser Ala
            260                 265                 270

Thr Ala Pro Ala Ala Ala Ala Ala Thr Thr Thr Ser Thr Thr Asn Ala
        275                 280                 285

Ala Ala Ala Ala Thr Ser Ala Ala Ala Ala Ala Gly Thr Ser Thr Thr
    290                 295                 300

Thr Thr Ser Ala Ala Ala Val Val Gln Thr Ser Ser Ser Ser Ser Ser
305                 310                 315                 320

Ala Pro Ser Ser Ala Ala Ala Ala Ala Thr Thr Thr Ala Ala Ala Ser
                325                 330                 335

Ala Arg Pro Thr Gly Cys Ser Ser Gly Arg Ser Arg Lys Gln Pro Arg
            340                 345                 350

Arg His Ala Arg Asp Met Val Val Ala Arg Gly Ala Glu Glu Ala Asn
        355                 360                 365
```

<210> SEQ ID NO 111
<211> LENGTH: 993
<212> TYPE: DNA
<213> ORGANISM: Thielavia terrestris

<400> SEQUENCE: 111

```
atgccgcccg cactccctca actcctaacc acggtcctga ccgccctcac cctcggttcc      60

accgccctcg cccactcaca cctcgcgtac attatcgtta acggcaagct ctaccagggc     120

ttcgacccgc gcccgcacca ggccaactac ccttcccggg tcgggtggtc caccggcgcc     180

gtcgacgacg gcttcgtcac gccggccaac tactccaccc cggacatcat ttgccacatc     240

gccggcacca gcccggccgg ccacgcgccc gtgcgcccgg gcgaccgcat ccacgtccag     300

tggaacggct ggccggtcgg ccacatcggt cccgtgctgt cgtacctcgc ccgctgcgag     360

tcggacacgg gctgcacggg ccagaacaag accgcgctgc ggtggaccaa gatcgacgac     420

tccagcccga ccatgcagaa cgtcgccggc gcgggcaccc agggcgaggg cacccccggc     480

aagcgctggg ccaccgacgt gctgatcgcc gccaacaaca gctggcaggt cgccgtgccg     540

gcggggctgc cgaccggcgc gtacgtgctg cgcaacgaga tcatcgcgct gcactacgcg     600
```

```
gcgaggaaga acggggcgca gaactatccg ctctgcatga acctgtgggt ggacgccagt    660

ggtgataata gtagtgtggc tgcaacgacg gcggcggtga cggcgggggg tctgcagatg    720

gatgcgtatg acgcgcgcgg gttctacaag gagaacgatc cgggcgtgct ggtcaatgtc    780

acggccgcgc tgtcgtcgta tgtcgtgccc gggccgacgg tggcggcggg cgccacgccg    840

gtgccgtacg cgcagcagag cccgagcgtg tcgacggcgg cgggcacgcc cgtcgtcgtt    900

acaaggacta gcgagacggc gccgtacacg ggcgccatga cgccgacggt tgcggcgagg    960

atgaagggga gggggtatga tcggcggggt tag                                 993
```

<210> SEQ ID NO 112
<211> LENGTH: 330
<212> TYPE: PRT
<213> ORGANISM: Thielavia terrestris

<400> SEQUENCE: 112

```
Met Pro Pro Ala Leu Pro Gln Leu Leu Thr Thr Val Leu Thr Ala Leu
1               5                   10                  15

Thr Leu Gly Ser Thr Ala Leu Ala His Ser His Leu Ala Tyr Ile Ile
            20                  25                  30

Val Asn Gly Lys Leu Tyr Gln Gly Phe Asp Pro Arg Pro His Gln Ala
        35                  40                  45

Asn Tyr Pro Ser Arg Val Gly Trp Ser Thr Gly Ala Val Asp Asp Gly
    50                  55                  60

Phe Val Thr Pro Ala Asn Tyr Ser Thr Pro Asp Ile Ile Cys His Ile
65                  70                  75                  80

Ala Gly Thr Ser Pro Ala Gly His Ala Pro Val Arg Pro Gly Asp Arg
                85                  90                  95

Ile His Val Gln Trp Asn Gly Trp Pro Val Gly His Ile Gly Pro Val
            100                 105                 110

Leu Ser Tyr Leu Ala Arg Cys Glu Ser Asp Thr Gly Cys Thr Gly Gln
        115                 120                 125

Asn Lys Thr Ala Leu Arg Trp Thr Lys Ile Asp Asp Ser Ser Pro Thr
    130                 135                 140

Met Gln Asn Val Ala Gly Ala Gly Thr Gln Gly Glu Gly Thr Pro Gly
145                 150                 155                 160

Lys Arg Trp Ala Thr Asp Val Leu Ile Ala Ala Asn Asn Ser Trp Gln
                165                 170                 175

Val Ala Val Pro Ala Gly Leu Pro Thr Gly Ala Tyr Val Leu Arg Asn
            180                 185                 190

Glu Ile Ile Ala Leu His Tyr Ala Ala Arg Lys Asn Gly Ala Gln Asn
        195                 200                 205

Tyr Pro Leu Cys Met Asn Leu Trp Val Asp Ala Ser Gly Asp Asn Ser
    210                 215                 220

Ser Val Ala Ala Thr Thr Ala Ala Val Thr Ala Gly Gly Leu Gln Met
225                 230                 235                 240

Asp Ala Tyr Asp Ala Arg Gly Phe Tyr Lys Glu Asn Asp Pro Gly Val
                245                 250                 255

Leu Val Asn Val Thr Ala Ala Leu Ser Ser Tyr Val Val Pro Gly Pro
            260                 265                 270

Thr Val Ala Ala Gly Ala Thr Pro Val Pro Tyr Ala Gln Gln Ser Pro
        275                 280                 285

Ser Val Ser Thr Ala Ala Gly Thr Pro Val Val Val Thr Arg Thr Ser
    290                 295                 300
```

```
Glu Thr Ala Pro Tyr Thr Gly Ala Met Thr Pro Thr Val Ala Ala Arg
305                 310                 315                 320

Met Lys Gly Arg Gly Tyr Asp Arg Arg Gly
                325                 330


<210> SEQ ID NO 113
<211> LENGTH: 1221
<212> TYPE: DNA
<213> ORGANISM: Thielavia terrestris

<400> SEQUENCE: 113

atgaagacat tcaccgccct cctggccgca gccggcctcg tcgccggcca tggatatgtc      60

gacaacgcca ccattggcgg ccagttttat caggtactct accgcttcac ccaaggtccg     120

ctggccacaa ctctataggt gtcataaatt aacaagccac cgtcccgcag ttctatcagg     180

tgtgctcgct accgaccatg tggtcccgtc tcagcaagcc actcacacgc ccatgatccc     240

ctagccttac gtcgacccgt atttagcaac cttggcacgt agtatttatt gtcccaaata     300

ttgagctgaa ctgcacctcc ctagaatccc gcggtgctaa cattctttca gcccgacagg     360

gtctctcgat ccatcccggg caacggcccg gtcacggacg tcactctcat cgacctgcag     420

tgcaacgcca attccacccc ggccaagctc cacgccactg ccgctgccgg ctcggacgtg     480

attctccgct ggacgctctg gcctgagtcg cacgttggcc ccgtcatcac ctacatggcc     540

cgctgccccg acacgggctg ccaggactgg atgccgggca cttcgtagga gcccatcttg     600

caccatatcc atttcaaccg gccacacgca ctgacccata tgtctgtcta cccctgcagt     660

gcggtctggt tcaagatcaa ggagggcggc cgcgacggca cttccaacac ctgggccgac     720

gtacgtgtac cccgtcccag agagccaaag cccccccttc aacaaagcaa acatctcaat     780

agcccgagcc tacgcactaa cccctctcct tccccctcga aaacacagac cccgctgatg     840

acggcgccca cctcgtacac gtacacgatc ccctcctgcc tgaagaaggg ctactacctg     900

gtccgccacg agatcatcgc gctgcacgcc gcctacacct accccggcgc gcagttctac     960

ccgggctgcc accagctcaa cgtcacgggc ggcgggtcca ccgtaccgtc gagcggcctg    1020

gtggcctttc ccggggcgta caagggcagt gaccccggga ttacgtacga tgcgtataaa    1080

ggtgggttgg ctggttggcc caggtcttgg tgatggggga atgtggtgat gaggtttatt    1140

atttgggatc ccgtggctaa cgtaaccctg ggtgtagcgc aaacgtacca gattcctggg    1200

ccggcggtct ttacttgctg a                                              1221


<210> SEQ ID NO 114
<211> LENGTH: 236
<212> TYPE: PRT
<213> ORGANISM: Thielavia terrestris

<400> SEQUENCE: 114

Met Lys Thr Phe Thr Ala Leu Leu Ala Ala Ala Gly Leu Val Ala Gly
1               5                   10                  15

His Gly Tyr Val Asp Asn Ala Thr Ile Gly Gly Gln Phe Tyr Gln Asn
            20                  25                  30

Pro Ala Val Leu Thr Phe Phe Gln Pro Asp Arg Val Ser Arg Ser Ile
        35                  40                  45

Pro Gly Asn Gly Pro Val Thr Asp Val Thr Leu Ile Asp Leu Gln Cys
    50                  55                  60

Asn Ala Asn Ser Thr Pro Ala Lys Leu His Ala Thr Ala Ala Ala Gly
65                  70                  75                  80
```

```
Ser Asp Val Ile Leu Arg Trp Thr Leu Trp Pro Glu Ser His Val Gly
                85                  90                  95

Pro Val Ile Thr Tyr Met Ala Arg Cys Pro Asp Thr Gly Cys Gln Asp
            100                 105                 110

Trp Met Pro Gly Thr Ser Ala Val Trp Phe Lys Ile Lys Glu Gly Gly
        115                 120                 125

Arg Asp Gly Thr Ser Asn Thr Trp Ala Asp Thr Pro Leu Met Thr Ala
    130                 135                 140

Pro Thr Ser Tyr Thr Tyr Thr Ile Pro Ser Cys Leu Lys Lys Gly Tyr
145                 150                 155                 160

Tyr Leu Val Arg His Glu Ile Ile Ala Leu His Ala Ala Tyr Thr Tyr
                165                 170                 175

Pro Gly Ala Gln Phe Tyr Pro Gly Cys His Gln Leu Asn Val Thr Gly
            180                 185                 190

Gly Gly Ser Thr Val Pro Ser Ser Gly Leu Val Ala Phe Pro Gly Ala
        195                 200                 205

Tyr Lys Gly Ser Asp Pro Gly Ile Thr Tyr Asp Ala Tyr Lys Ala Gln
    210                 215                 220

Thr Tyr Gln Ile Pro Gly Pro Ala Val Phe Thr Cys
225                 230                 235
```

<210> SEQ ID NO 115
<211> LENGTH: 933
<212> TYPE: DNA
<213> ORGANISM: Thielavia terrestris

<400> SEQUENCE: 115

```
atggccttgc tgctcttggc aggcttggcc attctggccg ggccggctca tgcccacggc      60

ggcctcgcca actacacagt gggcaacacc tggtataggg ggtgcgtaag gggggcaccg     120

acaacgcctg cttagtaact ccaccatttc gagcgggcta acaccgggcg cagctacgac     180

cccttcacgc cggcggccga ccagatcggc cagccgtgga tgatccaacg cgcgtgggac     240

tcgatcgacc cgatcttcag cgtcaacgac aaggcgctcg cctgcaacac cccggccacg     300

gcgccgacct cttacattcc catccgcgcg ggcgagaaca tcacggccgt gtactggtac     360

tggctgcacc cggtgggccc catgacggcg tggctggcgc ggtgcgacgg cgactgccgc     420

gacgccgacg tcaacgaggc gcgctggttc aagatctggg aggccggcct gctcagcggg     480

ccgaacctgg ccgagggcat gtggtaccag aaggcgttcc agaactggga cggcagcccg     540

gacctgtggc ccgtcacgat cccggccggg ctgaagagcg gcctgtacat gatccggcac     600

gagatcttgt cgatccacgt cgaggataaa ccgcagtttt atcccgagtg tgcgcatctg     660

aatgtgaccg gggtggggga cctgctgccg cctgatgagt tttggtgaa gttcccgggc      720

gcttacaaag aagatagtga gtgaaacgcg aagcttcggt agccattggg ttgcgctgat     780

ggaggttaga cccgtcgatc aagatcaata tctactcgga ccagtacgcc aatacaacgg     840

tgagtgtaac aggtcgagca aaaccaaaca gatgccgatg actgatgatc tcagaattac     900

acaattcccg gagggccgat atgggatggg tga                                  933
```

<210> SEQ ID NO 116
<211> LENGTH: 250
<212> TYPE: PRT
<213> ORGANISM: Thielavia terrestris

<400> SEQUENCE: 116

```
Met Ala Leu Leu Leu Leu Ala Gly Leu Ala Ile Leu Ala Gly Pro Ala
```

```
1               5                   10                  15

His Ala His Gly Gly Leu Ala Asn Tyr Thr Val Gly Asn Thr Trp Tyr
            20                  25                  30

Arg Gly Tyr Asp Pro Phe Thr Pro Ala Ala Asp Gln Ile Gly Gln Pro
        35                  40                  45

Trp Met Ile Gln Arg Ala Trp Asp Ser Ile Asp Pro Ile Phe Ser Val
    50                  55                  60

Asn Asp Lys Ala Leu Ala Cys Asn Thr Pro Ala Thr Ala Pro Thr Ser
65                  70                  75                  80

Tyr Ile Pro Ile Arg Ala Gly Glu Asn Ile Thr Ala Val Tyr Trp Tyr
                85                  90                  95

Trp Leu His Pro Val Gly Pro Met Thr Ala Trp Leu Ala Arg Cys Asp
            100                 105                 110

Gly Asp Cys Arg Asp Ala Asp Val Asn Glu Ala Arg Trp Phe Lys Ile
        115                 120                 125

Trp Glu Ala Gly Leu Leu Ser Gly Pro Asn Leu Ala Glu Gly Met Trp
    130                 135                 140

Tyr Gln Lys Ala Phe Gln Asn Trp Asp Gly Ser Pro Asp Leu Trp Pro
145                 150                 155                 160

Val Thr Ile Pro Ala Gly Leu Lys Ser Gly Leu Tyr Met Ile Arg His
                165                 170                 175

Glu Ile Leu Ser Ile His Val Glu Asp Lys Pro Gln Phe Tyr Pro Glu
            180                 185                 190

Cys Ala His Leu Asn Val Thr Gly Gly Gly Asp Leu Leu Pro Pro Asp
        195                 200                 205

Glu Phe Leu Val Lys Phe Pro Gly Ala Tyr Lys Glu Asp Asn Pro Ser
    210                 215                 220

Ile Lys Ile Asn Ile Tyr Ser Asp Gln Tyr Ala Asn Thr Thr Asn Tyr
225                 230                 235                 240

Thr Ile Pro Gly Gly Pro Ile Trp Asp Gly
                245                 250
```

<210> SEQ ID NO 117
<211> LENGTH: 1584
<212> TYPE: DNA
<213> ORGANISM: Thielavia terrestris

<400> SEQUENCE: 117

```
atgatgccgt cccttgttcg cttctcaatg ggtctggcga ccgccttcgc ctcgctgtcc     60

acagcacata ccgtcttcac cacgcttttc atcaacggcg tcgaccaagg ggacgggacc    120

tgcatccgca tggccaagaa gggcagcgtt tgcacccatc ccattgctgg tggcctcgac    180

agcccagaca tggcttgtgg tatgccctct gcgtttcccc tgcgagagct ttcctcgagc    240

taacccaatg ccgcgttgcc caggccgaga cggacaacaa gccgtggcat tcacctgccc    300

agccccggcg ggctccaagt tgagcttcga gttccgcatg tgggccgacg cctctcagcc    360

cggctctatc gacccatccc acctcggctc gacggcaatc tacctcaaac aagtctccaa    420

catcagctcc gactcggctg ccggccctgg ctggttcaag atctacgccg agggctacga    480

cacagccgcc aagaagtggg ccacagagaa gctcatcgac aacggcggcc tgctgagcat    540

cgagcttccg cccactctgc cggcgggata ctacctcgcc cgcagcgaga tcgtcaccat    600

ccagaacgtc accaacgacc acgtcgaccc gcagttctac gttggctgcg cacagctctt    660

cgtccagggg cctccgacca cccccaccgt cccgccagac agactcgtct ccatcccggg    720
```

```
ccacgtccat gcctccgacc cggggctgac cttcaacatc tggcgcgacg acccctccaa    780

gacggcctac accgtcgtcg gcccggcccc cttctccccc accgccgccc ccaccccac     840

ctccaccaac accaacgggc agcaacaaca acaacagcaa caggcgataa agcagacgga    900

cggcgtgatc cccgccgact gccagctcaa gaacgccaac tggtgcggcg ccgaggtgcc    960

cgcgtacgcc gacgaggccg gctgctgggc gtcgtcggcc gactgcttcg cccagctgga   1020

cgcctgctac acgtcggcgc cgcccacggg cagccgcggc tgccggctgt gggaggactg   1080

gtgcaccggc attcagcagg gctgccgcgc ggggcggtgg cgggggccgc cgccctttca   1140

tggggagggg gcagcagcgg aggtgtgaac ggttcgggga cgggtggcgg tggtggtggt   1200

ggtggtggtg gcactggctc ttcttcggct tctgccccga cggagacggc ctctgctggc   1260

cggggggcg caagaatagc tgccgtggcc ggctgcggag gcgggacagg agacatggtt    1320

gaagaggttt tcctctttta ttgggacgct tgcagcggct ggcgacggag ccgtggtggt   1380

ggttcgattc ttgcgaggct tatccttcat gtccttcttc cacttttgag accgaggcga   1440

gcccctcgag tccatttact tctcttccac ctgtacctca acttctgtta tccaggaacc   1500

agtggtttct ataatcgcct gagcattaaa ctaggcatat ggccaagcaa aatgtcgcct   1560

gatgtagcgc attacgtgaa ataa                                          1584
```

<210> SEQ ID NO 118
<211> LENGTH: 478
<212> TYPE: PRT
<213> ORGANISM: Thielavia terrestris

<400> SEQUENCE: 118

```
Met Met Pro Ser Leu Val Arg Phe Ser Met Gly Leu Ala Thr Ala Phe
1               5                   10                  15

Ala Ser Leu Ser Thr Ala His Thr Val Phe Thr Thr Leu Phe Ile Asn
            20                  25                  30

Gly Val Asp Gln Gly Asp Gly Thr Cys Ile Arg Met Ala Lys Lys Gly
        35                  40                  45

Ser Val Cys Thr His Pro Ile Ala Gly Gly Leu Asp Ser Pro Asp Met
    50                  55                  60

Ala Cys Gly Arg Asp Gly Gln Gln Ala Val Ala Phe Thr Cys Pro Ala
65                  70                  75                  80

Pro Ala Gly Ser Lys Leu Ser Phe Glu Phe Arg Met Trp Ala Asp Ala
                85                  90                  95

Ser Gln Pro Gly Ser Ile Asp Pro Ser His Leu Gly Ser Thr Ala Ile
            100                 105                 110

Tyr Leu Lys Gln Val Ser Asn Ile Ser Ser Asp Ser Ala Ala Gly Pro
        115                 120                 125

Gly Trp Phe Lys Ile Tyr Ala Glu Gly Tyr Asp Thr Ala Ala Lys Lys
    130                 135                 140

Trp Ala Thr Glu Lys Leu Ile Asp Asn Gly Gly Leu Leu Ser Ile Glu
145                 150                 155                 160

Leu Pro Pro Thr Leu Pro Ala Gly Tyr Tyr Leu Ala Arg Ser Glu Ile
                165                 170                 175

Val Thr Ile Gln Asn Val Thr Asn Asp His Val Asp Pro Gln Phe Tyr
            180                 185                 190

Val Gly Cys Ala Gln Leu Phe Val Gln Gly Pro Pro Thr Thr Pro Thr
        195                 200                 205

Val Pro Pro Asp Arg Leu Val Ser Ile Pro Gly His Val His Ala Ser
    210                 215                 220
```

```
Asp Pro Gly Leu Thr Phe Asn Ile Trp Arg Asp Asp Pro Ser Lys Thr
225                 230                 235                 240

Ala Tyr Thr Val Val Gly Pro Ala Pro Phe Ser Pro Thr Ala Ala Pro
                245                 250                 255

Thr Pro Thr Ser Thr Asn Thr Asn Gly Gln Gln Gln Gln Gln Gln Gln
            260                 265                 270

Gln Ala Ile Lys Gln Thr Asp Gly Val Ile Pro Ala Asp Cys Gln Leu
        275                 280                 285

Lys Asn Ala Asn Trp Cys Gly Ala Glu Val Pro Ala Tyr Ala Asp Glu
    290                 295                 300

Ala Gly Cys Trp Ala Ser Ser Ala Asp Cys Phe Ala Gln Leu Asp Ala
305                 310                 315                 320

Cys Tyr Thr Ser Ala Pro Pro Thr Gly Ser Arg Gly Cys Arg Leu Trp
                325                 330                 335

Glu Asp Trp Cys Thr Gly Ile Gln Gln Gly Cys Arg Ala Gly Arg Trp
            340                 345                 350

Arg Gly Pro Pro Pro Phe His Gly Glu Gly Ala Ala Ala Glu Thr Ala
        355                 360                 365

Ser Ala Gly Arg Gly Gly Ala Arg Ile Ala Ala Val Ala Gly Cys Gly
    370                 375                 380

Gly Gly Thr Gly Asp Met Val Glu Glu Val Phe Leu Phe Tyr Trp Asp
385                 390                 395                 400

Ala Cys Ser Gly Trp Arg Arg Ser Arg Gly Gly Gly Ser Ile Leu Ala
                405                 410                 415

Arg Leu Ile Leu His Val Leu Leu Pro Leu Leu Arg Pro Arg Arg Ala
            420                 425                 430

Pro Arg Val His Leu Leu Leu Phe His Leu Tyr Leu Asn Phe Cys Tyr
        435                 440                 445

Pro Gly Thr Ser Gly Phe Tyr Asn Arg Leu Ser Ile Lys Leu Gly Ile
    450                 455                 460

Trp Pro Ser Lys Met Ser Pro Asp Val Ala His Tyr Val Lys
465                 470                 475
```

<210> SEQ ID NO 119
<211> LENGTH: 868
<212> TYPE: DNA
<213> ORGANISM: Thielavia terrestris

<400> SEQUENCE: 119

```
atgcagctcc tcgtgggctt gctgcttgca gccgtggctg ctcgagcaca ttgtatttct     60

acccctttcc gcgtgcctcc cagcctcaag gcaagaagac gcacgcagca gctaacggac    120

cctatcagac acatttccca gactcgtggt aaatgggcag cccgaggaca aggactggtc    180

ggttacgcgc atgaccaaga acgcgcagag caagcaggga gtccaggacc cgaccagtcc    240

cgacattcgc tgctacacgt cgcagacggc gcctaacgtg gctacggtcc ctgccggagc    300

caccgtccat tacatatcga ctcagcagat caaccacccg ggcccgacgc agtactacct    360

cgccaaggta ccggcggggt cgtcggccaa gacgtgggac gggtcagggg ccgtctggtt    420

caagatctcg accaccatgc cttacttgga caacaacaag cagcttgtct ggccgaatca    480

gagtaggaac aattcccgct ccaatcttcg atttggcctt gagctacggc cgattgcatg    540

ggagagaccg ttgactgacg gggcaaccca accttcatca gacacgtaca cgacggtcaa    600

cacgaccatc cccgccgata cgcccagtgg ggaatacctc ctccgggtcg agcagatcgc    660
```

```
gctgcacctg gcctcgcagc ccaacggggc tcagttctac ctggcctgct cgcagatcca    720

gattacgggc ggcggcaacg gcacgcccgg cccgctagtc gcgttgccgg gggcgtacaa    780

gagcaacgac ccgggcattt tggtcaacat ctactctatg cagcccggcg attacaagcc    840

gcccgggccg ccggtgtgga gtggctga                                       868


<210> SEQ ID NO 120
<211> LENGTH: 230
<212> TYPE: PRT
<213> ORGANISM: Thielavia terrestris

<400> SEQUENCE: 120

Met Gln Leu Leu Val Gly Leu Leu Leu Ala Ala Val Ala Ala Arg Ala
1               5                   10                  15

His Tyr Thr Phe Pro Arg Leu Val Val Asn Gly Gln Pro Glu Asp Lys
            20                  25                  30

Asp Trp Ser Val Thr Arg Met Thr Lys Asn Ala Gln Ser Lys Gln Gly
        35                  40                  45

Val Gln Asp Pro Thr Ser Pro Asp Ile Arg Cys Tyr Thr Ser Gln Thr
    50                  55                  60

Ala Pro Asn Val Ala Thr Val Pro Ala Gly Ala Thr Val His Tyr Ile
65                  70                  75                  80

Ser Thr Gln Gln Ile Asn His Pro Gly Pro Thr Gln Tyr Tyr Leu Ala
                85                  90                  95

Lys Val Pro Ala Gly Ser Ser Ala Lys Thr Trp Asp Gly Ser Gly Ala
            100                 105                 110

Val Trp Phe Lys Ile Ser Thr Thr Met Pro Tyr Leu Asp Asn Asn Lys
        115                 120                 125

Gln Leu Val Trp Pro Asn Gln Asn Thr Tyr Thr Thr Val Asn Thr Thr
    130                 135                 140

Ile Pro Ala Asp Thr Pro Ser Gly Glu Tyr Leu Leu Arg Val Glu Gln
145                 150                 155                 160

Ile Ala Leu His Leu Ala Ser Gln Pro Asn Gly Ala Gln Phe Tyr Leu
                165                 170                 175

Ala Cys Ser Gln Ile Gln Ile Thr Gly Gly Gly Asn Gly Thr Pro Gly
            180                 185                 190

Pro Leu Val Ala Leu Pro Gly Ala Tyr Lys Ser Asn Asp Pro Gly Ile
        195                 200                 205

Leu Val Asn Ile Tyr Ser Met Gln Pro Gly Asp Tyr Lys Pro Pro Gly
    210                 215                 220

Pro Pro Val Trp Ser Gly
225                 230


<210> SEQ ID NO 121
<211> LENGTH: 1068
<212> TYPE: DNA
<213> ORGANISM: Thielavia terrestris

<400> SEQUENCE: 121

atgaagctgt acctggcggc ctttctaggc gccgtcgcca ccccgggagc gttcgctcat     60

cgtaggttcc ccgtctatct ccctaggggt agcaccacga ctaatttctc gtcgtccccc    120

tgtagaaatc cacgggattc tacttgtcaa cggcaccgaa acgccggaat ggaaatacgt    180

ccggtaatat ctaccttgct ctccttcttc cacaaccagc ctaacacatc atcagtgacg    240

tggcctggga gggcgcctac gaaccggaaa aatacccccaa caccgagttc tttaagacgc    300
```

```
ccccgcagac ggacatcaac aacccgaaca tcacctgcgg caggaacgcg ttcgactcgg    360

ccagcaagac tgagacggcc gacatactgg ccggctcaga ggtcggcttc cgcgtctcgt    420

gggacggcaa cggcaagtac ggcgtgttct ggcatcccgg gccggggcag atctacctct    480

ctcgtgctcc gaacgacgac ctggaggact accgcggcga cggagactgg ttcaagatcg    540

caaccggcgc cgccgtctcc aataccgagt ggctgctgtg gaacaagcat gacgtgagcc    600

ccaacattcc tcgcccaatc gatccccaac ctggtcacca tggcggcgtc cgggatgcaa    660

agagactaac tccagaggaa cctacctagt tcaacttcac catccccaag acgacgccgc    720

cgggcaagta cctgatgcgc atcgagcagt tcatgccctc cacggtcgaa tacagccagt    780

ggtacgtcaa ctgcgcccac gtcaacatca tcggccccgg cggaggcacg ccgacgggct    840

ttgccaggtt tcccggcacc tacactgttg acgatcccgg taagccggac ctaccggaca    900

cagaggcctc gggatagctt gctaaccttg tttgctctct ctctttttct ctcccgacta    960

ggcatcaagg tgccgttgaa ccagatcgtc aacagcggag agttgccgca ggaccaactg   1020

aggctgctcg agtacaagcc cccgggccca gcgctgtgga ctggttga                1068
```

```
<210> SEQ ID NO 122
<211> LENGTH: 257
<212> TYPE: PRT
<213> ORGANISM: Thielavia terrestris

<400> SEQUENCE: 122

Met Lys Leu Tyr Leu Ala Ala Phe Leu Gly Ala Val Ala Thr Pro Gly
1               5                   10                  15

Ala Phe Ala His Gln Ile His Gly Ile Leu Leu Val Asn Gly Thr Glu
            20                  25                  30

Thr Pro Glu Trp Lys Tyr Val Arg Asp Val Ala Trp Glu Gly Ala Tyr
        35                  40                  45

Glu Pro Glu Lys Tyr Pro Asn Thr Glu Phe Phe Lys Thr Pro Pro Gln
    50                  55                  60

Thr Asp Ile Asn Asn Pro Asn Ile Thr Cys Gly Arg Asn Ala Phe Asp
65                  70                  75                  80

Ser Ala Ser Lys Thr Glu Thr Ala Asp Ile Leu Ala Gly Ser Glu Val
                85                  90                  95

Gly Phe Arg Val Ser Trp Asp Gly Asn Gly Lys Tyr Gly Val Phe Trp
            100                 105                 110

His Pro Gly Pro Gly Gln Ile Tyr Leu Ser Arg Ala Pro Asn Asp Asp
        115                 120                 125

Leu Glu Asp Tyr Arg Gly Asp Gly Asp Trp Phe Lys Ile Ala Thr Gly
    130                 135                 140

Ala Ala Val Ser Asn Thr Glu Trp Leu Leu Trp Asn Lys His Asp Phe
145                 150                 155                 160

Asn Phe Thr Ile Pro Lys Thr Thr Pro Pro Gly Lys Tyr Leu Met Arg
                165                 170                 175

Ile Glu Gln Phe Met Pro Ser Thr Val Glu Tyr Ser Gln Trp Tyr Val
            180                 185                 190

Asn Cys Ala His Val Asn Ile Ile Gly Pro Gly Gly Gly Thr Pro Thr
        195                 200                 205

Gly Phe Ala Arg Phe Pro Gly Thr Tyr Thr Val Asp Asp Pro Gly Ile
    210                 215                 220

Lys Val Pro Leu Asn Gln Ile Val Asn Ser Gly Glu Leu Pro Gln Asp
225                 230                 235                 240
```

```
Gln Leu Arg Leu Leu Glu Tyr Lys Pro Pro Gly Pro Ala Leu Trp Thr
                245                 250                 255

Gly


<210> SEQ ID NO 123
<211> LENGTH: 871
<212> TYPE: DNA
<213> ORGANISM: Thermoascus crustaceus

<400> SEQUENCE: 123

atggcctttt cccagataat ggctattacc ggcgtttttc ttgcctctgc ttccctggtg      60

gctggccatg gctttgttca gaatatcgtg attgatggta aaaggtacct aactacctac     120

cttactatct gatgtcattt acaagaaagg gcacagacac aagcggcaaa aaaaagaaag     180

aaagaaagaa agaaaagaaag ctgacaaaaa ttcaacaagt tatggcgggt acatcgtgaa     240

ccaatatcca tacatgtcag atcctccgga ggtcgtcggc tggtctacca ccgcaaccga     300

cctcggattc gtggacggta ccggatacca aggacctgat atcatctgcc acaggggcgc     360

caagcctgca gccctgactg cccaagtggc cgccggagga accgtcaagc tggaatggac     420

tccatggcct gattctcacc acggcccggt gatcaactac cttgctcctt gcaacggtga     480

ctgttccacc gtggacaaga cccaattgaa attcttcaag atcgcccagg ccggtctcat     540

cgatgacaac agtcctcctg gtatctgggc ctcagacaat ctgatagcgg ccaacaacag     600

ctggactgtc accatcccaa ccacaactgc acctggaaac tatgttctaa ggcatgagat     660

cattgctctc cactcagctg ggaacaagga tggtgcgcag aactatcccc agtgcatcaa     720

cctgaaggtc actggaaatg gttctggcaa tcctcctgct ggtgctcttg gaacggcact     780

ctacaaggat acagatccgg gaattctgat caatatctac cagaaacttt ccagctatgt     840

tattcctggt cctgctttgt acactggtta g                                    871


<210> SEQ ID NO 124
<211> LENGTH: 251
<212> TYPE: PRT
<213> ORGANISM: Thermoascus crustaceus

<400> SEQUENCE: 124

Met Ala Phe Ser Gln Ile Met Ala Ile Thr Gly Val Phe Leu Ala Ser
1               5                   10                  15

Ala Ser Leu Val Ala Gly His Gly Phe Val Gln Asn Ile Val Ile Asp
            20                  25                  30

Gly Lys Ser Tyr Gly Gly Tyr Ile Val Asn Gln Tyr Pro Tyr Met Ser
        35                  40                  45

Asp Pro Pro Glu Val Val Gly Trp Ser Thr Thr Ala Thr Asp Leu Gly
    50                  55                  60

Phe Val Asp Gly Thr Gly Tyr Gln Gly Pro Asp Ile Ile Cys His Arg
65                  70                  75                  80

Gly Ala Lys Pro Ala Ala Leu Thr Ala Gln Val Ala Ala Gly Gly Thr
                85                  90                  95

Val Lys Leu Glu Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
        115                 120                 125

Thr Gln Leu Lys Phe Phe Lys Ile Ala Gln Ala Gly Leu Ile Asp Asp
    130                 135                 140

Asn Ser Pro Pro Gly Ile Trp Ala Ser Asp Asn Leu Ile Ala Ala Asn
```

```
145                 150                 155                 160

Asn Ser Trp Thr Val Thr Ile Pro Thr Thr Thr Ala Pro Gly Asn Tyr
                165                 170                 175

Val Leu Arg His Glu Ile Ile Ala Leu His Ser Ala Gly Asn Lys Asp
            180                 185                 190

Gly Ala Gln Asn Tyr Pro Gln Cys Ile Asn Leu Lys Val Thr Gly Asn
        195                 200                 205

Gly Ser Gly Asn Pro Pro Ala Gly Ala Leu Gly Thr Ala Leu Tyr Lys
    210                 215                 220

Asp Thr Asp Pro Gly Ile Leu Ile Asn Ile Tyr Gln Lys Leu Ser Ser
225                 230                 235                 240

Tyr Val Ile Pro Gly Pro Ala Leu Tyr Thr Gly
                245                 250


<210> SEQ ID NO 125
<211> LENGTH: 1102
<212> TYPE: DNA
<213> ORGANISM: Thermoascus crustaceus

<400> SEQUENCE: 125

atgtcattct cgaagatact tgctatcgct ggggccatta cctacgcatc ttcagctgcc      60

gctcatggtt atgtccaggg aattgttgtc gatggcagct agtatgtcac tctggatgga     120

accttcagca cgtactgtac taacaatcag cagctacggg ggatatatgg tgacccaata     180

tccctacacc gctcaacctc cggaactcat cgcctggtcc actaaagcaa ccgatcttgg     240

gtttgtggac ggcagtggct atacttctcc tgatatcatc tgccataagg gtgctgagcc     300

tggtgcccag agcgccaaag tggcagctgg agggaccgtt gagctgcagt ggacggcatg     360

gcccgagtct cacaagggcc cagttattga ctacctcgcc gcctgcgacg gggactgctc     420

atctgttgat aagactgcac taaagttctt taagattgac gagagtggtc tgattgacgg     480

caacggtgct ggaacatggg cctctgatac gttgatcaaa aataacaaca gctggactgt     540

caccatccca agcacaattg cttccggaaa ctacgtacta agacacgaaa taattgcgct     600

ccattctgcc ggaaacaaag atggtgctca gaactatccc cagtgtatca acctcgaggt     660

cactggtagt ggcaccgaaa accctgctgg cactctcgga acagcgcttt acacagacac     720

tgatcctggc cttctggtca acatctacca gggtctgtcc aactattcaa tccctggtcc     780

tgctctgtat agcggcaaca gtgataacgc tggttccctc aaccctacca ccacgccgtc     840

aattcagaat gctgctgctg ctccctccac ttccacagca tctgttgtca ctgattcttc     900

gtcagccacc cagactgcta gtgtcgccgc cacgactcca gcctccactt cggctgttac     960

agcctcacca gctcccgata ctggaagcga cgtaaccaaa tatctggatt cgatgagctc    1020

ggatgaggtc ctcaccctgg tgcgcgggac cctgtcttgg ctggtttcta acaagaaaca    1080

tgcgcgggat ctttctcact ga                                             1102


<210> SEQ ID NO 126
<211> LENGTH: 349
<212> TYPE: PRT
<213> ORGANISM: Thermoascus crustaceus

<400> SEQUENCE: 126

Met Ser Phe Ser Lys Ile Leu Ala Ile Ala Gly Ala Ile Thr Tyr Ala
1               5                   10                  15

Ser Ser Ala Ala Ala His Gly Tyr Val Gln Gly Ile Val Val Asp Gly
            20                  25                  30
```

-continued

```
Ser Tyr Tyr Gly Gly Tyr Met Val Thr Gln Tyr Pro Tyr Thr Ala Gln
        35                  40                  45

Pro Pro Glu Leu Ile Ala Trp Ser Thr Lys Ala Thr Asp Leu Gly Phe
    50                  55                  60

Val Asp Gly Ser Gly Tyr Thr Ser Pro Asp Ile Ile Cys His Lys Gly
65                  70                  75                  80

Ala Glu Pro Gly Ala Gln Ser Ala Lys Val Ala Ala Gly Gly Thr Val
                85                  90                  95

Glu Leu Gln Trp Thr Ala Trp Pro Glu Ser His Lys Gly Pro Val Ile
            100                 105                 110

Asp Tyr Leu Ala Ala Cys Asp Gly Asp Cys Ser Ser Val Asp Lys Thr
        115                 120                 125

Ala Leu Lys Phe Phe Lys Ile Asp Glu Ser Gly Leu Ile Asp Gly Asn
    130                 135                 140

Gly Ala Gly Thr Trp Ala Ser Asp Thr Leu Ile Lys Asn Asn Asn Ser
145                 150                 155                 160

Trp Thr Val Thr Ile Pro Ser Thr Ile Ala Ser Gly Asn Tyr Val Leu
                165                 170                 175

Arg His Glu Ile Ile Ala Leu His Ser Ala Gly Asn Lys Asp Gly Ala
            180                 185                 190

Gln Asn Tyr Pro Gln Cys Ile Asn Leu Glu Val Thr Gly Ser Gly Thr
        195                 200                 205

Glu Asn Pro Ala Gly Thr Leu Gly Thr Ala Leu Tyr Thr Asp Thr Asp
    210                 215                 220

Pro Gly Leu Leu Val Asn Ile Tyr Gln Gly Leu Ser Asn Tyr Ser Ile
225                 230                 235                 240

Pro Gly Pro Ala Leu Tyr Ser Gly Asn Ser Asp Asn Ala Gly Ser Leu
                245                 250                 255

Asn Pro Thr Thr Thr Pro Ser Ile Gln Asn Ala Ala Ala Ala Pro Ser
            260                 265                 270

Thr Ser Thr Ala Ser Val Val Thr Asp Ser Ser Ser Ala Thr Gln Thr
        275                 280                 285

Ala Ser Val Ala Ala Thr Thr Pro Ala Ser Thr Ser Ala Val Thr Ala
    290                 295                 300

Ser Pro Ala Pro Asp Thr Gly Ser Asp Val Thr Lys Tyr Leu Asp Ser
305                 310                 315                 320

Met Ser Ser Asp Glu Val Leu Thr Leu Val Arg Gly Thr Leu Ser Trp
                325                 330                 335

Leu Val Ser Asn Lys Lys His Ala Arg Asp Leu Ser His
            340                 345
```

```
<210> SEQ ID NO 127
<211> LENGTH: 1493
<212> TYPE: DNA
<213> ORGANISM: Thermoascus crustaceus

<400> SEQUENCE: 127

atgttgtcat tcattcccac caagtcagct gcgctgacga ctcttctact tcttggaaca      60

gctcatgctc acactttgat gaccaccatg tttgtggacg gcgtcaacca gggagatggt     120

gtctgcattc gcatgaacaa tgacggcgga actgccaata cctatatcca gcctatcacg     180

agcaaggata tcgcctgcgg taagtaccca gatgtcatca tactctgcca taacatccgt     240

catatctact agaatcggag caatgttaag tatttccagg catccaaggc gaaatcggcg     300
```

```
cctcccgagt ctgcccagtc aaggcatctt ccaccctaac cttccaattc cgcgagcaac    360

ccaacaaccc aaactcctcc cctctcgatc catcgcacaa aggccccgcc gcggtgtacc    420

tgaaaaaggt cgactccgcc atcgcgagca acaacgccgc cggagacagc tggttcaaga    480

tctgggagtc cgtctacgac gagtccacgg gcaaatgggg cacgaccaag atgatcgaga    540

acaacgggca catctccgtc aaggtgcccg atgatatcga gggtggttac tatcttgccc    600

ggacggagct gctggcgcta cattctgcgg atcaggggga tccgcagttc tatgttggct    660

gtgcgcagct gtttatcgat tcggatggga cggcgaaacc gcccactgtt tctattggag    720

aggggacgta cgatctgagc atgcctgcca tgacgtataa tatctgggag acaccgttgg    780

ctctgccgta tccgatgtat gggcctcctg tctatacgcc tggctctggt tctggatcag    840

tccgtgcgac gagctcttct gctgtcccta ctgcaaccga atcctctttt gtagaggaaa    900

gagcaaaccc cgtcacggca aacagtgttt attctgcaag ggcaaattc aaaacctgga     960

ttgataaact gtcatggcgc gggaaggtcc gtgagaacgt cagacaagcc gcgggaagaa   1020

gaagcactct cgtccagact gtgggtctaa agccaaaagg ctgcatcttc gtcaatggaa   1080

actggtgcgg cttcgaggtt cccgactaca acgatgcgga gagctgctgg gctgtatgtt   1140

cccctcctta gcctcttaca tccctaagta ctacatttga aaacaacaaa aagaaatgta   1200

tatactaact acgtacgctc tactctaggc ctccgacaac tgctggaaac agtccgacgc   1260

ctgctggaac aagacccaac ccacgggcta caataactgc cagatctggc aggacaagaa   1320

atgcaaggtc atccaggatt cctgtagcgg acccaacccg catggaccac cgaataaggg   1380

caaggatttg actccggagt ggccgccact gaagggctcg atggatacgt tctccaagcg   1440

tactatcggt taccgcgatt ggattgttag aaggagaggt gcatgagggt gta          1493
```

<210> SEQ ID NO 128
<211> LENGTH: 436
<212> TYPE: PRT
<213> ORGANISM: Thermoascus crustaceus

<400> SEQUENCE: 128

```
Met Leu Ser Phe Ile Pro Thr Lys Ser Ala Ala Leu Thr Thr Leu Leu
1               5                   10                  15

Leu Leu Gly Thr Ala His Ala His Thr Leu Met Thr Thr Met Phe Val
            20                  25                  30

Asp Gly Val Asn Gln Gly Asp Gly Val Cys Ile Arg Met Asn Asn Asp
        35                  40                  45

Gly Gly Thr Ala Asn Thr Tyr Ile Gln Pro Ile Thr Ser Lys Asp Ile
    50                  55                  60

Ala Cys Gly Ile Gln Gly Glu Ile Gly Ala Ser Arg Val Cys Pro Val
65                  70                  75                  80

Lys Ala Ser Ser Thr Leu Thr Phe Gln Phe Arg Glu Gln Pro Asn Asn
                85                  90                  95

Pro Asn Ser Ser Pro Leu Asp Pro Ser His Lys Gly Pro Ala Ala Val
            100                 105                 110

Tyr Leu Lys Lys Val Asp Ser Ala Ile Ala Ser Asn Asn Ala Ala Gly
        115                 120                 125

Asp Ser Trp Phe Lys Ile Trp Glu Ser Val Tyr Asp Glu Ser Thr Gly
    130                 135                 140

Lys Trp Gly Thr Thr Lys Met Ile Glu Asn Asn Gly His Ile Ser Val
145                 150                 155                 160

Lys Val Pro Asp Asp Ile Glu Gly Gly Tyr Tyr Leu Ala Arg Thr Glu
```

```
                165                 170                 175

Leu Leu Ala Leu His Ser Ala Asp Gln Gly Asp Pro Gln Phe Tyr Val
            180                 185                 190

Gly Cys Ala Gln Leu Phe Ile Asp Ser Asp Gly Thr Ala Lys Pro Pro
        195                 200                 205

Thr Val Ser Ile Gly Glu Gly Thr Tyr Asp Leu Ser Met Pro Ala Met
    210                 215                 220

Thr Tyr Asn Ile Trp Glu Thr Pro Leu Ala Leu Pro Tyr Pro Met Tyr
225                 230                 235                 240

Gly Pro Pro Val Tyr Thr Pro Gly Ser Gly Ser Gly Ser Val Arg Ala
                245                 250                 255

Thr Ser Ser Ser Ala Val Pro Thr Ala Thr Glu Ser Ser Phe Val Glu
            260                 265                 270

Glu Arg Ala Asn Pro Val Thr Ala Asn Ser Val Tyr Ser Ala Arg Gly
        275                 280                 285

Lys Phe Lys Thr Trp Ile Asp Lys Leu Ser Trp Arg Gly Lys Val Arg
    290                 295                 300

Glu Asn Val Arg Gln Ala Ala Gly Arg Arg Ser Thr Leu Val Gln Thr
305                 310                 315                 320

Val Gly Leu Lys Pro Lys Gly Cys Ile Phe Val Asn Gly Asn Trp Cys
                325                 330                 335

Gly Phe Glu Val Pro Asp Tyr Asn Asp Ala Glu Ser Cys Trp Ala Ala
            340                 345                 350

Ser Asp Asn Cys Trp Lys Gln Ser Asp Ala Cys Trp Asn Lys Thr Gln
        355                 360                 365

Pro Thr Gly Tyr Asn Asn Cys Gln Ile Trp Gln Asp Lys Lys Cys Lys
    370                 375                 380

Val Ile Gln Asp Ser Cys Ser Gly Pro Asn Pro His Gly Pro Pro Asn
385                 390                 395                 400

Lys Gly Lys Asp Leu Thr Pro Glu Trp Pro Pro Leu Lys Gly Ser Met
                405                 410                 415

Asp Thr Phe Ser Lys Arg Thr Ile Gly Tyr Arg Asp Trp Ile Val Arg
            420                 425                 430

Arg Arg Gly Ala
        435
```

<210> SEQ ID NO 129
<211> LENGTH: 1035
<212> TYPE: DNA
<213> ORGANISM: Aspergillus aculeatus

<400> SEQUENCE: 129

```
atgaagtata ttcctctcgt tattgcagtt gctgccggcc tggcacgtcc ggctactgcc     60

cactacatct tcagcaagct cgtgctgaac ggagaggcat ctgcggactg gcaatacatc    120

cgcgagacta ctcgcagcat agtctatgag ccgaccaagt acacctctac cttcgataac    180

ctaacaccca gcgatagcga cttccgctgt aatctcggtt ccttcagcaa tgctgcgaag    240

accgaggtcg ctgaggttgc ggcaggcgat accatcgcaa tgaagctatt ctacgacacc    300

agtattgcgc atcctggccc gggacaagtt tatatgtcca aggcaccgac cggcaatgtt    360

caggaatacc aaggagacgg ggattggttc aaaatctggg aaaagaccct ttgcaacacg    420

gatggtgatc tgactacaga ggcctggtgc acctggggca tgtcacagtt tgaatttcaa    480

atcccagctg cgaccccggc aggagagtac ctagtgcgcg ccgagcatat aggcctgcat    540
```

```
ggcgctcaag cgaacgaggc cgaattcttc tacagctgtg cgcagatcaa ggttacaggc    600

tcgggaactg gatctcccag tctcacgtat caaattcctg gtctctataa cgacactatg    660

accctgttca atggcctcaa tctttggact gattcagccg agaaggtgca gctggatttc    720

ctggagacgc caattgggga cgacgtgtgg agcggagcag gctcggggag cccatctgct    780

gccacctctt cgaccagcgg tgcaactctt gcagctcagg gtacaactac ctctgccgcg    840

catgctcagg cccagaccac cattaccacc agcaccagca ccatcacgtc tctcgaatca    900

gccagctcaa ccgatctcgt tgcgcagtat ggtcagtgcg gaggccttaa ctggtccggt    960

ccaaccgagt gtgagacacc ttatacctgt gtgcagcaga acccttacta ccatcaatgc   1020

gtgaattcgt gctga                                                    1035
```

<210> SEQ ID NO 130
<211> LENGTH: 344
<212> TYPE: PRT
<213> ORGANISM: Aspergillus aculeatus

<400> SEQUENCE: 130

```
Met Lys Tyr Ile Pro Leu Val Ile Ala Val Ala Ala Gly Leu Ala Arg
1               5                   10                  15

Pro Ala Thr Ala His Tyr Ile Phe Ser Lys Leu Val Leu Asn Gly Glu
            20                  25                  30

Ala Ser Ala Asp Trp Gln Tyr Ile Arg Glu Thr Thr Arg Ser Ile Val
        35                  40                  45

Tyr Glu Pro Thr Lys Tyr Thr Ser Thr Phe Asp Asn Leu Thr Pro Ser
    50                  55                  60

Asp Ser Asp Phe Arg Cys Asn Leu Gly Ser Phe Ser Asn Ala Ala Lys
65                  70                  75                  80

Thr Glu Val Ala Glu Val Ala Ala Gly Asp Thr Ile Ala Met Lys Leu
                85                  90                  95

Phe Tyr Asp Thr Ser Ile Ala His Pro Gly Pro Gly Gln Val Tyr Met
            100                 105                 110

Ser Lys Ala Pro Thr Gly Asn Val Gln Glu Tyr Gln Gly Asp Gly Asp
        115                 120                 125

Trp Phe Lys Ile Trp Glu Lys Thr Leu Cys Asn Thr Asp Gly Asp Leu
    130                 135                 140

Thr Thr Glu Ala Trp Cys Thr Trp Gly Met Ser Gln Phe Glu Phe Gln
145                 150                 155                 160

Ile Pro Ala Ala Thr Pro Ala Gly Glu Tyr Leu Val Arg Ala Glu His
                165                 170                 175

Ile Gly Leu His Gly Ala Gln Ala Asn Glu Ala Glu Phe Phe Tyr Ser
            180                 185                 190

Cys Ala Gln Ile Lys Val Thr Gly Ser Gly Thr Gly Ser Pro Ser Leu
        195                 200                 205

Thr Tyr Gln Ile Pro Gly Leu Tyr Asn Asp Thr Met Thr Leu Phe Asn
    210                 215                 220

Gly Leu Asn Leu Trp Thr Asp Ser Ala Glu Lys Val Gln Leu Asp Phe
225                 230                 235                 240

Leu Glu Thr Pro Ile Gly Asp Asp Val Trp Ser Gly Ala Gly Ser Gly
                245                 250                 255

Ser Pro Ser Ala Ala Thr Ser Ser Thr Ser Gly Ala Thr Leu Ala Ala
            260                 265                 270

Gln Gly Thr Thr Thr Ser Ala Ala His Ala Gln Ala Gln Thr Thr Ile
        275                 280                 285
```

```
Thr Thr Ser Thr Ser Thr Ile Thr Ser Leu Glu Ser Ala Ser Ser Thr
    290                 295                 300

Asp Leu Val Ala Gln Tyr Gly Gln Cys Gly Gly Leu Asn Trp Ser Gly
305                 310                 315                 320

Pro Thr Glu Cys Glu Thr Pro Tyr Thr Cys Val Gln Gln Asn Pro Tyr
                325                 330                 335

Tyr His Gln Cys Val Asn Ser Cys
            340


<210> SEQ ID NO 131
<211> LENGTH: 1170
<212> TYPE: DNA
<213> ORGANISM: Aspergillus aculeatus

<400> SEQUENCE: 131

atgaagtcct ctactttcgg tatgctcgct ctggcagcag cagccaagat ggtcgatgcc     60

cacaccaccg tcttcgccgt ctggatcaac ggcgaggacc agggtctggg caacagtgcc    120

agtggctaca tccggtctcc ccccagcaac agccccgtca aggacgtgac ctcgaccgac    180

atcacctgca acgtcaacgg cgaccaggcg gcggctaaga ccctctccgt caagggcggc    240

gacgtcgtca ccttcgagtg gcaccacgac agccgggacg cctccgacga catcatcgcc    300

tcctcccaca agggccccgt catggtctac atggccccga ccaccgccgg cagcagcggc    360

aagaactggg tcaagatcgc cgaggacgga tactccgacg gcacctgggc cgtcgacacc    420

ctgatcgcca acagcggcaa gcacaacatc accgtccccg acgtccccgc cggcgactac    480

ctcttccgcc cggagatcat cgccctccac gaggccgaga acgagggcgg cgcccagttc    540

tacatggagt gtgtccagtt caaggtcacc tccgacggtg ccaacactct gcccgacggt    600

gtcagcctgc ccggcgccta ctccgccact gaccccggta tcctcttcaa catgtacggc    660

tccttcgaca gctatcccat ccccggtccc tccgtctggg atggcactag ctctggctct    720

tcctcttctt cctcttcttc ctcttccagc tcttccgccg ccgctgccgt tgttgccacc    780

tcctcttcct cttcctctgc ttccatcgag gccgtgacca ccaagggtgc cgtcgccgcc    840

gtctccaccg ccgccgccgt ggctcctacc accaccaccg ctgcccccac caccttcgcc    900

acggccgtcg cctccaccaa gaaggccact gcctgccgca acaagaccaa gtcctcctcc    960

gctgccacca ccgccgccgc cgtcgccgag accacctctt ccaccgctgc cgccaccgct   1020

gctgcttcct ctgcctcttc cgcctccggc accgccggca agtacgagcg ctgcggtggc   1080

cagggctgga ccggtgccac cacctgcgtt gatggctgga cctgcaagca gtggaaccct   1140

tactactacc agtgcgttga gtctgcctag                                    1170


<210> SEQ ID NO 132
<211> LENGTH: 389
<212> TYPE: PRT
<213> ORGANISM: Aspergillus aculeatus

<400> SEQUENCE: 132

Met Lys Ser Ser Thr Phe Gly Met Leu Ala Leu Ala Ala Ala Ala Lys
1               5                   10                  15

Met Val Asp Ala His Thr Thr Val Phe Ala Val Trp Ile Asn Gly Glu
            20                  25                  30

Asp Gln Gly Leu Gly Asn Ser Ala Ser Gly Tyr Ile Arg Ser Pro Pro
        35                  40                  45

Ser Asn Ser Pro Val Lys Asp Val Thr Ser Thr Asp Ile Thr Cys Asn
```

```
    50                  55                  60

Val Asn Gly Asp Gln Ala Ala Ala Lys Thr Leu Ser Val Lys Gly Gly
65                  70                  75                  80

Asp Val Val Thr Phe Glu Trp His His Asp Ser Arg Asp Ala Ser Asp
                85                  90                  95

Asp Ile Ile Ala Ser Ser His Lys Gly Pro Val Met Val Tyr Met Ala
            100                 105                 110

Pro Thr Thr Ala Gly Ser Ser Gly Lys Asn Trp Val Lys Ile Ala Glu
        115                 120                 125

Asp Gly Tyr Ser Asp Gly Thr Trp Ala Val Asp Thr Leu Ile Ala Asn
    130                 135                 140

Ser Gly Lys His Asn Ile Thr Val Pro Asp Val Pro Ala Gly Asp Tyr
145                 150                 155                 160

Leu Phe Arg Pro Glu Ile Ile Ala Leu His Glu Ala Glu Asn Glu Gly
                165                 170                 175

Gly Ala Gln Phe Tyr Met Glu Cys Val Gln Phe Lys Val Thr Ser Asp
            180                 185                 190

Gly Ala Asn Thr Leu Pro Asp Gly Val Ser Leu Pro Gly Ala Tyr Ser
        195                 200                 205

Ala Thr Asp Pro Gly Ile Leu Phe Asn Met Tyr Gly Ser Phe Asp Ser
    210                 215                 220

Tyr Pro Ile Pro Gly Pro Ser Val Trp Asp Gly Thr Ser Ser Gly Ser
225                 230                 235                 240

Ser Ser Ser Ser Ser Ser Ser Ser Ser Ser Ser Ser Ala Ala Ala Ala
                245                 250                 255

Val Val Ala Thr Ser Ser Ser Ser Ser Ser Ala Ser Ile Glu Ala Val
            260                 265                 270

Thr Thr Lys Gly Ala Val Ala Ala Val Ser Thr Ala Ala Ala Val Ala
        275                 280                 285

Pro Thr Thr Thr Thr Ala Ala Pro Thr Thr Phe Ala Thr Ala Val Ala
    290                 295                 300

Ser Thr Lys Lys Ala Thr Ala Cys Arg Asn Lys Thr Lys Ser Ser Ser
305                 310                 315                 320

Ala Ala Thr Thr Ala Ala Ala Val Ala Glu Thr Thr Ser Ser Thr Ala
                325                 330                 335

Ala Ala Thr Ala Ala Ala Ser Ser Ala Ser Ser Ala Ser Gly Thr Ala
            340                 345                 350

Gly Lys Tyr Glu Arg Cys Gly Gly Gln Gly Trp Thr Gly Ala Thr Thr
        355                 360                 365

Cys Val Asp Gly Trp Thr Cys Lys Gln Trp Asn Pro Tyr Tyr Tyr Gln
    370                 375                 380

Cys Val Glu Ser Ala
385
```

<210> SEQ ID NO 133
<211> LENGTH: 1221
<212> TYPE: DNA
<213> ORGANISM: Aspergillus aculeatus

<400> SEQUENCE: 133

```
atgcgtcagg ctcagtcttt gtccctcttg acagctcttc tgtctgccac gcgtgtggct     60

ggacacggtc acgtcactaa cgttgtcgtc aacggtgttt actacgaggg cttcgatatc    120

aacagcttcc cctacgagtc cgatccccct aaggtggcgg cttggaccac tcctaacact    180
```

```
ggcaacggtt tcatttcccc cagcgactac ggtaccgatg acattatttg ccaccagaat    240

gccaccaacg cccaggccca cattgttgtt gcggctggtg acaagatcaa catccagtgg    300

accgcgtggc ccgattccca ccacggtcct gtccttgact acctcgctcg ctgcgacggt    360

gagtgtgaga cggttgataa gaccactctt gagtttttca agatcgacgg cgtcggtctc    420

atcagtgaca ccgaagtgcc cggtacctgg ggagatgacc agctgatcgc caacaacaac    480

agctggttgg tcgagatccc cccgaccatt gctcctggca actatgttct tcgccacgag    540

cttatcgctc tccacagcgc cggcactgaa gatggtgctc agaactaccc ccagtgtttc    600

aacctccagg tcactggctc cggtactgac gagcccgctg gtaccctcgg caccaagctc    660

tacactgagg atgaggctgg tatcgttgtg aacatctaca cctctctgtc ttcctatgcc    720

gtccccggcc ccacccagta cagcggcgcc gtctctgtca gccaatccac ttcggccatt    780

acctccaccg gaactgctgt tgtcggtagc ggcagcgctg ttgccacctc tgccgccgcg    840

gctaccacca gcgctgctgc ttcttctgcc gctgctgcta ccaccgctgc tgccgttacc    900

agcgccaatg ccaacactca gattgcccag cccagcagca gctcttctta ctcccagatc    960

gccgtgcagg tgccctcctc ctggaccacc cttgtgaccg tcactcctcc cgccgccgcc   1020

gccaccaccc ctgctgccgt ccctgagcct cagaccccct ctgccagctc tggagccacc   1080

actaccagca gcagcagcgg cgccgcccag tctctctacg gccagtgcgg tggtatcaac   1140

tggaccggag ctacctcttg cgttgagggc gctacttgct accagtacaa cccttactac   1200

taccagtgca tctctgccta a                                             1221


<210> SEQ ID NO 134
<211> LENGTH: 406
<212> TYPE: PRT
<213> ORGANISM: Aspergillus aculeatus

<400> SEQUENCE: 134

Met Arg Gln Ala Gln Ser Leu Ser Leu Leu Thr Ala Leu Leu Ser Ala
1               5                   10                  15

Thr Arg Val Ala Gly His Gly His Val Thr Asn Val Val Val Asn Gly
            20                  25                  30

Val Tyr Tyr Glu Gly Phe Asp Ile Asn Ser Phe Pro Tyr Glu Ser Asp
        35                  40                  45

Pro Pro Lys Val Ala Ala Trp Thr Thr Pro Asn Thr Gly Asn Gly Phe
    50                  55                  60

Ile Ser Pro Ser Asp Tyr Gly Thr Asp Asp Ile Ile Cys His Gln Asn
65                  70                  75                  80

Ala Thr Asn Ala Gln Ala His Ile Val Val Ala Ala Gly Asp Lys Ile
                85                  90                  95

Asn Ile Gln Trp Thr Ala Trp Pro Asp Ser His His Gly Pro Val Leu
            100                 105                 110

Asp Tyr Leu Ala Arg Cys Asp Gly Glu Cys Glu Thr Val Asp Lys Thr
        115                 120                 125

Thr Leu Glu Phe Phe Lys Ile Asp Gly Val Gly Leu Ile Ser Asp Thr
    130                 135                 140

Glu Val Pro Gly Thr Trp Gly Asp Asp Gln Leu Ile Ala Asn Asn Asn
145                 150                 155                 160

Ser Trp Leu Val Glu Ile Pro Pro Thr Ile Ala Pro Gly Asn Tyr Val
                165                 170                 175

Leu Arg His Glu Leu Ile Ala Leu His Ser Ala Gly Thr Glu Asp Gly
            180                 185                 190
```

```
Ala Gln Asn Tyr Pro Gln Cys Phe Asn Leu Gln Val Thr Gly Ser Gly
        195                 200                 205

Thr Asp Glu Pro Ala Gly Thr Leu Gly Thr Lys Leu Tyr Thr Glu Asp
    210                 215                 220

Glu Ala Gly Ile Val Val Asn Ile Tyr Thr Ser Leu Ser Ser Tyr Ala
225                 230                 235                 240

Val Pro Gly Pro Thr Gln Tyr Ser Gly Ala Val Ser Val Ser Gln Ser
                245                 250                 255

Thr Ser Ala Ile Thr Ser Thr Gly Thr Ala Val Val Gly Ser Gly Ser
            260                 265                 270

Ala Val Ala Thr Ser Ala Ala Ala Ala Thr Thr Ser Ala Ala Ala Ser
        275                 280                 285

Ser Ala Ala Ala Ala Thr Thr Ala Ala Ala Val Thr Ser Ala Asn Ala
    290                 295                 300

Asn Thr Gln Ile Ala Gln Pro Ser Ser Ser Ser Ser Tyr Ser Gln Ile
305                 310                 315                 320

Ala Val Gln Val Pro Ser Ser Trp Thr Thr Leu Val Thr Val Thr Pro
                325                 330                 335

Pro Ala Ala Ala Ala Thr Thr Pro Ala Ala Val Pro Glu Pro Gln Thr
            340                 345                 350

Pro Ser Ala Ser Ser Gly Ala Thr Thr Thr Ser Ser Ser Ser Gly Ala
        355                 360                 365

Ala Gln Ser Leu Tyr Gly Gln Cys Gly Gly Ile Asn Trp Thr Gly Ala
    370                 375                 380

Thr Ser Cys Val Glu Gly Ala Thr Cys Tyr Gln Tyr Asn Pro Tyr Tyr
385                 390                 395                 400

Tyr Gln Cys Ile Ser Ala
                405
```

<210> SEQ ID NO 135
<211> LENGTH: 1284
<212> TYPE: DNA
<213> ORGANISM: Aspergillus aculeatus

<400> SEQUENCE: 135

```
atgtctcttt ccaagattgc cactcttctg ctgggctcgg tctcgctggt cgctggtcat     60

gggtatgtct cgagcatcga ggtggacggt accacctatg gagggtactt ggtcgacact    120

tattactacg aatccgaccc gcccgagtta atcgcctggt ccacaaatgc cacggatgat    180

ggctatgtat cgccctccga ctacgagagc gtgaacatca tctgccacaa ggggtctgcg    240

cccggcgcgt tgtcggcccc tgtcgcgccc ggaggctggg tgcagatgac ctggaacacc    300

tggcccaccg accatcacgg ccctgtcatc acgtatatgg ccaattgcca cggttcttgc    360

gcagatgtgg acaagaccac cctcgagttc ttcaagatcg atgctggcgg cttgatcgat    420

gacacggacg tgcctggaac ttgggcgacc gatgagctca ttgaagatag ctatagtcgc    480

aacatcacta tccccagcga tattgccccc gggtactatg ttttgcgaca cgagatcatt    540

gctctgcaca gcgccgagaa cctggacgga gcccagaact acccccagtg catcaatctg    600

gaagtcaccg gcagcgagac agcaaccccg agtggcacct tgggcactgc tctgtacaag    660

gagaccgacc ccggcatcta tgttgacatc tggaacacgt tgagcacgta tactattccc    720

ggccccgcgc tgtacactgc tggtagcact gcgaccgcag ccgctgctgc cgataccacc    780

actacttctg ctggcaccac cgctgaggcc accaccgctg ccgccgccgt gagtaccacc    840
```

```
gcggacgctg ttccgaccga gtcttcagct ccttccgaga ccagcgcgac taccgcgaac    900

cctgctcggc ccactgccgg cagcgacatc cgcttccagc ccggtcaggt caaggctggt    960

gcttcagtca acaactcggc tactgagact tcctctggtg agtctgccac gacgaccaca   1020

acatcagtgg ccactgcggc ttcgagcgcg gattcgtcga cgacttctgg ggttttgagt   1080

ggcgcctgca gccaggaggg ctactggtac tgcaacgggg gcactgcgtt ccagcgctgt   1140

gtcaacgggg aatgggatgc gtcccagagt gtggctgcgg gcacggtctg caccgccggt   1200

atctcggaga ccatcaccat ttcagccgcc gccacgcgcc gggatgccat gcgtcgtcat   1260

ctggcgcgtc ccaagcgtca ctga                                          1284


<210> SEQ ID NO 136
<211> LENGTH: 427
<212> TYPE: PRT
<213> ORGANISM: Aspergillus aculeatus

<400> SEQUENCE: 136

Met Ser Leu Ser Lys Ile Ala Thr Leu Leu Leu Gly Ser Val Ser Leu
1               5                   10                  15

Val Ala Gly His Gly Tyr Val Ser Ser Ile Glu Val Asp Gly Thr Thr
            20                  25                  30

Tyr Gly Gly Tyr Leu Val Asp Thr Tyr Tyr Tyr Glu Ser Asp Pro Pro
        35                  40                  45

Glu Leu Ile Ala Trp Ser Thr Asn Ala Thr Asp Asp Gly Tyr Val Ser
    50                  55                  60

Pro Ser Asp Tyr Glu Ser Val Asn Ile Ile Cys His Lys Gly Ser Ala
65                  70                  75                  80

Pro Gly Ala Leu Ser Ala Pro Val Ala Pro Gly Gly Trp Val Gln Met
                85                  90                  95

Thr Trp Asn Thr Trp Pro Thr Asp His His Gly Pro Val Ile Thr Tyr
            100                 105                 110

Met Ala Asn Cys His Gly Ser Cys Ala Asp Val Asp Lys Thr Thr Leu
        115                 120                 125

Glu Phe Phe Lys Ile Asp Ala Gly Gly Leu Ile Asp Asp Thr Asp Val
    130                 135                 140

Pro Gly Thr Trp Ala Thr Asp Glu Leu Ile Glu Asp Ser Tyr Ser Arg
145                 150                 155                 160

Asn Ile Thr Ile Pro Ser Asp Ile Ala Pro Gly Tyr Tyr Val Leu Arg
                165                 170                 175

His Glu Ile Ile Ala Leu His Ser Ala Glu Asn Leu Asp Gly Ala Gln
            180                 185                 190

Asn Tyr Pro Gln Cys Ile Asn Leu Glu Val Thr Gly Ser Glu Thr Ala
        195                 200                 205

Thr Pro Ser Gly Thr Leu Gly Thr Ala Leu Tyr Lys Glu Thr Asp Pro
    210                 215                 220

Gly Ile Tyr Val Asp Ile Trp Asn Thr Leu Ser Thr Tyr Thr Ile Pro
225                 230                 235                 240

Gly Pro Ala Leu Tyr Thr Ala Gly Ser Thr Ala Thr Ala Ala Ala Ala
                245                 250                 255

Ala Asp Thr Thr Thr Thr Ser Ala Gly Thr Thr Ala Glu Ala Thr Thr
            260                 265                 270

Ala Ala Ala Ala Val Ser Thr Thr Ala Asp Ala Val Pro Thr Glu Ser
        275                 280                 285

Ser Ala Pro Ser Glu Thr Ser Ala Thr Thr Ala Asn Pro Ala Arg Pro
```

```
    290                 295                 300

Thr Ala Gly Ser Asp Ile Arg Phe Gln Pro Gly Gln Val Lys Ala Gly
305                 310                 315                 320

Ala Ser Val Asn Asn Ser Ala Thr Glu Thr Ser Ser Gly Glu Ser Ala
                325                 330                 335

Thr Thr Thr Thr Thr Ser Val Ala Thr Ala Ala Ser Ser Ala Asp Ser
            340                 345                 350

Ser Thr Thr Ser Gly Val Leu Ser Gly Ala Cys Ser Gln Glu Gly Tyr
        355                 360                 365

Trp Tyr Cys Asn Gly Gly Thr Ala Phe Gln Arg Cys Val Asn Gly Glu
    370                 375                 380

Trp Asp Ala Ser Gln Ser Val Ala Ala Gly Thr Val Cys Thr Ala Gly
385                 390                 395                 400

Ile Ser Glu Thr Ile Thr Ile Ser Ala Ala Ala Thr Arg Arg Asp Ala
                405                 410                 415

Met Arg Arg His Leu Ala Arg Pro Lys Arg His
            420                 425


<210> SEQ ID NO 137
<211> LENGTH: 804
<212> TYPE: DNA
<213> ORGANISM: Aspergillus aculeatus

<400> SEQUENCE: 137

atgcttgtca aactcatctc ttttctttca gctgctacca gcgtagctgc tcatggtcat      60

gtgtcaaaca ttgtgatcaa cggggtgtcc taccgcggat gggacatcaa ttcggaccct     120

tacaattcca accctccggt ggtggttgca tggcaaacac ccaacacagc taatggcttc     180

atctcccctg atgcatacga cacagatgat gttatttgcc atctgagcgc tacgaatgcc     240

agaggccacg cagtcgtcgc tgctggcgac aagatcagcc tccagtggac gacctggcct     300

gacagtcacc atggccctgt catcagctac ctagccaact gcggctccag ctgcgagaca     360

gtcgataaga ccaccctcga gttcttcaag atcgatggtg ttggcttggt ggatgagagc     420

aatcccctg gtatctgggg agacgatgag ctcattgcca acaacaactc ttggctggta     480

gagattccag ctagtatcgc gccaggatac tatgtgctgc gtcacgagtt gatcgctctg     540

catggagcag ggagtgagaa tggagcccag aattacatgc aatgtttcaa ccttcaggtt     600

actgggactg gcacggtcca gccttccggg gtcctgggca cggagctgta caaacccaca     660

gacgctggaa ttcttgtcaa tatctaccag tcgctctcca cctatgttgt tcctggcccg     720

accctgatcc cccaggccgt ttccctcgtt cagtcgagct ccaccattac cgcctcgggc     780

acggcagtga caaccacggc ttga                                            804


<210> SEQ ID NO 138
<211> LENGTH: 267
<212> TYPE: PRT
<213> ORGANISM: Aspergillus aculeatus

<400> SEQUENCE: 138

Met Leu Val Lys Leu Ile Ser Phe Leu Ser Ala Ala Thr Ser Val Ala
1               5                   10                  15

Ala His Gly His Val Ser Asn Ile Val Ile Asn Gly Val Ser Tyr Arg
            20                  25                  30

Gly Trp Asp Ile Asn Ser Asp Pro Tyr Asn Ser Asn Pro Pro Val Val
        35                  40                  45
```

```
Val Ala Trp Gln Thr Pro Asn Thr Ala Asn Gly Phe Ile Ser Pro Asp
    50                  55                  60

Ala Tyr Asp Thr Asp Asp Val Ile Cys His Leu Ser Ala Thr Asn Ala
65                  70                  75                  80

Arg Gly His Ala Val Val Ala Ala Gly Asp Lys Ile Ser Leu Gln Trp
                85                  90                  95

Thr Thr Trp Pro Asp Ser His His Gly Pro Val Ile Ser Tyr Leu Ala
            100                 105                 110

Asn Cys Gly Ser Ser Cys Glu Thr Val Asp Lys Thr Thr Leu Glu Phe
        115                 120                 125

Phe Lys Ile Asp Gly Val Gly Leu Val Asp Glu Ser Asn Pro Pro Gly
    130                 135                 140

Ile Trp Gly Asp Asp Glu Leu Ile Ala Asn Asn Asn Ser Trp Leu Val
145                 150                 155                 160

Glu Ile Pro Ala Ser Ile Ala Pro Gly Tyr Tyr Val Leu Arg His Glu
                165                 170                 175

Leu Ile Ala Leu His Gly Ala Gly Ser Glu Asn Gly Ala Gln Asn Tyr
            180                 185                 190

Met Gln Cys Phe Asn Leu Gln Val Thr Gly Thr Gly Thr Val Gln Pro
        195                 200                 205

Ser Gly Val Leu Gly Thr Glu Leu Tyr Lys Pro Thr Asp Ala Gly Ile
    210                 215                 220

Leu Val Asn Ile Tyr Gln Ser Leu Ser Thr Tyr Val Val Pro Gly Pro
225                 230                 235                 240

Thr Leu Ile Pro Gln Ala Val Ser Leu Val Gln Ser Ser Ser Thr Ile
                245                 250                 255

Thr Ala Ser Gly Thr Ala Val Thr Thr Thr Ala
            260                 265
```

```
<210> SEQ ID NO 139
<211> LENGTH: 822
<212> TYPE: DNA
<213> ORGANISM: Aspergillus aculeatus

<400> SEQUENCE: 139

atgaagtatc ttgcgatctt cgcggcagca gcagctggac tggcccgccc gacagcagcg      60

cactacatct tcagcaagct gattctggac ggcgaagtct ctgaggactg gcagtatatt     120

cgtaaaacca cccgggagac atgctatttg ccgaccaagt tcaccgacac cttcgacaac     180

ttgactccga acgaccagga tttccggtgc aatctcggct cgttcagcaa cgccgccaag     240

accgaagtgg ccgaggtgga agcgggctcc acgattggca tgcagctttt cgctggtagc     300

cacatgcgtc acccgggacc tgcgcaagtc ttcatgtcta aggccccgtc cggcaacgta     360

cagagctacg agggtgacgg ctcctggttc aagatctggg agcgtacact ctgcgacaaa     420

agtggcgatc tgactggaga tgcgtggtgt acatacggcc agaccgagat cgagtttcaa     480

atccccgagg cgaccccgac gggcgaatac ctggtccgag cggagcacat cggtcttcac     540

cgcgcacaga gtaatcaagc cgagttctac tacagctgcg cccaggtcaa ggtcacgggc     600

aatggtaccg gggtgccgag ccagacatat cagatccctg gcatgtacaa tgaccgctcg     660

gagcttttca acgggctgaa cttgtggtcc tactcggtgg agaacgtcga ggcagccatg     720

aagaattcta tcgtgggtga tgaaatttgg aatggaagtt ctgttccctc tgagtcccat     780

gtcccgaagt ataagaagag tcatgcttgt cgtgtttatt ga                        822
```

<210> SEQ ID NO 140
<211> LENGTH: 273
<212> TYPE: PRT
<213> ORGANISM: Aspergillus aculeatus

<400> SEQUENCE: 140

```
Met Lys Tyr Leu Ala Ile Phe Ala Ala Ala Ala Ala Gly Leu Ala Arg
1               5                   10                  15

Pro Thr Ala Ala His Tyr Ile Phe Ser Lys Leu Ile Leu Asp Gly Glu
            20                  25                  30

Val Ser Glu Asp Trp Gln Tyr Ile Arg Lys Thr Thr Arg Glu Thr Cys
        35                  40                  45

Tyr Leu Pro Thr Lys Phe Thr Asp Thr Phe Asp Asn Leu Thr Pro Asn
    50                  55                  60

Asp Gln Asp Phe Arg Cys Asn Leu Gly Ser Phe Ser Asn Ala Ala Lys
65                  70                  75                  80

Thr Glu Val Ala Glu Val Glu Ala Gly Ser Thr Ile Gly Met Gln Leu
                85                  90                  95

Phe Ala Gly Ser His Met Arg His Pro Gly Pro Ala Gln Val Phe Met
            100                 105                 110

Ser Lys Ala Pro Ser Gly Asn Val Gln Ser Tyr Glu Gly Asp Gly Ser
        115                 120                 125

Trp Phe Lys Ile Trp Glu Arg Thr Leu Cys Asp Lys Ser Gly Asp Leu
    130                 135                 140

Thr Gly Asp Ala Trp Cys Thr Tyr Gly Gln Thr Glu Ile Glu Phe Gln
145                 150                 155                 160

Ile Pro Glu Ala Thr Pro Thr Gly Glu Tyr Leu Val Arg Ala Glu His
                165                 170                 175

Ile Gly Leu His Arg Ala Gln Ser Asn Gln Ala Glu Phe Tyr Tyr Ser
            180                 185                 190

Cys Ala Gln Val Lys Val Thr Gly Asn Gly Thr Gly Val Pro Ser Gln
        195                 200                 205

Thr Tyr Gln Ile Pro Gly Met Tyr Asn Asp Arg Ser Glu Leu Phe Asn
    210                 215                 220

Gly Leu Asn Leu Trp Ser Tyr Ser Val Glu Asn Val Glu Ala Ala Met
225                 230                 235                 240

Lys Asn Ser Ile Val Gly Asp Glu Ile Trp Asn Gly Ser Ser Val Pro
                245                 250                 255

Ser Glu Ser His Val Pro Lys Tyr Lys Lys Ser His Ala Cys Arg Val
            260                 265                 270

Tyr
```

<210> SEQ ID NO 141
<211> LENGTH: 969
<212> TYPE: DNA
<213> ORGANISM: Aurantiporus alborubescens

<400> SEQUENCE: 141

```
atgcgaacca tcgccacgtt tgttacgctt gtagcctcag ttctccctgc ggtcctcgca      60

cacggaggtg tcctctccta ttcsaacggg gggaattggt actggggatg gaagccttac     120

aattcacctg acgggcagac caccatccaa cgcccgtggg caacatacaa tccgatcact     180

gatgcgacgg atcctaccat tgcttgcaac aacgacggga catctggagc tctgcagttg     240

actgcgacag tcgcggcggg atctgccatc acggcgtatt ggaaccaggt gtggccgcat     300

gataaagggc cgatgacgac atacctcgca caatgccccg gcagtacctg cacaggagtc     360
```

```
aacgcgaaga ctctgaaatg gttcaagatc gatcacgccg ggttgctttc tggtactgtc    420

tacagtggct cgtgggcatc aggcaagatg attgcacaga actcgacctg gacaactacc    480

attccagcga cggtgccttc agggaactat ctgatacgtt tcgagactat tgccctgcac    540

tctttgccag cgcaatttta ccctgagtgc gcacaaattc aaatcacggg cggaggttcc    600

cgtgctccaa ccgctgcaga gcttgttagc ttccctggcg cgtacagcaa caatgatcct    660

ggtgtcaaca ttgacatcta ctccaatgcc gcgcagagtg caaccacata cgtaatacca    720

ggacctccat tgtacggcgg tgcttccgga tctggtccat cttccgcgcc tccatcaagt    780

accccaggta gttcgtccac ttcccacggt cccacgtccg tcagcacgtc cagcagtgct    840

gcaccatcga cgacaggaac cgtgacgcag tacggtcagt gcggtggcat tggttgggct    900

ggagctaccg gctgtatctc accattcaag tgcacggtca tcaacgatta ttactaccag    960

tgcctctga                                                            969


<210> SEQ ID NO 142
<211> LENGTH: 322
<212> TYPE: PRT
<213> ORGANISM: Aurantiporus alborubescens

<400> SEQUENCE: 142

Met Arg Thr Ile Ala Thr Phe Val Thr Leu Val Ala Ser Val Leu Pro
1               5                   10                  15

Ala Val Leu Ala His Gly Gly Val Leu Ser Tyr Ser Asn Gly Gly Asn
            20                  25                  30

Trp Tyr Trp Gly Trp Lys Pro Tyr Asn Ser Pro Asp Gly Gln Thr Thr
        35                  40                  45

Ile Gln Arg Pro Trp Ala Thr Tyr Asn Pro Ile Thr Asp Ala Thr Asp
    50                  55                  60

Pro Thr Ile Ala Cys Asn Asn Asp Gly Thr Ser Gly Ala Leu Gln Leu
65                  70                  75                  80

Thr Ala Thr Val Ala Ala Gly Ser Ala Ile Thr Ala Tyr Trp Asn Gln
                85                  90                  95

Val Trp Pro His Asp Lys Gly Pro Met Thr Thr Tyr Leu Ala Gln Cys
            100                 105                 110

Pro Gly Ser Thr Cys Thr Gly Val Asn Ala Lys Thr Leu Lys Trp Phe
        115                 120                 125

Lys Ile Asp His Ala Gly Leu Leu Ser Gly Thr Val Tyr Ser Gly Ser
    130                 135                 140

Trp Ala Ser Gly Lys Met Ile Ala Gln Asn Ser Thr Trp Thr Thr Thr
145                 150                 155                 160

Ile Pro Ala Thr Val Pro Ser Gly Asn Tyr Leu Ile Arg Phe Glu Thr
                165                 170                 175

Ile Ala Leu His Ser Leu Pro Ala Gln Phe Tyr Pro Glu Cys Ala Gln
            180                 185                 190

Ile Gln Ile Thr Gly Gly Gly Ser Arg Ala Pro Thr Ala Ala Glu Leu
        195                 200                 205

Val Ser Phe Pro Gly Ala Tyr Ser Asn Asn Asp Pro Gly Val Asn Ile
    210                 215                 220

Asp Ile Tyr Ser Asn Ala Ala Gln Ser Ala Thr Thr Tyr Val Ile Pro
225                 230                 235                 240

Gly Pro Pro Leu Tyr Gly Gly Ala Ser Gly Ser Gly Pro Ser Ser Ala
                245                 250                 255
```

```
Pro Pro Ser Ser Thr Pro Gly Ser Ser Ser Thr Ser His Gly Pro Thr
            260                 265                 270

Ser Val Ser Thr Ser Ser Ser Ala Ala Pro Ser Thr Thr Gly Thr Val
        275                 280                 285

Thr Gln Tyr Gly Gln Cys Gly Gly Ile Gly Trp Ala Gly Ala Thr Gly
    290                 295                 300

Cys Ile Ser Pro Phe Lys Cys Thr Val Ile Asn Asp Tyr Tyr Tyr Gln
305                 310                 315                 320

Cys Leu


<210> SEQ ID NO 143
<211> LENGTH: 705
<212> TYPE: DNA
<213> ORGANISM: Aurantiporus alborubescens

<400> SEQUENCE: 143

atgaaggcta tcttggctat tttctcggcc cttgctccac ttgccgctgc gcattatacc      60

ttccctgatt ttattgtcaa cggaacaaca actgccgatt gggtctacat ccgagagacc     120

gcgaaccact actcgaatgg tcctgtaacc aacgtgaacg atccagaatt ccgatgctac     180

gagctggacc tgcaaaacac ggcagcgagt accctcaccg ccacggtctc tgcaggctcc     240

agcgtcggct ttaaagctaa cagcgccctt taccatcctg gttatctcga tgtgtatatg     300

tccaaagcga ccccagctgc taattcaccc agtgctggaa cggaccaaag ctggttcaag     360

gtctatgaat ccgctccggt cttcgcgaat ggggccctaa gcttcccttc ggagaacatc     420

caatctttca cgttcacaat cccgaagtcc cttcccagtg gccaatatct catccgtgtg     480

gaacacatcg ctctccactc cgccagtagc tacggaggtg cacaattcta catcagctgc     540

gctcaagtca atgtcgtcaa cggcgggaac ggaaacccag gaccgttagt caagattccc     600

ggcgtttaca ctgggaacga gcctggcatc ctcatcaaca tctacagctt cccaccgggt     660

ttcagtggct accaatcccc gggacctgct gtgtggcgtg gttga                     705


<210> SEQ ID NO 144
<211> LENGTH: 234
<212> TYPE: PRT
<213> ORGANISM: Aurantiporus alborubescens

<400> SEQUENCE: 144

Met Lys Ala Ile Leu Ala Ile Phe Ser Ala Leu Ala Pro Leu Ala Ala
1               5                   10                  15

Ala His Tyr Thr Phe Pro Asp Phe Ile Val Asn Gly Thr Thr Thr Ala
            20                  25                  30

Asp Trp Val Tyr Ile Arg Glu Thr Ala Asn His Tyr Ser Asn Gly Pro
        35                  40                  45

Val Thr Asn Val Asn Asp Pro Glu Phe Arg Cys Tyr Glu Leu Asp Leu
    50                  55                  60

Gln Asn Thr Ala Ala Ser Thr Leu Thr Ala Thr Val Ser Ala Gly Ser
65                  70                  75                  80

Ser Val Gly Phe Lys Ala Asn Ser Ala Leu Tyr His Pro Gly Tyr Leu
                85                  90                  95

Asp Val Tyr Met Ser Lys Ala Thr Pro Ala Ala Asn Ser Pro Ser Ala
            100                 105                 110

Gly Thr Asp Gln Ser Trp Phe Lys Val Tyr Glu Ser Ala Pro Val Phe
        115                 120                 125

Ala Asn Gly Ala Leu Ser Phe Pro Ser Glu Asn Ile Gln Ser Phe Thr
```

```
    130                 135                 140

Phe Thr Ile Pro Lys Ser Leu Pro Ser Gly Gln Tyr Leu Ile Arg Val
145                 150                 155                 160

Glu His Ile Ala Leu His Ser Ala Ser Ser Tyr Gly Gly Ala Gln Phe
                165                 170                 175

Tyr Ile Ser Cys Ala Gln Val Asn Val Val Asn Gly Gly Asn Gly Asn
            180                 185                 190

Pro Gly Pro Leu Val Lys Ile Pro Gly Val Tyr Thr Gly Asn Glu Pro
        195                 200                 205

Gly Ile Leu Ile Asn Ile Tyr Ser Phe Pro Pro Gly Phe Ser Gly Tyr
    210                 215                 220

Gln Ser Pro Gly Pro Ala Val Trp Arg Gly
225                 230


<210> SEQ ID NO 145
<211> LENGTH: 702
<212> TYPE: DNA
<213> ORGANISM: Trichophaea saccata

<400> SEQUENCE: 145

atgacgcccc tgaaactccg cccccttctc ctcctggtgc tttccacgac cctcagcctc      60

gtgcacgcgc actatcgctt ctacgaactg atcgccaacg gggccaccca cgcttccttc     120

gaatacatcc gccaatgggt gcccatctac agcaactctc ccgtaaccga cgtcaccagc     180

gtcaacctcc gctgcaacgt caacgccact cccgccgccg aggtgatcac cgttgctgcc     240

ggtagcaccg tcggcttcgt agcagacaca acagtaacgc accccggtgc gttcaccgcg     300

tacatggcga aagcgcccga agacatcacg gaatgggatg gcaacgggga ctggttcaag     360

atctgggaga agggtccaac gagtataacc agtagcggga taacctggga cgtcacggat     420

acccaatgga ccttcaccat cccttccgcg acaccaaacg gtcaatacct actccgcttc     480

gagcacatag cgctccacgc cgccagcacc gtgggggtg ctcaattcta catgtcgtgc      540

gcgcagatac aagtaacgaa cggcggcaac gggagtcccg ggcccaccat caagttcccg     600

ggcggataca gcgccacaga ccccggtatc ctgatcaata tctattatcc catccccact     660

agttacacta ttcctggtcc accggtttgg accggtaagt aa                        702


<210> SEQ ID NO 146
<211> LENGTH: 233
<212> TYPE: PRT
<213> ORGANISM: Trichophaea saccata

<400> SEQUENCE: 146

Met Thr Pro Leu Lys Leu Arg Pro Leu Leu Leu Leu Val Leu Ser Thr
1               5                   10                  15

Thr Leu Ser Leu Val His Ala His Tyr Arg Phe Tyr Glu Leu Ile Ala
            20                  25                  30

Asn Gly Ala Thr His Ala Ser Phe Glu Tyr Ile Arg Gln Trp Val Pro
        35                  40                  45

Ile Tyr Ser Asn Ser Pro Val Thr Asp Val Thr Ser Val Asn Leu Arg
    50                  55                  60

Cys Asn Val Asn Ala Thr Pro Ala Ala Glu Val Ile Thr Val Ala Ala
65                  70                  75                  80

Gly Ser Thr Val Gly Phe Val Ala Asp Thr Thr Val Thr His Pro Gly
                85                  90                  95

Ala Phe Thr Ala Tyr Met Ala Lys Ala Pro Glu Asp Ile Thr Glu Trp
```

```
            100                 105                 110

Asp Gly Asn Gly Asp Trp Phe Lys Ile Trp Glu Lys Gly Pro Thr Ser
        115                 120                 125

Ile Thr Ser Ser Gly Ile Thr Trp Asp Val Thr Asp Thr Gln Trp Thr
    130                 135                 140

Phe Thr Ile Pro Ser Ala Thr Pro Asn Gly Gln Tyr Leu Leu Arg Phe
145                 150                 155                 160

Glu His Ile Ala Leu His Ala Ala Ser Thr Val Gly Gly Ala Gln Phe
                165                 170                 175

Tyr Met Ser Cys Ala Gln Ile Gln Val Thr Asn Gly Gly Asn Gly Ser
            180                 185                 190

Pro Gly Pro Thr Ile Lys Phe Pro Gly Gly Tyr Ser Ala Thr Asp Pro
        195                 200                 205

Gly Ile Leu Ile Asn Ile Tyr Tyr Pro Ile Pro Thr Ser Tyr Thr Ile
    210                 215                 220

Pro Gly Pro Pro Val Trp Thr Gly Lys
225                 230
```

<210> SEQ ID NO 147
<211> LENGTH: 714
<212> TYPE: DNA
<213> ORGANISM: Trichophaea saccata

<400> SEQUENCE: 147

```
atgaaatgcc ttctctccct ccttctcgcc gcgacagcgg tctccgctca cacgatcttc     60

caagaaatcg gcataaacgg ggtgatgcaa gctcgctacg actacatgcg gctgccgtcc    120

tacgacggtc ccattacgga cgtaacgagc acctacatgg cgtgcaacgg tggtcccaat    180

ccattggtcc aaatctcgaa cgacgtcgct ttcgtaaaag ccggcgacag catcacgctg    240

caatgggcgc aaacgttgac gacagatttc aacacggggc tgatcatcga tccatcgcac    300

ttgggtcctg tgatggtcta catggccaaa gtaccctccg ccaccggtcc gatccccaac    360

agcggctggt tcaaaatcta cgaagacggc tacgacccga caacaaagac atggcggta    420

accaagctca tcaacaacaa gggaaaagtg accgtcacca tcccatcgtg tctaccggca    480

ggggactact tgctgcgcgg tgaaatcatt gccttgcacg cggctagtac ctatccaggc    540

gcacagtttt acatggagtg tgcgcagttg cggcttacca gtggcggcac taagatgcct    600

accacgtata acattccggg gatctattcg cccactgatc cgggtgttac gttcaatctt    660

tacaatggat tcacgagtta taccattcct ggcccaaggc cgtttacatg ctag          714
```

<210> SEQ ID NO 148
<211> LENGTH: 237
<212> TYPE: PRT
<213> ORGANISM: Trichophaea saccata

<400> SEQUENCE: 148

```
Met Lys Cys Leu Leu Ser Leu Leu Leu Ala Ala Thr Ala Val Ser Ala
1               5                   10                  15

His Thr Ile Phe Gln Glu Ile Gly Ile Asn Gly Val Met Gln Ala Arg
            20                  25                  30

Tyr Asp Tyr Met Arg Leu Pro Ser Tyr Asp Gly Pro Ile Thr Asp Val
        35                  40                  45

Thr Ser Thr Tyr Met Ala Cys Asn Gly Gly Pro Asn Pro Leu Val Gln
    50                  55                  60

Ile Ser Asn Asp Val Ala Phe Val Lys Ala Gly Asp Ser Ile Thr Leu
```

```
65                  70                  75                  80

Gln Trp Ala Gln Thr Leu Thr Thr Asp Phe Asn Thr Gly Leu Ile Ile
                85                  90                  95

Asp Pro Ser His Leu Gly Pro Val Met Val Tyr Met Ala Lys Val Pro
            100                 105                 110

Ser Ala Thr Gly Pro Ile Pro Asn Ser Gly Trp Phe Lys Ile Tyr Glu
        115                 120                 125

Asp Gly Tyr Asp Pro Thr Thr Lys Thr Trp Ala Val Thr Lys Leu Ile
    130                 135                 140

Asn Asn Lys Gly Lys Val Thr Val Thr Ile Pro Ser Cys Leu Pro Ala
145                 150                 155                 160

Gly Asp Tyr Leu Leu Arg Gly Glu Ile Ile Ala Leu His Ala Ala Ser
                165                 170                 175

Thr Tyr Pro Gly Ala Gln Phe Tyr Met Glu Cys Ala Gln Leu Arg Leu
            180                 185                 190

Thr Ser Gly Gly Thr Lys Met Pro Thr Thr Tyr Asn Ile Pro Gly Ile
        195                 200                 205

Tyr Ser Pro Thr Asp Pro Gly Val Thr Phe Asn Leu Tyr Asn Gly Phe
    210                 215                 220

Thr Ser Tyr Thr Ile Pro Gly Pro Arg Pro Phe Thr Cys
225                 230                 235


<210> SEQ ID NO 149
<211> LENGTH: 1455
<212> TYPE: DNA
<213> ORGANISM: Penicillium thomii

<400> SEQUENCE: 149

atgtctctgt ctaagatttc tggattgatc ctcggatctg ctgccttggt ggctggccac     60

ggttacgtga gcggaatcgt cgttgacgat acctactatg gtggatacct tgtcacccag    120

taccccttatg agagtgacgc cccagagctc attgcctggt cggagcaaga gaccgatctg   180

ggttacatcg atggctctga gtatgccaac tccaacatca tctgtcacaa ggaggccaaa    240

cctggtgctt tggaagcacc cgttaaggct ggtggctccg tcgagctcca gtggaccact    300

tggcctacca gccaccacgg tcctgtcatt acctacatgg ccaactgtaa cggcgactgt    360

gacgacgttg acaagactac tttgcagttc ttcaagattg accagggtgg tttgatcagc    420

gataccaccg agcccggtac ctgggcaact gacaacctca tcgccaacaa caatagccgt    480

actgtcaccg tccccagcga cattgccgat ggaaactacg tcctccgtca cgagatcatt    540

gccctccact ccgccgggga gaccaacggt gcccagaact acccccaatg tatcaacttg    600

aaggtcactg gcggcggtag cgctactcct tctggtaccc tgggtaccgc cctgtacaag    660

aacaccgacc ccggtatcct gatcaacatc tacacttccc tcagcaccta cgatatcccc    720

ggcccaaccc tgtacactgc cggcgccgcc gctgctaccg ctgcctccac ggctgcctct    780

tccaccgccg ctgccgttac tactgccgac gccgtcacta ccgccgctgc cgtcaccagc    840

agctctgcat ccgtggaagt tgtgcccaca actactccca gctcatcaat cgtcagtgcc    900

ttcccaacct ggagcccctc ttctacccca cccttctcca actcttccaa cggatggcgt    960

ccgtcattca gccgcggacc tggtggcccc cgcttcacat ctgctcctgc tcctcagttc   1020

tccgctccta gcggcgctca gcagaagcag tctgccactg ctaccccccat cgtggctacc  1080

cctgtcgtga tcaccatgac cgagaccagc acctcctggg tcaccgaaat ggttactctt   1140

actgacaagt ctgttgtgca gaccaccagc gctgtcccag tcgtcgtcgc cgccaccact   1200
```

```
acccttaccg agggaagcga gcctgctcag acagcctccc ccagcgttgt ctccggctcc   1260

tctagctccg gctctagctc ctcatctacc accaccacct caaagacctc aactggatcc   1320

gactacgtct ccagcgactg gatgtcttac ctcagctcct tgagcgctgc tgaggtcctc   1380

cagatgctgc gccagacctt ccgttggatg gtcagcaacg acaaggtgca cgctcgtgat   1440

attaccatca actag                                                    1455


<210> SEQ ID NO 150
<211> LENGTH: 484
<212> TYPE: PRT
<213> ORGANISM: Penicillium thomii

<400> SEQUENCE: 150

Met Ser Leu Ser Lys Ile Ser Gly Leu Ile Leu Gly Ser Ala Ala Leu
1               5                   10                  15

Val Ala Gly His Gly Tyr Val Ser Gly Ile Val Val Asp Asp Thr Tyr
            20                  25                  30

Tyr Gly Gly Tyr Leu Val Thr Gln Tyr Pro Tyr Glu Ser Asp Ala Pro
        35                  40                  45

Glu Leu Ile Ala Trp Ser Glu Gln Glu Thr Asp Leu Gly Tyr Ile Asp
    50                  55                  60

Gly Ser Glu Tyr Ala Asn Ser Asn Ile Ile Cys His Lys Glu Ala Lys
65                  70                  75                  80

Pro Gly Ala Leu Glu Ala Pro Val Lys Ala Gly Gly Ser Val Glu Leu
                85                  90                  95

Gln Trp Thr Thr Trp Pro Thr Ser His His Gly Pro Val Ile Thr Tyr
            100                 105                 110

Met Ala Asn Cys Asn Gly Asp Cys Asp Asp Val Asp Lys Thr Thr Leu
        115                 120                 125

Gln Phe Phe Lys Ile Asp Gln Gly Gly Leu Ile Ser Asp Thr Thr Glu
    130                 135                 140

Pro Gly Thr Trp Ala Thr Asp Asn Leu Ile Ala Asn Asn Asn Ser Arg
145                 150                 155                 160

Thr Val Thr Val Pro Ser Asp Ile Ala Asp Gly Asn Tyr Val Leu Arg
                165                 170                 175

His Glu Ile Ile Ala Leu His Ser Ala Gly Glu Thr Asn Gly Ala Gln
            180                 185                 190

Asn Tyr Pro Gln Cys Ile Asn Leu Lys Val Thr Gly Gly Gly Ser Ala
        195                 200                 205

Thr Pro Ser Gly Thr Leu Gly Thr Ala Leu Tyr Lys Asn Thr Asp Pro
    210                 215                 220

Gly Ile Leu Ile Asn Ile Tyr Thr Ser Leu Ser Thr Tyr Asp Ile Pro
225                 230                 235                 240

Gly Pro Thr Leu Tyr Thr Ala Gly Ala Ala Ala Ala Thr Ala Ala Ser
                245                 250                 255

Thr Ala Ala Ser Ser Thr Ala Ala Ala Val Thr Thr Ala Asp Ala Val
            260                 265                 270

Thr Thr Ala Ala Ala Val Thr Ser Ser Ser Ala Ser Val Glu Val Val
        275                 280                 285

Pro Thr Thr Thr Pro Ser Ser Ser Ile Val Ser Ala Phe Pro Thr Trp
    290                 295                 300

Ser Pro Ser Ser Thr Pro Pro Phe Ser Asn Ser Ser Asn Gly Trp Arg
305                 310                 315                 320
```

```
Pro Ser Phe Ser Arg Gly Pro Gly Gly Pro Arg Phe Thr Ser Ala Pro
                325                 330                 335

Ala Pro Gln Phe Ser Ala Pro Ser Gly Ala Gln Gln Lys Gln Ser Ala
            340                 345                 350

Thr Ala Thr Pro Ile Val Ala Thr Pro Val Val Ile Thr Met Thr Glu
        355                 360                 365

Thr Ser Thr Ser Trp Val Thr Glu Met Val Thr Leu Thr Asp Lys Ser
    370                 375                 380

Val Val Gln Thr Thr Ser Ala Val Pro Val Val Val Ala Ala Thr Thr
385                 390                 395                 400

Thr Leu Thr Glu Gly Ser Glu Pro Ala Gln Thr Ala Ser Pro Ser Val
                405                 410                 415

Val Ser Gly Ser Ser Ser Ser Gly Ser Ser Ser Ser Ser Thr Thr Thr
            420                 425                 430

Thr Ser Lys Thr Ser Thr Gly Ser Asp Tyr Val Ser Ser Asp Trp Met
        435                 440                 445

Ser Tyr Leu Ser Ser Leu Ser Ala Ala Glu Val Leu Gln Met Leu Arg
    450                 455                 460

Gln Thr Phe Arg Trp Met Val Ser Asn Asp Lys Val His Ala Arg Asp
465                 470                 475                 480

Ile Thr Ile Asn
```

<210> SEQ ID NO 151
<211> LENGTH: 1021
<212> TYPE: DNA
<213> ORGANISM: Talaromyces stipitatus

<400> SEQUENCE: 151

```
atgccttcca ctaaagttgc tgctctatct gccgtcctgg ctttggcctc cacggttgct     60

ggccatggct ttgtgcaaaa tattgtcatt gacggtaaat cgtaagtgac ttgcttttgt    120

actatagagc tagataaata cttatactaa ataattcagc tacactggct acctcgtgaa    180

ccagtatcct taccagtcca acccaccagc tgttattggg tggtcaacca ctgcaaccga    240

cttgggattt gtcgatggat ctggatacac caacccggat atcatctgcc acaaaaacgc    300

caaacccggt cagctttctg ctccggttgc cgcaggaggc aaggttgagc tcgaatggac    360

aacatggccc gagagccatc acggccctgt catcagctat ctcgccaatt gcaatggcga    420

ttgtactacc gtggataaga cgaagctcga atttgtcaaa atcgatcagc ggggtctgat    480

cgacgacagc aatcctcccg gtacatgggc cgccgaccag ctcatcgccg ccaacaacag    540

ctggactgta actattcccg agagcatcgc gcctggaaac tacgtccttc gccacgaaat    600

catcgctctt cactccgcca acaacgcaac cggagctcaa aactaccctc aatgcatcaa    660

cttgcaaatc actggcagcg ggacggccaa cccatctggt acccctggcg agaaactcta    720

taccccaact gacccaggta tcttggtcaa catctaccag tcattgtcgt cttatgttat    780

tcccggtccg actttgtgga gtggtgctgc agcgcacgtt gttgccactg cagccggttc    840

tgctactggg gttgcttctg ccaccgctac tccgaccact cttgtgactg ccgtttcatc    900

gcctaccggt gctccttcag tggtgactcc tgaggctcct tcagtaacct cgttcgcccc    960

agtggtgact gttactgatg tcgttactgt gactaccgtc atcactacta ctatctctta   1020

g                                                                   1021
```

<210> SEQ ID NO 152
<211> LENGTH: 320

<212> TYPE: PRT
<213> ORGANISM: Talaromyces stipitatus

<400> SEQUENCE: 152

```
Met Pro Ser Thr Lys Val Ala Ala Leu Ser Ala Val Leu Ala Leu Ala
1               5                   10                  15

Ser Thr Val Ala Gly His Gly Phe Val Gln Asn Ile Val Ile Asp Gly
            20                  25                  30

Lys Ser Tyr Thr Gly Tyr Leu Val Asn Gln Tyr Pro Tyr Gln Ser Asn
        35                  40                  45

Pro Pro Ala Val Ile Gly Trp Ser Thr Thr Ala Thr Asp Leu Gly Phe
    50                  55                  60

Val Asp Gly Ser Gly Tyr Thr Asn Pro Asp Ile Ile Cys His Lys Asn
65                  70                  75                  80

Ala Lys Pro Gly Gln Leu Ser Ala Pro Val Ala Ala Gly Gly Lys Val
                85                  90                  95

Glu Leu Glu Trp Thr Thr Trp Pro Glu Ser His His Gly Pro Val Ile
            100                 105                 110

Ser Tyr Leu Ala Asn Cys Asn Gly Asp Cys Thr Thr Val Asp Lys Thr
        115                 120                 125

Lys Leu Glu Phe Val Lys Ile Asp Gln Arg Gly Leu Ile Asp Asp Ser
    130                 135                 140

Asn Pro Pro Gly Thr Trp Ala Ala Asp Gln Leu Ile Ala Ala Asn Asn
145                 150                 155                 160

Ser Trp Thr Val Thr Ile Pro Glu Ser Ile Ala Pro Gly Asn Tyr Val
                165                 170                 175

Leu Arg His Glu Ile Ile Ala Leu His Ser Ala Asn Asn Ala Thr Gly
            180                 185                 190

Ala Gln Asn Tyr Pro Gln Cys Ile Asn Leu Gln Ile Thr Gly Ser Gly
        195                 200                 205

Thr Ala Asn Pro Ser Gly Thr Pro Gly Glu Lys Leu Tyr Thr Pro Thr
    210                 215                 220

Asp Pro Gly Ile Leu Val Asn Ile Tyr Gln Ser Leu Ser Ser Tyr Val
225                 230                 235                 240

Ile Pro Gly Pro Thr Leu Trp Ser Gly Ala Ala Ala His Val Val Ala
                245                 250                 255

Thr Ala Ala Gly Ser Ala Thr Gly Val Ala Ser Ala Thr Ala Thr Pro
            260                 265                 270

Thr Thr Leu Val Thr Ala Val Ser Ser Pro Thr Gly Ala Pro Ser Val
        275                 280                 285

Val Thr Pro Glu Ala Pro Ser Val Thr Ser Phe Ala Pro Val Val Thr
    290                 295                 300

Val Thr Asp Val Val Thr Val Thr Thr Val Ile Thr Thr Thr Ile Ser
305                 310                 315                 320
```

<210> SEQ ID NO 153
<211> LENGTH: 1145
<212> TYPE: DNA
<213> ORGANISM: Aspergillus fumigatus

<400> SEQUENCE: 153

```
atgcgtttct cccttgccgc caccgctctt ctcgctggcc tggccacggc agcgccttcg      60

agcaacaaga acaacgtcaa tcttgataag cttgctcggc gtaatggcat gctttggttc     120

ggcactgcag ccgatatccc tggtacctca gaaacaaccg acaagcctta tctgagcatc     180
```

```
ctgcgcaagc agttcggcga aatgacaccc gcaaacgcat tgaaggtgag ccagagtgat    240

agtacacctc atctcgtgtc ggcgctgacc agacgatgtt attcacatag ttcatgtata    300

ccgagcccga gcagaatgtc ttcaacttca ctcaagggga ctacttcatg gacttggccg    360

atcactatgg tcacgccgtg cgctgccata acctcgtctg ggccagccaa gtgtccgact    420

gggtcacctc caggaactgg accgccacag aactcaaaga agtgatgaag aaccacatat    480

tcaagaccgt ccaacatttt ggcaagcgct gctacgcgtg ggacgtcgtc aatgaagcta    540

ttaatgggga cgggaccttt tcctccagtg tgtggtacga cacaattggc gaggaatact    600

tctaccttgc attccagtat gcccaggaag ccctggcgca gattcacgcc aaccaggtca    660

agctttacta taacgactat ggcattgaga accccggccc caaggcagat gctgttctga    720

agctagtcgc cgagttgcgg aagcggggca ttcgcattga cggagtcggt ctcgagtccc    780

acttcatcgt cggcgagact ccttcgctgg ctgaccagct cgccaccaag aaggcttata    840

tcgaggccgg acttgaggtc gccatcaccg aacttgacgt ccgcttttct caggccccgt    900

tctacaccgc cgaggcccaa aagcagcagg ctgccgacta ctatgctagc gtcgccagtt    960

gcaagcatgc cggaccgcgc tgtgttggtg ttgtagtctg ggatttcgat gacgcctact   1020

cgtggattcc gggtaccttc gagggacagg gtggcgcctg tctatataat gagacactcg   1080

aggtgaagcc ggccttctat gctgctgccg aggcgttgga gaacaagccc tgcactgtat   1140

gctag                                                               1145
```

<210> SEQ ID NO 154
<211> LENGTH: 364
<212> TYPE: PRT
<213> ORGANISM: Aspergillus fumigatus

<400> SEQUENCE: 154

```
Met Arg Phe Ser Leu Ala Ala Thr Ala Leu Leu Ala Gly Leu Ala Thr
1               5                   10                  15

Ala Ala Pro Ser Ser Asn Lys Asn Asn Val Asn Leu Asp Lys Leu Ala
            20                  25                  30

Arg Arg Asn Gly Met Leu Trp Phe Gly Thr Ala Ala Asp Ile Pro Gly
        35                  40                  45

Thr Ser Glu Thr Thr Asp Lys Pro Tyr Leu Ser Ile Leu Arg Lys Gln
    50                  55                  60

Phe Gly Glu Met Thr Pro Ala Asn Ala Leu Lys Val Ser Gln Ser Asp
65                  70                  75                  80

Phe Met Tyr Thr Glu Pro Glu Gln Asn Val Phe Asn Phe Thr Gln Gly
                85                  90                  95

Asp Tyr Phe Met Asp Leu Ala Asp His Tyr Gly His Ala Val Arg Cys
            100                 105                 110

His Asn Leu Val Trp Ala Ser Gln Val Ser Asp Trp Val Thr Ser Arg
        115                 120                 125

Asn Trp Thr Ala Thr Glu Leu Lys Glu Val Met Lys Asn His Ile Phe
    130                 135                 140

Lys Thr Val Gln His Phe Gly Lys Arg Cys Tyr Ala Trp Asp Val Val
145                 150                 155                 160

Asn Glu Ala Ile Asn Gly Asp Gly Thr Phe Ser Ser Ser Val Trp Tyr
                165                 170                 175

Asp Thr Ile Gly Glu Glu Tyr Phe Tyr Leu Ala Phe Gln Tyr Ala Gln
            180                 185                 190

Glu Ala Leu Ala Gln Ile His Ala Asn Gln Val Lys Leu Tyr Tyr Asn
```

```
        195                 200                 205

Asp Tyr Gly Ile Glu Asn Pro Gly Pro Lys Ala Asp Ala Val Leu Lys
    210                 215                 220

Leu Val Ala Glu Leu Arg Lys Arg Gly Ile Arg Ile Asp Gly Val Gly
225                 230                 235                 240

Leu Glu Ser His Phe Ile Val Gly Glu Thr Pro Ser Leu Ala Asp Gln
                245                 250                 255

Leu Ala Thr Lys Lys Ala Tyr Ile Glu Ala Gly Leu Glu Val Ala Ile
            260                 265                 270

Thr Glu Leu Asp Val Arg Phe Ser Gln Ala Pro Phe Tyr Thr Ala Glu
        275                 280                 285

Ala Gln Lys Gln Gln Ala Ala Asp Tyr Tyr Ala Ser Val Ala Ser Cys
    290                 295                 300

Lys His Ala Gly Pro Arg Cys Val Gly Val Val Val Trp Asp Phe Asp
305                 310                 315                 320

Asp Ala Tyr Ser Trp Ile Pro Gly Thr Phe Glu Gly Gln Gly Gly Ala
                325                 330                 335

Cys Leu Tyr Asn Glu Thr Leu Glu Val Lys Pro Ala Phe Tyr Ala Ala
            340                 345                 350

Ala Glu Ala Leu Glu Asn Lys Pro Cys Thr Val Cys
        355                 360
```

<210> SEQ ID NO 155
<211> LENGTH: 1400
<212> TYPE: DNA
<213> ORGANISM: Aspergillus fumigatus

<400> SEQUENCE: 155

```
atggtcgtcc tcagcaagct cgtcagcagc attctctttg tctccctggt ttcggcgggc     60

gtgatcgacg aacgccaggc agccggcatc aaccaggcgt ttacctccca tggcaagaag    120

tactttggca ccgccagtga ccaagctctg ctccagaagt cgcagaatga ggccattgtg    180

cgcaaagact ttggccagct gacgccggag aatagcatga agtgggatgc gactgagcgt    240

aggtctctcg gccactgtgg ctgacgttaa cttgttgaca tgactgtctg tgtagcatcg    300

caaggaagat tcaacttcgc tggtgctgat ttcctggtat gcaatctgct catctcggtc    360

gagctcctgc tgaaggacaa taaataggtc aactatgcaa aacagaatgg caagaaggtc    420

cgcggacaca ccttaggtat tcatgcgccc tcacggcatt tcgaggatac agccaagctg    480

acagtgtagt ctggcactcc caactcccgt cctgggtgtc ggctatcagc gacaaaaaca    540

ccctgacctc ggtgctgaag aaccacatca ccaccgtcat gacccggtac aagggccaga    600

tctacgcctg ggtatttgc cctctatccc acacaatgcc agccccagct aatagctgca    660

aaggacgtcg tcaacgagat cttcaacgag gacggctccc tccgcgacag cgtcttctcc    720

cgcgtgctgg gcgaggactt tgtgcggatt gccttcgaga cggcgcgctc tgtggatccc    780

tcggcgaagc tgtacatcaa cgattacaag taagcttgtg gttttgtcga gagatgtact    840

ccgtcctgga tctgaccatc acagtctcga ctcggctagc tatggcaaaa cccaggggat    900

ggtgagatat gtcaagaagt ggctggctgc gggcattcct atcgatggaa tcggtgagca    960

caggtcgcgg agctgtgtgt gatgattgta cgctgactct tcctgaaggc actcaaaccc   1020

accttggtgc gggtgcttcg tccagcgtca aaggataagt ctccttggtt ttcttgccta   1080

cgtaacgctg acccccgtg tacagcattg actgctcttg cgtcttccgg cgtctctgag    1140

gtcgccatta ccgagctgga tatcgcgggt gcgagctccc aggactacgt caatgtatgt   1200
```

```
ctcctgattg ccagtggcag ggtcatcgat actaatagaa acaggtcgtc aaggcatgcc   1260

tggatgtccc caagtgtgtg ggaatcaccg tctgggggt gtcggacagg gactcgtggc   1320

gctccggctc gtctccgctg ctgttcgaca gcaactacca gcccaaggcg gcgtataatg   1380

ccatcattgc tgctctctga                                               1400


<210> SEQ ID NO 156
<211> LENGTH: 323
<212> TYPE: PRT
<213> ORGANISM: Aspergillus fumigatus

<400> SEQUENCE: 156

Met Val Val Leu Ser Lys Leu Val Ser Ser Ile Leu Phe Val Ser Leu
1               5                   10                  15

Val Ser Ala Gly Val Ile Asp Glu Arg Gln Ala Ala Gly Ile Asn Gln
            20                  25                  30

Ala Phe Thr Ser His Gly Lys Lys Tyr Phe Gly Thr Ala Ser Asp Gln
        35                  40                  45

Ala Leu Leu Gln Lys Ser Gln Asn Glu Ala Ile Val Arg Lys Asp Phe
    50                  55                  60

Gly Gln Leu Thr Pro Glu Asn Ser Met Lys Trp Asp Ala Thr Glu Ala
65                  70                  75                  80

Ser Gln Gly Arg Phe Asn Phe Ala Gly Ala Asp Phe Leu Val Asn Tyr
                85                  90                  95

Ala Lys Gln Asn Gly Lys Lys Val Arg Gly His Thr Leu Trp His Ser
            100                 105                 110

Gln Leu Pro Ser Trp Val Ser Ala Ile Ser Asp Lys Asn Thr Leu Thr
        115                 120                 125

Ser Val Leu Lys Asn His Ile Thr Thr Val Met Thr Arg Tyr Lys Gly
    130                 135                 140

Gln Ile Tyr Ala Trp Asp Val Val Asn Glu Ile Phe Asn Glu Asp Gly
145                 150                 155                 160

Ser Leu Arg Asp Ser Val Phe Ser Arg Val Leu Gly Glu Asp Phe Val
                165                 170                 175

Arg Ile Ala Phe Glu Thr Ala Arg Ser Val Asp Pro Ser Ala Lys Leu
            180                 185                 190

Tyr Ile Asn Asp Tyr Lys Leu Asp Ser Ala Ser Tyr Gly Lys Thr Gln
        195                 200                 205

Gly Met Val Arg Tyr Val Lys Lys Trp Leu Ala Ala Gly Ile Pro Ile
    210                 215                 220

Asp Gly Ile Gly Gln Thr His Leu Gly Ala Gly Ala Ser Ser Ser Val
225                 230                 235                 240

Lys Gly Ala Leu Thr Ala Leu Ala Ser Ser Gly Val Ser Glu Val Ala
                245                 250                 255

Ile Thr Glu Leu Asp Ile Ala Gly Ala Ser Ser Gln Asp Tyr Val Asn
            260                 265                 270

Val Val Lys Ala Cys Leu Asp Val Pro Lys Cys Val Gly Ile Thr Val
        275                 280                 285

Trp Gly Val Ser Asp Arg Asp Ser Trp Arg Ser Gly Ser Ser Pro Leu
    290                 295                 300

Leu Phe Asp Ser Asn Tyr Gln Pro Lys Ala Ala Tyr Asn Ala Ile Ile
305                 310                 315                 320

Ala Ala Leu
```

<210> SEQ ID NO 157
<211> LENGTH: 1415
<212> TYPE: DNA
<213> ORGANISM: Aspergillus fumigatus

<400> SEQUENCE: 157

```
atggtccatc tatcttcatt ggcagcagcc ctggctgctc tgcctctgta tgtttaccca      60

ctcacgagag gaggaacagc tttgacattg ctatagtgta tatggagctg gcctgaacac     120

agcagccaaa gccaaaggac taaagtactt tggttccgcc acggacaatc cagagctcac     180

ggactctgcg tatgtcgcgc aactgagcaa caccgatgat tttggtcaaa tcacacccgg     240

aaactccatg aaggtttgct tacgtctgcc tccctggagc attgcctcaa aagctaattg     300

gttgttttgt ttggatagtg ggatgccacc gagccttctc agaattcttt ttcgttcgca     360

aatggagacg ccgtggtcaa tctggcgaac aagaatggcc agctgatgcg atgccatact     420

ctggtctggc acagtcagct accgaactgg ggtatgtaaa cgtcttgtct attctcaaat     480

actctctaac agttgacagt ctctagcggg tcatggacca atgcgaccct tttggcggcc     540

atgaagaatc atatcaccaa tgtggttact cactacaagg ggaagtgcta cgcctgggat     600

gttgtcaatg aaggtttgtt gctccatcta tcctcaatag ttcttttgaa actgacaagc     660

ctgtcaatct agccctgaac gaggacggta ctttccgtaa ctctgtcttc taccagatca     720

tcggcccagc atacattcct attgcgttcg ccacggctgc tgccgcagat cccgacgtga     780

aactctacta caacgactac aacattgaat actcaggcgc caaagcgact gctgcgcaga     840

atatcgtcaa gatgatcaag gcctacggcg cgaagatcga cggcgtcggc ctccaggcac     900

actttatcgt cggcagcact ccgagtcaat cggatctgac gaccgtcttg aagggctaca     960

ctgctctcgg cgttgaggtg gcctataccg aacttgacat ccgcatgcag ctgccctcga    1020

ccgccgcaaa gctggcccag cagtccactg acttccaagg cgtggccgca gcatgcgtta    1080

gcaccactgg ctgcgtgggt gtcactatct gggactggac cgacaagtac tcctgggtcc    1140

ccagcgtgtt ccaaggctac ggcgccccat tgccttggga tgagaactat gtgaagaagc    1200

cagcgtacga tggcctgatg gcgggtcttg gagcaagcgg ctccggcacc acaacgacca    1260

ctactactac ttctactacg acaggaggta cggaccctac tggagtcgct cagaaatggg    1320

gacagtgtgg cggtattggc tggaccgggc caacaacttg tgtcagtggt accacttgcc    1380

aaaagctgaa tgactggtac tcacagtgcc tgtaa                               1415
```

<210> SEQ ID NO 158
<211> LENGTH: 397
<212> TYPE: PRT
<213> ORGANISM: Aspergillus fumigatus

<400> SEQUENCE: 158

```
Met Val His Leu Ser Ser Leu Ala Ala Ala Leu Ala Ala Leu Pro Leu
1               5                   10                  15

Val Tyr Gly Ala Gly Leu Asn Thr Ala Ala Lys Ala Lys Gly Leu Lys
            20                  25                  30

Tyr Phe Gly Ser Ala Thr Asp Asn Pro Glu Leu Thr Asp Ser Ala Tyr
        35                  40                  45

Val Ala Gln Leu Ser Asn Thr Asp Asp Phe Gly Gln Ile Thr Pro Gly
    50                  55                  60

Asn Ser Met Lys Trp Asp Ala Thr Glu Pro Ser Gln Asn Ser Phe Ser
65                  70                  75                  80
```

```
Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
            100                 105                 110

Val Ser Ser Gly Ser Trp Thr Asn Ala Thr Leu Leu Ala Ala Met Lys
        115                 120                 125

Asn His Ile Thr Asn Val Val Thr His Tyr Lys Gly Lys Cys Tyr Ala
    130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Ala Asp Pro Asp Val Lys Leu Tyr Tyr Asn Asp
            180                 185                 190

Tyr Asn Ile Glu Tyr Ser Gly Ala Lys Ala Thr Ala Ala Gln Asn Ile
        195                 200                 205

Val Lys Met Ile Lys Ala Tyr Gly Ala Lys Ile Asp Gly Val Gly Leu
    210                 215                 220

Gln Ala His Phe Ile Val Gly Ser Thr Pro Ser Gln Ser Asp Leu Thr
225                 230                 235                 240

Thr Val Leu Lys Gly Tyr Thr Ala Leu Gly Val Glu Val Ala Tyr Thr
                245                 250                 255

Glu Leu Asp Ile Arg Met Gln Leu Pro Ser Thr Ala Ala Lys Leu Ala
            260                 265                 270

Gln Gln Ser Thr Asp Phe Gln Gly Val Ala Ala Ala Cys Val Ser Thr
        275                 280                 285

Thr Gly Cys Val Gly Val Thr Ile Trp Asp Trp Thr Asp Lys Tyr Ser
    290                 295                 300

Trp Val Pro Ser Val Phe Gln Gly Tyr Gly Ala Pro Leu Pro Trp Asp
305                 310                 315                 320

Glu Asn Tyr Val Lys Lys Pro Ala Tyr Asp Gly Leu Met Ala Gly Leu
                325                 330                 335

Gly Ala Ser Gly Ser Gly Thr Thr Thr Thr Thr Thr Thr Thr Ser Thr
            340                 345                 350

Thr Thr Gly Gly Thr Asp Pro Thr Gly Val Ala Gln Lys Trp Gly Gln
        355                 360                 365

Cys Gly Gly Ile Gly Trp Thr Gly Pro Thr Thr Cys Val Ser Gly Thr
    370                 375                 380

Thr Cys Gln Lys Leu Asn Asp Trp Tyr Ser Gln Cys Leu
385                 390                 395
```

<210> SEQ ID NO 159
<211> LENGTH: 2564
<212> TYPE: DNA
<213> ORGANISM: Trichoderma reesei

<400> SEQUENCE: 159

```
ggacagccgg acgcaatggt gaataacgca gctcttctcg ccgccctgtc ggctctcctg      60

cccacggccc tggcgcagaa caatcaaaca tacgccaact actctgctca gggccagcct     120

gatctctacc ccgagacact tgccacgctc acactctcgt tccccgactg cgaacatggc     180

cccctcaaga acaatctcgt ctgtgactca tcggccggct atgtagagcg agcccaggcc     240

ctcatctcgc tcttcaccct cgaggagctc attctcaaca cgcaaaactc gggccccggc     300

gtgcctcgcc tgggtcttcc gaactaccaa gtctggaatg aggctctgca cggcttggac     360
```

```
cgcgccaact tcgccaccaa gggcggccag ttcgaatggg cgacctcgtt ccccatgccc    420

atcctcacta cggcggccct caaccgcaca ttgatccacc agattgccga catcatctcg    480

acccaagctc gagcattcag caacagcggc cgttacggtc tcgacgtcta tgcgccaaac    540

gtcaatggct tccgaagccc cctctggggc cgtggccagg agacgcccgg cgaagacgcc    600

tttttcctca gctccgccta tacttacgag tacatcacgg gcatccaggg tggcgtcgac    660

cctgagcacc tcaaggttgc cgccacggtg aagcactttg ccggatacga cctcgagaac    720

tggaacaacc agtcccgtct cggtttcgac gccatcataa ctcagcagga cctctccgaa    780

tactacactc cccagttcct cgctgcggcc cgttatgcaa agtcacgcag cttgatgtgc    840

gcatacaact ccgtcaacgg cgtgcccagc tgtgccaaca gcttcttcct gcagacgctt    900

ttgcgcgaga gctggggctt ccccgaatgg ggatacgtct cgtccgattg cgatgccgtc    960

tacaacgttt tcaaccctca tgactacgcc agcaaccagt cgtcagccgc cgccagctca   1020

ctgcgagccg gcaccgatat cgactgcggt cagacttacc cgtggcacct caacgagtcc   1080

tttgtggccg gcgaagtctc ccgcggcgag atcgagcggt ccgtcacccg tctgtacgcc   1140

aacctcgtcc gtctcggata cttcgacaag aagaaccagt accgctcgct cggttggaag   1200

gatgtcgtca agactgatgc ctggaacatc tcgtacgagg ctgctgttga gggcatcgtc   1260

ctgctcaaga acgatggcac tctccctctg tccaagaagg tgcgcagcat tgctctgatc   1320

ggaccatggg ccaatgccac aacccaaatg caaggcaact actatggccc tgccccatac   1380

ctcatcagcc ctctggaagc tgctaagaag gccggctatc acgtcaactt tgaactcggc   1440

acagagatcg ccggcaacag caccactggc tttgccaagg ccattgctgc cgccaagaag   1500

tcggatgcca tcatctacct cggtggaatt gacaacacca ttgaacagga gggcgctgac   1560

cgcacggaca ttgcttggcc cggtaatcag ctggatctca tcaagcagct cagcgaggtc   1620

ggcaaacccc ttgtcgtcct gcaaatgggc ggtggtcagg tagactcatc ctcgctcaag   1680

agcaacaaga aggtcaactc cctcgtctgg ggcggatatc ccggccagtc gggaggcgtt   1740

gccctcttcg acattctctc tggcaagcgt gctcctgccg gccgactggt caccactcag   1800

tacccggctg agtatgttca ccaattcccc cagaatgaca tgaacctccg acccgatgga   1860

aagtcaaacc ctggacagac ttacatctgg tacaccggca aacccgtcta cgagtttggc   1920

agtggtctct tctacaccac cttcaaggag actctcgcca gccaccccaa gagcctcaag   1980

ttcaacacct catcgatcct ctctgctcct caccccggat acacttacag cgagcagatt   2040

cccgtcttca ccttcgaggc caacatcaag aactcgggca agacggagtc ccatatacg    2100

gccatgctgt ttgttcgcac aagcaacgct ggcccagccc cgtacccgaa caagtggctc   2160

gtcggattcg accgacttgc cgacatcaag cctggtcact cttccaagct cagcatcccc   2220

atccctgtca gtgctctcgc ccgtgttgat tctcacggaa accggattgt ataccccggc   2280

aagtatgagc tagccttgaa caccgacgag tctgtgaagc ttgagtttga gttggtggga   2340

gaagaggtaa cgattgagaa ctggccgttg gaggagcaac agatcaagga tgctacacct   2400

gacgcataag ggttttaatg atgttgttat gacaaacggg tagagtagtt aatgatggaa   2460

taggaagagg ccatagtttt ctgtttgcaa accatttttg ccattgcgaa aaaaaaaaaa   2520

aaaaaaaaaa aaaaaaaaaa aaaaaaaaaa aaaaaaaaaa aaaa                    2564
```

<210> SEQ ID NO 160
<211> LENGTH: 780
<212> TYPE: PRT

<213> ORGANISM: Trichoderma reesei

<400> SEQUENCE: 160

```
Met Val Asn Asn Ala Ala Leu Leu Ala Ala Leu Ser Ala Leu Leu Pro
1               5                   10                  15

Thr Ala Leu Ala Gln Asn Asn Gln Thr Tyr Ala Asn Tyr Ser Ala Gln
            20                  25                  30

Gly Gln Pro Asp Leu Tyr Pro Glu Thr Leu Ala Thr Leu Thr Leu Ser
        35                  40                  45

Phe Pro Asp Cys Glu His Gly Pro Leu Lys Asn Asn Leu Val Cys Asp
    50                  55                  60

Ser Ser Ala Gly Tyr Val Glu Arg Ala Gln Ala Leu Ile Ser Leu Phe
65                  70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
            100                 105                 110

Gly Leu Asp Arg Ala Asn Phe Ala Thr Lys Gly Gly Gln Phe Glu Trp
        115                 120                 125

Ala Thr Ser Phe Pro Met Pro Ile Leu Thr Thr Ala Ala Leu Asn Arg
    130                 135                 140

Thr Leu Ile His Gln Ile Ala Asp Ile Ile Ser Thr Gln Ala Arg Ala
145                 150                 155                 160

Phe Ser Asn Ser Gly Arg Tyr Gly Leu Asp Val Tyr Ala Pro Asn Val
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Ala Tyr Thr Tyr Glu Tyr Ile Thr
        195                 200                 205

Gly Ile Gln Gly Gly Val Asp Pro Glu His Leu Lys Val Ala Ala Thr
    210                 215                 220

Val Lys His Phe Ala Gly Tyr Asp Leu Glu Asn Trp Asn Asn Gln Ser
225                 230                 235                 240

Arg Leu Gly Phe Asp Ala Ile Ile Thr Gln Gln Asp Leu Ser Glu Tyr
                245                 250                 255

Tyr Thr Pro Gln Phe Leu Ala Ala Ala Arg Tyr Ala Lys Ser Arg Ser
            260                 265                 270

Leu Met Cys Ala Tyr Asn Ser Val Asn Gly Val Pro Ser Cys Ala Asn
        275                 280                 285

Ser Phe Phe Leu Gln Thr Leu Leu Arg Glu Ser Trp Gly Phe Pro Glu
    290                 295                 300

Trp Gly Tyr Val Ser Ser Asp Cys Asp Ala Val Tyr Asn Val Phe Asn
305                 310                 315                 320

Pro His Asp Tyr Ala Ser Asn Gln Ser Ser Ala Ala Ala Ser Ser Leu
                325                 330                 335

Arg Ala Gly Thr Asp Ile Asp Cys Gly Gln Thr Tyr Pro Trp His Leu
            340                 345                 350

Asn Glu Ser Phe Val Ala Gly Glu Val Ser Arg Gly Glu Ile Glu Arg
        355                 360                 365

Ser Val Thr Arg Leu Tyr Ala Asn Leu Val Arg Leu Gly Tyr Phe Asp
    370                 375                 380

Lys Lys Asn Gln Tyr Arg Ser Leu Gly Trp Lys Asp Val Val Lys Thr
385                 390                 395                 400
```

```
Asp Ala Trp Asn Ile Ser Tyr Glu Ala Ala Val Glu Gly Ile Val Leu
                405                 410                 415

Leu Lys Asn Asp Gly Thr Leu Pro Leu Ser Lys Lys Val Arg Ser Ile
            420                 425                 430

Ala Leu Ile Gly Pro Trp Ala Asn Ala Thr Thr Gln Met Gln Gly Asn
        435                 440                 445

Tyr Tyr Gly Pro Ala Pro Tyr Leu Ile Ser Pro Leu Glu Ala Ala Lys
    450                 455                 460

Lys Ala Gly Tyr His Val Asn Phe Glu Leu Gly Thr Glu Ile Ala Gly
465                 470                 475                 480

Asn Ser Thr Thr Gly Phe Ala Lys Ala Ile Ala Ala Ala Lys Lys Ser
                485                 490                 495

Asp Ala Ile Ile Tyr Leu Gly Gly Ile Asp Asn Thr Ile Glu Gln Glu
            500                 505                 510

Gly Ala Asp Arg Thr Asp Ile Ala Trp Pro Gly Asn Gln Leu Asp Leu
        515                 520                 525

Ile Lys Gln Leu Ser Glu Val Gly Lys Pro Leu Val Val Leu Gln Met
    530                 535                 540

Gly Gly Gly Gln Val Asp Ser Ser Ser Leu Lys Ser Asn Lys Lys Val
545                 550                 555                 560

Asn Ser Leu Val Trp Gly Gly Tyr Pro Gly Gln Ser Gly Gly Val Ala
                565                 570                 575

Leu Phe Asp Ile Leu Ser Gly Lys Arg Ala Pro Ala Gly Arg Leu Val
            580                 585                 590

Thr Thr Gln Tyr Pro Ala Glu Tyr Val His Gln Phe Pro Gln Asn Asp
        595                 600                 605

Met Asn Leu Arg Pro Asp Gly Lys Ser Asn Pro Gly Gln Thr Tyr Ile
    610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
                645                 650                 655

Asn Thr Ser Ser Ile Leu Ser Ala Pro His Pro Gly Tyr Thr Tyr Ser
            660                 665                 670

Glu Gln Ile Pro Val Phe Thr Phe Glu Ala Asn Ile Lys Asn Ser Gly
        675                 680                 685

Lys Thr Glu Ser Pro Tyr Thr Ala Met Leu Phe Val Arg Thr Ser Asn
    690                 695                 700

Ala Gly Pro Ala Pro Tyr Pro Asn Lys Trp Leu Val Gly Phe Asp Arg
705                 710                 715                 720

Leu Ala Asp Ile Lys Pro Gly His Ser Ser Lys Leu Ser Ile Pro Ile
                725                 730                 735

Pro Val Ser Ala Leu Ala Arg Val Asp Ser His Gly Asn Arg Ile Val
            740                 745                 750

Tyr Pro Gly Lys Tyr Glu Leu Ala Leu Asn Thr Asp Glu Ser Val Lys
        755                 760                 765

Leu Glu Phe Glu Leu Val Gly Glu Glu Val Thr Ile
    770                 775                 780
```

<210> SEQ ID NO 161
<211> LENGTH: 2376
<212> TYPE: DNA
<213> ORGANISM: Aspergillus fumigatus

<400> SEQUENCE: 161

```
atggcggttg ccaaatctat tgctgccgtg ctggtagcac tgttgcctgg tgcgcttgct     60
caggcgaata caagctatgt tgattacaat gtggaggcga atccggatct cacccctcag    120
tcggtcgcta cgattgacct gtcctttccc gactgcgaga atggaccgct cagcaagact    180
ctcgtttgcg acacgtcggc tcggccgcat gaccgagctg ctgccctggt ttccatgttc    240
accttcgagg agctggtgaa caacacaggc aacactagcc ctggtgttcc aagacttggt    300
ctccctccgt accaagtatg gagcgaggct ctccatggac ttgaccgcgc caacttcaca    360
aacgagggag agtacagctg ggccacctcg ttccccatgc ctatcctgac aatgtcggcc    420
ttgaaccgaa ccctgatcaa ccagatcgcg accatcatcg caactcaagg acgagctttc    480
aataacgttg ggcggtatgg gctggacgtg tacgccccga atataaatgc attcagatcg    540
gctatgtggg gaagaggtca agagaccccc ggagaagacg cttactgcct ggcatcggcg    600
tatgcgtacg agtatatcac tggcatccag ggtggtgttg atccggaaca cctcaagttg    660
gtggccactg ccaaacacta tgcgggctac gatcttgaga actgggacgg tcactcccgt    720
ttgggcaacg atatgaacat tacacagcag gaactttccg aatactacac ccctcagttc    780
cttgttgcag ccagagacgc caaagtgcac agtgtcatgt gctcctacaa cgcggtaaat    840
ggggtgccca gctgcgcaaa ctcgttcttc ctccagaccc tcctccgtga cacattcggc    900
ttcgtcgagg atggttatgt atccagcgac tgcgactcgg cgtacaatgt ctggaacccg    960
cacgagtttg cggccaacat cacgggggcc gctgcagact ctatccgggc ggggacggac   1020
attgattgcg gcactactta tcaatactat ttcggcgaag cctttgacga gcaagaggtc   1080
acccgtgcag aaatcgaaag aggtgtgatc cgcctgtaca gcaacttggt gcgtctcggc   1140
tatttcgatg gcaatggaag cgtgtatcgg gacctgacgt ggaatgatgt cgtgaccacg   1200
gatgcctgga atatctcata cgaagccgct gtagaaggca ttgtcctact gaagaacgat   1260
ggaaccttgc ctctcgccaa gtcggtccgc agtgttgcat tgattgggcc ctggatgaat   1320
gtgacgactc agcttcaggg caactacttt ggaccggcgc cttatctgat tagtccgttg   1380
aatgccttcc agaattctga cttcgacgtg aactacgctt tcggcacgaa catttcatcc   1440
cactccacag atgggttttc cgaggcgttg tctgctgcga agaaatccga cgtcatcata   1500
ttcgcgggcg ggattgacaa cactttggaa gcagaagcca tggatcgcat gaatatcaca   1560
tggcccggca atcagctaca gctcatcgac cagttgagcc aactcggcaa accgctgatc   1620
gtcctccaga tgggcggcgg ccaagtcgac tcctcctcgc tcaagtccaa caagaatgtc   1680
aactccctga tctggggtgg ataccccgga caatccggcg ggcaggctct cctagacatc   1740
atcaccggca agcgcgcccc cgccggccga ctcgtggtca cgcagtaccc ggccgaatac   1800
gcaacccagt tccccgccac cgacatgagc ctgcggcctc acggcaataa tcccggccag   1860
acctacatgt ggtacaccgg caccccccgtc tacgagtttg gccacgggct cttctacacg   1920
accttccacg cctccctccc tggcaccggc aaggacaaga cctccttcaa catccaagac   1980
ctcctcacgc agccgcatcc gggcttcgca aacgtcgagc aaatgccttt gctcaacttc   2040
accgtgacga tcaccaatac cggcaaggtc gcttccgact acactgctat gctcttcgcg   2100
aacaccaccg cgggacctgc tccatacccg aacaagtggc tcgtcggctt cgaccggctg   2160
gcgagcctgg aaccgcacag gtcgcagact atgaccatcc ccgtgactat cgacagcgtg   2220
gctcgtacgg atgaggccgg caatcgggtt ctctacccgg gaaagtacga gttggccctg   2280
aacaatgagc ggtcggttgt ccttcagttt gtgctgacag gccgagaggc tgtgattttc   2340
```

```
aagtggcctg tagagcagca gcagatttcg tctgcg                          2376


<210> SEQ ID NO 162
<211> LENGTH: 792
<212> TYPE: PRT
<213> ORGANISM: Aspergillus fumigatus

<400> SEQUENCE: 162

Met Ala Val Ala Lys Ser Ile Ala Ala Val Leu Val Ala Leu Leu Pro
1               5                   10                  15

Gly Ala Leu Ala Gln Ala Asn Thr Ser Tyr Val Asp Tyr Asn Val Glu
            20                  25                  30

Ala Asn Pro Asp Leu Thr Pro Gln Ser Val Ala Thr Ile Asp Leu Ser
        35                  40                  45

Phe Pro Asp Cys Glu Asn Gly Pro Leu Ser Lys Thr Leu Val Cys Asp
    50                  55                  60

Thr Ser Ala Arg Pro His Asp Arg Ala Ala Ala Leu Val Ser Met Phe
65                  70                  75                  80

Thr Phe Glu Glu Leu Val Asn Asn Thr Gly Asn Thr Ser Pro Gly Val
                85                  90                  95

Pro Arg Leu Gly Leu Pro Pro Tyr Gln Val Trp Ser Glu Ala Leu His
            100                 105                 110

Gly Leu Asp Arg Ala Asn Phe Thr Asn Glu Gly Glu Tyr Ser Trp Ala
        115                 120                 125

Thr Ser Phe Pro Met Pro Ile Leu Thr Met Ser Ala Leu Asn Arg Thr
    130                 135                 140

Leu Ile Asn Gln Ile Ala Thr Ile Ile Ala Thr Gln Gly Arg Ala Phe
145                 150                 155                 160

Asn Asn Val Gly Arg Tyr Gly Leu Asp Val Tyr Ala Pro Asn Ile Asn
                165                 170                 175

Ala Phe Arg Ser Ala Met Trp Gly Arg Gly Gln Glu Thr Pro Gly Glu
            180                 185                 190

Asp Ala Tyr Cys Leu Ala Ser Ala Tyr Ala Tyr Glu Tyr Ile Thr Gly
        195                 200                 205

Ile Gln Gly Gly Val Asp Pro Glu His Leu Lys Leu Val Ala Thr Ala
    210                 215                 220

Lys His Tyr Ala Gly Tyr Asp Leu Glu Asn Trp Asp Gly His Ser Arg
225                 230                 235                 240

Leu Gly Asn Asp Met Asn Ile Thr Gln Gln Glu Leu Ser Glu Tyr Tyr
                245                 250                 255

Thr Pro Gln Phe Leu Val Ala Ala Arg Asp Ala Lys Val His Ser Val
            260                 265                 270

Met Cys Ser Tyr Asn Ala Val Asn Gly Val Pro Ser Cys Ala Asn Ser
        275                 280                 285

Phe Phe Leu Gln Thr Leu Leu Arg Asp Thr Phe Gly Phe Val Glu Asp
    290                 295                 300

Gly Tyr Val Ser Ser Asp Cys Asp Ser Ala Tyr Asn Val Trp Asn Pro
305                 310                 315                 320

His Glu Phe Ala Ala Asn Ile Thr Gly Ala Ala Ala Asp Ser Ile Arg
                325                 330                 335

Ala Gly Thr Asp Ile Asp Cys Gly Thr Thr Tyr Gln Tyr Tyr Phe Gly
            340                 345                 350

Glu Ala Phe Asp Glu Gln Glu Val Thr Arg Ala Glu Ile Glu Arg Gly
        355                 360                 365
```

```
Val Ile Arg Leu Tyr Ser Asn Leu Val Arg Leu Gly Tyr Phe Asp Gly
    370                 375                 380

Asn Gly Ser Val Tyr Arg Asp Leu Thr Trp Asn Asp Val Val Thr Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ala Lys Ser Val Arg Ser Val
            420                 425                 430

Ala Leu Ile Gly Pro Trp Met Asn Val Thr Thr Gln Leu Gln Gly Asn
        435                 440                 445

Tyr Phe Gly Pro Ala Pro Tyr Leu Ile Ser Pro Leu Asn Ala Phe Gln
    450                 455                 460

Asn Ser Asp Phe Asp Val Asn Tyr Ala Phe Gly Thr Asn Ile Ser Ser
465                 470                 475                 480

His Ser Thr Asp Gly Phe Ser Glu Ala Leu Ser Ala Ala Lys Lys Ser
                485                 490                 495

Asp Val Ile Ile Phe Ala Gly Gly Ile Asp Asn Thr Leu Glu Ala Glu
            500                 505                 510

Ala Met Asp Arg Met Asn Ile Thr Trp Pro Gly Asn Gln Leu Gln Leu
        515                 520                 525

Ile Asp Gln Leu Ser Gln Leu Gly Lys Pro Leu Ile Val Leu Gln Met
    530                 535                 540

Gly Gly Gly Gln Val Asp Ser Ser Ser Leu Lys Ser Asn Lys Asn Val
545                 550                 555                 560

Asn Ser Leu Ile Trp Gly Gly Tyr Pro Gly Gln Ser Gly Gly Gln Ala
                565                 570                 575

Leu Leu Asp Ile Ile Thr Gly Lys Arg Ala Pro Ala Gly Arg Leu Val
            580                 585                 590

Val Thr Gln Tyr Pro Ala Glu Tyr Ala Thr Gln Phe Pro Ala Thr Asp
        595                 600                 605

Met Ser Leu Arg Pro His Gly Asn Asn Pro Gly Gln Thr Tyr Met Trp
    610                 615                 620

Tyr Thr Gly Thr Pro Val Tyr Glu Phe Gly His Gly Leu Phe Tyr Thr
625                 630                 635                 640

Thr Phe His Ala Ser Leu Pro Gly Thr Gly Lys Asp Lys Thr Ser Phe
                645                 650                 655

Asn Ile Gln Asp Leu Leu Thr Gln Pro His Pro Gly Phe Ala Asn Val
            660                 665                 670

Glu Gln Met Pro Leu Leu Asn Phe Thr Val Thr Ile Thr Asn Thr Gly
        675                 680                 685

Lys Val Ala Ser Asp Tyr Thr Ala Met Leu Phe Ala Asn Thr Thr Ala
    690                 695                 700

Gly Pro Ala Pro Tyr Pro Asn Lys Trp Leu Val Gly Phe Asp Arg Leu
705                 710                 715                 720

Ala Ser Leu Glu Pro His Arg Ser Gln Thr Met Thr Ile Pro Val Thr
                725                 730                 735

Ile Asp Ser Val Ala Arg Thr Asp Glu Ala Gly Asn Arg Val Leu Tyr
            740                 745                 750

Pro Gly Lys Tyr Glu Leu Ala Leu Asn Asn Glu Arg Ser Val Val Leu
        755                 760                 765

Gln Phe Val Leu Thr Gly Arg Glu Ala Val Ile Phe Lys Trp Pro Val
    770                 775                 780

Glu Gln Gln Gln Ile Ser Ser Ala
```

785 790

<210> SEQ ID NO 163
<211> LENGTH: 37
<212> TYPE: DNA
<213> ORGANISM: Aspergillus fumigatus

<400> SEQUENCE: 163
actggattta ccatgacttt gtccaagatc acttcca 37

<210> SEQ ID NO 164
<211> LENGTH: 40
<212> TYPE: DNA
<213> ORGANISM: Aspergillus fumigatus

<400> SEQUENCE: 164
tcacctctag ttaattaagc gttgaacagt gcaggaccag 40

<210> SEQ ID NO 165
<211> LENGTH: 17
<212> TYPE: DNA
<213> ORGANISM: Aspergillus fumigatus

<400> SEQUENCE: 165
tgtcccttgt cgatgcg 17

<210> SEQ ID NO 166
<211> LENGTH: 17
<212> TYPE: DNA
<213> ORGANISM: Aspergillus fumigatus

<400> SEQUENCE: 166
cacatgactt ggcttcc 17

<210> SEQ ID NO 167
<211> LENGTH: 37
<212> TYPE: DNA
<213> ORGANISM: Aspergillus fumigatus

<400> SEQUENCE: 167
ggactgcgca ccatgacttt gtccaagatc acttcca 37

<210> SEQ ID NO 168
<211> LENGTH: 38
<212> TYPE: DNA
<213> ORGANISM: Aspergillus fumigatus

<400> SEQUENCE: 168
gccacggagc ttaattaatt aagcgttgaa cagtgcag 38

<210> SEQ ID NO 169
<211> LENGTH: 37
<212> TYPE: DNA
<213> ORGANISM: Aspergillus fumigatus

<400> SEQUENCE: 169
cgcggtagtg gcgcggtcga ccgaatgtag gattgtt 37

```
<210> SEQ ID NO 170
<211> LENGTH: 36
<212> TYPE: DNA
<213> ORGANISM: Aspergillus fumigatus

<400> SEQUENCE: 170

ttaccaattg gcgcgccact accgcgttcg agaaga                              36
```

METHODS FOR OBTAINING POSITIVE TRANSFORMANTS OF A FILAMENTOUS FUNGAL HOST CELL

CROSS-REFERENCE TO RELATED APPLICATIONS

This application is a divisional application of U.S. application Ser. No. 15/197,049 filed Jun. 29, 2016, now U.S. Pat. No. 10,190,109, which is a divisional application of U.S. application Ser. No. 14/238,681 filed Mar. 24, 2014, now U.S. Pat. No. 9,404,101, which is a 35 U.S.C. § 371 national application of PCT/US2012/052146 filed Aug. 23, 2012, which claims priority or the benefit under 35 U.S.C. § 119 of U.S. Provisional Application No. 61/526,804 filed on Aug. 24, 2011, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to methods for increasing the generation of positive transformants of a filamentous fungal host cell expressing multiple recombinant polypeptides.

Description of the Related Art

Recombinant production of a polypeptide in a filamentous fungal host cell may provide for a more desirable vehicle for producing the polypeptide in commercially relevant quantities. The recombinant production of a polypeptide is generally accomplished by constructing an expression cassette in which the DNA coding for the polypeptide is placed under the expression control of a promoter from a regulated gene. The expression cassette is introduced into the host cell, usually by plasmid-mediated transformation. Production of the polypeptide is then achieved by culturing the transformed host cell under inducing conditions necessary for the proper functioning of the promoter contained on the expression cassette.

Filamentous fungal cells may be transformed with a vector by a process involving protoplast formation, transformation of the protoplasts, and regeneration of the cell wall in a manner known per se. Co-transformation of two or more vectors expressing multiple recombinant proteins does not efficiently provide positive transformants producing significant amounts of the multiple recombinant polypeptides.

There is a need in the art for methods that improve the efficiency of obtaining positive transformants producing significant amounts of multiple recombinant polypeptides to reduce the number of transformants to be screened compared to positive transformants generated by co-transformation of vectors for each of the multiple recombinant polypeptides.

The present invention provides improved methods for the generation of positive transformants of a filamentous fungal host cell expressing multiple recombinant polypeptides.

SUMMARY OF THE INVENTION

The present invention relates to methods for obtaining positive transformants of a filamentous fungal host cell, comprising:

(a) transforming into a population of cells of the filamentous fungal host a tandem construct comprising (i) one or more (e.g., several) selectable markers, (ii) a first polynucleotide encoding a first polypeptide having biological activity operably linked to a first promoter and a first terminator, and (iii) a second polynucleotide encoding a second polypeptide having biological activity operably linked to a second promoter and a second terminator, wherein the tandem construct integrates by ectopic integration;

(b) selecting transformants based on the one or more (e.g., several) selectable markers, wherein the number of positive transformants for the first and second polypeptides having biological activity obtained by transformation of the tandem construct is higher compared to the number of positive transformants obtained by co-transformation of separate constructs for each of the first and second polynucleotides; and (c) isolating a transformant of the filamentous fungal host cell comprising the tandem construct expressing the first and second polypeptides having biological activity.

The present invention also relates to filamentous fungal host cells, comprising: a tandem construct comprising (i) one or more (e.g., several) selectable markers, (ii) a first polynucleotide encoding a first polypeptide having biological activity operably linked to a first promoter and a first terminator, and (iii) a second polynucleotide encoding a second polypeptide having biological activity operably linked to a second promoter and a second terminator, wherein the tandem construct integrated by ectopic integration.

The present invention also relates to methods of producing multiple recombinant polypeptides having biological activity, comprising:

(a) cultivating a filamentous fungal host cell transformed with a tandem construct comprising (i) one or more (e.g., several) selectable markers, (ii) a first polynucleotide encoding a first polypeptide having biological activity operably linked to a first promoter and a first terminator, and (iii) a second polynucleotide encoding a second polypeptide having biological activity operably linked to a second promoter and a second terminator, wherein the tandem construct integrates by ectopic integration, under conditions conducive for production of the polypeptides; and optionally (b) recovering the first and second polypeptides having biological activity.

The present invention further relates to tandem constructs and expression vectors comprising (i) one or more (e.g., several) selectable markers, (ii) a first polynucleotide encoding a first polypeptide having biological activity operably linked to a first promoter and a first terminator, and (iii) a second polynucleotide encoding a second polypeptide having biological activity operably linked to a second promoter and a second terminator.

DEFINITIONS

Figure 1:
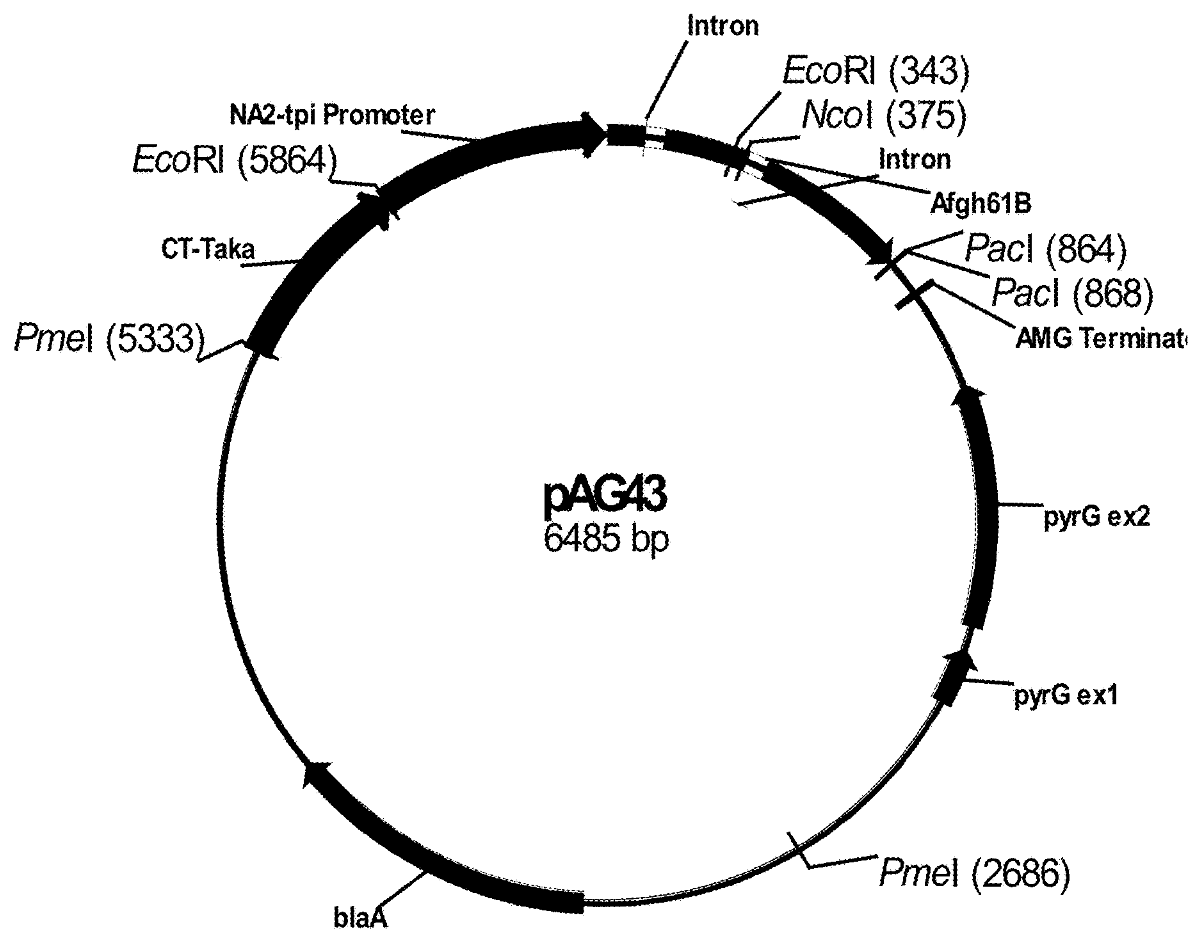
FIG. 1 shows a restriction map of plasmid pAG43.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, J. Bacteriol. 180: 243-249. One unit of alpha-glucuronidase equals the amount of enzyme capable of releasing 1 μmole of glucuronic or 4-O-methylglucuronic acid per minute at pH 5, 40° C.

Aspartic protease: The term "aspartic protease" means a protease that uses an aspartate residue(s) for catalyzing the hydrolysis of peptide bonds in peptides and proteins. Aspartic proteases are a family of protease enzymes that use an aspartate residue for catalytic hydrolysis of their peptide substrates. In general, they have two highly-conserved aspartates in the active site and are optimally active at acidic pH (Szecsi, 1992, *Scand. J. Clin. Lab. In vest*. Suppl. 210: 5-22). For purposes of the present invention, aspartic protease activity is determined according to the procedure described by Aikawa et al., 2001, *J. Biochem.* 129: 791-794.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a polypeptide. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Ectopic integration: The term "ectopic integration" means the insertion of a nucleic acid into the genome of a microorganism at a non-targeted site or at a site other than its usual chromosomal locus, i.e., random integration.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Flanking: The term "flanking" means DNA sequences extending on either side of a specific DNA sequence, locus, or gene. The flanking DNA is immediately adjacent to another DNA sequence, locus, or gene that is to be integrated into the genome of a filamentous fungal cell.

Fragment: The term "fragment" means a polypeptide having one or more (e.g., several) amino acids absent from the amino and/or carboxyl terminus of a mature polypeptide main; wherein the fragment has enzyme activity. In one aspect, a fragment contains at least 85%, e.g., at least 90% or at least 95% of the amino acid residues of the mature polypeptide of an enzyme.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology,* 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Homologous repeat: The term "homologous repeat" means a fragment of DNA that is repeated at least twice in the recombinant DNA introduced into a host cell and which can facilitate the loss of the DNA, i.e., selectable marker that is inserted between two homologous repeats, by homologous recombination.

Host cell: The term "host cell" means any cell type that is susceptible to transformation, transfection, transduction, or the like with a nucleic acid construct or expression vector comprising a polynucleotide encoding a polypeptide. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having enzyme activity.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more (e.g., several) control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsvrd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Positive transformants: The term "positive transformants" means transformants from a population of cells of a filamentous fungal host transformed with a tandem construct of the present invention or co-transformed with multiple constructs, wherein the transformants produce two or more (e.g., several) recombinant polypeptides encoded by the tandem construct or the multiple constructs.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having enzyme activity. In one aspect, a subsequence contains at least 85%, e.g., at least 90% or at least 95% of the nucleotides of the mature polypeptide coding sequence of an enzyme.

Subtilisin-like serine protease: The term "subtilisin-like serine protease" means a protease with a substrate specificity similar to subtilisin that uses a serine residue for catalyzing the hydrolysis of peptide bonds in peptides and proteins. Subtilisin-like proteases (subtilases) are serine proteases characterized by a catalytic triad of the three amino acids aspartate, histidine, and serine. The arrangement of these catalytic residues is shared with the prototypical subtilisin from *Bacillus licheniformis* (Siezen and Leunissen, 1997, *Protein Science* 6: 501-523). Subtilisin-like serine protease activity can be determined using a synthetic substrate, N-succinyl-L-Ala-L-Ala-L-Pro-L-Phe-p-nitroanilide (AAPF) (Bachem AG, Bubendorf, Switzerland) in 100 mM NaCl-100 mM MOPS pH 7.0 at 50° C. for 3 hours and then the absorbance at 405 nm is measured.

Transformant: The term "transformant" means a cell which has taken up extracellular DNA (foreign, artificial or modified) and expresses the gene(s) contained therein.

Transformation: The term "transformation" means the introduction of extracellular DNA into a cell, i.e., the genetic alteration of a cell resulting from the direct uptake, incorporation and expression of exogenous genetic material (exogenous DNA) from its surroundings and taken up through the cell membrane(s).

Transformation efficiency: The term "transformation efficiency" means the efficiency by which cells can take up the extracellular DNA and express the gene(s) contained therein, which is calculated by dividing the number of positive transformants expressing the gene(s) by the amount of DNA used during a transformation procedure.

Trypsin-like serine protease: The term "trypsin-like serine protease" means a protease with a substrate specificity similar to trypsin that uses a serine residue for catalyzing the hydrolysis of peptide bonds in peptides and proteins. For purposes of the present invention, trypsin-like serine protease activity is determined according to the procedure described by Dienes et al., 2007, *Enzyme and Microbial Technology* 40: 1087-1094.

Variant: The term "variant" means a polypeptide having enzyme activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune, FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

The present invention relates to methods for obtaining positive transformants of a filamentous fungal host cell, comprising: (a) transforming into a population of cells of the filamentous fungal host a tandem construct comprising (i) one or more (e.g., several) selectable markers, (ii) a first polynucleotide encoding a first polypeptide having biological activity operably linked to a first promoter and a first terminator, and (iii) a second polynucleotide encoding a second polypeptide having biological activity operably linked to a second promoter and a second terminator, wherein the tandem construct integrates by ectopic integration; (b) selecting transformants based on the one or more (e.g., several) selectable markers, wherein the number of positive transformants for the first and second polypeptides having biological activity obtained by transformation of the tandem construct is higher compared to the number of positive transformants obtained by co-transformation of separate constructs for each of the first and second polynucleotides; and (c) isolating a transformant of the filamentous fungal host cell comprising the tandem construct expressing the first and second polypeptides having biological activity.

An advantage of the methods of the present invention is an increase in the transformation efficiency of obtaining positive transformants producing significant amounts of two or more (e.g., several) recombinant polypeptides, which reduces the number of transformants that need to be generated and screened. Using a tandem construct of the present invention expressing two or more recombinant polypeptides results in a higher number of the transformants producing the two or more recombinant polypeptides in significant amounts when compared to transformants generated by co-transformation of separate constructs for each of the two or more recombinant polypeptides, e.g., two or more individual expression constructs.

In one aspect, the number of positive transformants for the first and second polypeptides having biological activity obtained by transformation of a tandem construct of the present invention is increased at least 1.1-fold, e.g., at least 1.25-fold, at least 1.5-fold, at least 2-fold, at least 2.5-fold, at least 3-fold, at least 4-fold, at least 5-fold, or at least 10-fold compared to the number of positive transformants obtained by co-transformation of separate constructs for each of the first and second polypeptides having biological activity.

Tandem Constructs

The present invention also relates to tandem constructs comprising (i) one or more (e.g., several) selectable markers, (ii) a first polynucleotide encoding a first polypeptide having biological activity operably linked to a first promoter and a first terminator, and (iii) a second polynucleotide encoding a second polypeptide having biological activity operably linked to a second promoter and a second terminator. The tandem constructs can be constructed by operably linking one or more (e.g., several) control sequences to each polynucleotide of the construct that direct the expression of the coding sequence in a filamentous fungal host cell under conditions compatible with the control sequences. Manipulation of each polynucleotide prior to insertion into a vector may be desirable or necessary depending on the expression vector. The techniques for modifying polynucleotides utilizing recombinant DNA methods are well known in the art.

The control sequence may be a promoter, a polynucleotide that is recognized by a filamentous fungal host cell for expression of a polynucleotide encoding a polypeptide. The promoter contains transcriptional control sequences that mediate the expression of the polypeptide. The promoter may be any polynucleotide that shows transcriptional activity in the filamentous fungal host cell including mutant, truncated, and hybrid promoters, and may be obtained from genes encoding extracellular or intracellular polypeptides either homologous or heterologous to the host cell.

In one aspect, the promoters in the tandem constructs are different promoters. In another aspect, two or more of the promoters in the tandem constructs are the same promoter.

Examples of suitable promoters for directing transcription of the constructs in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147, which is incorporated herein in its entirety.

The control sequence may also be a transcription terminator, which is recognized by a filamentous fungal host cell to terminate transcription. The terminator is operably linked to the 3'-terminus of the polynucleotide encoding the polypeptide. Any terminator that is functional in the host cell may be used in the present invention.

In one aspect, the terminators in the tandem constructs are different terminators. In another aspect, two or more of the terminators in the tandem constructs are the same terminator.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

The control sequence may also be a leader, a nontranslated region of an mRNA that is important for translation by the host cell. The leader is operably linked to the 5'-terminus of the polynucleotide encoding the polypeptide. Any leader that is functional in a filamentous fungal host cell may be used.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3'-terminus of the polynucleotide and, when transcribed, is recognized by a filamentous fungal host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus nigerglucoamylase, Aspergillus niger* alpha-glucosidase *Aspergillus oryzae* TAKA amylase, *Fusarium oxysporum* trypsin-like protease, *Trichoderma reesei* cellobiohydrolase I, *Trichoderma reesei* cellobiohydrolase II, and *Trichoderma reesei* endoglucanase V.

The control sequence may also be a signal peptide coding region that encodes a signal peptide linked to the N-terminus of a polypeptide and directs the polypeptide into a cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a filamentous fungal host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, *Rhizomucor miehei* aspartic proteinase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, and *Trichoderma reesei* endoglucanase V.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Myceliophthora thermophila* laccase (WO 95/33836) and *Rhizomucor miehei* aspartic proteinase.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of a filamentous fungal host cell. Examples of regulatory sequences are those that cause expression of the gene to be turned on or off in response to a chemical or physical stimulus, including the presence of a regulatory compound. Regulatory sequences in filamentous fungi include the *Aspergillus niger* glucoamylase promoter, *Aspergillus oryzae* TAKA alpha-amylase promoter, *Aspergillus oryzae* glucoamylase promoter, *Trichoderma reesei* cellobiohydrolase I promoter, and *Trichoderma reesei* cellobiohydrolase II promoter. Other examples of regulatory sequences are those that allow for gene amplification. In these cases, the polynucleotide encoding the polypeptide would be operably linked with the regulatory sequence.

The tandem constructs of the present invention preferably contain one or more (e.g., several) selectable markers that permit easy selection of transformed cells. A selectable marker is a gene the product of which provides for biocide or viral resistance, resistance to heavy metals, prototrophy to auxotrophs, and the like. Examples of selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes. Examples of bacterial selectable markers are markers that confer antibiotic resistance such as ampicillin, chloramphenicol, kanamycin, neomycin, spectinomycin, or tetracycline resistance.

The one or more (e.g., several) selectable markers may be a dual selectable marker system as described in WO 2010/039889 A2, which is incorporated herein by reference in its entirety. In one aspect, the one or more (e.g., several) selectable markers is a hph-tk dual selectable marker system.

In each tandem construct of the present invention, the one or more selectable markers are different markers, unless a selectable marker is reused as described herein.

One or more (e.g., several) of the selectable markers may be reused for introducing a new tandem construct into the filamentous fungal host cell. A tandem construct of the present invention may further comprise a first homologous repeat flanking 5' of the one or more (e.g., several) selectable markers and a second homologous repeat flanking 3' of the one or more selectable markers, wherein the first homologous repeat and the second homologous repeat undergo homologous recombination to excise the one or more selectable markers. Upon the excision of the one or more selectable markers, the one or more selectable markers can be reused in a new tandem construct.

In one aspect, the first and second homologous repeats are identical. In another aspect, the first and second homologous repeats have a sequence identity of at least 70%, e.g., at least 75%, at least 80%, at least 81%, at least 82%, at least 83% y, at least 84%, at least 85%, at least 86%, at least 87%, at least 88%, at least 89%, at least 90%, at least 91%, at least 92%, at least 93%, at least 94%, at least 95%, at least 96%, at least 97%, at least 97%, at least 98%, or at least 99% to each other. In another aspect, the first and second homologous repeats are each at least 50 bp, e.g., at least 100 bp, at least 200 bp, at least 400 bp, at least 800 bp, at least 1000 bp, at least 1500 bp, or at least 2000 bp. The fragment containing one repeat may be longer than the fragment containing the other repeat.

The tandem constructs of the present invention may further comprise one or more (e.g., several) additional polynucleotides encoding other polypeptides having biological activity. For example, a tandem construct may contain one additional polynucleotide, two additional polynucleotides, three additional polynucleotides, etc.

Polypeptides Having Biological Activity

The polypeptides may be any polypeptides having a biological activity of interest. The term "polypeptide" is not meant herein to refer to a specific length of the encoded product and, therefore, encompasses peptides, oligopeptides, and proteins. The term "polypeptide" also encompasses two or more polypeptides combined to form the encoded product. The polypeptides also include fusion polypeptides, which comprise a combination of partial or complete polypeptide sequences obtained from at least two different polypeptides wherein one or more (e.g., several) may be heterologous to the filamentous fungal host cell. The polypeptides further include naturally occurring allelic and engineered variations of the below-mentioned polypeptides and hybrid polypeptides.

In one aspect, the polypeptides having biological activity may be different polypeptides. In another aspect, two or more of the polypeptides having biological activity are the same polypeptide.

In another aspect, the polypeptides are selected from the group consisting of an antibody, an antigen, an antimicrobial peptide, an enzyme, a growth factor, a hormone, an immunodilator, a neurotransmitter, a receptor, a reporter protein, a structural protein, or a transcription factor.

In another aspect, the enzyme is selected from the group consisting of an oxidoreductase, a transferase, a hydrolase, a lyase, an isomerase, and a ligase. In another aspect, the enzyme is selected from the group consisting of an acetylmannan esterase, acetyxylan esterase, am inopeptidase, alpha-amylase, alpha-galactosidase, alpha-glucosidase, alpha-1,6-transglucosidase, arabinanase, arabinofuranosidase, beta-galactosidase, beta-glucosidase, beta-xylosidase, carbohydrase, carboxypeptidase, catalase, cellobiohydrolase, cellulase, chitinase, coumaric acid esterase, cyclodextrin glycosyltransferase, cutinase, deoxyribonuclease, endoglucanase, esterase, feruloyl esterase, GH61 polypeptide having cellulolytic enhancing activity, glucocerebrosidase, glucose oxidase, glucuronidase, glucuronoyl esterase, haloperoxidase, hemicellulase, invertase, isomerase, laccase, ligase, lipase, mannanase, mannosidase, mutanase, oxidase, pectinolytic enzyme, peroxidase, phospholipase, phytase, phenoloxidase, polyphenoloxidase, proteolytic enzyme, ribonuclease, transglutaminase, urokinase, and xylanase.

In another aspect, the polypeptides are selected from the group consisting of an albumin, a collagen, a tropoelastin, an elastin, and a gelatin.

In another aspect, the polypeptides are selected from the group consisting of a cellulase, a cip1 protein, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is one or more enzymes selected from the group consisting of an endoglucanase, a cellobiohydrolase, and a beta-glucosidase. In another aspect, the hemicellulase is one or more enzymes selected from the group consisting of a xylanase, an acetylxylan esterase, a feruloyl esterase, an arabinofuranosidase, a xylosidase, and a glucuronidase.

In another aspect, one of the polypeptides is a cellulase. In another aspect, one of the polypeptides is an endoglucanase. In another aspect, one of the polypeptides is a cellobiohydrolase. In another aspect, one of the polypeptides is a beta-glucosidase. In another aspect, one of the polypeptides is a GH61 polypeptide having cellulolytic enhancing activity. In another aspect, one of the polypeptides is a cip1 protein. In another aspect, one of the polypeptides is an esterase, In another aspect, one of the polypeptides is an expansin. In another aspect, one of the polypeptides is a laccase. In another aspect, one of the polypeptides is a ligninolytic enzyme. In another aspect, one of the polypeptides is a pectinase, In another aspect, one of the polypeptides is a peroxidase. In another aspect, one of the polypeptides is a protease. In another aspect, one of the polypeptides is a swollenin.

In another aspect, one of the polypeptides is a hemicellulase. In another aspect, one of the polypeptides is a xylanase. In another aspect, one of the polypeptides is a beta-xylosidase. In another aspect, one of the polypeptides is an acetyxylan esterase. In another aspect, one of the polypeptides is a feruloyl esterase. In another aspect, one of the polypeptides is an arabinofuranosidase. In another aspect, one of the polypeptides is a glucuronidase. In another aspect, one of the polypeptides is an acetylmannan esterase. In another aspect, one of the polypeptides is an arabinanase. In another aspect, one of the polypeptides is a coumaric acid esterase. In another aspect, one of the polypeptides is a galactosidase. In another aspect, one of the polypeptides is a glucuronoyl esterase. In another aspect, one of the polypeptides is a mannanase. In another aspect, one of the polypeptides is a mannosidase.

Examples of endoglucanases as one of the polypeptides having biological activity, include, but are not limited to, a *Trichoderma reesei* endoglucanase I (Penttila et al., 1986*, Gene* 45: 253-263; *Trichoderma reesei* Cel7B endoglucanase I; GENBANK™ accession no. M15665; SEQ ID NO: 2); *Trichoderma reesei* endoglucanase II (Saloheimo, et al., 1988*, Gene* 63:11-22; *Trichoderma reesei* Cel5A endoglucanase II; GENBANK™ accession no. M19373; SEQ ID NO: 4); *Trichoderma reesei* endoglucanase III (Okada et al., 1988*, Appl. Environ. Microbiol.* 64: 555-563; GENBANK™ accession no. AB003694; SEQ ID NO: 6); *Trichoderma reesei* endoglucanase V (Saloheimo et al., 1994*, Molecular Microbiology* 13: 219-228; GENBANK™ accession no. Z33381; SEQ ID NO: 8); *Aspergillus aculeatus* endoglucanase (Ooi et al., 1990*, Nucleic Acids Research* 18: 5884); *Aspergillus kawachii* endoglucanase (Sakamoto et al., 1995*, Current Genetics* 27: 435-439); *Erwinia carotovara* endoglucanase (Saarilahti et al., 1990*, Gene* 90: 9-14); *Fusarium oxysporum* endoglucanase (GENBANK™ accession no. L29381); *Humicola grisea* var. *thermoidea* endoglucanase (GENBANK™ accession no. AB003107); *Melanocarpus albomyces* endoglucanase (GENBANK™ accession no. MAL515703); *Neurospora crassa* endoglucanase (GENBANK™ accession no. XM_324477); *Humicola insolens* endoglucanase V (SEQ ID NO: 10); *Myceliophthora thermophila* CBS 117.65 endoglucanase (SEQ ID NO: 12); basidiomycete CBS 495.95 endoglucanase (SEQ ID NO: 14); basidiomycete CBS 494.95 endoglucanase (SEQ ID NO: 16); *Thielavia terrestris* NRRL 8126 CEL6B endoglucanase (SEQ ID NO: 18); *Thielavia terrestris* NRRL 8126 CEL6C endoglucanase (SEQ ID NO: 20); *Thielavia terrestris* NRRL 8126 CEL7C endoglucanase (SEQ ID NO: 22); *Thielavia terrestris* NRRL 8126 CEL7E endoglucanase (SEQ ID NO: 24); *Thielavia terrestris* NRRL 8126 CEL7F endoglucanase (SEQ ID NO: 26); *Cladorrhinum foecundissimum* ATCC 62373 CEL7A endoglucanase (SEQ ID NO: 28); and *Trichoderma reesei* strain No. VTT-D-80133 endoglucanase (SEQ ID NO: 30; GENBANK™ accession no. M15665). The endoglucanases of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30 described above are encoded by the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, and SEQ ID NO: 29, respectively.

Examples of cellobiohydrolases as one of the polypeptides having biological activity include, but are not limited to, *Trichoderma reesei* cellobiohydrolase I (SEQ ID NO: 32), *Trichoderma reesei* cellobiohydrolase II (SEQ ID NO: 34), *Humicola insolens* cellobiohydrolase I (SEQ ID NO: 36), *Myceliophthora thermophila* cellobiohydrolase II (WO 2009/042871; SEQ ID NO: 38 and SEQ ID NO: 40), *Thielavia terrestris* cellobiohydrolase II (CEL6A, WO 2006/074435; SEQ ID NO: 42), *Chaetomium thermophilum* cellobiohydrolase I (SEQ ID NO: 44), *Chaetomium thermophilum* cellobiohydrolase II (SEQ ID NO: 46), *Aspergillus fumigatus* cellobiohydrolase I (SEQ ID NO: 48), and *Aspergillus fumigatus* cellobiohydrolase II (SEQ ID NO: 50). The cellobiohydrolases of SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, and SEQ ID NO: 50, described above are encoded by the mature polypeptide coding sequence of SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, and SEQ ID NO: 49, respectively.

Examples of beta-glucosidases as one of the polypeptides having biological activity include, but are not limited to, beta-glucosidases from *Aspergillus oryzae* (WO 2002/095014; SEQ ID NO: 52), *Aspergillus fumigatus* (WO 2005/047499; SEQ ID NO: 54), *Penicillium brasilianum* IBT 20888 (WO 2007/019442 and WO 2010/088387; SEQ ID NO: 56), *Aspergillus niger* (Dan et al., 2000, *J. Biol. Chem.* 275: 4973-4980; SEQ ID NO: 58), and *Aspergillus aculeatus* (Kawaguchi et al., 1996, *Gene* 173: 287-288; SEQ ID NO: 60). The beta-glucosidases of SEQ ID NO: 52, SEQ ID NO: 54, SEQ ID NO: 56, SEQ ID NO: 58, and SEQ ID NO: 60 described above are encoded by the mature polypeptide coding sequence of SEQ ID NO: 51, SEQ ID NO: 53, SEQ ID NO: 55, SEQ ID NO: 57, and SEQ ID NO: 59, respectively.

The beta-glucosidase may also be a fusion protein. In one aspect, the beta-glucosidase is an *Aspergillus oryzae* beta-glucosidase variant BG fusion protein (WO 2008/057637; SEQ ID NO: 62) or an *Aspergillus oryzae* beta-glucosidase fusion protein (WO 2008/057637; SEQ ID NO: 64). The beta-glucosidase fusion proteins of SEQ ID NO: 62 and SEQ ID NO: 64 are encoded by SEQ ID NO: 61 and SEQ ID NO: 63, respectively.

Examples of other endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593.

Examples of GH61 polypeptides having cellulolytic enhancing activity as one of the polypeptides having biological activity include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504). In one aspect, the GH61 polypeptides having cellulolytic enhancing activity include, but are not limited to, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132; SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, or SEQ ID NO: 152, or the mature polypeptide thereof. The GH61 polypeptides described above are encoded by the mature polypeptide coding sequence of SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, or SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, or SEQ ID NO: 151, respectively.

Examples of xylanases as one of the polypeptides having biological activity include, but are not limited to, xylanases from *Aspergillus aculeatus* (GeneSeqP:AAR63790; WO 94/21785), *Aspergillus fumigatus* (WO 2006/078256; SEQ ID NO: 154, SEQ ID NO: 156, and SEQ ID NO: 158, *Penicillium pinophilum* (WO 2011/041405), *Penicillium* sp. (WO 2010/126772), *Thielavia terrestris* NRRL 8126 (WO 2009/079210), and *Trichophaea saccata GH*10 (WO 2011/057083). The xylanases described above are encoded by the mature polypeptide coding sequence of SEQ ID NO: 153, SEQ ID NO: 155, and SEQ ID NO: 157, respectively.

Examples of beta-xylosidases as one of the polypeptides having biological activity include, but are not limited to, beta-xylosidases from *Neurospora crassa* (SwissProt accession number Q7SOW4), *Trichoderma reesei* (UniProtKB/TrEMBL accession number Q92458; SEQ ID NO: 160), *Aspergillus fumigatus* (SEQ ID NO; 162), and *Talaromyces emersonii* (SwissProt accession number Q8X212). The beta-xylosidases described above are encoded by the mature polypeptide coding sequence of SEQ ID NO: 159 and SEQ ID NO: 161, respectively.

Examples of acetylxylan esterases as one of the polypeptides having biological activity include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number Q0UHJ1), and *Thielavia terrestris* NRRL 8126 (WO 2009/042846).

Examples of feruloyl esterases (ferulic acid esterases) as one of the polypeptides having biological activity include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases as one of the polypeptides having biological activity include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases as one of the polypeptides having biological activity include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number Q0CJP9), *Humicola insolens* (WO 2010/014706), *Penicillium aurantiogriseum* (WO 2009/068565), *Talaromyces emersonii* (UniProt accession number Q8X211), and *Trichoderma reesei* (Uniprot accession number Q99024).

The accession numbers are incorporated herein by reference in their entirety.

Expression Vectors

The present invention also relates to expression vectors comprising a tandem construct of the present invention. A tandem construct may be inserted into a vector or the various components of a tandem construct may be joined together to produce a recombinant expression vector. The vector may include one or more (e.g., several) convenient restriction sites to allow for insertion of polynucleotides at such sites. In creating the expression vector, the coding sequences are located in the vector so that the coding sequences are operably linked with the appropriate control sequences for expression.

The recombinant expression vector may be any vector (e.g., a plasmid or virus) that can be conveniently subjected to recombinant DNA procedures and can bring about expression of the polynucleotides. The choice of the vector will typically depend on the compatibility of the vector with the host cell into which the vector is to be introduced. The vector may be a linear or closed circular plasmid.

The vector preferably contains one or more (e.g., several) selectable markers that permit easy selection of transformed cells. Examples of selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes. Examples of bacterial selectable markers are markers that confer antibiotic resistance such as ampicillin, chloramphenicol, kanamycin, neomycin, spectinomycin, or tetracycline resistance.

The procedures used to ligate the elements described above to construct the recombinant expression vectors are well known to one skilled in the art (see, e.g., Sambrook et al., 1989, *Molecular Cloning, A Laboratory Manual,* 2d edition, Cold Spring Harbor, N.Y.).

Filamentous Fungal Host Cells

The present invention also relates to filamentous fungal host cells, comprising: a tandem construct comprising (i) one or more (e.g., several) selectable markers, (ii) a first polynucleotide encoding a first polypeptide having biological activity operably linked to a first promoter and a first terminator, and (iii) a second polynucleotide encoding a second polypeptide having biological activity operably linked to a second promoter and a second terminator, wherein the tandem construct integrated by ectopic integration.

The tandem construct or an expression vector comprising the tandem construct is introduced into a filamentous fungal host cell so that the construct is maintained as a chromosomal integrant. The term "host cell" encompasses any progeny of a parent cell that is not identical to the parent cell due to mutations that occur during replication. The choice of a host cell will to a large extent depend upon the gene encoding the polypeptide and its source.

The host cell may be any filamentous fungal cell useful in the recombinant production of polypeptides. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subver-*

*mispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

In one aspect, the filamentous fungal host cell is *Aspergillus oryzae*. In another aspect, the filamentous fungal host cell is *Aspergillus niger*. In another aspect, the filamentous fungal host cell is *Fusarium venenatum*. In another aspect, the filamentous fungal host cell is *Trichoderma reesei*. In another aspect, the filamentous fungal host cell is *Trichoderma longibrachiatum*.

In another aspect, the filamentous fungal host cell is *Trichoderma reesei* RutC30. In another aspect, the filamentous fungal host cell is *Trichoderma reesei* TV10. In another aspect, the filamentous fungal host cell is a mutant of *Trichoderma reesei* RutC30. In another aspect, the filamentous fungal host cell is a mutant of *Trichoderma reesei* TV10. In another aspect, the filamentous fungal host cell is a morphological mutant of *Trichoderma reesei*. See, for example, WO 97/26330, which is incorporated herein by reference in its entirety.

In another aspect, the filamentous fungal host cell is a *Trichoderma* strain comprising one or more (e.g., several) genes selected from the group consisting of a first subtilisin-like serine protease gene, a first aspartic protease gene, a trypsin-like serine protease gene, a second subtilisin-like serine protease gene, and a second aspartic protease gene, wherein the one or more (e.g., several) genes are modified rendering the mutant strain deficient in the production of one or more (e.g., several) enzymes selected from the group consisting of a first subtilisin-like serine protease, a first aspartic protease, a trypsin-like serine protease, a second subtilisin-like serine protease, and a second aspartic protease, respectively, compared to the parent *Trichoderma* strain when cultivated under identical conditions, as described in WO 2011/075677, which is incorporated herein by reference in its entirety.

Filamentous fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 1996/00787.

Methods of Production

The present invention also relates to methods of producing multiple recombinant polypeptides having biological activity, comprising:

(a) cultivating a filamentous fungal host cell transformed with a tandem construct comprising (i) one or more (e.g., several) selectable markers, (ii) a first polynucleotide encoding a first polypeptide having biological activity operably linked to a first promoter and a first terminator, and (iii) a second polynucleotide encoding a second polypeptide having biological activity operably linked to a second promoter and a second terminator, wherein the tandem construct integrates by ectopic integration, under conditions conducive for production of the polypeptides; and optionally (b) recovering the first and second polypeptides having biological activity.

The filamentous fungal host cells are cultivated in a nutrient medium suitable for production of the polypeptides using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptides to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptides are secreted into the nutrient medium, the polypeptides can be recovered directly from the medium. If the polypeptides are not secreted, they can be recovered from cell lysates.

The polypeptides may be detected using methods known in the art that are specific for the polypeptides. These detection methods include, but are not limited to, use of specific antibodies, formation of an enzyme product, or disappearance of an enzyme substrate. For example, enzyme assays may be used to determine the activity of the polypeptides.

The polypeptides may be recovered using methods known in the art. For example, the polypeptides may be recovered from the nutrient medium by conventional procedures including, but not limited to, collection, centrifugation, filtration, extraction, spray-drying, evaporation, or precipitation. In one aspect, the whole fermentation broth is recovered.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

The present invention is further described by the following examples that should not be construed as limiting the scope of the invention.

EXAMPLES

Strain

*Trichoderma reesei* strain 981-O-8 (D4) is a mutagenized strain of *Trichoderma reesei* RutC30 (ATCC 56765; Montenecourt and Eveleigh, 1979, *Adv. Chem. Ser.* 181: 289-301).

Media and Buffer Solutions

2XYT plus ampicillin plates were composed of 16 g of tryptone, 10 g of yeast extract, 5 g of sodium chloride, 15 g of Bacto agar, and deionized water to 1 liter. One ml of a 100 mg/ml solution of ampicillin was added after the autoclaved medium was cooled to 55° C.

COVE salt solution was composed of 26 g of KCl, 26 g of $MgSO_4.7H_2O$, 76 g of $KH_2PO_4$, 50 ml of COVE trace metals solution, and deionized water to 1 liter.

COVE trace metals solution was composed of 0.04 g of $NaB_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

COVE plates were composed of 342.3 g of sucrose, 20 ml of COVE salt solution, 10 ml of 1 M acetamide, 10 ml of 1.5 M CsCl, 25 g of Noble agar (Difco), and deionized water to 1 liter.

COVE2 plates were composed of 30 g of sucrose, 20 ml of COVE salt solution, 10 ml of 1 M acetamide, 25 g of Noble agar (Difco), and deionized water to 1 liter.

*Trichoderma* trace metals solution was composed of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, 336 g of citric acid, and deionized water to 1 liter.

CIM medium was composed of 20 g of cellulose, 10 g of corn steep solids, 1.45 g of $(NH_4)_2SO_4$, 2.08 g of $KH_2PO_4$, 0.28 g of $CaCl_2$), 0.42 g of $MgSO_4.7H_2O$, 0.42 ml of *Trichoderma* trace metals solution, 1-2 drops of antifoam, and deionized water to 1 liter; pH adjusted to 6.0.

YP medium was composed of 10 g of yeast extract, 20 g of Bacto peptone, and deionized water to 1 liter.

PEG buffer was composed of 500 g of polyethylene glycol 4000 (PEG 4000), 10 mM $CaCl_2$, 10 mM Tris-HCl pH 7.5, and deionized water to 1 liter; filter sterilized.

STC was composed of 1 M sorbitol, 10 mM $CaCl_2$, and 10 mM Tris-HCl, pH 7.5; filter sterilized.

Example 1: Cloning of an *Aspergillus fumigatus* GH61B Polypeptide Gene

A tblastn search (Altschul et al., 1997, *Nucleic Acids Res.* 25: 3389-3402) of the *Aspergillus fumigatus* partial genome sequence (The Institute for Genomic Research, Rockville, Md., USA) was performed using as query several known GH61 polypeptides including the *Thermoascus aurantiacus* GH61A polypeptide (GeneSeqP Accession Number AEC05922). Several genes were identified as putative Family GH61 homologs based upon a high degree of similarity to the query sequences at the amino acid level. One genomic region of approximately 850 bp with greater than 70% sequence identity to the *Thermoascus aurantiacus* GH61A polypeptide sequence at the amino acid level was chosen for further study.

*A. fumigatus* NN051616 was grown and harvested as described in U.S. Pat. No. 7,244,605. Frozen mycelia were ground, by mortar and pestle, to a fine powder and genomic DNA was isolated using a DNEASY® Plant Maxi Kit (QIAGEN Inc., Valencia, Calif., USA) according to manufacturer's instructions.

Two synthetic oligonucleotide primers shown below were designed to PCR amplify the *A. fumigatus* GH61B polypeptide coding sequence from the genomic DNA. An IN-FUSION® Cloning Kit (Clontech Laboratories, Inc., Mountain View, Calif., USA) was used to clone the fragment directly into the expression vector pAILo2 (WO 2004/099228), without the need for restriction digestion and ligation.

```
Forward primer:
                                        (SEQ ID NO: 163)
5'-ACTGGATTTACCATGACTTTGTCCAAGATCACTTCCA-3'

Reverse primer:
                                        (SEQ ID NO: 164)
5'-TCACCTCTAGTTAATTAAGCGTTGAACAGTGCAGGACCAG-3'
```

Bold letters represent coding sequence. The remaining sequences are homologous to the insertion sites of pAILo2.

Fifty picomoles of each of the primers above were used in a PCR reaction composed of 204 ng of *A. fumigatus* genomic DNA, 1× Pfx Amplification Buffer (Invitrogen, Carlsbad, Calif., USA), 1.5 μl of a 10 mM blend of dATP, dTTP, dGTP, and dCTP, 2.5 units of PLATINUM® Pfx DNA Polymerase (Invitrogen Corp., Carlsbad, Calif., USA), and 1 μl of 50 mM $MgSO_4$ in a final volume of 50 μl. The amplification was performed using an EPPENDORF® MASTERCYCLER® 5333 epgradient S (Eppendorf Scientific, Inc., Westbury, N.Y., USA) programmed for 1 cycle at 94° C. for 3 minutes; and 30 cycles each at 94° C. for 30 seconds, 56° C. for 30 seconds, and 72° C. for 1 minutes. The heat block was then held at 72° C. for 15 minutes followed by a 4° C. soak cycle. The reaction products were isolated by 1.0% agarose gel electrophoresis using 40 mM Tris base, 20 mM sodium acetate, 1 mM disodium EDTA (TAE) buffer where an approximately 850 bp product band was excised from the gel and purified using a MINELUTE® Gel Extraction Kit (QIAGEN Inc., Valencia, Calif., USA) according to the manufacturer's instructions.

The 850 bp fragment was then cloned into pAILo2 using an IN-FUSION® Cloning Kit. Plasmid pAILo2 was digested with Nco I and Pac I. The plasmid fragment was purified by gel electrophoresis as above and a QIAQUICK® Gel Purification Kit (QIAGEN Inc., Valencia, Calif., USA). The gene fragment and the digested vector were combined together in a reaction described below resulting in the expression plasmid pAG43 (FIG. 1) in which transcription of the *A. fumigatus* GH61B polypeptide coding sequence was under the control of the NA2-tpi promoter. The NA2-tpi promoter is a modified promoter from the *Aspergillus niger* neutral alpha-amylase gene in which the untranslated leader has been replaced by an untranslated leader from the *Aspergillus nidulans* triose phosphate isomerase gene. The recombination reaction (20 μl) was composed of 1× IN-FUSION® Reaction Buffer (Clontech Laboratories, Inc., Mountain View, Calif., USA), 1×BSA (Clontech Laboratories, Inc., Mountain View, Calif., USA), 1 μl of IN-FUSION® Enzyme (diluted 1:10) (Clontech Laboratories, Inc., Mountain View, Calif., USA), 166 ng of pAILo2 digested with Nco I and Pac I, and 110 ng of the *A. fumigatus* GH61B polypeptide purified PCR product. The reaction was incubated at 37° C. for 15 minutes followed by 15 minutes at 50° C. The reaction was diluted with 40 μl of 10 mM Tris-0.1 M EDTA buffer and 2.5 μl of the diluted reaction was used to transform *E. coli* XL10 SOLOPACK® Gold Competent Cells (Stratagene, La Jolla, Calif., USA) according to the manufacturer's instructions. An *E. coli* transformant containing pAG43 (GH61B polypeptide coding sequence) was identified by restriction enzyme digestion and plasmid DNA was prepared using a BIOROBOT® 9600 (QIAGEN Inc., Valencia, Calif., USA).

DNA sequencing of the 862 bp PCR fragment was performed with an Applied Biosystems Model 377 XL Automated DNA Sequencer (Applied Biosystems, Carlsbad, Calif., USA) using dye-terminator chemistry (Giesecke et al., 1992, *Journal of Virology Methods* 38: 47-60) and primer walking strategy. The following vector specific primers were used for sequencing:

```
pAllo2 5 Seq:
                                    (SEQ ID NO: 165)
5'-TGTCCCTTGTCGATGCG 3'

pAllo2 3 Seq:
                                    (SEQ ID NO: 166)
5'-CACATGACTTGGCTTCC 3'
```

Nucleotide sequence data were scrutinized for quality and all sequences were compared to each other with assistance of PHRED/PHRAP software (University of Washington, Seattle, Wash., USA).

A gene model for the *A. fumigatus* sequence was constructed based on similarity of the encoded protein to the *Thermoascus aurantiacus* GH61A protein (GeneSeqP Accession Number AEC05922). The nucleotide sequence and deduced amino acid sequence of the *A. fumigatus* GH61B polypeptide coding sequence are shown in SEQ ID NO: 93 (DNA sequence) and SEQ ID NO: 94 (deduced amino acid sequence). The genomic fragment encodes a polypeptide of 250 amino acids, interrupted by 2 introns of 53 and 56 bp. The % G+C content of the coding sequence and the mature coding sequence are 53.9% and 57%, respectively. Using the SignalP software program (Nielsen et al., 1997, *Protein Engineering* 10: 1-6), a signal peptide of 21 residues was predicted. The predicted mature protein contains 221 amino acids with a predicted molecular mass of 23.39 kDa.

Example 2: Construction of pSMai214 for Expression of the *Aspergillus fumigatus* GH61B Polypeptide The *Aspergillus fumigatus* GH61B polypeptide coding sequence was amplified from plasmid pAG43 (Example 1) using the gene-specific forward and reverse primers shown below. The region in italics represents vector homology to the site of insertion for an IN-FUSION® reaction.

```
Forward primer:
                                    (SEQ ID NO: 167)
5'-GGACTGCGCACCATGACTTTGTCCAAGATCACTTCCA-3'

Reverse primer:
                                    (SEQ ID NO: 168)
5'-GCCACGGAGCTTAATTAATTAAGCGTTGAACAGTGCAG-3'
```

Fifty picomoles of each of the primers above were used in a PCR reaction composed of 10 ng of pAG43 DNA, 1× Pfx Amplification Buffer, 1.5 μl of a 10 mM blend of dATP, dTTP, dGTP, and dCTP, 2.5 units of PLATINUM® Pfx DNA Polymerase, and 1 μl of 50 mM $MgSO_4$ in a final volume of 50 μl. The amplification was performed using an EPPENDORF® MASTERCYCLER® 5333 epgradient S programmed for 1 cycle at 98° C. for 3 minutes; and 30 cycles each at 98° C. for 30 seconds, 56° C. for 30 seconds, and 72° C. for 1 minute. The heat block was then held at 72° C. for 15 minutes. The PCR products were separated by 1% agarose gel electrophoresis using TAE buffer where an approximately 0.9 kb fragment was excised from the gel and extracted using a MINELUTE® Gel Extraction Kit according to the manufacturer's protocol.

Plasmid pMJ09 (WO 2005/047499) was digested with Nco I and Pac I, isolated by 1.0% agarose gel electrophoresis in 1 mM disodium EDTA-50 mM Tris base-50 mM boric acid (TBE) buffer, excised from the gel, and extracted using a QIAQUICK® Gel Extraction Kit (QIAGEN Inc., Valencia, Calif., USA) according to the manufacturer's instructions.

Figure 2:
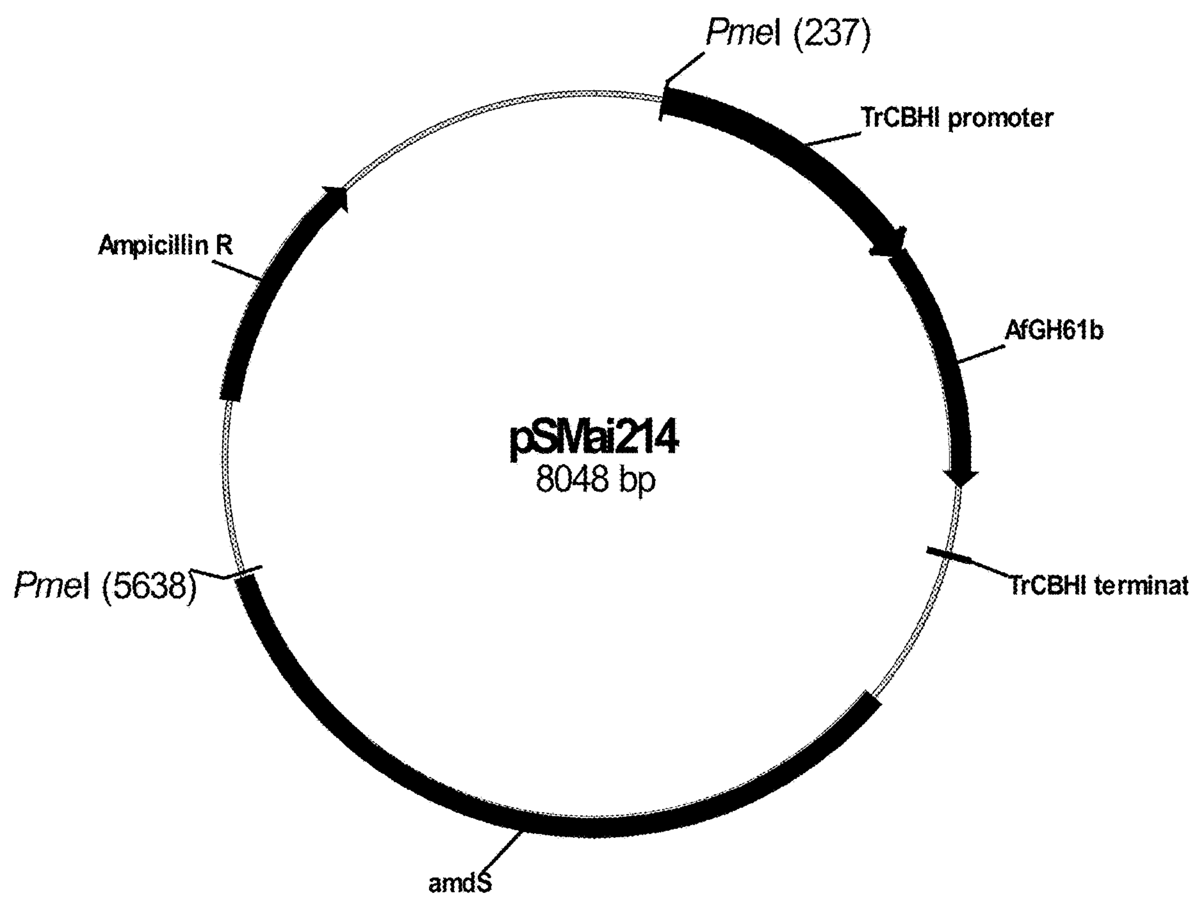
FIG. 2 shows a restriction map of plasmid pSMai214.

The 0.9 kb PCR product was inserted into the gel-purified Nco I/Pac I digested pMJ09 using an IN-FUSION® PCR Cloning Kit according to the manufacturer's protocol. The IN-FUSION® reaction was composed of 1× IN-FUSION® Reaction Buffer, 100 ng of the gel-purified Nco I/Pac I digested pMJ09, 37 ng of the 0.9 kb PCR product, 2 μl of 500 μg/ml BSA, and 1 μl of IN-FUSION® Enzyme in a 20 μl reaction volume. The reaction was incubated for 15 minutes at 37° C. and 15 minutes at 50° C. After the incubation period 30 μl of TE buffer were added to the reaction. A 2.5 μl aliquot was used to transform SOLOPACK® Gold Supercompetent Cells (Agilent Technologies, Inc., Cedar Creek, Tex., USA) according to the manufacturer's protocol. Transformants were screened by sequencing and one clone containing the insert with no PCR errors was identified and designated pSMai214 (FIG. 2). Plasmid pSMai214 can be digested with Pme I to generate an approximately 5.4 kb fragment for *T. reesei* transformation. The 5.4 kb fragment contains the expression cassette composed of the *T. reesei* Cel7A cellobiohydrolase I gene promoter, *A. fumigatus* GH61B polypeptide coding sequence, *T. reesei* Cel7A cellobiohydrolase I gene terminator, and *Aspergillus nidulans* acetamidase (amdS) gene.

Example 3: Construction of a Tandem Construct pDM287 for Expression of Both *Aspergillus fumigatus* CEL3A Beta-Glucosidase and *Aspergillus fumigatus* GH61B Polypeptide An *A. fumigatus* GH61B polypeptide expression cassette was amplified from plasmid pSMai214 using the gene-specific forward and reverse primers shown below. The region in italics represents vector homology to the site of insertion for an IN-FUSION® reaction.

```
Forward primer:
                                    (SEQ ID NO: 169)
5'-CGCGGTAGTGGCGCGGTCGACCGAATGTAGGATTGTT-3'

Reverse primer:
                                    (SEQ ID NO: 170)
5'-TTACCAATTGGCGCGCCACTACCGCGTTCGAGAAGA-3'
```

Fifty picomoles of each of the primers above were used in a PCR reaction composed of 25 ng of pSMai214 DNA, 1× PHUSION™ High-Fidelity Hot Start DNA Polymerase Buffer (Finnzymes Oy, Espoo, Finland), 1 μl of a 10 mM blend of dATP, dTTP, dGTP, and dCTP, and 1 unit of PHUSION™ High-Fidelity Hot Start DNA Polymerase (Finnzymes Oy, Espoo, Finland) in a final volume of 50 μl. The amplification was performed using an EPPENDORF® MASTERCYCLER® 5333 epgradient S programmed for 1 cycle at 98° C. for 30 seconds; 35 cycles each at 98° C. for 10 seconds, 60° C. for 30 seconds, and 72° C. for 1 minute 30 seconds; and 1 cycle at 72° C. for 10 minutes. PCR products were separated by 0.8% agarose gel electrophoresis using TAE buffer where an approximately 2.3 kb fragment was excised from the gel and extracted using a NUCLEOSPIN® Extract II Kit (Macherey-Nagel, Inc., Bethlehem, Pa., USA) according to the manufacturer's protocol.

Figure 3:
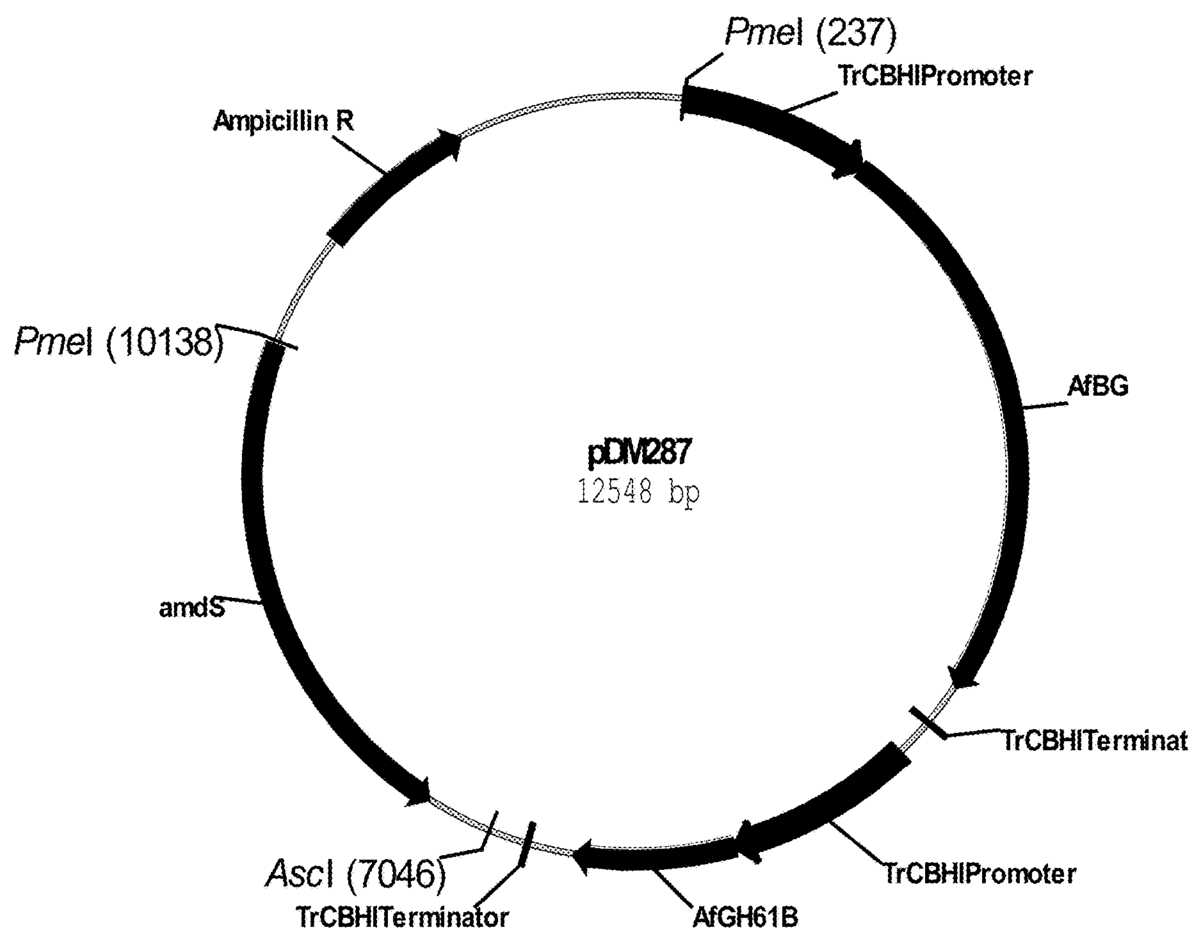
FIG. 3 shows a restriction map of plasmid pDM287.

The approximately 2.3 kb PCR product was inserted into Asc I-digested pEJG107 (WO 2005/047499) using an IN-FUSION® Advantage PCR Cloning Kit (Clontech Laboratories, Inc., Mountain View, Calif., USA) according to the manufacturer's protocol. Plasmid pEJG107 comprises an *Aspergillus fumigatus* CEL3A beta-glucosidase encoding sequence (SEQ ID NO: 53 [DNA sequence] and SEQ ID NO: 54 [deduced amino acid sequence]). The IN-FUSION® reaction was composed of 1× IN-FUSION® Reaction Buffer, 125 ng of the Asc I-digested pEJG107, 90 ng of the 2.33 kb PCR product, and 1 μl of IN-FUSION® Enzyme in a 10 μl reaction volume. The reaction was incubated for 15 minutes at 37° C. followed by 15 minutes at 50° C. After the incubation period 40 μl of TE were added to the reaction. A 2 μl aliquot was used to transform ONE SHOT® TOP10 competent cells (Invitrogen, Carlsbad, Calif., USA) according to the manufacturer's protocol. The *E. coli* transformation reactions were spread onto 2XYT plus ampicillin plates. The transformants were screened by sequencing and one clone containing the insert with no PCR errors was identified and designated pDM287 (FIG. 3). Plasmid pDM287 can be digested with Pme I to generate an approximately 9.9 kb fragment for *T. reesei* transformation. The 9.9 kb fragment contains two expression cassettes composed of (1) the *T. reesei* Cel7A cellobiohydrolase I gene promoter, *A. fumigatus* CEL3A beta-glucosidase coding sequence, and *T. reesei* Cel7A cellobiohydrolase I gene terminator; and (2) the *T. reesei* Cel7A cellobiohydrolase I gene promoter, *A. fumigatus* GH61B polypeptide coding sequence, and *T. reesei* Cel7A cellobiohydrolase I gene terminator. The 9.9 kb fragment also contains the *Aspergillus nidulans* acetamidase (amdS) gene.

Example 4: *Trichoderma reesei* Protoplast Generation and Transformation

Protoplast preparation and transformation were performed using a modified protocol by Penttila et al., 1987, *Gene* 61: 155-164. Briefly, *Trichoderma reesei* strain 981-O-8 (D4) was cultivated in 25 ml of YP medium supplemented with 2% (w/v) glucose and 10 mM uridine at 27° C. for 17 hours with gentle agitation at 90 rpm. Mycelia were collected by filtration using a Vacuum Driven Disposable Filtration System (Millipore, Bedford, Mass., USA) and washed twice with deionized water and twice with 1.2 M sorbitol. Protoplasts were generated by suspending the washed mycelia in 20 ml of 1.2 M sorbitol containing 15 mg of GLUCANEX® 200 G (Novozymes A/S, Bagsvaerd, Denmark) per ml and 0.36 units of chitinase (Sigma Chemical Co., St. Louis, Mo., USA) per ml for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemocytometer and resuspended to a final concentration of $1\times10^8$ protoplasts/ml in STC. Excess protoplasts were stored in a Cryo 1° C. Freezing Container (Nalgene, Rochester, N.Y., USA) at −80° C.

Approximately 100 μg of transforming plasmid (pSMai214, pDM287, or pEJG107) were digested with Pme I. The digestion reaction was purified by 0.8% agarose gel electrophoresis in TAE buffer. A DNA band containing the expression cassette of pSMai214, pDM287, or pEJG107, and the *Aspergillus nidulans* acetamidase (amdS) gene, was excised from the gel and extracted using a NUCLEOSPIN® Extract II Kit according to the manufacturer's suggested protocol.

The resulting purified DNA [1 μg of the 9.9 kb Pme I digested pDM287 (tandem transformation) or 1 μg of the 7.6 kb Pme I digested pEJG107 plus 1 μg of the 5.4 kb Pme digested pSMai214 (co-transformation)] was added to 100 μl of the protoplast solution and mixed gently. PEG buffer (250 μl) was added, and the reaction was mixed and incubated at 34° C. for 30 minutes. STC (3 ml) was then added, and the reaction was mixed and then spread onto COVE plates for amdS selection. The plates were incubated at 28° C. for 6-11 days.

Example 5: Evaluation of *Trichoderma reesei* Transformants Expressing *Aspergillus fumigatus* CEL3A Beta-Glucosidase and *Aspergillus fumigatus* GH 61B Polypeptide

Figure 4A:
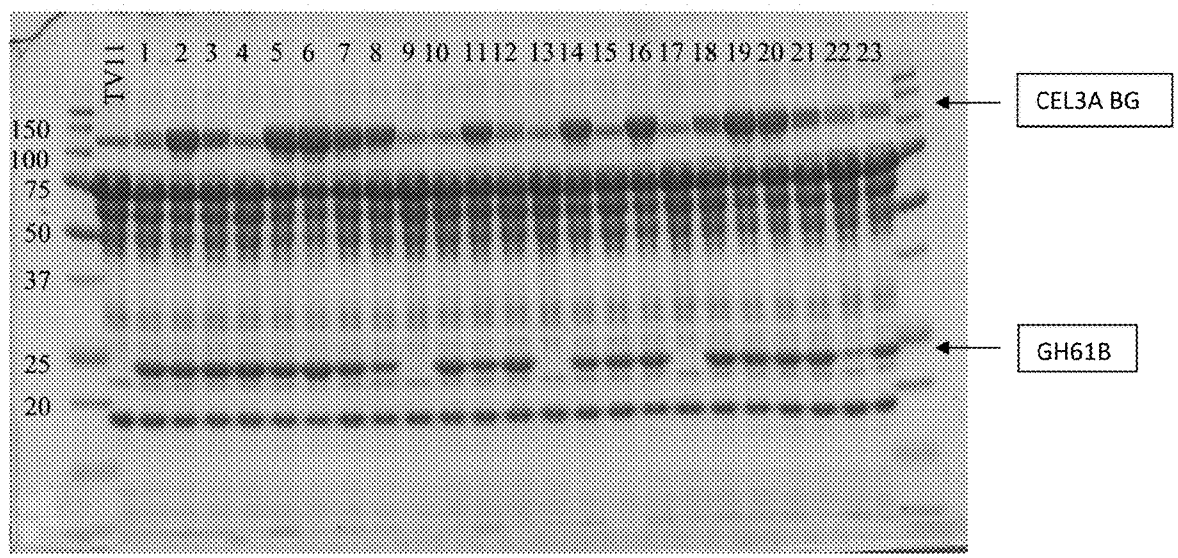
FIGS. 4A-4D shows SDS-PAGE profiles of 45 transformants of pDM287 (transformation of tandem construct; 4A and 4B) and 45 transformants of pEJG107+pSMai214 (co-transformation; 4C and 4D).
Figure 4B:
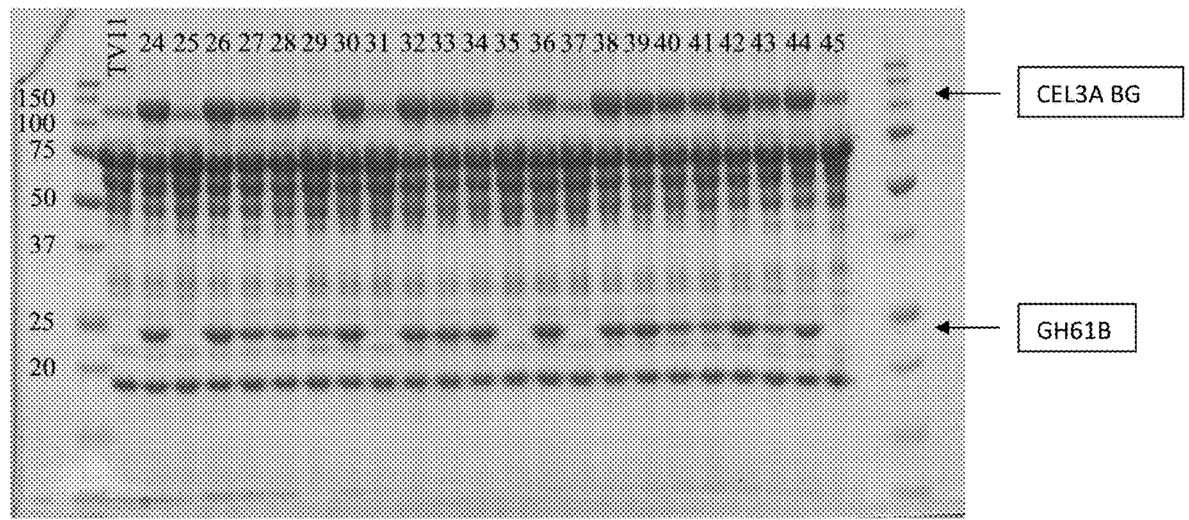
Figures 4C, 4D:
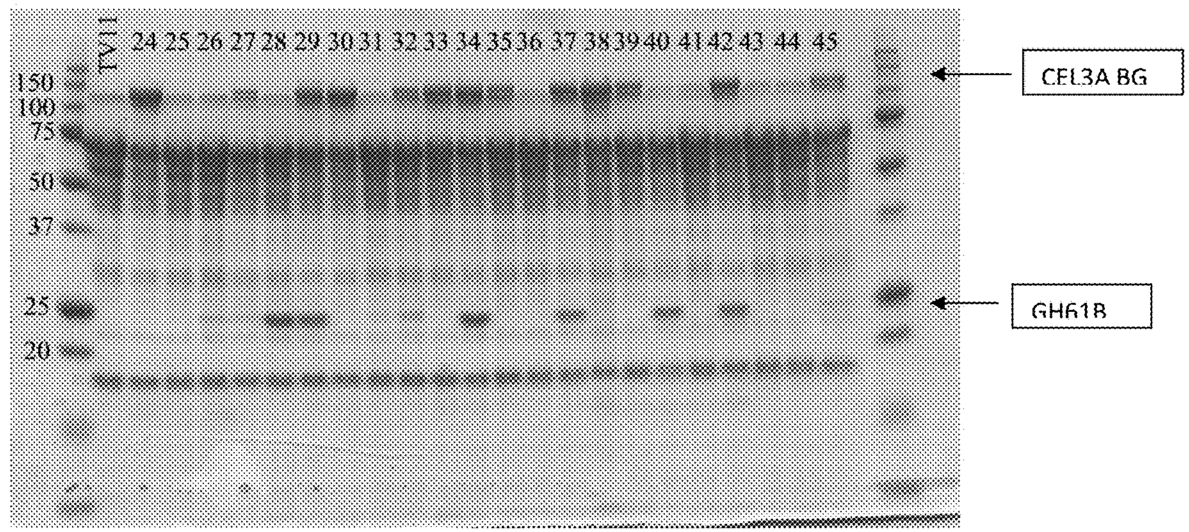

*Trichoderma reesei* transformants (Example 4) were transferred from COVE transformation plates to COVE2 plates supplemented with 10 mM uridine using an inoculation loop and incubated 5-7 days at 28° C. Spores were collected with an inoculating loop and transferred to 25 ml of CIM medium in a 125 ml plastic shake flask. The shake flask cultures were incubated for 5 days at 28° C., 200 rpm. A 1 ml aliquot of each culture was centrifuged at 13,400×g in a microcentrifuge and culture supernatant was recovered. Five μl of each culture supernatant were analyzed by SDS-PAGE using a CRITERION® 8-16% Tris-HCl Gel (Bio-Rad Laboratories, Hercules, Calif., USA) according to the manufacturer's instructions. The resulting gel was stained with BIO-SAFE™ Coomassie (Bio-Rad Laboratories, Hercules, Calif., USA). FIGS. 4A-4D show the SDS-PAGE profiles of the cultures of 45 transformants of pDM287 (tandem construct; FIGS. 4A and 4B) and 45 transformants of pEJG107+pSMai214 (co-transformation; 4C and 4D). The results demonstrated that the transformants produced major protein bands of approximately 130 kDa corresponding to the *A. fumigatus* CEL3A beta-glucosidase and approximately 24 kDa corresponding to the *A. fumigatus* GH61B polypeptide. A negative control sample, consisting of untransformed *T. reesei* strain 981-O-8 (D4) culture supernatant, showed no prominent bands at approximately 130 kDa and approximately 24 kDa.

The results in FIGS. 4A-4D and summarized below demonstrated that transformation with the tandem construct pDM287 yielded more positive transformants for *A. fumigatus* beta-glucosidase and *A. fumigatus* GH61B polypeptide production than co-transformation with pEJG107 and pSMai214.

| Transforming DNA | Number of transformants positive for *A. fumigatus* beta-glucosidase and *A. fumigatus* GH61B polypeptide production by SDS-PAGE |
|---|---|
| pDM287 (tandem construct) | 33 of 45 (73%) |
| pEJG107 + pSMai214 (co-transformation) | 13 of 45 (29%) |

Example 6: Beta-Glucosidase Assay of *Trichoderma reesei* Transformants Expressing *Aspergillus fumigatus* CEL3A Beta-Glucosidase and *Aspergillus fumigatus* GH61B Polypeptide The culture supernatants of Example 5 were assayed for beta-glucosidase activity using a BIOMEK® 3000, a BIOMEK® NX, and an ORCA® robotic arm (Beckman Coulter, Inc, Fullerton, Calif., USA). Culture supernatants were diluted appropriately in 0.1 M succinate, 0.01% TRITON® X-100 (4-(1,1,3,3-tetramethylbutyl)phenyl-polyethylene glycol) buffer pH 5.0 (sample buffer) followed by a series of dilutions from 0-fold to ⅓-fold to ⅙-fold of the diluted sample. A total of 20 μl of each dilution was transferred to a 96-well flat bottom plate. Two hundred microliters of a p-nitrophenyl-beta-D-glucopyranoside substrate solution (1 mg of p-nitrophenyl-beta-D-glucopyranoside per ml of 0.1 M succinate pH 5.0) were added to each well and then incubated at ambient temperature for 45 minutes. Upon completion of the incubation period 50 μl of quenching buffer (1 M Tris buffer pH 9) were added to each well. An endpoint was measured at an optical density of 405 nm for the 96-well plate.

Figure 5:
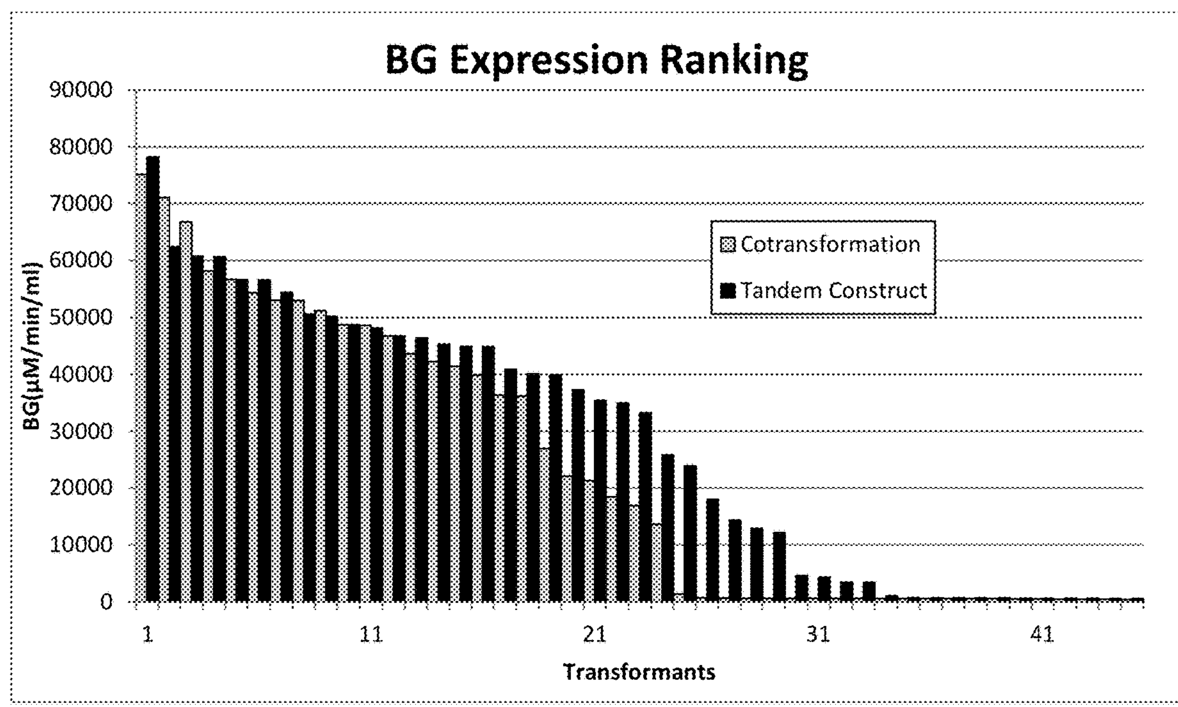
FIG. 5 shows a comparison of positive transformants for beta-glucosidase activity: between 45 transformants of pDM287 and 45 transformants of pEJG107+pSMai214.

The results shown in FIG. 5 confirmed the SDS-PAGE results of Example 5 that transformation with the tandem construct pDM287 yielded more positive transformants for *A. fumigatus* beta-glucosidase and *A. fumigatus* GH61B polypeptide production than co-transformation with pEJG107 and pSMai214.

The present invention is further described by the following numbered paragraphs:

[1] A method for obtaining positive transformants of a filamentous fungal host cell, comprising: (a) transforming into a population of cells of the filamentous fungal host a tandem construct comprising (i) one or more selectable markers, (ii) a first polynucleotide encoding a first polypeptide having biological activity operably linked to a first promoter and a first terminator, and (iii) a second polynucleotide encoding a second polypeptide having biological activity operably linked to a second promoter and a second terminator; (b) selecting transformants based on the one or more selectable markers, wherein the number of positive transformants for the first and second polypeptides having biological activity obtained by transformation of the tandem construct is higher compared to the number of positive transformants obtained by co-transformation of separate constructs for each of the first and second polynucleotides; and (c) isolating a transformant of the filamentous fungal host cell comprising the tandem construct expressing the first and second polypeptides having biological activity.

[2] The method of paragraph 1, wherein the number of positive transformants for the first and second polypeptides having biological activity obtained by transformation of the tandem construct is increased at least 1.1-fold, e.g., at least 1.25-fold, at least 1.5-fold, at least 2-fold, at least 2.5-fold, at least 3-fold, at least 4-fold, at least 5-fold, or at least 10-fold, compared to the number of positive transformants obtained by co-transformation of separate constructs for each of the first and second polynucleotides.

[3] The method of paragraph 1 or 2, wherein the tandem construct integrates by ectopic integration into the chromosome of the filamentous fungal host cell.

[4] The method of any of paragraphs 1-3, wherein the tandem construct is contained in an expression vector.

[5] The method of any of paragraphs 1-4, wherein the tandem construct further comprises a first homologous repeat flanking 5' of the one or more selectable markers and a second homologous repeat flanking 3' of the one or more selectable markers, wherein the first homologous repeat and the second homologous repeat undergo homologous recombination to excise the one or more selectable markers.

[6] The method of paragraph 5, wherein the first and second homologous repeats are identical or have a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 97%, at least 98%, or at least 99% to each other.

[7] The method of paragraph 5 or 6, wherein the first and second homologous repeats are each at least 50 bp, e.g., at least 100 bp, at least 200 bp, at least 400 bp, at least 800 bp, at least 1000 bp, at least 1500 bp, or at least 2000 bp.

[8] The method of any of paragraphs 5-7, wherein upon the excision of the one or more selectable markers, the one or more selectable markers can be reused for introducing another tandem construct into the filamentous fungal host cell.

[9] The method of any of paragraphs 1-8, wherein the polypeptides having biological activity are different polypeptides.

[10] The method of any of paragraphs 1-8, wherein the polypeptides having biological activity are the same polypeptide.

[11] The method of any of paragraphs 1-10, wherein the promoters are different promoters.

[12] The method of any of paragraphs 1-10, wherein the promoters are the same promoter.

[13] The method of any of paragraphs 1-12, wherein the terminators are different terminators.

[14] The method of any of paragraphs 1-12, wherein the terminators are the same terminator.

[15] The method of any of paragraphs 1-14, wherein the filamentous fungal cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* cell.

[16] The method of paragraph 15, wherein the *Trichoderma* strain is selected from the group consisting of *Trichoderma harzianum, Trichoderma koningii, Trichoderma longibrachiatum, Trichoderma reesei*, and *Trichoderma viride.*

[17] The method of paragraph 15, wherein the *Trichoderma* strain is *Trichoderma reesei.*

[18] A filamentous fungal host cell, comprising: a tandem construct comprising (i) one or more selectable markers, (ii) a first polynucleotide encoding a first polypeptide having biological activity operably linked to a first promoter and a first terminator, and (iii) a second polynucleotide encoding a second polypeptide having biological activity operably linked to a second promoter and a second terminator.

[19] The filamentous fungal host cell of paragraph 18, wherein the tandem construct integrated by ectopic integration into the chromosome of the filamentous fungal host cell.

[20] The filamentous fungal host cell of paragraph 18 or 19, wherein the tandem construct is contained in an expression vector.

[21] The filamentous fungal host cell of any of paragraphs 18-20, wherein the tandem construct further comprises a first homologous repeat flanking 5' of the one or more selectable markers and a second homologous repeat flanking 3' of the one or more selectable markers, wherein the first homologous repeat and the second homologous repeat undergo homologous recombination to excise the one or more selectable markers.

[22] The filamentous fungal host cell of paragraph 21, wherein the first and second homologous repeats are identical or have a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 97%, at least 98%, or at least 99% to each other.

[23] The filamentous fungal host cell of paragraph 21 or 22, wherein the first and second homologous repeats are each at least 50 bp, e.g., at least 100 bp, at least 200 bp, at least 400 bp, at least 800 bp, at least 1000 bp, at least 1500 bp, or at least 2000 bp.

[24] The filamentous fungal host cell of any of paragraphs 21-23, wherein upon the excision of the one or more selectable markers, the one or more selectable markers can be reused for introducing another tandem construct into the filamentous fungal host cell.

[25] The filamentous fungal host cell of any of paragraphs 18-24, wherein the polypeptides having biological activity are different polypeptides.

[26] The filamentous fungal host cell of any of paragraphs 18-24, wherein the polypeptides having biological activity are the same polypeptide.

[27] The filamentous fungal host cell of any of paragraphs 18-26, wherein the promoters are different promoters.

[28] The filamentous fungal host cell of any of paragraphs 18-26, wherein the promoters are the same promoter.

[29] The filamentous fungal host cell of any of paragraphs 18-28, wherein the terminators are different terminators.

[30] The filamentous fungal host cell of any of paragraphs 18-28, wherein the terminators are the same terminator.

[31] The filamentous fungal host cell of any of paragraphs 18-30, wherein the filamentous fungal cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* cell.

[32] The filamentous fungal host cell of paragraph 31, wherein the *Trichoderma* strain is selected from the group consisting of *Trichoderma harzianum, Trichoderma koningii, Trichoderma longibrachiatum, Trichoderma reesei*, and *Trichoderma viride*.

[33] The filamentous fungal host cell of paragraph 31, wherein the *Trichoderma* strain is *Trichoderma reesei*.

[34] A method of producing multiple recombinant polypeptides having biological activity, comprising: cultivating a filamentous fungal host cell transformed with a tandem construct comprising (i) one or more selectable markers, (ii) a first polynucleotide encoding a first polypeptide having biological activity operably linked to a first promoter and a first terminator, and (iii) a second polynucleotide encoding a second polypeptide having biological activity operably linked to a second promoter and a second terminator, under conditions conducive for production of the polypeptides.

[35] The method of paragraph 34, further comprising recovering the first and second polypeptides having biological activity.

[36] The method of paragraph 34 or 35, wherein the tandem construct integrated by ectopic integration into the chromosome of the filamentous fungal host cell.

[37] The method of any of paragraphs 34-36, wherein the tandem construct is contained in an expression vector.

[38] The method of any of paragraphs 34-37, wherein the tandem construct further comprises a first homologous repeat flanking 5' of the one or more selectable markers and a second homologous repeat flanking 3' of the one or more selectable markers, wherein the first homologous repeat and the second homologous repeat undergo homologous recombination to excise the one or more selectable markers.

[39] The method of paragraph 38, wherein the first and second homologous repeats are identical or have a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 97%, at least 98%, or at least 99% to each other.

[40] The method of paragraph 38 or 39, wherein the first and second homologous repeats are each at least 50 bp, e.g., at least 100 bp, at least 200 bp, at least 400 bp, at least 800 bp, at least 1000 bp, at least 1500 bp, or at least 2000 bp.

[41] The method of any of paragraphs 37-40, wherein upon the excision of the one or more selectable markers, the one or more selectable markers can be reused for introducing another tandem construct into the filamentous fungal host cell.

[42] The method of any of paragraphs 34-41, wherein the polypeptides having biological activity are different polypeptides.

[43] The method of any of paragraphs 34-41, wherein the polypeptides having biological activity are the same polypeptide.

[44] The method of any of paragraphs 34-43, wherein the promoters are different promoters.

[45] The method of any of paragraphs 34-43, wherein the promoters are the same promoter.

[46] The method of any of paragraphs 34-45, wherein the terminators are different terminators.

[47] The method of any of paragraphs 34-45, wherein the terminators are the same terminator.

[48] The method of any of paragraphs 34-47, wherein the filamentous fungal cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* cell.

[49] The method of paragraph 48, wherein the *Trichoderma* strain is selected from the group consisting of *Trichoderma harzianum, Trichoderma koningii, Trichoderma longibrachiatum, Trichoderma reesei*, and *Trichoderma viride*.

[50] The method of paragraph 48, wherein the *Trichoderma* strain is *Trichoderma reesei*.

[51] A tandem construct comprising (i) one or more selectable markers, (ii) a first polynucleotide encoding a first polypeptide having biological activity operably linked to a first promoter and a first terminator, and (iii) a second polynucleotide encoding a second polypeptide having biological activity operably linked to a second promoter and a second terminator.

[52] The tandem construct of paragraph 51, wherein the tandem construct further comprises a first homologous repeat flanking 5' of the one or more selectable markers and a second homologous repeat flanking 3' of the one or more selectable markers, wherein the first homologous repeat and the second homologous repeat undergo homologous recombination to excise the one or more selectable markers.

[53] The tandem construct of paragraph 52, wherein the first and second homologous repeats are identical or have a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 97%, at least 98%, or at least 99% to each other.

[54] The tandem construct of paragraph 52 or 53, wherein the first and second homologous repeats are each at least 50 bp, e.g., at least 100 bp, at least 200 bp, at least 400 bp, at least 800 bp, at least 1000 bp, at least 1500 bp, or at least 2000 bp.

[55] The tandem construct of any of paragraphs 52-54, wherein upon the excision of the one or more selectable markers, the one or more selectable markers can be reused for introducing another tandem construct into the filamentous fungal host cell.

[56] The tandem construct of any of paragraphs 51-55, wherein the polypeptides having biological activity are different polypeptides.

[57] The tandem construct of any of paragraphs 51-55, wherein the polypeptides having biological activity are the same polypeptide.

[58] The tandem construct of any of paragraphs 51-57, wherein the promoters are different promoters.

[59] The tandem construct of any of paragraphs 51-57, wherein the promoters are the same promoter.

[60] The method of any of paragraphs 51-59, wherein the terminators are different terminators.

[61] The method of any of paragraphs 51-59, wherein the terminators are the same terminator.

[62] An expression vector comprising the tandem construct of any of paragraph 51-61.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A tandem construct comprising (i) one or more selectable markers, (ii) a first polynucleotide encoding a first polypeptide having biological activity operably linked to a first promoter and a first terminator, (iii) a second polynucleotide encoding a second polypeptide having biological activity operably linked to a second promoter and a second terminator, and (iv) a first homologous repeat flanking 5' of the one or more selectable markers and a second homologous repeat flanking 3' of the one or more selectable markers, wherein the first homologous repeat and the second homologous repeat undergo homologous recombination to excise the one or more selectable markers, wherein the tandem construct integrates by ectopic integration into the chromosome of a filamentous fungal host cell.

2. The tandem construct of claim 1, wherein the first and second homologous repeats are identical or have a sequence identity of at least 70% to each other.

3. The tandem construct of claim 1, wherein the first and second homologous repeats are each at least 50 bp.

4. The tandem construct of claim 1, wherein upon the excision of the one or more selectable markers, the one or more selectable markers can be reused for introducing another tandem construct into the filamentous fungal host cell.

5. The tandem construct of claim 1, wherein the polypeptides having biological activity are different polypeptides.

6. The tandem construct of claim 1, wherein the polypeptides having biological activity are the same polypeptide.

7. The tandem construct of claim 1, wherein the promoters are different promoters.

8. The tandem construct of claim 1, wherein the promoters are the same promoter.

9. The tandem construct of claim 1, wherein the terminators are different terminators.

10. The tandem construct of claim 1, wherein the terminators are the same terminator.

11. The tandem construct of claim 1, wherein the filamentous fungal cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* cell.

12. The tandem construct of claim 11, wherein the *Trichoderma* strain is selected from the group consisting of *Trichoderma harzianum, Trichoderma koningii, Trichoderma longibrachiatum, Trichoderma reesei*, and *Trichoderma viride*.

13. The tandem construct of claim 11, wherein the filamentous fungal cell is *Trichoderma reesei*.

* * * * *